US011008392B2

(12) United States Patent
Iwamoto et al.

(10) Patent No.: US 11,008,392 B2
(45) Date of Patent: May 18, 2021

(54) HANP-FC-CONTAINING MOLECULAR CONJUGATE

(71) Applicant: DAIICHI SANKYO COMPANY, LIMITED, Tokyo (JP)

(72) Inventors: Mitsuhiro Iwamoto, Tokyo (JP); Shohei Oishi, Tokyo (JP); Yukiko Sekiguchi, Tokyo (JP); Hiroyuki Chaya, Tokyo (JP); Ryuki Miyauchi, Tokyo (JP); Takeshi Honda, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 103 days.

(21) Appl. No.: 16/314,411

(22) PCT Filed: Jun. 30, 2017

(86) PCT No.: PCT/JP2017/024206
§ 371 (c)(1),
(2) Date: Dec. 29, 2018

(87) PCT Pub. No.: WO2018/003983
PCT Pub. Date: Jan. 4, 2018

(65) Prior Publication Data
US 2019/0169293 A1 Jun. 6, 2019

(30) Foreign Application Priority Data

Jul. 1, 2016 (JP) .............................. JP2016-131450

(51) Int. Cl.

| A61K 47/60 | (2017.01) |
| C12N 15/09 | (2006.01) |
| C07K 19/00 | (2006.01) |
| A61K 39/395 | (2006.01) |
| C07K 16/28 | (2006.01) |
| A61P 9/12 | (2006.01) |
| C07K 14/58 | (2006.01) |
| A61K 38/22 | (2006.01) |
| A61K 47/68 | (2017.01) |
| C12P 19/18 | (2006.01) |
| C12P 1/00 | (2006.01) |
| A61P 9/04 | (2006.01) |
| A61P 13/12 | (2006.01) |
| C07K 16/00 | (2006.01) |
| A61P 9/10 | (2006.01) |
| A61P 9/14 | (2006.01) |
| C07K 16/12 | (2006.01) |
| A61K 38/00 | (2006.01) |

(52) U.S. Cl.
CPC ............ *C07K 16/283* (2013.01); *A61K 38/22* (2013.01); *A61K 39/395* (2013.01); *A61K 47/60* (2017.08); *A61K 47/68* (2017.08); *A61P 9/04* (2018.01); *A61P 9/10* (2018.01); *A61P 9/12* (2018.01); *A61P 9/14* (2018.01); *A61P 13/12* (2018.01); *C07K 14/58* (2013.01); *C07K 16/00* (2013.01); *C07K 19/00* (2013.01); *C12N 15/09* (2013.01); *C12P 1/00* (2013.01); *C12P 19/18* (2013.01); *A61K 38/00* (2013.01); *C07K 16/12* (2013.01)

(58) Field of Classification Search
None
See application file for complete search history.

(56) References Cited

U.S. PATENT DOCUMENTS

2018/0208915 A1    7/2018  Kawaguchi et al.

FOREIGN PATENT DOCUMENTS

| EP | 2 949 665 A | 12/2015 |
| WO | WO-2008/079995 A2 | 7/2008 |
| WO | WO-2008/154226 A1 | 12/2008 |
| WO | WO-2013/120066 A1 | 8/2013 |
| WO | WO-2015/157446 A1 | 10/2015 |

OTHER PUBLICATIONS

Office Action dated Feb. 4, 2020 for corresponding Canadian Application No. 3,029,605.
Agarwal et al, Site-Specific Antibody-Drug Conjugates: The Nexus of Bioorthogonal Chemistry, Protein Engineering, and Drug Development, Bioconjugate Chemistry, 2015,vol. 26, pp. 176-192.
Chang et al, Subtiligase: A tool for semisynthesis of proteins, Proc. Natl. Acad. Sci., 1994, vol. 91, pp. 12544-12547.
Huang et al, Chemoenzymatic Glycoengineering of Intact IgG Antibodies for Gain of Functions, Journal of the American Chemical Society, 2012, vol. 134, pp. 12308-12318.
Is Hydroxyapatite Useful in Purification of Antibody?, Biompact, 2014, vol. 3.
Kontos et al, Drug development: longer-lived proteins, Chem Soc Rev, 2012, vol. 41, pp. 2686-2695.
Kuroski De Bold et al, Characterization of a long-acting recombinant human serum albumin-atrial natriuretic factor (ANF) expressed in Pichia pastoris, Regulatory Peptides, 2012, pp. 7-10.
Mezo et al, Atrial Natriuretic Peptide-Fc, ANP-Fc, Fusion Proteins: Semisynthesis, In Vitro Activity and Pharmacokinetics in Rats, Bioconjugate Chem, 2012, pp. 518-526.
Nesher et al, Reversible Pegylation Prolongs the Hypotensive Effect of Atrial Natriuretic Peptide, Bioconjugate Chem, 2008, vol. 19, pp. 342-348.
Parsons et al, Optimal Synthetic Glycosylation of a Therapeutic Antibody, Glycoproteins, 2016, vol. 55, pp. 2361-2367.
Richter et al, Subcutaneous Absorption of Biotherapeutics: Knowns and Unknowns, Drug Metabolism & Disposition, 2014, vol. 42, pp. 1881-1889.
Iwamoto et al.; "Generation of efficient mutants of endoglycosidase from *Streptococcus pyogenes* and their application in a novel one-pot transglycosylation reaction for antibody modification"; PLOS ONE; Feb. 23, 2018 (Feb. 23, 2018); p. 1-13.

(Continued)

*Primary Examiner* — Padmavathi Baskar
(74) *Attorney, Agent, or Firm* — Foley & Lardner LLP

(57) ABSTRACT

The present invention provides a conjugate comprising a hANP peptide bonded via a polyethylene glycol linker to a glycan attached to Asn297 of a Fc-containing molecule (N297 glycan), or a pharmaceutically acceptable salt thereof, a medicament comprising the same as an active ingredient, a method for producing the same, etc.

8 Claims, 28 Drawing Sheets

Specification includes a Sequence Listing.

(56) References Cited

OTHER PUBLICATIONS

Tang et al.; "One-pot N-glycosylation remodeling of IgG with non-natural sialylglycopeptides enables glycosite-specific and dual-payload antibody-drug conjugates"; vol. 14; Electronic Supplementary Material (ESI) for Organic & Biomolecular Chemistry; 2016; pp. S1-S70.
Extended European Search Report dated Nov. 27, 2019 for corresponding Application No. 17820337.8.
Iwamoto et al,"Pharmacokinetic and Pharmacodynamic Profiles of Glyco-Modified Atrial Natriuretic Peptide Derivatives Synthesized Using Chemo-enzymatic Synthesis Approaches", Bioconjugate Chemistry, vol. 29, No. 8, Aug. 3, 2018 (Aug. 3, 2018), pp. 2829-2837, XP055641868.
Nesher et al, "Reversible pegylation prolongs the hypotensive effect of atrial natriuretic peptide", Bioconjugate Chemistry, American Chemical Society, US, vol. 19, No. 1, Jan. 1, 2008 (Jan. 1, 2008), pp. 342-348, XP002493772.
Canadian Intellectual Property Office, "Office Action," issued in connection with Canadian Patent Application No. 3,029,605, dated Feb. 16, 2021.

[Figure 1]
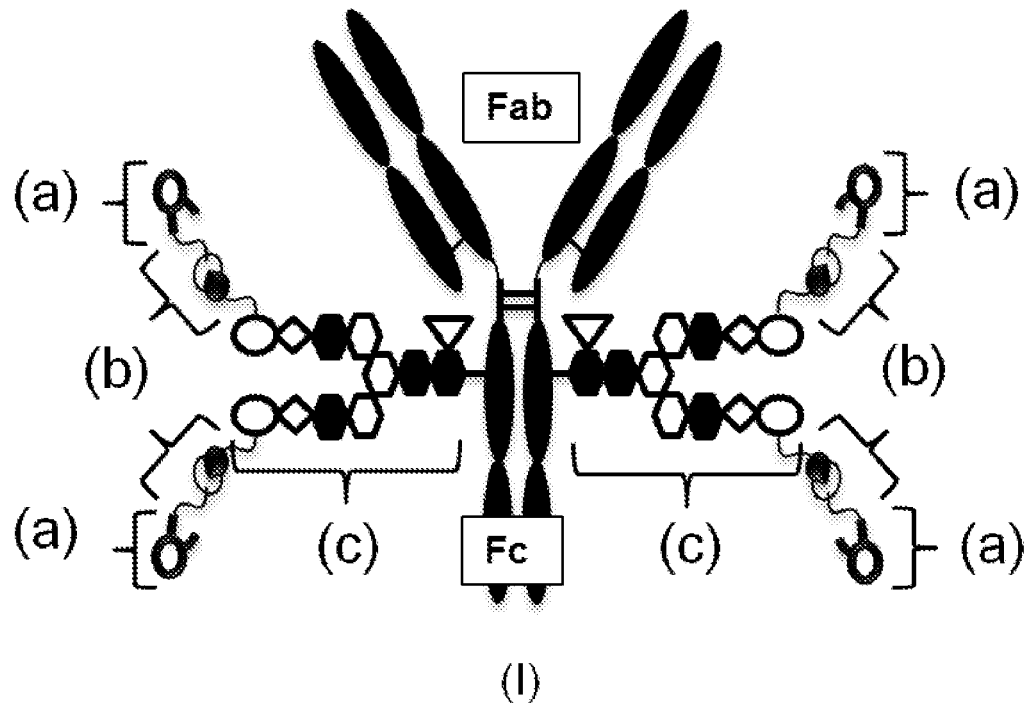
[Figure 2A]
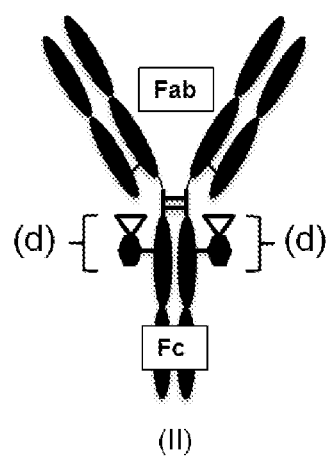
[Figure 2B]
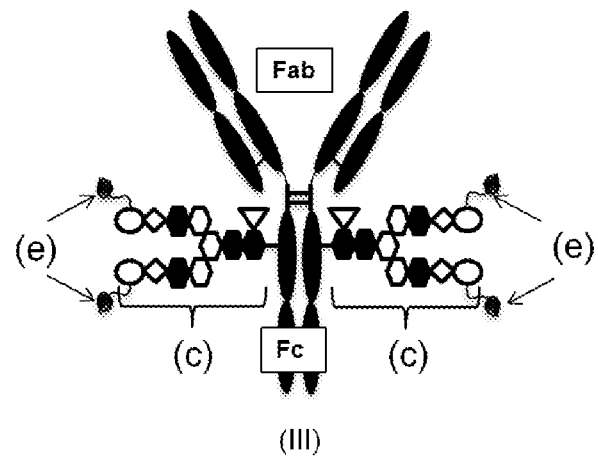

[Figure 3A]
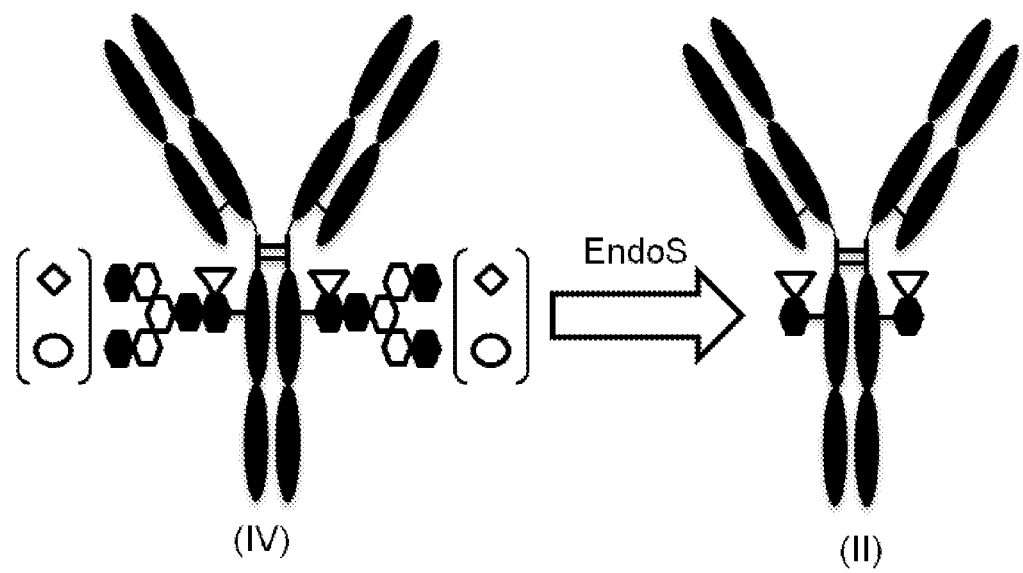
[Figure 3B]
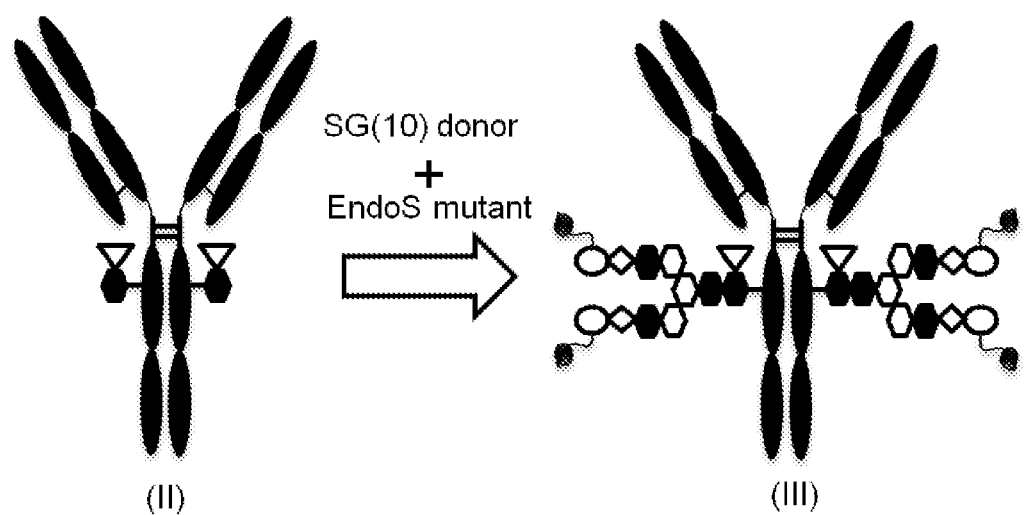

[Figure 4]
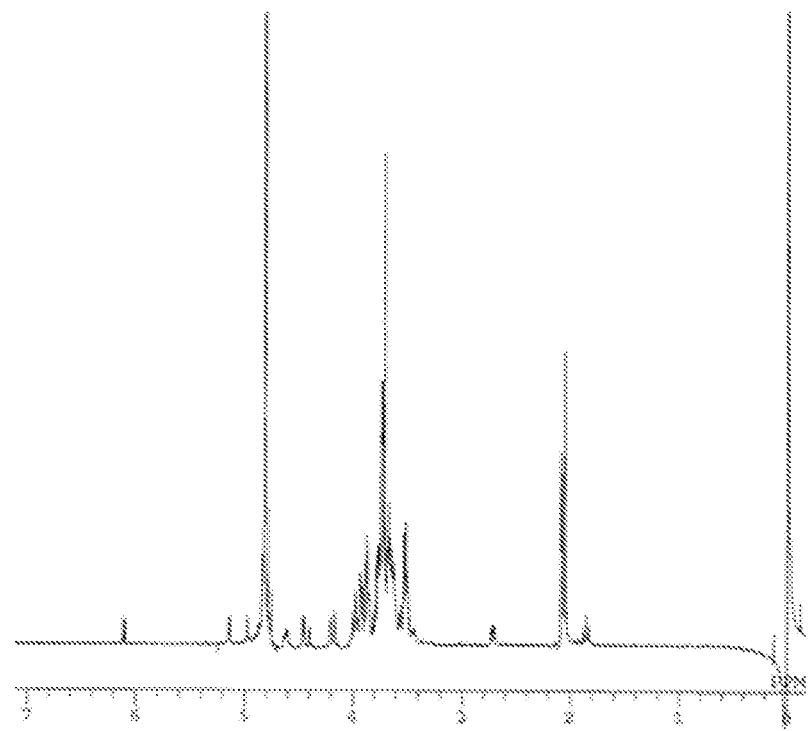
[Figure 5]
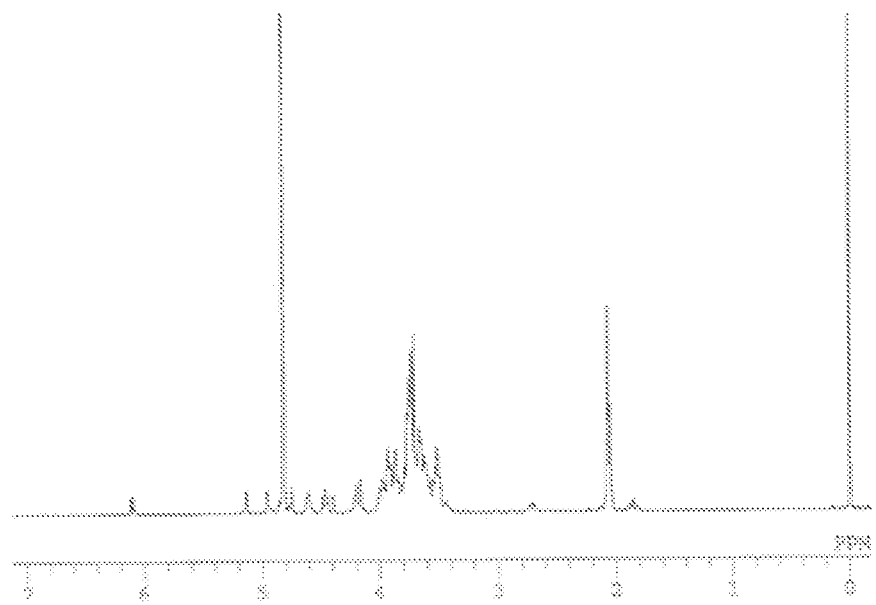

[Figure 6]
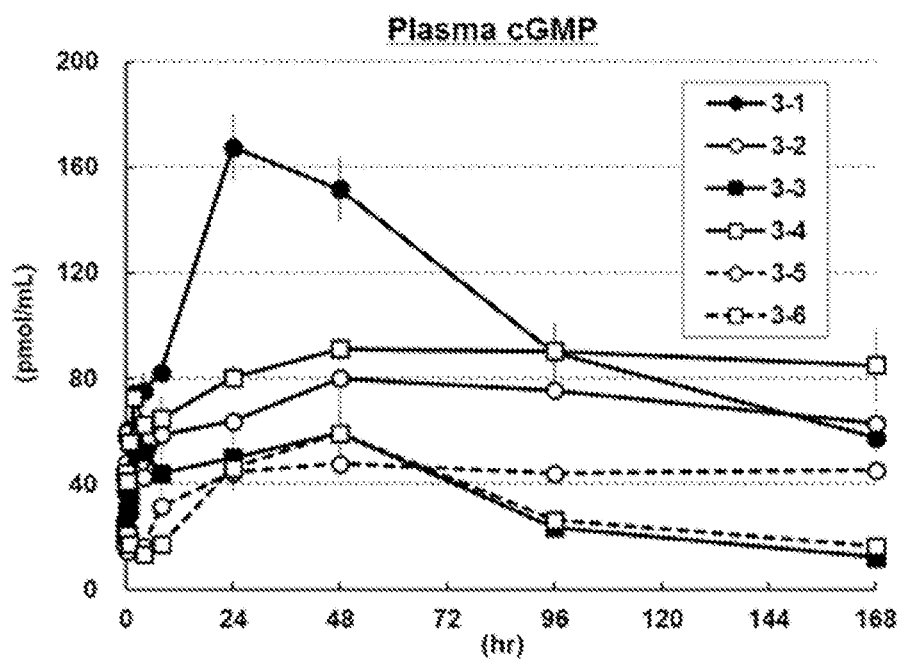
[Figure 7]
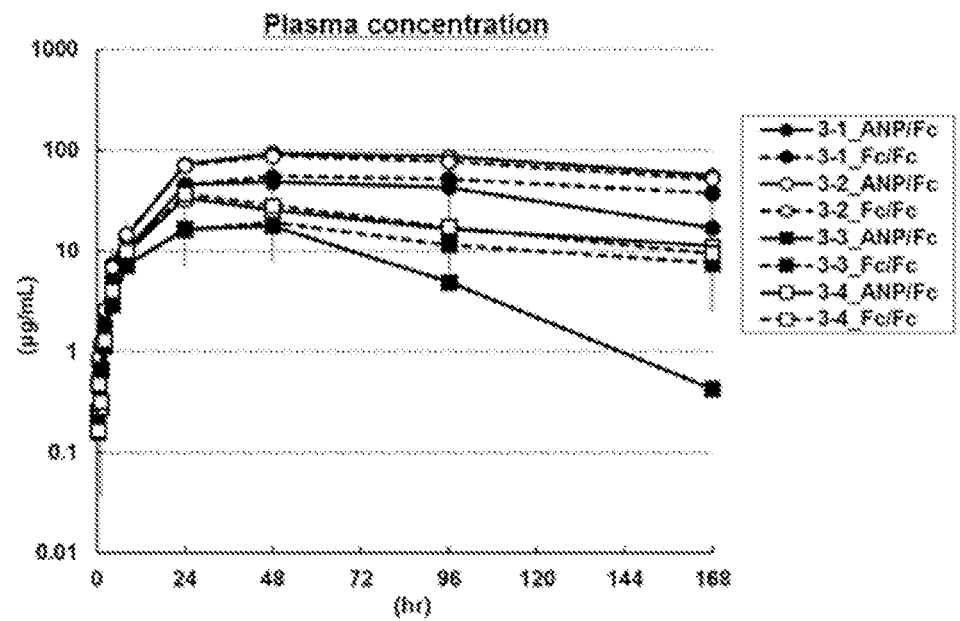

[Figure 8]
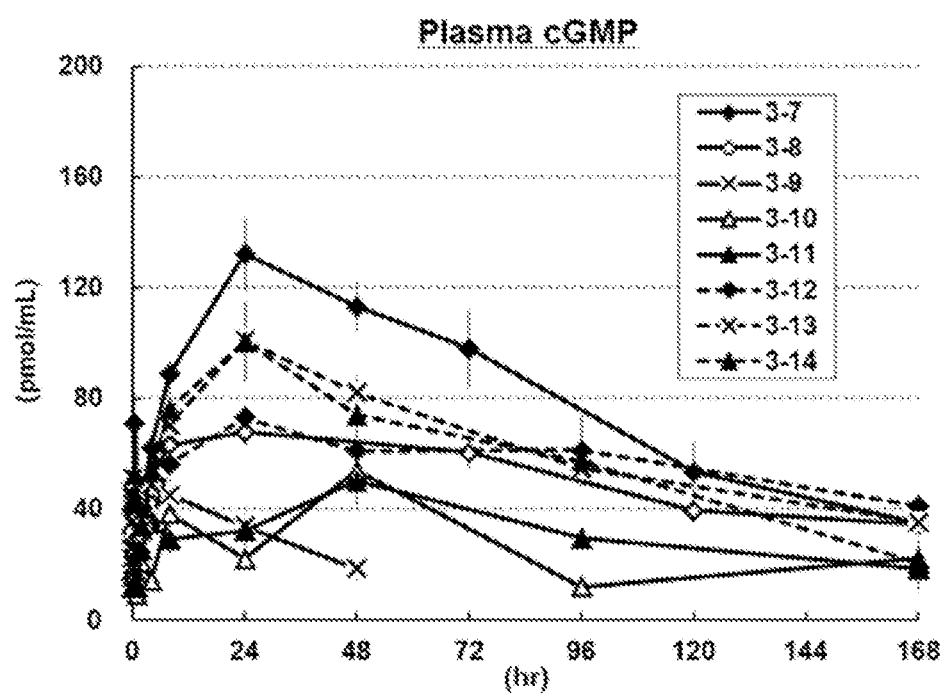
[Figure 9]
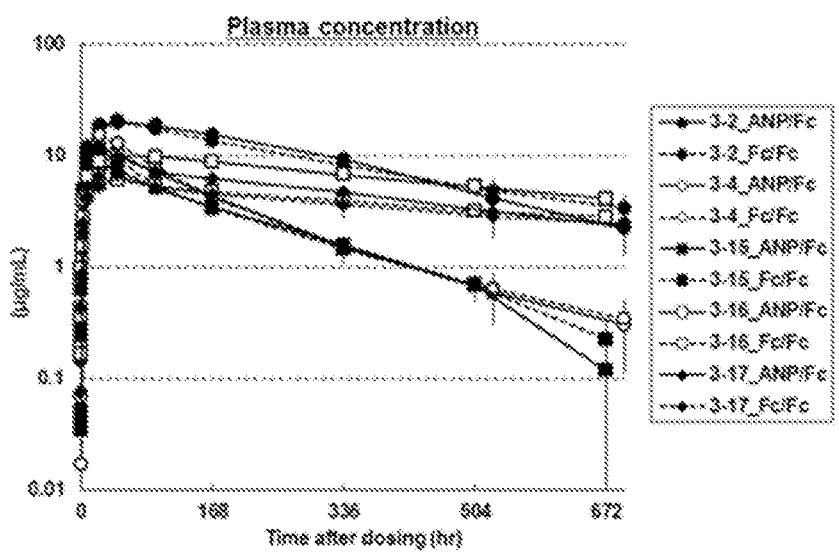

(Formula 37)

Compound 1-1

(Formula 38)

Compound 1-2

(Formula 39)

(Formula 40)

(Formula 41)

Compound 1-5

(Formula 42)

Compound 1-6

(Formula 43)

Compound 1-7

(Formula 44)

Compound 1-8

(Figure 45)

Compound 1-9

(Formula 46)

Compound 1-10

(Formula 47)

Compound 1-11

(Formula 48)

Compound 1-12

(Formula 49)

Compound 1-13

(Formula 50)

Compound 1-14

(Formula 51)

(Formula 52)

(Formula 53)

(Formula 54)

Compound 3-1

(Figure 55)

(Formula 56)

Compound 3-2

(Formula 57)

(Formula 58)

(Formula 59)

(Formula 60)

Compound 3-3

(Formula 61)

(Formula 62)

Compound 3-4

(Formula 63)

(Formula 64)

(Formula 65)

(Formula 66)

(Formula 67)

(Formula 68)

Compound 3-6

(Formula 69)

(Formula 70)

(Formula 71)

(Formula 72)

(Formula 73)

Compound 3-16

(Formula 74)

(Formula 75)

(Formula 76)

SEQUENCE LISTING

<160> NUMBER OF SEQ ID NOS: 19

<210> SEQ ID NO 1
<211> LENGTH: 28
<212> TYPE: PRT
<213> ORGANISM: Homo sapiens

<400> SEQUENCE: 1

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 2
<211> LENGTH: 1422
<212> TYPE: DNA
<213> ORGANISM: Artificial Sequence
<220> FEATURE:
<223> OTHER INFORMATION: Nucleotide encoding the heavy chain of anti-LPS
      mAb-A
<220> FEATURE:
<221> NAME/KEY: CDS
<222> LOCATION: (1)..(1422)
<223> OTHER INFORMATION: Encoding polypeptides including a signal
      sequence (19 aa) followed by Heavy chain of mAb-A (20-474: 455 aa)

<400> SEQUENCE: 2 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys
            20                  25                  30 cca ggc gcc agc gtg aag gtg tcc tgc aag gcc agc ggc tac acc ttt     144
Pro Gly Ala Ser Val Lys Val Ser Cys Lys Ala Ser Gly Tyr Thr Phe
        35                  40                  45 acc agc tac tgg atc aac tgg gtg cgc cag gcc cct gga cag ggc ctg     192
Thr Ser Tyr Trp Ile Asn Trp Val Arg Gln Ala Pro Gly Gln Gly Leu
    50                  55                  60 gaa tgg atg ggc aac atc tac ccc ggc agc agc atc aac tac aac         240
Glu Trp Met Gly Asn Ile Tyr Pro Gly Ser Ser Ser Ile Asn Tyr Asn
65                  70                  75                  80 gag aag ttc aag agc cgc gtg acc atc acc gcc gac acc agc aca agc     288
Glu Lys Phe Lys Ser Arg Val Thr Ile Thr Ala Asp Thr Ser Thr Ser
                85                  90                  95 acc gcc tac atg gaa ctg agc agc ctg cgg agc gag gac acc gcc gtg     336
Thr Ala Tyr Met Glu Leu Ser Ser Leu Arg Ser Glu Asp Thr Ala Val
            100                 105                 110 tac tac tgc gcc cgg acc atc tac aac tac ggc agc tcc ggc tac aat     384
Tyr Tyr Cys Ala Arg Thr Ile Tyr Asn Tyr Gly Ser Ser Gly Tyr Asn
        115                 120                 125 tac gcc atg gac tac tgg ggc cag ggc acc ctg gtg acc gtg agc tca     432
Tyr Ala Met Asp Tyr Trp Gly Gln Gly Thr Leu Val Thr Val Ser Ser
    130                 135                 140

```
gcc tcc acc aag ggc cca agc gtc ttc ccc ctg gca ccc tcc tcc aag        480
Ala Ser Thr Lys Gly Pro Ser Val Phe Pro Leu Ala Pro Ser Ser Lys
145                 150                 155                 160 agc acc tct ggc ggc aca gcc gcc ctg ggc tgc ctg gtc aag gac tac        528
Ser Thr Ser Gly Gly Thr Ala Ala Leu Gly Cys Leu Val Lys Asp Tyr
                165                 170                 175 ttc ccc gaa ccc gtg acc gtg agc tgg aac tca ggc gcc ctg acc agc        576
Phe Pro Glu Pro Val Thr Val Ser Trp Asn Ser Gly Ala Leu Thr Ser
            180                 185                 190 ggc gtg cac acc ttc ccc gct gtc ctg cag tcc tca gga ctc tac tcc        624
Gly Val His Thr Phe Pro Ala Val Leu Gln Ser Ser Gly Leu Tyr Ser
        195                 200                 205 ctc agc agc gtg gtg acc gtg ccc tcc agc agc ttg ggc acc cag acc        672
Leu Ser Ser Val Val Thr Val Pro Ser Ser Ser Leu Gly Thr Gln Thr
    210                 215                 220 tac atc tgc aac gtg aat cac aag ccc agc aac acc aag gtg gac aag        720
Tyr Ile Cys Asn Val Asn His Lys Pro Ser Asn Thr Lys Val Asp Lys
225                 230                 235                 240 aga gtt gag ccc aaa tct tgt gac aaa act cac aca tgc cca ccc tgc        768
Arg Val Glu Pro Lys Ser Cys Asp Lys Thr His Thr Cys Pro Pro Cys
                245                 250                 255 cca gca cct gaa ctc ctg ggg gga ccc tca gtc ttc ctc ttc ccc cca        816
Pro Ala Pro Glu Leu Leu Gly Gly Pro Ser Val Phe Leu Phe Pro Pro
            260                 265                 270 aaa ccc aag gac acc ctc atg atc tcc cgg acc cct gag gtc aca tgc        864
Lys Pro Lys Asp Thr Leu Met Ile Ser Arg Thr Pro Glu Val Thr Cys
        275                 280                 285 gtg gtg gtg gac gtg agc cac gaa gac cct gag gtc aag ttc aac tgg        912
Val Val Val Asp Val Ser His Glu Asp Pro Glu Val Lys Phe Asn Trp
    290                 295                 300 tac gtg gac ggc gtg gag gtg cat aat gcc aag aca aag ccc cgg gag        960
Tyr Val Asp Gly Val Glu Val His Asn Ala Lys Thr Lys Pro Arg Glu
305                 310                 315                 320 gag cag tac aac agc acg tac cgg gtg gtc agc gtc ctc acc gtc ctg       1008
Glu Gln Tyr Asn Ser Thr Tyr Arg Val Val Ser Val Leu Thr Val Leu
                325                 330                 335 cac cag gac tgg ctg aat ggc aag gag tac aag tgc aag gtc tcc aac       1056
His Gln Asp Trp Leu Asn Gly Lys Glu Tyr Lys Cys Lys Val Ser Asn
            340                 345                 350 aaa gcc ctc cca gcc ccc atc gag aaa acc atc tcc aaa gcc aaa ggc       1104
Lys Ala Leu Pro Ala Pro Ile Glu Lys Thr Ile Ser Lys Ala Lys Gly
        355                 360                 365 cag ccc cgg gaa cca cag gtg tac acc ctg ccc cca tcc cgg gag gag       1152
Gln Pro Arg Glu Pro Gln Val Tyr Thr Leu Pro Pro Ser Arg Glu Glu
    370                 375                 380 atg acc aag aac cag gtc agc ctg acc tgc ctg gtc aaa ggc ttc tat       1200
Met Thr Lys Asn Gln Val Ser Leu Thr Cys Leu Val Lys Gly Phe Tyr
385                 390                 395                 400 ccc agc gac atc gcc gtg gag tgg gag agc aat ggc cag ccc gag aac       1248
Pro Ser Asp Ile Ala Val Glu Trp Glu Ser Asn Gly Gln Pro Glu Asn
                405                 410                 415 aac tac aag acc acc cct ccc gtg ctg gac tcc gac ggc tcc ttc ttc       1296
Asn Tyr Lys Thr Thr Pro Pro Val Leu Asp Ser Asp Gly Ser Phe Phe
            420                 425                 430 ctc tac agc aag ctc acc gtg gac aag agc agg tgg cag cag ggc aac       1344
Leu Tyr Ser Lys Leu Thr Val Asp Lys Ser Arg Trp Gln Gln Gly Asn
        435                 440                 445 gtc ttc tca tgc tcc gtg atg cat gag gct ctg cac aac cac tac acc       1392
Val Phe Ser Cys Ser Val Met His Glu Ala Leu His Asn His Tyr Thr
```

```
                450             455             460
cag aag agc ctc tcc ctg tct ccc ggc aaa                          1422
Gln Lys Ser Leu Ser Leu Ser Pro Gly Lys
465                 470

<210> SEQ ID NO 3
<211> LENGTH: 474
<212> TYPE: PRT
<213> ORGANISM: Artificial Sequence
<220> FEATURE:
<223> OTHER INFORMATION: Synthetic Construct

<400> SEQUENCE: 3

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Ile Asn Trp Val Arg Gln Ala Pro Gly Gln Gly Leu
    50                  55                  60

Glu Trp Met Gly Asn Ile Tyr Pro Gly Ser Ser Ile Asn Tyr Asn
65                  70                  75                  80

Glu Lys Phe Lys Ser Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Thr Ile Tyr Asn Tyr Gly Ser Ser Gly Tyr Asn
        115                 120                 125

Tyr Ala Met Asp Tyr Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335
```

```
His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Glu Glu
        370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470
```

<210> SEQ ID NO 4
<211> LENGTH: 702
<212> TYPE: DNA
<213> ORGANISM: Artificial Sequence
<220> FEATURE:
<223> OTHER INFORMATION: Nucleotides encoding the light chain of anti-
    LPS mAb-A
<220> FEATURE:
<221> NAME/KEY: CDS
<222> LOCATION: (1)..(702)
<223> OTHER INFORMATION: Encoding polypeptides including a signal
    sequence (20 aa) followed by light chain of mAb-A (21-234: 214 aa)

<400> SEQUENCE: 4

```
atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc gac atc gtg atg acc cag agc cct gac agc ctg gcc      96
Gly Ala Tyr Gly Asp Ile Val Met Thr Gln Ser Pro Asp Ser Leu Ala
            20                  25                  30 gtg tct ctg gga gag aga gcc acc atc aac tgc aag gcc agc gag aac     144
Val Ser Leu Gly Glu Arg Ala Thr Ile Asn Cys Lys Ala Ser Glu Asn
        35                  40                  45 gtg ggc aac agc gtg tcc tgg tat cag cag aag ccc ggc cag ccc ccc     192
Val Gly Asn Ser Val Ser Trp Tyr Gln Gln Lys Pro Gly Gln Pro Pro
    50                  55                  60 aag ctg ctg atc tac ggc gcc agc aac aga tac acc ggc gtg ccc gat     240
Lys Leu Leu Ile Tyr Gly Ala Ser Asn Arg Tyr Thr Gly Val Pro Asp
65                  70                  75                  80 aga ttc agc ggc agc ggc tct ggc acc gac ttc acc ctg aca atc agc     288
Arg Phe Ser Gly Ser Gly Ser Gly Thr Asp Phe Thr Leu Thr Ile Ser
                85                  90                  95 tcc ctg cag gcc gag gac gtg gcc gtg tac tac tgt ggc cag agc tac     336
Ser Leu Gln Ala Glu Asp Val Ala Val Tyr Tyr Cys Gly Gln Ser Tyr
            100                 105                 110 agc tac ccc tac acc ttc ggc cag ggc acc aag gtg gaa atc aag cgt     384
Ser Tyr Pro Tyr Thr Phe Gly Gln Gly Thr Lys Val Glu Ile Lys Arg
        115                 120                 125 acg gtg gcc gcc ccc tcc gtg ttc atc ttc ccc ccc tcc gac gag cag     432
Thr Val Ala Ala Pro Ser Val Phe Ile Phe Pro Pro Ser Asp Glu Gln
    130                 135                 140
```

```
ctg aag tcc ggc acc gcc tcc gtg gtg tgc ctg ctg aat aac ttc tac    480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc    528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc    576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag    624
Tyr Ser Leu Ser Ser Thr Leu Thr Leu Ser Lys Ala Asp Tyr Glu Lys
        195                 200                 205 cac aag gtg tac gcc tgc gag gtg acc cac cag ggc ctg agc tcc ccc    672
His Lys Val Tyr Ala Cys Glu Val Thr His Gln Gly Leu Ser Ser Pro
    210                 215                 220 gtc acc aag agc ttc aac agg ggg gag tgt                            702
Val Thr Lys Ser Phe Asn Arg Gly Glu Cys
225                 230
```

<210> SEQ ID NO 5
<211> LENGTH: 234
<212> TYPE: PRT
<213> ORGANISM: Artificial Sequence
<220> FEATURE:
<223> OTHER INFORMATION: Synthetic Construct

<400> SEQUENCE: 5

```
Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Lys Ala Ser Glu Asn
            35                  40                  45

Val Gly Asn Ser Val Ser Trp Tyr Gln Gln Lys Pro Gly Gln Pro Pro
        50                  55                  60

Lys Leu Leu Ile Tyr Gly Ala Ser Asn Arg Tyr Thr Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Ala Glu Asp Val Ala Val Tyr Tyr Cys Gly Gln Ser Tyr
            100                 105                 110

Ser Tyr Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 6
<211> LENGTH: 1097
<212> TYPE: DNA
<213> ORGANISM: Artificial Sequence
<220> FEATURE:
<223> OTHER INFORMATION: Nucleotide sequence encoding the heavy chain of
      CLCH-1
<220> FEATURE:
<221> NAME/KEY: CDS
<222> LOCATION: (26)..(1072)
<223> OTHER INFORMATION: Encoding polypeptides including a signal
      sequence (19 aa) followed by CH-A (20-349: 330 aa)

<400> SEQUENCE: 6

| ccagcctccg gactctagag ccacc atg aag cac ctg tgg ttc ttt ctg ctg | 52 |
| | Met Lys His Leu Trp Phe Phe Leu Leu | |
| | 1               5                   | |

| ctg gtg gcc gct ccc aga tgg gtg ctg agc gcc tct aca aag ggc ccc | 100 |
| Leu Val Ala Ala Pro Arg Trp Val Leu Ser Ala Ser Thr Lys Gly Pro | |
| 10              15                  20                  25      | |

| agc gtg ttc cct ctg gcc cct agc agc aag agc aca tct ggc gga aca | 148 |
| Ser Val Phe Pro Leu Ala Pro Ser Ser Lys Ser Thr Ser Gly Gly Thr | |
|         30                  35                  40              | |

| gcc gcc ctg ggc tgc ctc gtg aag gac tac ttt ccc gag ccc gtg acc | 196 |
| Ala Ala Leu Gly Cys Leu Val Lys Asp Tyr Phe Pro Glu Pro Val Thr | |
|                 45                  50                  55      | |

| gtg tcc tgg aac tct ggc gct ctg aca agc ggc gtg cac acc ttt cca | 244 |
| Val Ser Trp Asn Ser Gly Ala Leu Thr Ser Gly Val His Thr Phe Pro | |
|             60                  65                  70          | |

| gcc gtg ctg cag agc agc ggc ctg tac tct ctg agc agc gtc gtg aca | 292 |
| Ala Val Leu Gln Ser Ser Gly Leu Tyr Ser Leu Ser Ser Val Val Thr | |
|         75                  80                  85              | |

| gtg ccc agc agc tct ctg ggc acc cag acc tac atc tgc aac gtg aac | 340 |
| Val Pro Ser Ser Ser Leu Gly Thr Gln Thr Tyr Ile Cys Asn Val Asn | |
| 90                  95                  100                 105 | |

| cac aag ccc agc aac acc aag gtg gac aag cgg gtg gaa ccc aag agc | 388 |
| His Lys Pro Ser Asn Thr Lys Val Asp Lys Arg Val Glu Pro Lys Ser | |
|                 110                 115                 120     | |

| tgc gac aag acc cac acc tgt ccc cct tgt cct gcc ccc gaa ctg ctg | 436 |
| Cys Asp Lys Thr His Thr Cys Pro Pro Cys Pro Ala Pro Glu Leu Leu | |
|             125                 130                 135         | |

| gga ggc cct tcc gtg ttc ctg ttc ccc cca aag ccc aag gac acc ctg | 484 |
| Gly Gly Pro Ser Val Phe Leu Phe Pro Pro Lys Pro Lys Asp Thr Leu | |
|         140                 145                 150             | |

| atg atc agc cgg acc ccc gaa gtg acc tgc gtg gtg gtg gat gtg tcc | 532 |
| Met Ile Ser Arg Thr Pro Glu Val Thr Cys Val Val Val Asp Val Ser | |
| 155                 160                 165                     | |

| cac gag gac cct gaa gtg aag ttc aat tgg tac gtg gac ggc gtg gaa | 580 |
| His Glu Asp Pro Glu Val Lys Phe Asn Trp Tyr Val Asp Gly Val Glu | |
| 170                 175                 180                 185 | |

| gtg cac aac gcc aag acc aag cct aga gag gaa cag tac aac agc acc | 628 |
| Val His Asn Ala Lys Thr Lys Pro Arg Glu Glu Gln Tyr Asn Ser Thr | |
|                 190                 195                 200     | |

| tac cgg gtg gtg tcc gtg ctg aca gtg ctg cac cag gac tgg ctg aac | 676 |
| Tyr Arg Val Val Ser Val Leu Thr Val Leu His Gln Asp Trp Leu Asn | |
|             205                 210                 215         | |

| ggc aaa gag tac aag tgc aag gtg tcc aac aag gcc ctg cct gcc ccc | 724 |
| Gly Lys Glu Tyr Lys Cys Lys Val Ser Asn Lys Ala Leu Pro Ala Pro | |
|         220                 225                 230             | |

| atc gag aaa acc atc agc aag gcc aag ggc cag ccc cgc gaa ccc cag | 772 |
| Ile Glu Lys Thr Ile Ser Lys Ala Lys Gly Gln Pro Arg Glu Pro Gln | |
| 235                 240                 245                     | |

```
gtg tac aca ctg ccc cca agc cgg gaa gag atg acc aag aac cag gtg      820
Val Tyr Thr Leu Pro Pro Ser Arg Glu Glu Met Thr Lys Asn Gln Val
250                 255                 260                 265 tcc ctg acc tgt ctc gtg aaa ggc ttc tac ccc tcc gat atc gcc gtg      868
Ser Leu Thr Cys Leu Val Lys Gly Phe Tyr Pro Ser Asp Ile Ala Val
                270                 275                 280 gaa tgg gag agc aac ggc cag ccc gag aac aac tac aag acc acc ccc      916
Glu Trp Glu Ser Asn Gly Gln Pro Glu Asn Asn Tyr Lys Thr Thr Pro
                285                 290                 295 cct gtg ctg gac agc gac ggc tca ttc ttc ctg tac agc aag ctg acc      964
Pro Val Leu Asp Ser Asp Gly Ser Phe Phe Leu Tyr Ser Lys Leu Thr
                300                 305                 310 gtg gac aag agc cgg tgg cag cag ggc aac gtg ttc agc tgc agc gtg     1012
Val Asp Lys Ser Arg Trp Gln Gln Gly Asn Val Phe Ser Cys Ser Val
                315                 320                 325 atg cac gag gcc ctg cac aac cac tac acc cag aag tcc ctg agc ctg     1060
Met His Glu Ala Leu His Asn His Tyr Thr Gln Lys Ser Leu Ser Leu
330                 335                 340                 345 agc ccc ggc aaa tgagtttaaa cggggaggc taact                          1097
Ser Pro Gly Lys <210> SEQ ID NO 7
<211> LENGTH: 349
<212> TYPE: PRT
<213> ORGANISM: Artificial Sequence
<220> FEATURE:
<223> OTHER INFORMATION: Synthetic Construct

<400> SEQUENCE: 7

Met Lys His Leu Trp Phe Phe Leu Leu Leu Val Ala Ala Pro Arg Trp
1               5                   10                  15

Val Leu Ser Ala Ser Thr Lys Gly Pro Ser Val Phe Pro Leu Ala Pro
                20                  25                  30

Ser Ser Lys Ser Thr Ser Gly Gly Thr Ala Ala Leu Gly Cys Leu Val
            35                  40                  45

Lys Asp Tyr Phe Pro Glu Pro Val Thr Val Ser Trp Asn Ser Gly Ala
        50                  55                  60

Leu Thr Ser Gly Val His Thr Phe Pro Ala Val Leu Gln Ser Ser Gly
65                  70                  75                  80

Leu Tyr Ser Leu Ser Ser Val Val Thr Val Pro Ser Ser Ser Leu Gly
                85                  90                  95

Thr Gln Thr Tyr Ile Cys Asn Val Asn His Lys Pro Ser Asn Thr Lys
            100                 105                 110

Val Asp Lys Arg Val Glu Pro Lys Ser Cys Asp Lys Thr His Thr Cys
        115                 120                 125

Pro Pro Cys Pro Ala Pro Glu Leu Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220
```

```
Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
            245                 250                 255

Arg Glu Glu Met Thr Lys Asn Gln Val Ser Leu Thr Cys Leu Val Lys
                260                 265                 270

Gly Phe Tyr Pro Ser Asp Ile Ala Val Glu Trp Glu Ser Asn Gly Gln
            275                 280                 285

Pro Glu Asn Asn Tyr Lys Thr Thr Pro Pro Val Leu Asp Ser Asp Gly
        290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys
                340                 345
```

```
<210> SEQ ID NO 8
<211> LENGTH: 425
<212> TYPE: DNA
<213> ORGANISM: Artificial Sequence
<220> FEATURE:
<223> OTHER INFORMATION: Nucleotide sequence encoding the light chain of
      CLCH-A
<220> FEATURE:
<221> NAME/KEY: CDS
<222> LOCATION: (26)..(400)
<223> OTHER INFORMATION: Encoding polypeptides including a signal
      sequence (20 aa) followed by CL-A (21-125: 105 aa)

<400> SEQUENCE: 8
```

```
ccagcctccg gactctagag ccacc atg gtg ctg cag acc cag gtg ttc atc         52
                            Met Val Leu Gln Thr Gln Val Phe Ile
                            1               5 agc ctg ctg ctg tgg atc agc ggc gcc tat ggc gtg gca gcc cct agc        100
Ser Leu Leu Leu Trp Ile Ser Gly Ala Tyr Gly Val Ala Ala Pro Ser
 10              15                  20                  25 gtg ttc atc ttc cca ccc agc gac gag cag ctg aag tct ggc aca gcc        148
Val Phe Ile Phe Pro Pro Ser Asp Glu Gln Leu Lys Ser Gly Thr Ala
                 30                  35                  40 agc gtc gtg tgc ctg ctg aac aac ttc tac ccc cgc gag gcc aag gtg        196
Ser Val Val Cys Leu Leu Asn Asn Phe Tyr Pro Arg Glu Ala Lys Val
             45                  50                  55 cag tgg aag gtg gac aat gcc ctg cag agc ggc aac agc cag gaa agc        244
Gln Trp Lys Val Asp Asn Ala Leu Gln Ser Gly Asn Ser Gln Glu Ser
 60                  65                  70 gtg acc gag cag gac agc aag gac tcc acc tac agc ctg agc agc acc        292
Val Thr Glu Gln Asp Ser Lys Asp Ser Thr Tyr Ser Leu Ser Ser Thr
     75                  80                  85 ctg acc ctg agc aag gcc gac tac gag aag cac aag gtg tac gcc tgc        340
Leu Thr Leu Ser Lys Ala Asp Tyr Glu Lys His Lys Val Tyr Ala Cys
 90                  95                 100                 105 gaa gtg acc cac cag ggc ctg tct agc ccc gtg acc aag agc ttc aac        388
Glu Val Thr His Gln Gly Leu Ser Ser Pro Val Thr Lys Ser Phe Asn
                 110                 115                 120 cgg ggc gag tgt tgagtttaaa cggggaggc taact                             425
Arg Gly Glu Cys
            125
```

```
<210> SEQ ID NO 9
```

<211> LENGTH: 125
<212> TYPE: PRT
<213> ORGANISM: Artificial Sequence
<220> FEATURE:
<223> OTHER INFORMATION: Synthetic Construct

<400> SEQUENCE: 9

```
Met Val Leu Gln Thr Gln Val Phe Ile Ser Leu Leu Leu Trp Ile Ser
1               5                   10                  15

Gly Ala Tyr Gly Val Ala Ala Pro Ser Val Phe Ile Phe Pro Pro Ser
                20                  25                  30

Asp Glu Gln Leu Lys Ser Gly Thr Ala Ser Val Val Cys Leu Leu Asn
            35                  40                  45

Asn Phe Tyr Pro Arg Glu Ala Lys Val Gln Trp Lys Val Asp Asn Ala
        50                  55                  60

Leu Gln Ser Gly Asn Ser Gln Glu Ser Val Thr Glu Gln Asp Ser Lys
65                  70                  75                  80

Asp Ser Thr Tyr Ser Leu Ser Ser Thr Leu Thr Leu Ser Lys Ala Asp
                85                  90                  95

Tyr Glu Lys His Lys Val Tyr Ala Cys Glu Val Thr His Gln Gly Leu
            100                 105                 110

Ser Ser Pro Val Thr Lys Ser Phe Asn Arg Gly Glu Cys
        115                 120                 125
```

<210> SEQ ID NO 10
<211> LENGTH: 1047
<212> TYPE: DNA
<213> ORGANISM: Artificial Sequence
<220> FEATURE:
<223> OTHER INFORMATION: Nucleotide sequence encoding the heavy chain of CLCH-B (LALA form)
<220> FEATURE:
<221> NAME/KEY: CDS
<222> LOCATION: (1)..(1047)
<223> OTHER INFORMATION: Encoding polypeptides including a signal sequence (19 aa) followed by CH-B (20-349: 330 aa)

<400> SEQUENCE: 10

```
atg aag cac ctg tgg ttc ttt ctg ctg ctg gtg gcc gct ccc aga tgg      48
Met Lys His Leu Trp Phe Phe Leu Leu Leu Val Ala Ala Pro Arg Trp
1               5                   10                  15 gtg ctg agc gcc tct aca aag ggc ccc agc gtg ttc cct ctg gcc cct      96
Val Leu Ser Ala Ser Thr Lys Gly Pro Ser Val Phe Pro Leu Ala Pro
                20                  25                  30 agc agc aag agc aca tct ggc gga aca gcc gcc ctg ggc tgc ctc gtg     144
Ser Ser Lys Ser Thr Ser Gly Gly Thr Ala Ala Leu Gly Cys Leu Val
            35                  40                  45 aag gac tac ttt ccc gag ccc gtg acc gtg tcc tgg aac tct ggc gct     192
Lys Asp Tyr Phe Pro Glu Pro Val Thr Val Ser Trp Asn Ser Gly Ala
        50                  55                  60 ctg aca agc ggc gtg cac acc ttt cca gcc gtg ctg cag agc agc ggc     240
Leu Thr Ser Gly Val His Thr Phe Pro Ala Val Leu Gln Ser Ser Gly
65                  70                  75                  80 ctg tac tct ctg agc agc gtc gtg aca gtg ccc agc agc tct ctg ggc     288
Leu Tyr Ser Leu Ser Ser Val Val Thr Val Pro Ser Ser Ser Leu Gly
                85                  90                  95 acc cag acc tac atc tgc aac gtg aac cac aag ccc agc aac acc aag     336
Thr Gln Thr Tyr Ile Cys Asn Val Asn His Lys Pro Ser Asn Thr Lys
            100                 105                 110 gtg gac aag cgg gtg gaa ccc aag agc tgc gac aag acc cac acc tgt     384
Val Asp Lys Arg Val Glu Pro Lys Ser Cys Asp Lys Thr His Thr Cys
        115                 120                 125
```

| | | | | | | | | | | | | | | | | |
|---|---|---|---|---|---|---|---|---|---|---|---|---|---|---|---|---|
| ccc | cct | tgt | cct | gcc | ccc | gaa | gcc | gcg | gga | ggc | cct | tcc | gtg | ttc | ctg | 432 |
| Pro | Pro | Cys | Pro | Ala | Pro | Glu | Ala | Ala | Gly | Gly | Pro | Ser | Val | Phe | Leu | |
| | 130 | | | | 135 | | | | | 140 | | | | | | |
| ttc | ccc | cca | aag | ccc | aag | gac | acc | ctg | atg | atc | agc | cgg | acc | ccc | gaa | 480 |
| Phe | Pro | Pro | Lys | Pro | Lys | Asp | Thr | Leu | Met | Ile | Ser | Arg | Thr | Pro | Glu | |
| 145 | | | | 150 | | | | | 155 | | | | | 160 | | |
| gtg | acc | tgc | gtg | gtg | gtg | gat | gtg | tcc | cac | gag | gac | cct | gaa | gtg | aag | 528 |
| Val | Thr | Cys | Val | Val | Val | Asp | Val | Ser | His | Glu | Asp | Pro | Glu | Val | Lys | |
| | | | | 165 | | | | | 170 | | | | | 175 | | |
| ttc | aat | tgg | tac | gtg | gac | ggc | gtg | gaa | gtg | cac | aac | gcc | aag | acc | aag | 576 |
| Phe | Asn | Trp | Tyr | Val | Asp | Gly | Val | Glu | Val | His | Asn | Ala | Lys | Thr | Lys | |
| | | 180 | | | | | 185 | | | | | 190 | | | | |
| cct | aga | gag | gaa | cag | tac | aac | agc | acc | tac | cgg | gtg | gtg | tcc | gtg | ctg | 624 |
| Pro | Arg | Glu | Glu | Gln | Tyr | Asn | Ser | Thr | Tyr | Arg | Val | Val | Ser | Val | Leu | |
| | | 195 | | | | | 200 | | | | | 205 | | | | |
| aca | gtg | ctg | cac | cag | gac | tgg | ctg | aac | ggc | aaa | gag | tac | aag | tgc | aag | 672 |
| Thr | Val | Leu | His | Gln | Asp | Trp | Leu | Asn | Gly | Lys | Glu | Tyr | Lys | Cys | Lys | |
| 210 | | | | | 215 | | | | | 220 | | | | | | |
| gtg | tcc | aac | aag | gcc | ctg | cct | gcc | ccc | atc | gag | aaa | acc | atc | agc | aag | 720 |
| Val | Ser | Asn | Lys | Ala | Leu | Pro | Ala | Pro | Ile | Glu | Lys | Thr | Ile | Ser | Lys | |
| 225 | | | | 230 | | | | | 235 | | | | | 240 | | |
| gcc | aag | ggc | cag | ccc | cgc | gaa | ccc | cag | gtg | tac | aca | ctg | ccc | cca | agc | 768 |
| Ala | Lys | Gly | Gln | Pro | Arg | Glu | Pro | Gln | Val | Tyr | Thr | Leu | Pro | Pro | Ser | |
| | | | | 245 | | | | | 250 | | | | | 255 | | |
| cgg | gaa | gag | atg | acc | aag | aac | cag | gtg | tcc | ctg | acc | tgt | ctc | gtg | aaa | 816 |
| Arg | Glu | Glu | Met | Thr | Lys | Asn | Gln | Val | Ser | Leu | Thr | Cys | Leu | Val | Lys | |
| | | | | 260 | | | | | 265 | | | | | 270 | | |
| ggc | ttc | tac | ccc | tcc | gat | atc | gcc | gtg | gaa | tgg | gag | agc | aac | ggc | cag | 864 |
| Gly | Phe | Tyr | Pro | Ser | Asp | Ile | Ala | Val | Glu | Trp | Glu | Ser | Asn | Gly | Gln | |
| | | | 275 | | | | | 280 | | | | | 285 | | | |
| ccc | gag | aac | aac | tac | aag | acc | acc | ccc | cct | gtg | ctg | gac | agc | gac | ggc | 912 |
| Pro | Glu | Asn | Asn | Tyr | Lys | Thr | Thr | Pro | Pro | Val | Leu | Asp | Ser | Asp | Gly | |
| | 290 | | | | | 295 | | | | | 300 | | | | | |
| tca | ttc | ttc | ctg | tac | agc | aag | ctg | acc | gtg | gac | aag | agc | cgg | tgg | cag | 960 |
| Ser | Phe | Phe | Leu | Tyr | Ser | Lys | Leu | Thr | Val | Asp | Lys | Ser | Arg | Trp | Gln | |
| 305 | | | | | 310 | | | | | 315 | | | | | 320 | |
| cag | ggc | aac | gtg | ttc | agc | tgc | agc | gtg | atg | cac | gag | gcc | ctg | cac | aac | 1008 |
| Gln | Gly | Asn | Val | Phe | Ser | Cys | Ser | Val | Met | His | Glu | Ala | Leu | His | Asn | |
| | | | | 325 | | | | | 330 | | | | | 335 | | |
| cac | tac | acc | cag | aag | tcc | ctg | agc | ctg | agc | ccc | ggc | aaa | | | | 1047 |
| His | Tyr | Thr | Gln | Lys | Ser | Leu | Ser | Leu | Ser | Pro | Gly | Lys | | | | |
| | | | 340 | | | | | 345 | | | | | | | | |

<210> SEQ ID NO 11
<211> LENGTH: 349
<212> TYPE: PRT
<213> ORGANISM: Artificial Sequence
<220> FEATURE:
<223> OTHER INFORMATION: Synthetic Construct

<400> SEQUENCE: 11

Met Lys His Leu Trp Phe Phe Leu Leu Leu Val Ala Ala Pro Arg Trp
1               5                   10                  15

Val Leu Ser Ala Ser Thr Lys Gly Pro Ser Val Phe Pro Leu Ala Pro
            20                  25                  30

Ser Ser Lys Ser Thr Ser Gly Gly Thr Ala Ala Leu Gly Cys Leu Val
        35                  40                  45

Lys Asp Tyr Phe Pro Glu Pro Val Thr Val Ser Trp Asn Ser Gly Ala
    50                  55                  60

```
Leu Thr Ser Gly Val His Thr Phe Pro Ala Val Leu Gln Ser Ser Gly
 65                  70                  75                  80

Leu Tyr Ser Leu Ser Ser Val Val Thr Val Pro Ser Ser Ser Leu Gly
             85                  90                  95

Thr Gln Thr Tyr Ile Cys Asn Val Asn His Lys Pro Ser Asn Thr Lys
            100                 105                 110

Val Asp Lys Arg Val Glu Pro Lys Ser Cys Asp Lys Thr His Thr Cys
        115                 120                 125

Pro Pro Cys Pro Ala Pro Glu Ala Ala Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys
            340                 345
```

```
<210> SEQ ID NO 12
<211> LENGTH: 30
<212> TYPE: DNA
<213> ORGANISM: Artificial Sequence
<220> FEATURE:
<223> OTHER INFORMATION: Forward primer of CHLALA-F

<400> SEQUENCE: 12
gcgggaggcc cttccgtgtt cctgttcccc                                      30

<210> SEQ ID NO 13
<211> LENGTH: 31
<212> TYPE: DNA
<213> ORGANISM: Artificial Sequence
<220> FEATURE:
<223> OTHER INFORMATION: Reverse primer of CHLALA-R

<400> SEQUENCE: 13
ggcttcgggg gcaggacaag ggggacaggt g                                    31
```

<210> SEQ ID NO 14
<211> LENGTH: 779
<212> TYPE: DNA
<213> ORGANISM: Artificial Sequence
<220> FEATURE:
<223> OTHER INFORMATION: Nucleotide sequence encoding Fc fragment (wild type)
<220> FEATURE:
<221> NAME/KEY: CDS
<222> LOCATION: (26)..(754)
<223> OTHER INFORMATION: Encoding polypeptide containing a signal sequence (20 aa) followed by Fc-B (223 aa)

<400> SEQUENCE: 14

```
ccagcctccg gactctagag ccacc atg gtg ctg cag acc cag gtg ttc atc      52
                             Met Val Leu Gln Thr Gln Val Phe Ile
                               1               5 agc ctg ctg ctg tgg atc agc ggc gcc tac ggc acc tgt cct cca tgt     100
Ser Leu Leu Leu Trp Ile Ser Gly Ala Tyr Gly Thr Cys Pro Pro Cys
 10              15                  20                  25 cct gct cca gag ctg ctg ggc gga cct agc gtg ttc ctg ttc ccc cca     148
Pro Ala Pro Glu Leu Leu Gly Gly Pro Ser Val Phe Leu Phe Pro Pro
                 30                  35                  40 aag ccc aag gac acc ctg atg atc agc cgg acc ccc gaa gtg acc tgc     196
Lys Pro Lys Asp Thr Leu Met Ile Ser Arg Thr Pro Glu Val Thr Cys
         45                  50                  55 gtg gtg gtg gat gtg tcc cac gag gac cct gaa gtg aag ttc aat tgg     244
Val Val Val Asp Val Ser His Glu Asp Pro Glu Val Lys Phe Asn Trp
     60                  65                  70 tac gtg gac ggc gtg gaa gtg cac aac gcc aag acc aag ccc aga gag     292
Tyr Val Asp Gly Val Glu Val His Asn Ala Lys Thr Lys Pro Arg Glu
 75                  80                  85 gaa cag tac aac agc acc tac cgg gtg gtg tcc gtg ctg acc gtg ctg     340
Glu Gln Tyr Asn Ser Thr Tyr Arg Val Val Ser Val Leu Thr Val Leu
 90                  95                 100                 105 cac cag gac tgg ctg aac ggc aaa gag tac aag tgc aag gtg tcc aac     388
His Gln Asp Trp Leu Asn Gly Lys Glu Tyr Lys Cys Lys Val Ser Asn
                110                 115                 120 aag gcc ctg cct gcc ccc atc gag aaa acc atc agc aag gcc aag ggc     436
Lys Ala Leu Pro Ala Pro Ile Glu Lys Thr Ile Ser Lys Ala Lys Gly
             125                 130                 135 cag ccc cgc gaa ccc cag gtg tac aca ctg ccc cct agc agg gac gag     484
Gln Pro Arg Glu Pro Gln Val Tyr Thr Leu Pro Pro Ser Arg Asp Glu
         140                 145                 150 ctg acc aag aac cag gtg tcc ctg acc tgt ctc gtg aag ggc ttc tac     532
Leu Thr Lys Asn Gln Val Ser Leu Thr Cys Leu Val Lys Gly Phe Tyr
     155                 160                 165 ccc tcc gat atc gcc gtg gaa tgg gag agc aac ggc cag ccc gag aac     580
Pro Ser Asp Ile Ala Val Glu Trp Glu Ser Asn Gly Gln Pro Glu Asn
170                 175                 180                 185 aac tac aag acc acc ccc cct gtg ctg gac agc gac ggc tca ttc ttc     628
Asn Tyr Lys Thr Thr Pro Pro Val Leu Asp Ser Asp Gly Ser Phe Phe
                190                 195                 200 ctg tac agc aag ctg aca gtg gac aag agc cgg tgg cag cag ggc aac     676
Leu Tyr Ser Lys Leu Thr Val Asp Lys Ser Arg Trp Gln Gln Gly Asn
             205                 210                 215 gtg ttc agc tgc agc gtg atg cac gag gcc ctg cac aac cac tac acc     724
Val Phe Ser Cys Ser Val Met His Glu Ala Leu His Asn His Tyr Thr
         220                 225                 230 cag aag tcc ctg agc ctg agc ccc ggc aaa tgagtttaaa cggggaggc         774
Gln Lys Ser Leu Ser Leu Ser Pro Gly Lys
     235                 240
```

<210> SEQ ID NO 15
<211> LENGTH: 243
<212> TYPE: PRT
<213> ORGANISM: Artificial Sequence
<220> FEATURE:
<223> OTHER INFORMATION: Synthetic Construct

<400> SEQUENCE: 15

Met Val Leu Gln Thr Gln Val Phe Ile Ser Leu Leu Leu Trp Ile Ser
1               5                   10                  15

Gly Ala Tyr Gly Thr Cys Pro Pro Cys Pro Ala Pro Glu Leu Leu Gly
            20                  25                  30

Gly Pro Ser Val Phe Leu Phe Pro Pro Lys Pro Lys Asp Thr Leu Met
        35                  40                  45

Ile Ser Arg Thr Pro Glu Val Thr Cys Val Val Val Asp Val Ser His
    50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
            100                 105                 110

Lys Glu Tyr Lys Cys Lys Val Ser Asn Lys Ala Leu Pro Ala Pro Ile
        115                 120                 125

Glu Lys Thr Ile Ser Lys Ala Lys Gly Gln Pro Arg Glu Pro Gln Val
    130                 135                 140

Tyr Thr Leu Pro Pro Ser Arg Asp Glu Leu Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
            180                 185                 190

Val Leu Asp Ser Asp Gly Ser Phe Phe Leu Tyr Ser Lys Leu Thr Val
        195                 200                 205

Asp Lys Ser Arg Trp Gln Gln Gly Asn Val Phe Ser Cys Ser Val Met
    210                 215                 220

His Glu Ala Leu His Asn His Tyr Thr Gln Lys Ser Leu Ser Leu Ser
225                 230                 235                 240

Pro Gly Lys

<210> SEQ ID NO 16
<211> LENGTH: 741
<212> TYPE: DNA
<213> ORGANISM: Artificial Sequence
<220> FEATURE:
<223> OTHER INFORMATION: Nucleotide sequence encoding Fc-A (LALA form)
<220> FEATURE:
<221> NAME/KEY: CDS
<222> LOCATION: (1)..(741)
<223> OTHER INFORMATION: Encoding a signal peptide (20 aa) and Fc-A (227
      aa)

<400> SEQUENCE: 16 atg gtg ctg cag acc cag gtg ttc atc agc ctg ctg ctg tgg atc agc      48
Met Val Leu Gln Thr Gln Val Phe Ile Ser Leu Leu Leu Trp Ile Ser
1               5                   10                  15 ggc gcc tac ggc gac aaa act cac acc tgt cct cca tgt cct gct cca      96

```
Gly Ala Tyr Gly Asp Lys Thr His Thr Cys Pro Pro Cys Pro Ala Pro
            20                  25                  30 gag gcc gcg ggc gga cct agc gtg ttc ctg ttc ccc cca aag ccc aag    144
Glu Ala Ala Gly Gly Pro Ser Val Phe Leu Phe Pro Pro Lys Pro Lys
        35                  40                  45 gac acc ctg atg atc agc cgg acc ccc gaa gtg acc tgc gtg gtg gtg    192
Asp Thr Leu Met Ile Ser Arg Thr Pro Glu Val Thr Cys Val Val Val
 50                  55                  60 gat gtg tcc cac gag gac cct gaa gtg aag ttc aat tgg tac gtg gac    240
Asp Val Ser His Glu Asp Pro Glu Val Lys Phe Asn Trp Tyr Val Asp
65                  70                  75                  80 ggc gtg gaa gtg cac aac gcc aag acc aag ccc aga gag gaa cag tac    288
Gly Val Glu Val His Asn Ala Lys Thr Lys Pro Arg Glu Glu Gln Tyr
                85                  90                  95 aac agc acc tac cgg gtg gtg tcc gtg ctg acc gtg ctg cac cag gac    336
Asn Ser Thr Tyr Arg Val Val Ser Val Leu Thr Val Leu His Gln Asp
            100                 105                 110 tgg ctg aac ggc aaa gag tac aag tgc aag gtg tcc aac aag gcc ctg    384
Trp Leu Asn Gly Lys Glu Tyr Lys Cys Lys Val Ser Asn Lys Ala Leu
        115                 120                 125 cct gcc ccc atc gag aaa acc atc agc aag gcc aag ggc cag ccc cgc    432
Pro Ala Pro Ile Glu Lys Thr Ile Ser Lys Ala Lys Gly Gln Pro Arg
130                 135                 140 gaa ccc cag gtg tac aca ctg ccc cct agc agg gac gag ctg acc aag    480
Glu Pro Gln Val Tyr Thr Leu Pro Pro Ser Arg Asp Glu Leu Thr Lys
145                 150                 155                 160 aac cag gtg tcc ctg acc tgt ctc gtg aag ggc ttc tac ccc tcc gat    528
Asn Gln Val Ser Leu Thr Cys Leu Val Lys Gly Phe Tyr Pro Ser Asp
                165                 170                 175 atc gcc gtg gaa tgg gag agc aac ggc cag ccc gag aac aac tac aag    576
Ile Ala Val Glu Trp Glu Ser Asn Gly Gln Pro Glu Asn Asn Tyr Lys
            180                 185                 190 acc acc ccc cct gtg ctg gac agc gac ggc tca ttc ttc ctg tac agc    624
Thr Thr Pro Pro Val Leu Asp Ser Asp Gly Ser Phe Phe Leu Tyr Ser
        195                 200                 205 aag ctg aca gtg gac aag agc cgg tgg cag cag ggc aac gtg ttc agc    672
Lys Leu Thr Val Asp Lys Ser Arg Trp Gln Gln Gly Asn Val Phe Ser
    210                 215                 220 tgc agc gtg atg cac gag gcc ctg cac aac cac tac acc cag aag tcc    720
Cys Ser Val Met His Glu Ala Leu His Asn His Tyr Thr Gln Lys Ser
225                 230                 235                 240 ctg agc ctg agc ccc ggc aaa                                        741
Leu Ser Leu Ser Pro Gly Lys
                245
```

<210> SEQ ID NO 17
<211> LENGTH: 247
<212> TYPE: PRT
<213> ORGANISM: Artificial Sequence
<220> FEATURE:
<223> OTHER INFORMATION: Synthetic Construct

<400> SEQUENCE: 17

```
Met Val Leu Gln Thr Gln Val Phe Ile Ser Leu Leu Leu Trp Ile Ser
1               5                   10                  15

Gly Ala Tyr Gly Asp Lys Thr His Thr Cys Pro Pro Cys Pro Ala Pro
            20                  25                  30

Glu Ala Ala Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
```

```
                 50                  55                  60
Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Leu His Gln Asp
                100                 105                 110

Trp Leu Asn Gly Lys Glu Tyr Lys Cys Lys Val Ser Asn Lys Ala Leu
            115                 120                 125

Pro Ala Pro Ile Glu Lys Thr Ile Ser Lys Ala Lys Gly Gln Pro Arg
        130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 18
<211> LENGTH: 48
<212> TYPE: DNA
<213> ORGANISM: Artificial Sequence
<220> FEATURE:
<223> OTHER INFORMATION: Forward primer of FcLALA-F

<400> SEQUENCE: 18
tgtcctgctc cagaggccgc gggcggacct agcgtgttcc tgttcccc            48

<210> SEQ ID NO 19
<211> LENGTH: 51
<212> TYPE: DNA
<213> ORGANISM: Artificial Sequence
<220> FEATURE:
<223> OTHER INFORMATION: Reverse primer of Fc05-R

<400> SEQUENCE: 19
tggaggacag gtgtgagttt tgtcgccgta ggcgccgctg atccacagca g          51
```

HANP-FC-CONTAINING MOLECULAR CONJUGATE

CROSS-REFERENCE TO RELATED APPLICATIONS

The present application is a national phase of International Application No. PCT/JP2017/024206, filed Jun. 30, 2017, which claims priority to Japanese Patent Application No. 2016-131450, filed on Jul. 1, 2016. Each of the above-referenced applications is hereby incorporated by reference into the present application in their entirety.

SEQUENCE LISTING

The instant application contains a Sequence Listing which has been submitted in ASCII format via EFS-Web and is hereby incorporated by reference in its entirety. Said ASCII copy, created on Nov. 15, 2018, is named 098065-0214 SL.txt and is 51,681 bytes in size.

TECHNICAL FIELD

The present invention relates to a conjugate comprising a hANP peptide loaded on a Fc-containing molecule serving as a carrier, whereby the hANP peptide gradually migrates into blood after subcutaneous administration and the duration time of the pharmacological effect of hANP is drastically prolonged, a medicament containing the same as an active ingredient, a method for producing the conjugate, etc.

BACKGROUND ART

Human atrial natriuretic peptides (hANPs) are biologically active peptides having a vasodilatory effect, a diuretic effect, a cell growth inhibitory effect, a venous return lowering effect, and a sympathetic activity inhibitory effect. Native hANP rapidly loses its activity in blood, for example, through cleavage by neutral endopeptidase (NEP) in the blood. In Japan, hANP is clinically applied as a therapeutic drug for acute heart failure, but needs to be continuously administered via intravenous infusion or the like, under blood pressure monitoring, for the purpose of avoiding a sharp drop in blood pressure after administration.

Endogenous biologically active peptides such as hANP have very high selectivity for their specific receptors and can therefore be expected to have high efficacy and safety. On the other hand, such biologically active peptides are known to have a very short half-life in blood because the biologically active peptide are rapidly metabolized by various metabolic enzymes during systemic circulation or rapidly excreted by glomerular filtration in the kidney. Hence, attempts have been made to prolong the half-lives in blood of such peptides by imparting metabolic enzyme resistance thereto or circumventing renal excretion. Examples thereof include various methods such as a glycosylated peptide (Patent Literature 1), a fusion polypeptide (Patent Literature 2), an albumin fusion peptide (Patent Literature 3 and Non Patent Literature 1), an immunoglobulin Fc fusion peptide (Patent Literature 4 and Non Patent Literature 2), and a polyethylene glycol (PEG)-modified peptide (Non Patent Literatures 3 and 4).

Antibody drugs have a very long half-life in blood as compared with peptide drugs or protein drugs, through a recycling mechanism mediated by a neonatal Fc receptor (FcRn) (Non Patent Literature 5). Hence, fusion peptides expected to produce a similar recycling effect have also been considered as a means of prolonging the half-life of hANP (Patent Literatures 3 and 4 and Non Patent Literatures 1 and 2). However, it has been suggested that when hANP, which is rapidly metabolized in blood, is directly loaded onto a carrier protein, the hANP moiety on the carrier undergoes metabolism during circulation. Thus, "hANP-protein fusions" are difficult to retain in the blood at a level equivalent to the retention, in the blood, of the carrier protein moiety (Non Patent Literature 2).

In recent years, the technical development of antibody-drug conjugates has been actively performed, and various synthesis methods have been reported (Non Patent Literatures 6, 7, and 8). However, if a conjugation method that diminishes the compatibility of a carrier protein with a drug moiety to be loaded thereon is adopted, the carrier moiety or the drug moiety might be destabilized so that the half-life in blood is not prolonged or agglutination is increased. Therefore, it is very important to select the optimum conjugation method or linker. In general, biopharmaceuticals are known to migrate gradually into the blood by subcutaneous administration rather than intravenous administration (Non Patent Literature 9). However, it is difficult to predict the pharmacokinetics of chemically-modified antibodies.

Thus, there is a demand for the development of hANP formulations that possess all of the following: gradual migration into the blood, a sufficient retention time in the blood, and maintenance of activity necessary for pharmacological effects.

CITATION LIST

Patent Literature

Patent Literature 1: PCT International Patent Application Publication No. WO2014/115797 A1
Patent Literature 2: U.S. Patent Application Publication No. US2006-036227
Patent Literature 3: U.S. Patent Application Publication No. US2007-0162986 A1
Patent Literature 4: PCT International Patent Application Publication No. WO2008/154226 A1 Non Patent Literature
Non Patent Literature 1: Regulatory Peptides, 2012, 175, 7-10
Non Patent Literature 2: Bioconjugate Chem., 2012, 23, 518-526
Non Patent Literature 3: Proc. Natl. Acad. Sci. USA 1994, 91, 12544-12548
Non Patent Literature 4: Bioconjugate Chem., 2008, 19, 342-348
Non Patent Literature 5: Chem. Soc. Rev., 2012, 41, 2686-2695
Non Patent Literature 6: Bioconjugate Chem., 2015, 26, 176-192
Non Patent Literature 7: J. Am. Chem. Soc., 2012, 134, 12308-12318
Non Patent Literature 8: Angew. Chem. Int. Ed., 2016, 55, 2361-2367
Non Patent Literature 9: Drug Metab. Dispos., 2014, 42,1881-1889

SUMMARY OF INVENTION

Technical Problem

An object of the present invention is to find an improved form of hANP that possesses both drug efficacy and safety in subcutaneous administration.

Solution to Problem

The present inventors have conducted diligent studies on an improved form of hANP that possesses both drug efficacy and safety in subcutaneous administration, and consequently found that: a conjugate comprising a hANP peptide linked via a particular PEG linker to a glycan attached to an Asn residue corresponding to position 297 of an IgG heavy chain elevated the intracellular cGMP concentration in GC-A receptor-expressing cells, prolonged the duration time in the blood of the hANP peptide when administered to rats, and sustainably elevated the cGMP concentration in the blood even 168 hours or later after administration of the conjugate; a conjugate employing glycosylated hANP as the hANP peptide has particularly favorable physical properties; etc. The present inventors have conducted further studies, thereby reaching the completion of the present invention.

The present invention provides the following: (1) A conjugate comprising a hANP peptide bonded via a polyethylene glycol linker (L(PEG)) to a glycan attached to Asn297 of a Fc-containing molecule (N297 glycan), or a pharmaceutically acceptable salt thereof, wherein:

the hANP peptide optionally lacks 1 to 5 amino acids consecutively from the N terminus and/or one C terminal amino acid in the amino acid sequence represented by SEQ ID NO: 1 and is optionally glycosylated at either one or both of its N terminus and C terminus;

the L(PEG) is a linker structure comprising 10 to 35 ethylene glycol structures and optionally comprising an additional binding structure and/or modifying structure;

the Fc-containing molecule is a molecule having an amino acid sequence corresponding to a human IgG Fc region and having no ability to bind specifically to a human biomolecule; and the N297 glycan is a glycan N297-(Fuc)SG, N297-(Fuc)MSG1 or N297-(Fuc)MSG2 having a structure represented by the following formula:

[Formula 1]

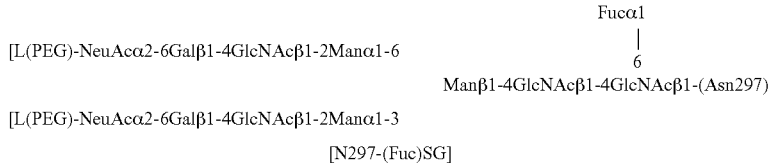

[N297-(Fuc)SG]

wherein [L(PEG)] represents that L(PEG) binds to carbonyl groups bonded to the 2-positions of sialic acid residues at the non-reducing ends of both the 1-3 and 1-6 branched chains of β-Man,

[Formula 2]

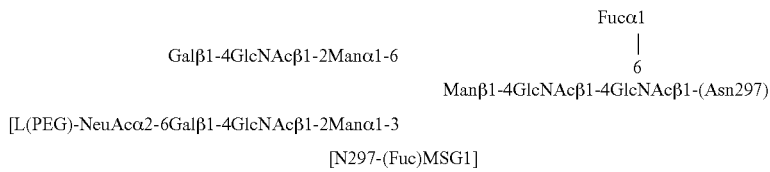

[N297-(Fuc)MSG1]

wherein [L(PEG)] represents that L(PEG) binds to a carbonyl group bonded to the 2-position of a sialic acid residue at the non-reducing end of the 1-3 branched chain of β-Man, and

[Formula 3]

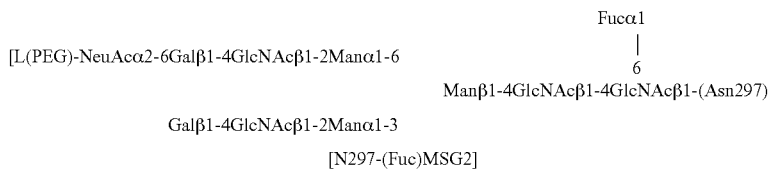

[N297-(Fuc)MSG2]

wherein [L(PEG)] represents that L(PEG) binds to a carbonyl group bonded to the 2-position of a sialic acid residue at the non-reducing end of the 1-6 branched chain of β-Man.

(2) The conjugate according to (1) or a pharmaceutically acceptable salt thereof, wherein the hANP peptide is hANP (1-28), hANP(2-28), hANP(3-28), hANP(1-27), hANP(2-27) or hANP(3-27).

(3) The conjugate according to (1) or (2) or a pharmaceutically acceptable salt thereof, wherein the hANP peptide is a glycosylated peptide in which asparagine or glutamine with its side chain attached through a N-glycosidic bond to any of glycans AG5, AG7, AG9 and SG represented by the following formula is bonded to the N terminus or C terminus of the peptide:

[Formula 4]

Manα1-6

Manβ1-4GlcNAcβ1-4GlcNAcβ1-(N/Q)

Manα1-3         [AG5]

[Formula 5]

GlcNAcβ1-2Manα1-6

Manβ1-4GlcNAcβ1-4GlcNAcβ1-(N/Q)

GlcNAcβ1-2Manα1-3         [AG7]

[Formula 6]

Galβ1-4GlcNAcβ1-2Manα1-6

Manβ1-4GlcNAcβ1-4GlcNAcβ1-(N/Q)

Galβ1-4GlcNAcβ1-2Manα1-3         [AG9]

[Formula 7]

NeuAcα2-6Galβ1-4GlcNAcβ1-2Manα1-6

Manβ1-4GlcNAcβ1-4GlcNAcβ1-(N/Q)

NeuAcα2-6Galβ1-4GlcNAcβ1-2Manα1-3         [SG]

wherein "-(N/Q)" represents binding to the side chain of asparagine or glutamine through a N-glycosidic bond.

(4) The conjugate according to (3) or a pharmaceutically acceptable salt thereof, wherein the hANP peptide is hANP (1-28) in which asparagine with its side chain attached to a glycan SG through a N-glycosidic bond is bonded to the N terminus of the peptide.

(5) The conjugate according to (1) or a pharmaceutically acceptable salt thereof, wherein the L(PEG) is a linker structure comprising 25 to 30 ethylene glycol structures and comprising an amide bond and a 1,2,3-triazole ring as binding structures.

(6) The conjugate according to (1) or a pharmacologically acceptable salt thereof, wherein the L(PEG) is a linker structure represented by any of the following formulas:

[Formula 8]

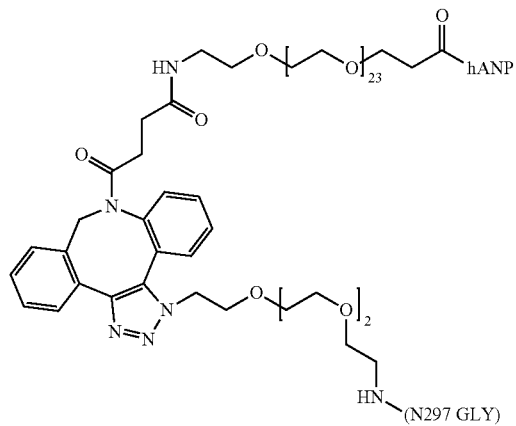

L(PEG) A1

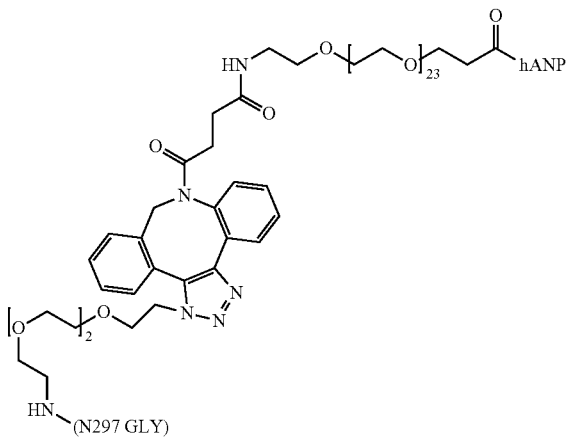

L(PEG) A2

[Formula 9]
L(PEG) B1
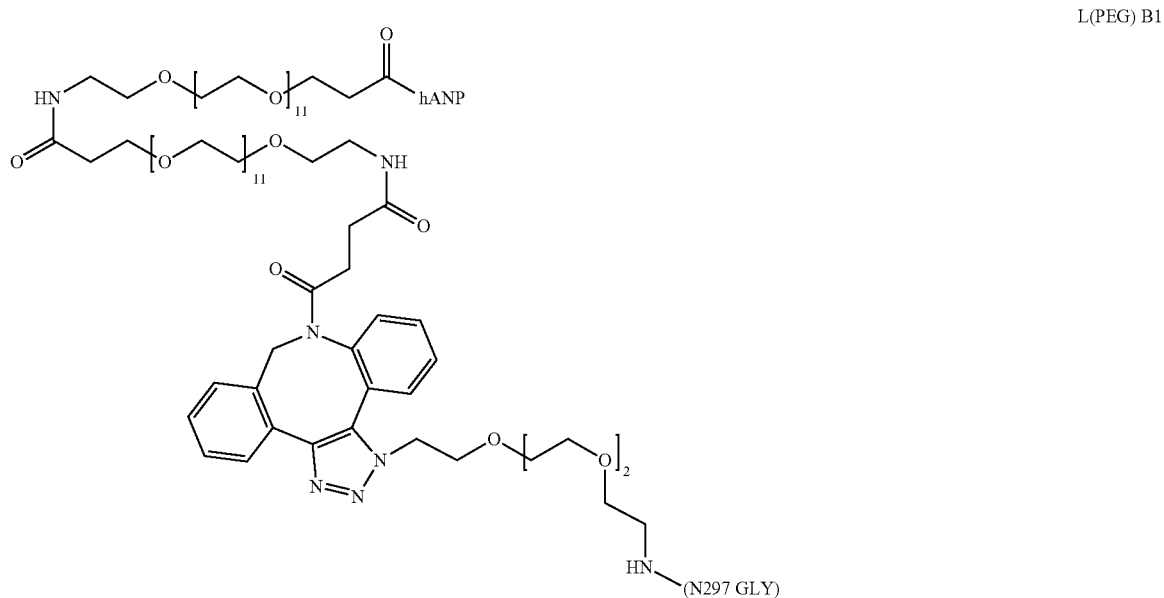
L(PEG) B2
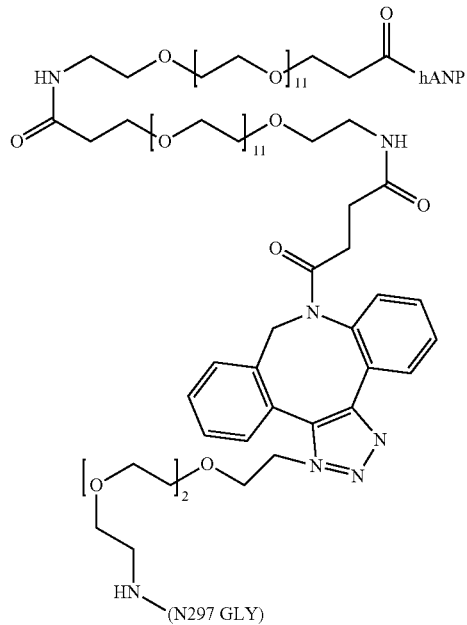

[Formula 10]
L(PEG) C1
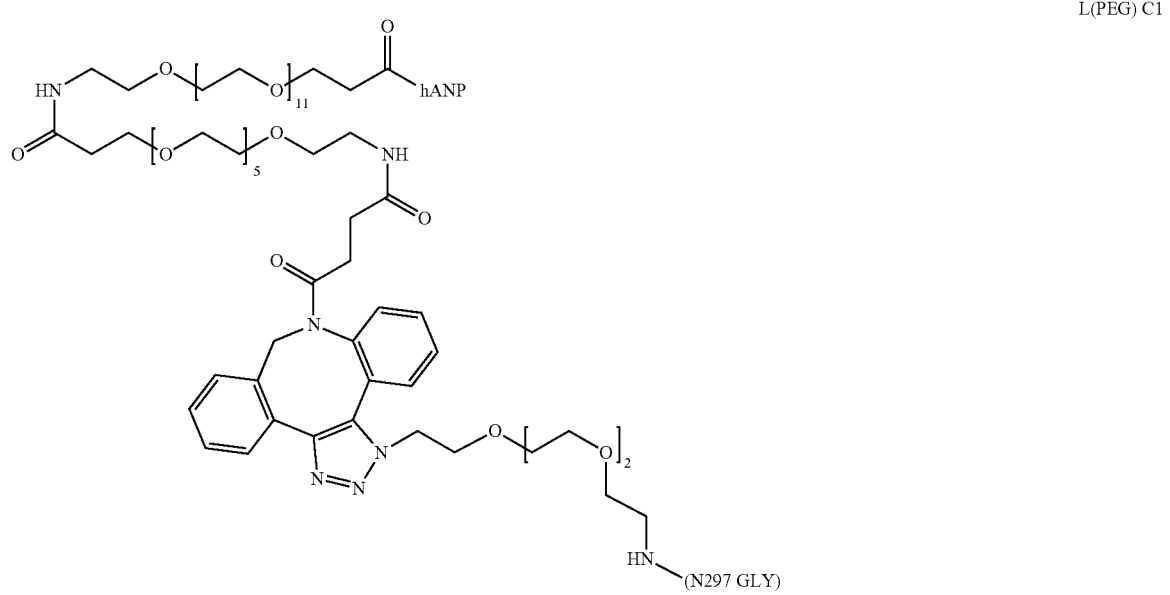
L(PEG) C2
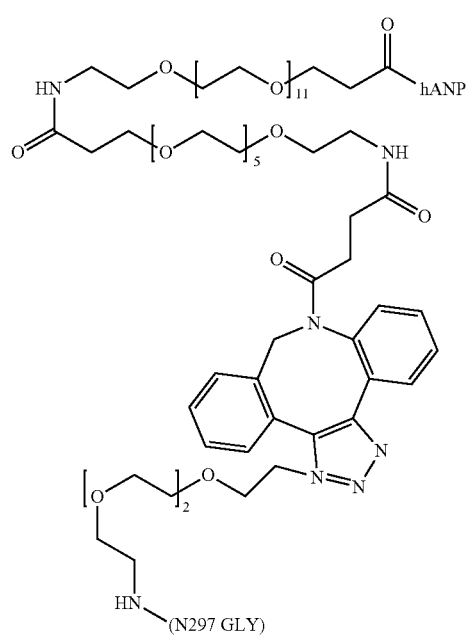

[Formula 11]
L(PEG) D1
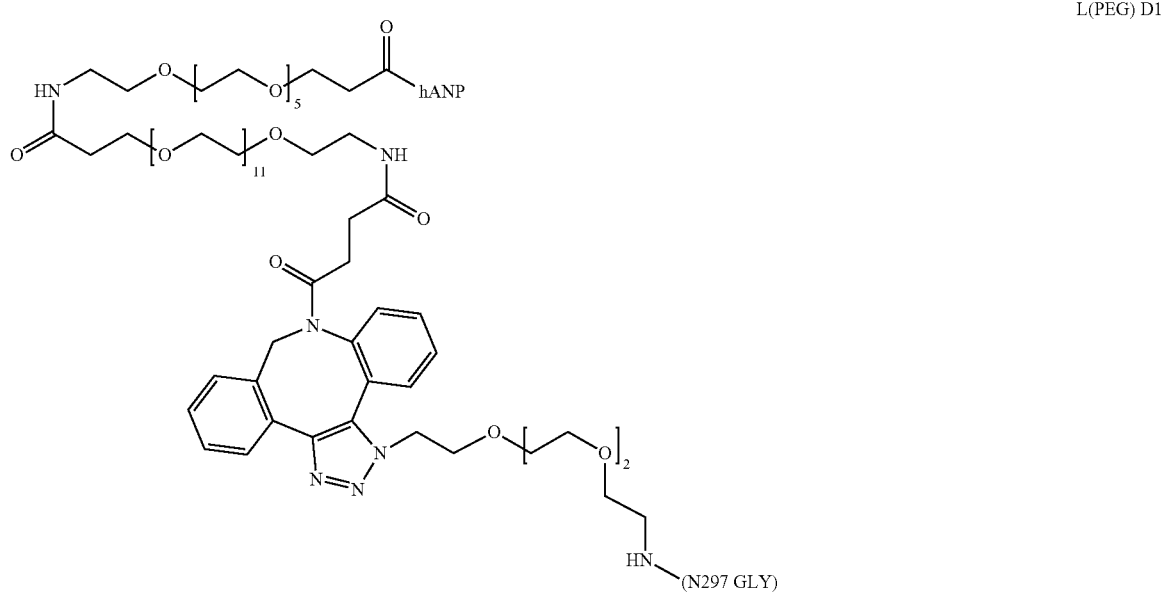
L(PEG) D2
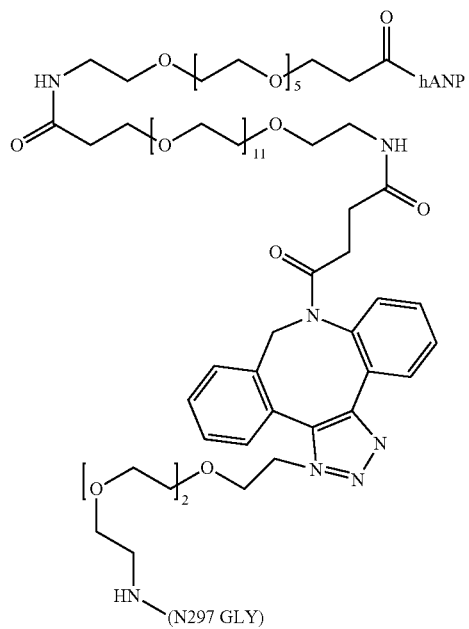

[Formula 12]
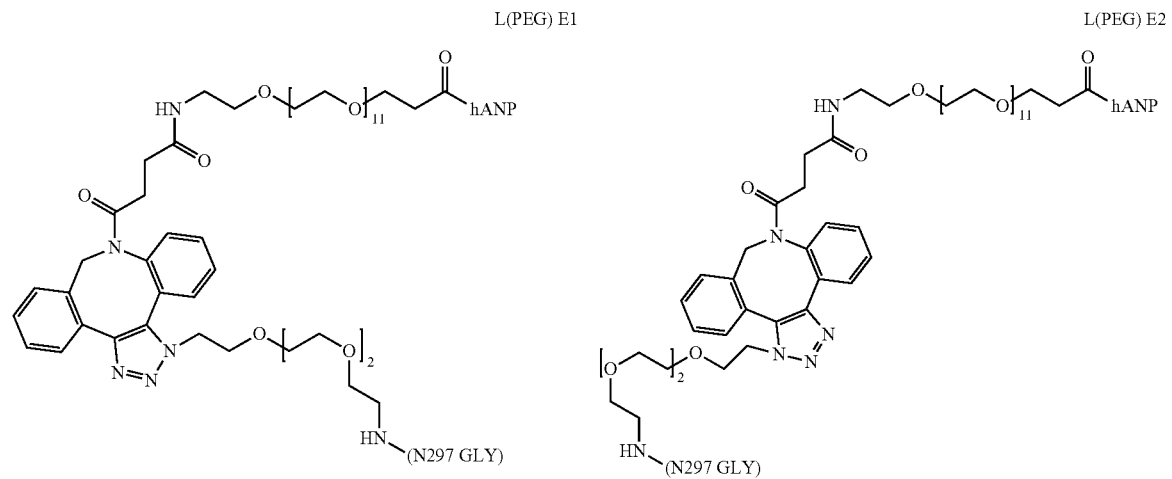
[Formula 13]
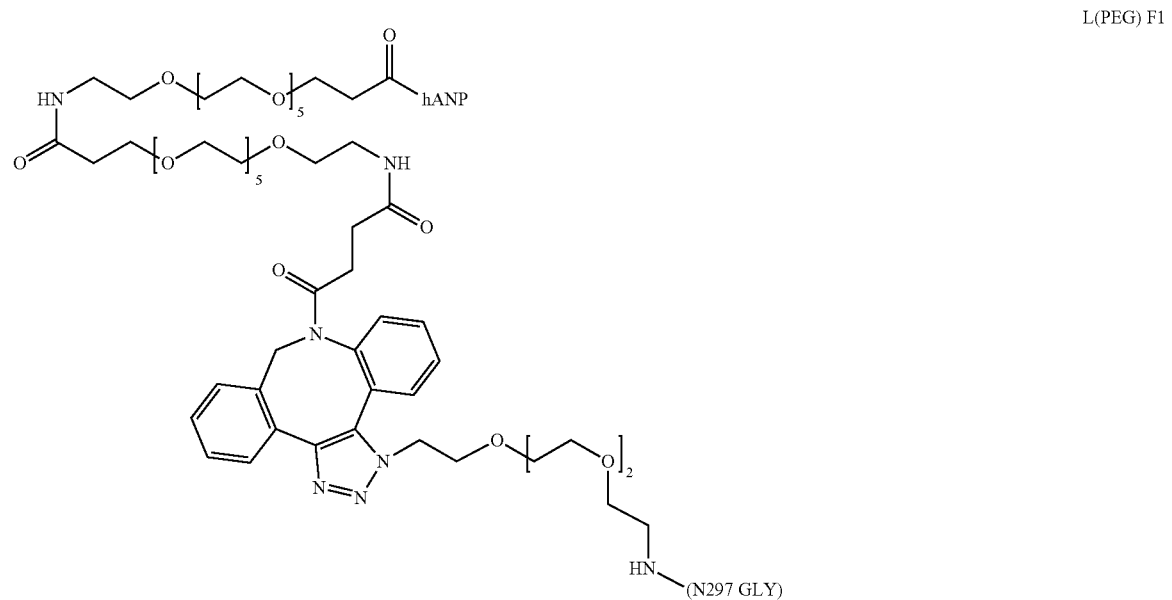

-continued
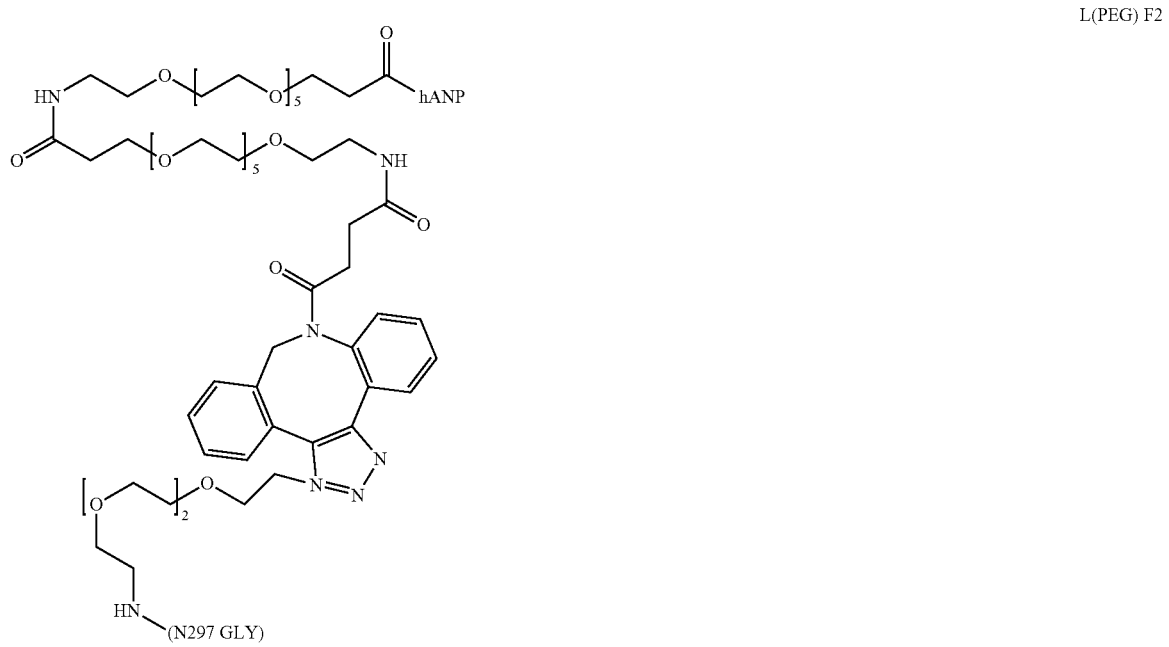
L(PEG) F2
[Formula 14]
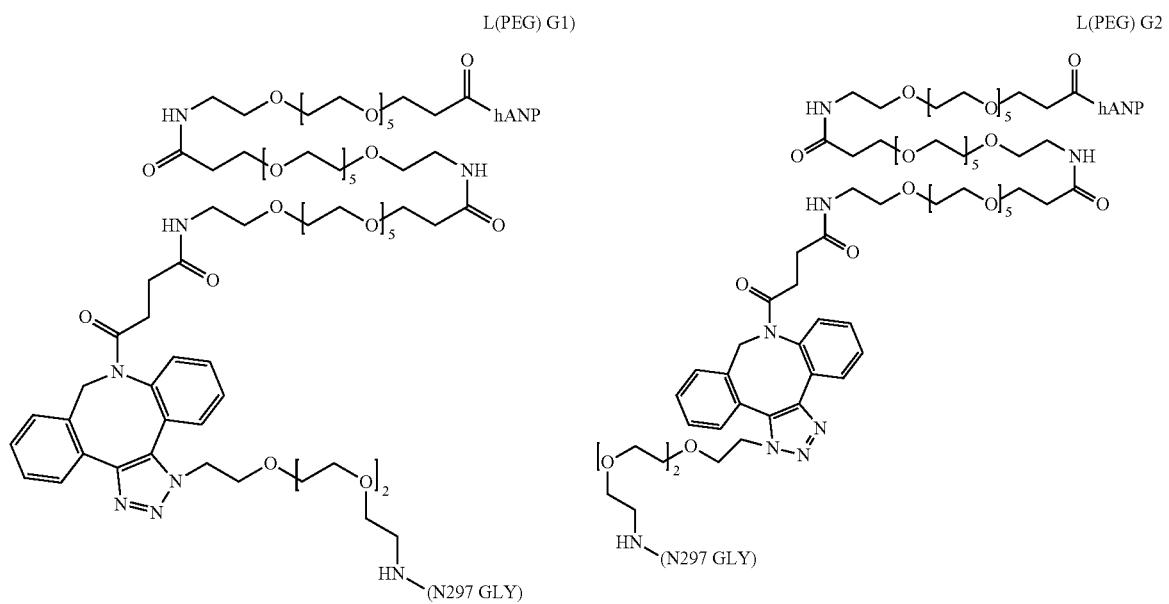
L(PEG) G1
L(PEG) G2

-continued

[Formula 15]

L(PEG) H1)

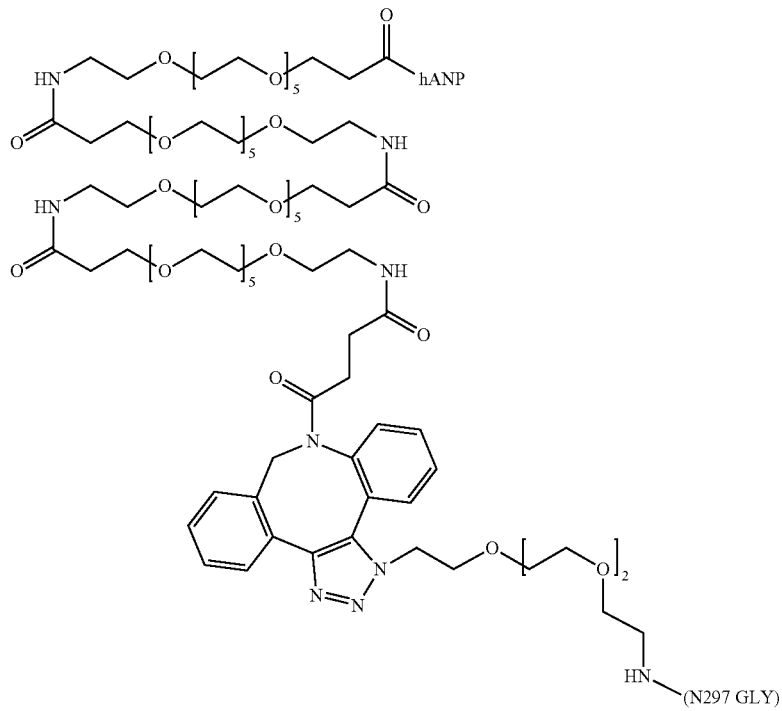

L(PEG) H2

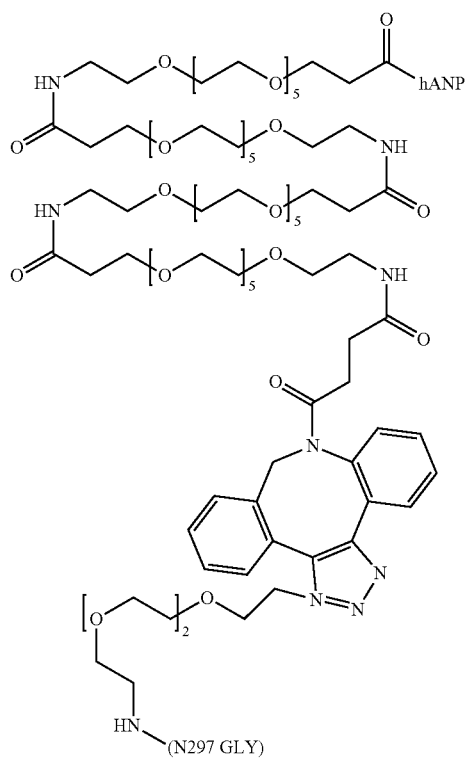

wherein "hANP" represents binding to the N terminus of the hANP peptide; "N297 GLY" represents binding to the non-reducing end of the N297-attached glycan; each linker structure has geometric isomeric structures formed during bond formation at the 1,2,3-triazole ring site, as shown in structures L(PEG)-X1 and L(PEG)-X2 (these are collectively referred to as L(PEG)-X (X being A, B, C, D, E, F, G or H)) in the formulas; and either only any one of the structures is present in the linkers in one molecule of the conjugate, or two structures coexist as linkers in one molecule of the conjugate.

(7) The conjugate according to (1) or a pharmaceutically acceptable salt thereof, wherein the Fc-containing molecule is a human IgG monoclonal antibody directed to a substance other than a human biogenic substance as an antigen, or a fragment or an engineered form of human IgG having a human IgG Fc region and lacking variable regions.

(8) The conjugate according to (7) or a pharmaceutically acceptable salt thereof, wherein the Fc-containing molecule is Fc derived from human IgG or CLCH consisting of human IgG constant regions.

(9) The conjugate according to (7) or a pharmaceutically acceptable salt thereof, wherein the Fc-containing molecule is an antibody consisting of a combination of a heavy chain consisting of an amino acid sequence from amino acid positions 20 to 474 of SEQ ID NO: 3 and a light chain consisting of an amino acid sequence from amino acid positions 21 to 234 of SEQ ID NO: 5 (mAb-A), CLCH consisting of a combination of a heavy chain consisting of an amino acid sequence from amino acid positions 20 to 349 of SEQ ID NO: 7 and a light chain consisting of an amino acid sequence from amino acid positions 21 to 125 of SEQ ID NO: 9 (CLCH-A), CLCH consisting of a combination of a heavy chain consisting of an amino acid sequence from amino acid positions 20 to 349 of SEQ ID NO: 11 and a light chain consisting of an amino acid sequence from amino acid positions 21 to 125 of SEQ ID NO: 9 (CLCH-B), a Fc fragment consisting of an amino acid sequence from amino acid positions 21 to 243 of SEQ ID NO: 15 (Fc-B), or a Fc fragment consisting of an amino acid sequence from amino acid positions 21 to 247 of SEQ ID NO: 17 (Fc-A), or an engineered form of any such antibody. (10) The conjugate according to (1) or a pharmaceutically acceptable salt thereof, wherein the hANP peptide is hANP(1-28) or (SG-)Asn-hANP(1-28), the PEG linker is L(PEG)-A, L(PEG)-B, L(PEG)-C, L(PEG)-D, L(PEG)-E, L(PEG)-F, L(PEG)-G or L(PEG)-H, the Fc-containing molecule is mAb-A, CLCH-A, CLCH-B, Fc-A or Fc-B, and the N297 glycan is N297-(Fuc)SG.

(11) The conjugate according to (1) or a pharmaceutically acceptable salt thereof, wherein the hANP peptide is (SG-)Asn-hANP(1-28), the PEG linker is L(PEG)-B, the Fc-containing molecule is Fc-A or Fc-B, and the N297 glycan is N297-(Fuc)SG.

(12) A medicament comprising the conjugate according to any of (1) to (11) or a pharmaceutically acceptable salt thereof as an active ingredient.

(13) The medicament according to (12), wherein the medicament is a therapeutic agent or a prophylactic agent for a disease treatable by the activation of GC-A.

(14) The medicament according to (12), wherein the medicament is a therapeutic agent or a prophylactic agent for hypertension, acute heart failure, chronic heart failure, acute renal failure, or chronic renal failure.

(15) A method for producing the conjugate according to any of (1) to (11), comprising the following steps:

step A: the step of treating a Fc-containing molecule produced in an animal cell with hydrolase to produce a (Fucα1,6)GlcNAc-Fc-containing molecule;

step B1: the step of reacting a glycan donor molecule with the (Fucα1,6)GlcNAc-Fc-containing molecule in the presence of glycosyltransferase to synthesize a SG type glycan-remodeled Fc-containing molecule with an azide group introduced in the sialic acid, wherein the glycan donor contains SG(10) or MSG(9) with an azide group introduced sialic acid and having oxazoline at the reducing end, or step B2: the step of reacting a glycan donor molecule, the glycan donor molecule being (SG-)Asn or (MSG-)Asn with an azide group introduced in sialic acid thereof, with the (Fucα1,6)GlcNAc-Fc-containing molecule in the presence of two endoglycosidases to synthesize a SG type glycan-remodeled Fc-containing molecule with the azide group introduced in the sialic acid; and step C: the step of reacting a linker molecule having a hANP peptide on one side and DBCO on the other side with the SG type glycan-remodeled Fc-containing molecule with the azide group introduced in the sialic acid, prepared in step B to synthesize the conjugate according to any of (1) to (11).

(16) The production method according to (15), further comprising the step of purifying the (Fucα1,6)GlcNAc-Fc-containing molecule from the reaction solution of step A by a step involving purification using a hydroxyapatite column.

(17) A method for treating or preventing a disease treatable by the activation of GC-A, comprising administering the conjugate according to any of (1) to (11) or a pharmaceutically acceptable salt thereof as an active ingredient to a subject in need of the administration.

(18) The conjugate according to any of (1) to (11) or a pharmaceutically acceptable salt thereof for use in the treatment or prevention of a disease treatable by the activation of GC-A.

(19) Use of the conjugate according to any of (1) to (11) or a pharmaceutically acceptable salt thereof for the production of a therapeutic agent or a prophylactic agent for a disease treatable by the activation of GC-A.

In the aspects (17) to (19), the disease treatable by the activation of GC-A is preferably hypertension, acute heart failure, chronic heart failure, acute renal failure, or chronic renal failure.

Advantageous Effects of Invention

The conjugate of the present invention possesses all of the following: gradual migration into the blood, a long-term half-life in the blood and long-term maintenance of a pharmacological effect when subcutaneously administered. Therefore, the conjugate of the present invention is clinically applicable to diseases on which heretofore known hANP formulations have no therapeutic effect and enables the development of drugs that offer improved convenience to patients. Furthermore, the conjugate of the present invention, exploiting a glycosylated hANP peptide as the hANP peptide, exhibited drastically suppressed agglutination and favorable physical properties. Therefore, its application to a range of forms of formulations is expected.

BRIEF DESCRIPTION OF DRAWINGS

FIG. 1 schematically shows the conjugate of the present invention (molecule (I)). The moiety (a) depicts a hANP peptide, the moiety (b) depicts a PEG linker, and the moiety (c) depicts a N297 glycan (wherein the open ellipse depicts NeuAc(Sia), the open hexagon depicts Man, the filled hexagon depicts GlcNAc, the open rhomboid depicts Gal, and the open inverted triangle depicts Fuc). The Y shape depicts a Fc-containing molecule, which is illustrated as full-length IgG containing Fab for the sake of convenience. However, the Fc-containing molecule in the conjugate of the present invention can be any molecule having Fc region to which the N297 glycan is bonded. In this schematic diagram, the N297 glycan is indicated as N297-(Fuc)SG for the sake of convenience and is shown in a form in which PEG linkers are bonded to sialic acid residues at the non-reducing ends of all branched chains. However, N297-(Fuc)MSG adopted as the N297 glycan may have sialic acid bonded to the PEG linker in any one of the two branched chains and have no sialic acid at the non-reducing end of the other branched chain. Such a notation is applied throughout the present specification, unless otherwise specified.

FIG. 2 is a schematic diagram showing the structures of a (Fucα1,6)GlcNAc-Fc-containing molecule (molecule (II) of FIG. 2A) and a SG type glycan remodeling Fc-containing molecule (molecule (III) of FIG. 2B), which are intermediates for the production of the conjugate of the present invention. In both the drawings, the Y shape depicts the same Fc-containing molecule as in FIG. 1. In FIG. 2A, the moiety (d) depicts a N297 glycan consisting only of GlcNAc having α-glycosidic bonds at the 1- and 6-positions of Fuc. In FIG. 2B, the moiety (c) depicts the same N297 glycan as in FIG. 1, and the moiety (e) depicts a terminal functional group (an azide group is exemplified herein, though the functional group is not limited thereto) that is a partial structure of a PEG linker and is subjected to binding to another linker molecule. The binding pattern of the PEG linker is as described in FIG. 1.

FIG. 3A Each of FIGS. 3A and 3B is a schematic diagram of the step of producing a SG type glycan remodeling Fc-containing molecule from a Fc-containing molecule produced in an animal cell. In the drawings, the molecules (II) and (III) depict a (Fucα1,6)GlcNAc-Fc-containing molecule and a SG type glycan remodeling Fc-containing molecule, respectively, as in FIG. 2. The molecule (IV) is a Fc-containing molecule produced in an animal cell and is a mixture of molecules having heterogeneous N297 glycans. FIG. 3A shows the step of treating heterogeneous N297 glycans in the molecule (IV) with hydrolase such as EndoS to prepare a homogeneous (Fucα1,6)GlcNAc-Fc-containing molecule (II). The SG type glycan donor molecule used herein has PEG linker-modified sialic acid at the non-reducing end of SG(10), MSG1(9) or MSG2(9). In the prepared SG type N297 glycan remodeling Fc-containing molecule, sialic acid at the non-reducing end is also similarly modified, as described in FIG. 2B. In the drawings, the donor molecule is indicated in a form using SG(10) for the sake of convenience. However, a remodeling Fc-containing molecule in which a linker molecule having a functional group at any one of the two non-reducing ends of the N297 glycan is bonded to a remodeling antibody is synthesized as the molecule (III) by using MSG1(9) or MSG2(9) as the glycan donor.

FIG. 3B Each of FIGS. 3A and 3B is a schematic diagram of the step of producing a SG type glycan remodeling Fc-containing molecule from a Fc-containing molecule produced in an animal cell. In the drawings, the molecules (II) and (III) depict a (Fucα1,6)GlcNAc-Fc-containing molecule and a SG type glycan remodeling Fc-containing molecule, respectively, as in FIG. 2. The molecule (IV) is a Fc-containing molecule produced in an animal cell and is a mixture of molecules having heterogeneous N297 glycans. FIG. 3B shows the step of transglycosylating a glycan of a SG type glycan donor molecule to GlcNAc of a N297 glycan in the Fc-containing molecule (II) by use of glycosyltransferase such as an EndoS D233Q mutant to prepare a SG type glycan remodeling Fc-containing molecule (III). The SG type glycan donor molecule used herein has PEG linker-modified sialic acid at the non-reducing end of SG(10), MSG1(9) or MSG2(9). In the prepared SG type N297 glycan remodeling Fc-containing molecule, sialic acid at the non-reducing end is also similarly modified, as described in FIG. 2B. In the drawings, the donor molecule is indicated in a form using SG(10) for the sake of convenience. However, a remodeling Fc-containing molecule in which a linker molecule having a functional group at any one of the two non-reducing ends of the N297 glycan is bonded to a remodeling antibody is synthesized as the molecule (III) by using MSG1(9) or MSG2(9) as the glycan donor.

FIG. 4 shows a NMR chart of compound 1-10 ([$N_3$-PEG (3)]$_2$-SG(10)-Ox).

FIG. 5 shows a NMR chart of compound 1-11 ([$N_3$-PEG (3)]-MSG1(9)-Ox).

FIG. 6 is a graph showing time-dependent change in the plasma cGMP concentrations of rats given subcutaneous administration of the conjugate of the present invention. The abscissa shows the time (h) elapsed after administration, and the ordinate shows the cGMP concentration (pmol/mL). Each data was indicated by mean±standard deviation (n=2 to 4). The solid line with a filled circle shows the results about compound 3-1, the solid line with an open circle shows the results about compound 3-2, the solid line with a filled square shows the results about compound 3-3, the solid line with an open square shows the results about compound 3-4, the broken line with an open circle shows the results about compound 3-5, and the broken line with an open square shows the results about compound 3-6.

FIG. 7 is a graph showing time-dependent change in the amounts of all human Fc-containing molecules and conjugates detected in the plasma of rats given subcutaneous administration of the conjugate of the present invention. The abscissa shows the time (h) elapsed after administration, and the ordinate shows the detected matter concentration (μg/mL). Each data was indicated by mean±standard deviation (n=3 to 4). The filled circle shows the results about compound 3-1, the open circle shows the results about compound 3-2, the filled square shows the results about compound 3-3, and the open square shows the results about compound 3-4. For each compound, the solid line depicts the amount of the conjugate detected, and the broken line depicts the amount of the human Fc-containing molecule detected. For each compound, the overlap between the solid line and the broken line shows that the conjugate is sustained in blood without degrading only the hANP(1-28) moiety more rapidly than the Fc-containing molecule or without dissociating hANP(1-28) from the Fc-containing molecule.

FIG. 8 is a graph showing time-dependent change in the plasma cGMP concentrations of rats given subcutaneous administration of the conjugate of the present invention. The abscissa shows the time (h) elapsed after administration, and the ordinate shows the cGMP concentration (pmol/mL). Each data was indicated by mean±standard deviation (n=2 to 4). The solid line with a filled rhomboid shows the results about compound 3-7, the solid line with an open rhomboid shows the results about compound 3-8, the solid line with an x-mark shows the results about compound 3-9, the solid line with an open triangle shows the results about compound 3-10, the solid line with a filled triangle shows the results about compound 3-11, the broken line with a filled rhomboid shows the results about compound 3-12, the broken line with an x-mark shows the results about compound 3-13, and the broken line with a filled triangle shows the results about compound 3-14.

FIG. 9 is a graph showing time-dependent change in the amounts of all human Fc-containing molecules and conjugates detected in the plasma of monkeys given subcutaneous administration of the conjugate of the present invention. The abscissa shows the time (h) elapsed after administration, and the ordinate shows the detected matter concentration (μg/mL). Each data was indicated by mean±standard deviation (n=3 to 4). The filled circle shows the results about compound 3-2, the open circle shows the results about compound 3-4, the filled square shows the results about compound 3-15, the open square shows the results about compound 3-16, and the filled rhomboid shows the results about compound 3-17. For each compound, the solid line depicts the amount of the conjugate detected, and the broken line depicts the amount of the human Fc-containing molecule detected, as in FIG. 7

DESCRIPTION OF EMBODIMENTS

Figure 10:
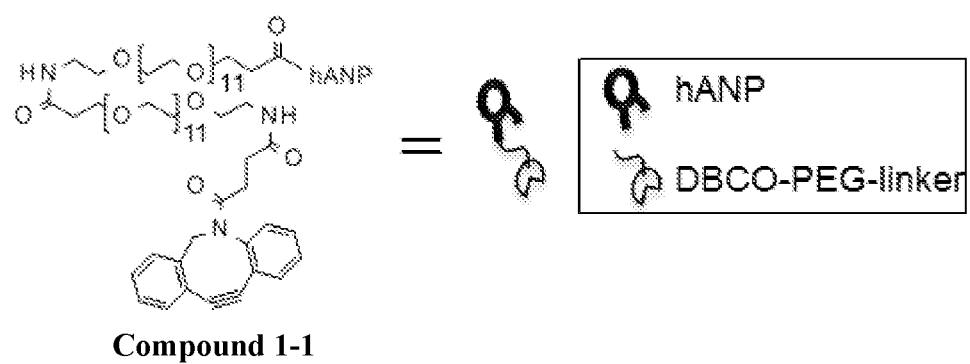
FIG. 10 shows Formula 37 (i.e., Compound 1-1), wherein the schematic diagram on the right of the structural formula shows the corresponding structure in the schematic diagram of the conjugate or the intermediate shown in the reaction schemes of FIGS. 1 to 3 and Example 3.

Hereinafter, the present invention will be described in detail.

The present invention provides a conjugate comprising a hANP peptide linked via a PEG linker to a N-linked glycan attached to asparagine (Asn297) conserved in a Fc-containing molecule (N297 glycan), or a pharmaceutically acceptable salt thereof. The conjugate of the present invention is a large molecule in which a plurality of structural units such as the hANP peptide, the PEG linker, the Fc-containing molecule, and partial structures constituting them are linked. A schematic diagram of this structure is shown in FIG. 1.

In the present invention, the term "linked", when describing a plurality of structural units means that these structural units are bonded directly through a covalent bond or indirectly via a linker so that the structural units exist in one molecule. The chemical structure that links the structural units is not particularly limited.

The structural units constituting the conjugate of the present invention have a very large molecular weight and a complicated structure and therefore, may also be described in a simplified form through the use of symbols for the sake of convenience. In such symbolic description, the hANP peptide is referred to as "hANP", the PEG linker is referred to as "L(PEG)" or "PEG(n)" ("n" being the number of consecutive ethylene glycol units (structural units ($-CH_2-CH_2-O-$)) contained therein), the N297 glycan contained in the Fc-containing molecule is referred to as "N297 GLY", and the Fc-containing molecule is referred to as "mAb", "CLCH", or "Fc". The glycan is also indicated by "SG", etc., as mentioned later. Each bond between the structural units may be omitted from a symbolic description for a general binding pattern, whereas a characteristic structure or functional group may be indicated by an expression usually used in the field of organic synthetic chemistry.

In the notation of the conjugate of the present invention or a partial structure thereof, the N terminus (amino group) and the C terminus (carboxyl group) of an amino acid or a peptide are indicated on the left and on the right, respectively, unless otherwise specified. An amino acid or a peptide with the symbol "*" on the right (e.g., Gln*) represents that contrary to this rule, the C terminus and the N terminus are indicated on the left and on the right, respectively.

In the notation of an amino acid, an amino group and a carboxyl group, which are structures essential to an amino acid, directly bonded to the central carbon atom (α carbon) are referred to as an "α amino group" and an "α carboxyl group", respectively.

In the notation of the conjugate or a partial structure thereof in the present specification, when an amino acid or a peptide is linked at its N terminal amino group to another linker, a symbol representing the structural unit to be linked is indicated with a hyphen and without parentheses on the left side of a symbol representing this peptide or amino acid. In this case, the hyphen represents the amide bond formed between the amino group of the peptide or the amino acid and the carboxyl group carried by the linker structure. For example, a structure where SG is linked to the amino group of Asn is referred to as "SG-Asn".

By contrast, when an amino acid or a peptide is linked at its C terminal carboxyl group to another structural unit in the present specification, a symbol representing the structural unit to be linked is indicated with a hyphen and without parentheses on the right side of a symbol representing this amino acid or peptide. In this case, the hyphen represents the amide bond formed between the C terminal carboxyl group of the peptide or the amino acid and the amino group (or azide group) carried by the linker structure. For example, a structure where SG is linked to the carboxyl group of Tyr is referred to as "Tyr-SG".

When an amino acid is linked at its side chain to a glycan in the present specification, the partial structure is referred to as, for example, "(SG-)Asn" with the side chain moiety included in the parentheses.

In the present invention, the "glycan" means a structural unit of two or more monosaccharides bonded to each other through a glycosidic bond. A specific monosaccharide or glycan is also indicated by an abbreviation, for example, "GlcNAc-" or "SG-". When the glycan is represented by a structural formula with these abbreviations, an oxygen atom or a nitrogen atom belonging to the glycosidic bond at the reducing end with another structural unit is excluded from the abbreviations representing the glycan, unless otherwise defined.

In the present specification, the monosaccharide serving as the basic unit of the glycan is indicated in its ring structure where a carbon atom bonded to an oxygen atom constituting the ring and directly bonded to the hydroxy group (or the oxygen atom belonging to the glycosidic bond) is defined as the 1-position (2-position only for sialic acid) for the sake of convenience, unless otherwise specified. The compounds of Examples are named in the light of their whole chemical structures, so that this rule is not necessarily applicable thereto.

The monosaccharide contained in the glycan is not particularly limited as long as the monosaccharide has the basic structure of a sugar. Various monosaccharides such as 6-membered and 5-membered sugars can be used. The monosaccharide may be a naturally occurring sugar or may be an artificially synthesized sugar. A naturally occurring sugar is preferred. Examples of the monosaccharide can include glucose (Glu), fructose (Fru), mannose (Man), galactose (Gal), glucosamine (Glc), N-acetylglucosamine (GlcNAc), glucuronic acid (GlucA), neuraminic acid (Neu), sialic acid/N-acetylneuraminic acid (Sia/NeuNAc/Neu5Ac), galactosamine, N-acetylgalactosamine (GalNAc), xylose (Xyl), iduronic acid (IdoA), fucose (Fuc), aldotriose, glyceraldehyde, aldotetrose, erythrose, threose, aldopentose, ribose, lyxose, arabinose, aldohexose, allose, talose, gulose, aldose, idose, ketotriose, dihydroxyacetone, ketotetrose, erythrulose, ketopentose, xylulose, ribulose, ketohexose, psicose, sorbose, and tagatose.

When the glycan is indicated by a symbol (e.g., GLY, SG, or GlcNAc) in the present specification, this symbol also includes carbon at the reducing end and excludes N or O belonging to the N- or O-glycosidic bond, unless otherwise defined. Likewise, when the hANP peptide is indicated by a symbol (e.g., hANP or hANP(1-28)), the symbol also includes N terminal —NH and C terminal C=O as a rule. The N terminus and the C terminus are indicated on the left and on the right, respectively, unless otherwise specified. Specifically, an unmodified hANP peptide is referred to as H-hANP-OH.

<hANP Peptide>

In the present invention, the "hANP peptide" means a peptide consisting of an amino acid sequence comprising at least amino acids at the 7- to 27-positions in the amino acid sequence of human atrial natriuretic peptide (SEQ ID NO: 1; hereinafter, referred to as native hANP or hANP(1-28)), which is a biologically active peptide consisting of 28 amino acids. The native hANP exerts its biological activity by binding to a GC-A receptor (Chinkers M, et al., Nature 338; 78-83, 1989)) expressed on the cell surface, activating guanylate cyclase present in the intracellular domain of the receptor, and elevating the intracellular cGMP concentration. As for the native hANP, α-hANP described in Biochem. Biophys. Res. Commun., vol. 118, p. 131, 1984, has been approved for manufacture and sale under the generic name of "carperitide" in Japan and is commercially available (trade name: HANP). α-hANP is also generally known as Human pro-ANP[99-126].

Native hANP has an intramolecular ring structure formed by Cys residues at the 7- and 23-positions of SEQ ID NO: 1 through a disulfide bond. It is known that this ring structure and the C terminal amino acids up to the Arg residue at the 27-position are important for the activation of the GC-A receptor by hANP (Silver, M A, Curr. Opin. Nephrol. Hypertens. (2006), 15, p. 14-21; and A. Calderone, Minerva Endocrinol. (2004), 29, p. 113-127). hANP(7-27) consisting of this ring structure is therefore considered as the minimum unit for activating GC-A. The hANP peptide of the present invention is a peptide consisting of an amino acid sequence that may lack 1 to 6 amino acids consecutively from the N terminus and/or an amino acid at the 28-position in SEQ ID NO: 1), and is preferably a peptide that may lack at least one of the amino acid sites of the 1-position, the 1- and 2-positions, and the 28-position of SEQ ID NO: 1, more preferably a peptide consisting of an amino acid sequence that may lack an amino acid at the 1-position or amino acids at the 1- and 2-positions of SEQ ID NO: 1 (hANP(2-28), hANP(3-28), etc.), most preferably a peptide consisting of the amino acid sequence of SEQ ID NO: 1 (hANP(1-28)).

In the present invention, the peptide shown in SEQ ID NO: 1 is referred to as "hANP(1-28)", the peptide lacking an amino acid at the 1-position of SEQ ID NO: 1 is referred to as "hANP(2-28)", and the peptide lacking amino acids at the 1- and 2-positions of SEQ ID NO: 1 is referred to as "hANP(3-28)", for example. Other peptides lacking a portion of amino acids are also referred to in a manner corresponding to that shown above.

The number of hANP molecules in one molecule of the conjugate of the present invention varies depending on the structure of the N297 glycan bonded to the Fc-containing molecule or the PEG linker and is usually 2 or 4.

In the conjugate of the present invention, the PEG linker can be bonded to the hANP peptide through, for example, an amide bond with the N terminal α-amino group or the C terminal α-carboxyl group. Preferably, the PEG linker is bonded to the N terminus of the hANP peptide.

In the conjugate of the present invention, the hANP peptide may be glycosylated. Various forms of the glycosylation of the hANP peptide are described in Patent Literature 1. Diverse glycosylated peptides can be applied to the present invention through the use of these forms of glycosylation. A glycan structurally similar to a glycan present in the bodies of humans is appropriately adopted as the glycan for use in the modification of the hANP peptide.

Glycans contained in natural glycoproteins are broadly classified into N-linked glycans attached to asparagine of a glycoprotein and O-linked glycans attached to serine or threonine thereof, both of which have their characteristic basic structures. Naturally, the N-linked glycan is bonded through a N-glycosidic bond to the amino acid side chain of a protein, while the O-linked glycan is bonded through an O-glycosidic bond thereto. Artificial glycans can be bonded to other compounds through any glycosidic bond. Thus, the type of glycosidic bond is not limited by the structure of such a glycan. For example, the glycan is azidated at its reducing end, and this azidated glycan can be reacted with a compound having a carboxyl group in the presence of triphenylphosphine to bond the compound having the desired structure to the glycan through a N-glycosidic bond. Alternatively, the glycan can be reacted with a compound having a hydroxy group, such as an alcohol, to bond the glycan to the desired compound through an O-glycosidic bond.

The basic structure of the N-linked glycan is represented by the following structural formula and sequence. A glycan having this glycan structure is designated as AG5.

[Formula 16]

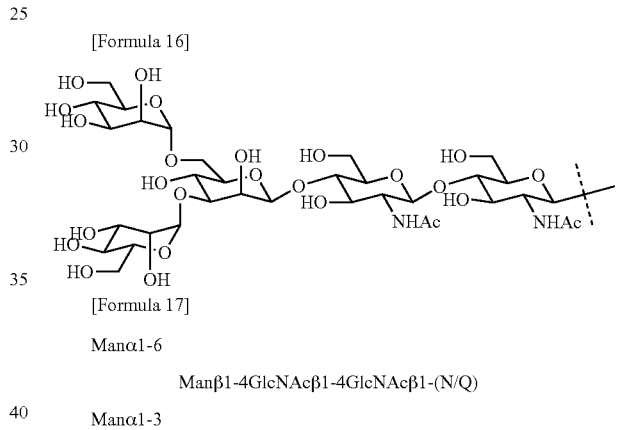

[Formula 17]

Manα1-6

Manβ1-4GlcNAcβ1-4GlcNAcβ1-(N/Q)

Manα1-3 wherein "-(N/Q)" represents binding to the side chain of Asn or Gln through a N-glycosidic bond.

Most of the N-linked glycans have this basic structure. Its non-reducing end or branched sugar may be further bonded to another sugar.

Human glycans or human-compatible glycans are glycans known to exhibit no antigenicity in the bodies of humans. For example, high-mannose, complex, and composite forms of N-linked glycans are known. The high-mannose form is a glycan having a mannose-rich structure composed of a plurality of consecutive mannose residues at the non-reducing end of the N-linked basic structure. The complex form is a glycan having a Galβ1-4GlcNAc motif structure at the non-reducing end of the N-linked basic structure. The composite glycan is a glycan having a Galβ1-4GlcNAc motif structure at the non-reducing end of the N-linked basic structure and also having a mannose-rich structure composed of a plurality of mannose residues.

The N-linked complex glycan is typically a glycan contained in sialyl glycopeptide (hereinafter, referred to as "SGP") contained in chicken egg yolk. Examples thereof can include sialyl glycan (hereinafter, referred to as "SG") having a structure represented by the following structural formula and sequence:

[Formula 18]

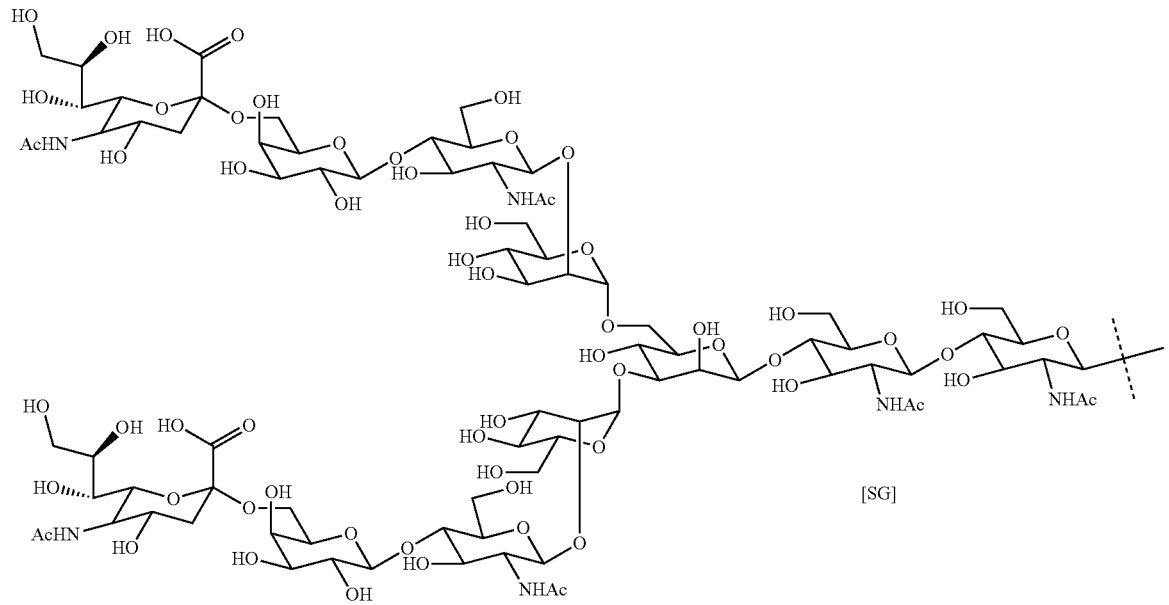

[SG]

[Formula 19]

NeuAcα2-6Galβ1-4GlcNAcβ1-2Manα1-6
                                                Manβ1-4GlcNAcβ1-4GlcNAcβ1-(N\Q)
NeuAcα2-6Galβ1-4GlcNAcβ1-2Manα1-3

[SG]

wherein "-(N/Q)" represents binding to the side chain of Asn or Gln through a N-glycosidic bond.

SGP can be isolated and purified from chicken egg yolk according to common methods, for example, a method described in WO2011/0278681. Alternatively, a purified product of SGP is commercially available (Tokyo Chemical Industry Co., Ltd. or Fushimi Pharmaceutical Co., Ltd.) and can be purchased. Also, for example, disialooctasaccharide (manufactured by Tokyo Chemical Industry Co., Ltd.) consisting only of a glycan lacking one GlcNAc at the reducing end of the glycan moiety of SG (hereinafter, this glycan is referred to as "SG(10)") is commercially available. In the present specification, a glycan structure lacking sialic acid at the non-reducing end of only any one of the two branched chains of SG(10) β-Man is referred to as MSG(9), a glycan structure having sialic acid only in the 1-3 branched chain of the glycan is referred to as MSG1(9), and a glycan structure having sialic acid only in the 1-6 branched chain of the glycan is referred to as MSG2(9).

The glycan engineered at the reducing end by the replacement of GlcNAc at the reducing end of SG with another sugar can be prepared using the disialosaccharide through the use of a known transglycosylation reaction. The glycan engineered at the reducing end by the replacement of GlcNAc at the reducing end of SG with Glc is referred to as SG(Glc). The glycan engineered at the reducing end by the replacement of GlcNAc at the reducing end of SG with Man is referred to as SG(Man).

Specific examples of the engineered glycan that may be used as the glycan of the present invention can include AG9 (a structural formula and a sequence of AG9 are given below) which lacks Neu5Ac residues at the two non-reducing ends as a result of the neuraminidase treatment of SG, AG(7) (a structural formula and a sequence of AG7 are given below) which lacks Gal residues at the two non-reducing ends as a result of the galactosidase treatment of AG9, and AG5 (glycan having the N-linked basic structure, described above) which lacks GlcNAc residues at the two non-reducing ends as a result of the further treatment of AG7 with N-acetylglucosaminidase. Also, glycans engineered at the reducing ends of AG(9), AG(7) and AG(5) (e.g. AG(9-Glc) with GlcNAc at the reducing end of AG(9) replaced with Glc, and AG(9-Man) with GlcNAc at the reducing end of AG(9) replaced with Man) can be obtained by the same treatment as above using the glycan engineered at the reducing end of SG (e.g., SG(Glc) or SG(Man)) instead of SG and can be adopted for the glycosylation of the present invention.

[Formula 20]
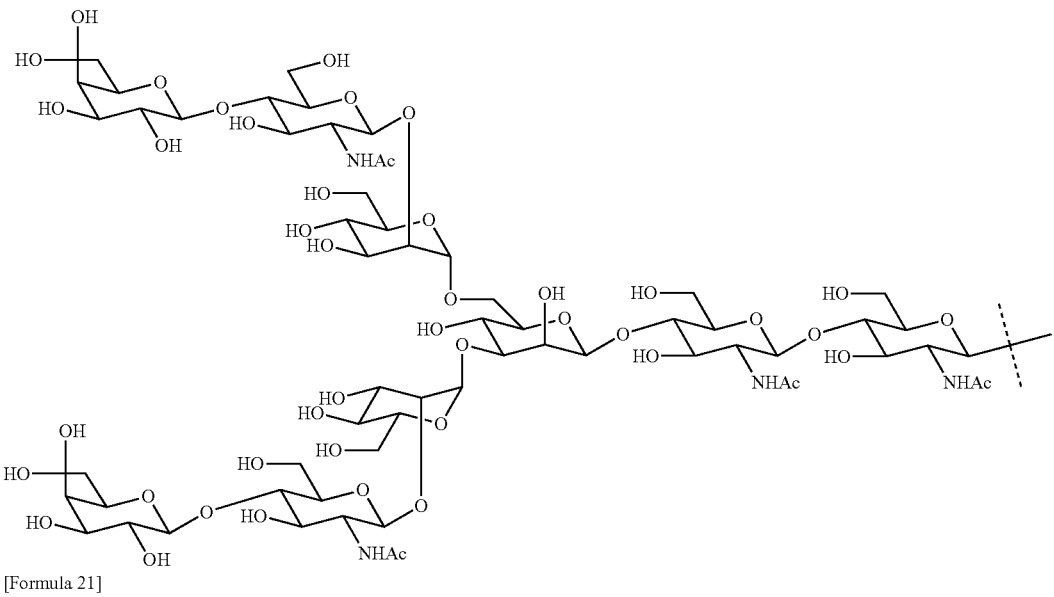
[AG9]
[Formula 21]
Galβ1-4GlcNAcβ1-2Manα1-6  
                            Manβ1-4GlcNAcβ1-4GlcNAcβ1-(N/Q)  
Galβ1-4GlcNAcβ1-2Manα1-3
[AG9]
wherein "-(N/Q)" represents binding to the side chain of Asn or Gln through a N-glycosidic bond.
wherein "-(N/Q)" represents binding to the side chain of Asn or Gln through a N-glycosidic bond.
[Formula 22]
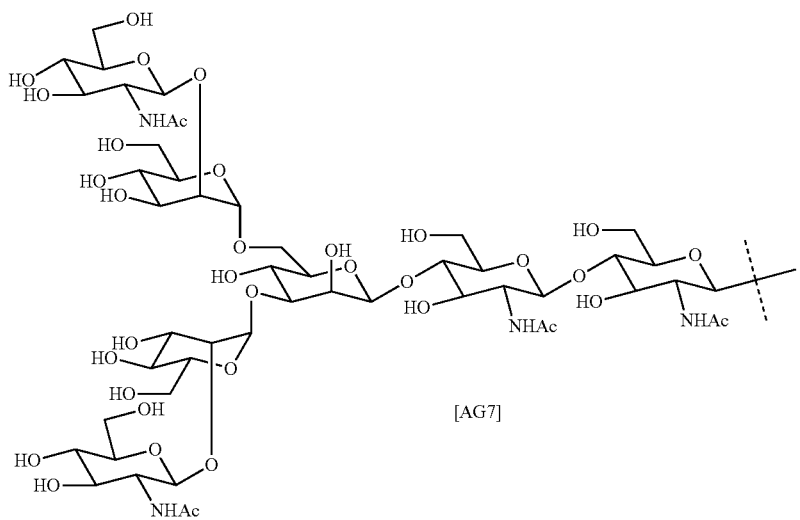
[AG7]
[Formula 23]
GlcNAcβ1-2Manα1-6  
                    Manβ1-4GlcNAcβ1-4GlcNAcβ1-(N\Q)  
GlcNAcβ1-2Manα1-3  
              [AG7]

In the conjugate of the present invention, there is no upper limit on the number of glycans bonded to the hANP peptide. The number of glycans is, for example, 3 or fewer, preferably 2 or 1. The glycans attached to the hANP peptide may have the same structure or may be a mixture of glycans differing in structure. Preferably, all of these glycans have the same glycan structure.

One example of the glycosylated hANP peptide of the present invention can include a hANP peptide comprising a N-linked glycan, as mentioned above, attached to the side chain of Asn or Gln through a N-glycosidic bond ("(GLY-)Asn" or "(GLY-)Gln". In such a peptide, any one or a plurality of amino acids at the 1- to 5- and 28-positions of the amino acid sequence of SEQ ID NO: 1 may be replaced with (GLY-)Asn or (GLY-)Gln. Alternatively, (GLY-)Asn or (GLY-)Gln may be bonded through a peptide bond to any one or both of the N-terminus and C-terminus of a peptide consisting of a consecutive amino acid sequence comprising the 6- to 27-positions of SEQ ID NO: 1. Such a peptide is preferably a peptide with (GLY-)Asn or (GLY-)Gln bonded through a peptide bond to the N terminus and/or C terminus of hANP(1-28), hANP(2-28), hANP(3-28), hANP(4-28), hANP(5-28), or hANP(6-28), more preferably a peptide with (SG-)Asn or (SG-)Gln bonded through a peptide bond to the N terminus of hANP(1-28), hANP(2-28) or hANP(3-28), even more preferably (SG-)Asn-hANP(1-28).

In the present invention, in the case of using a naturally occurring glycoprotein- or glycolipid-derived glycan as the glycan for use in the modification of the hANP peptide, this glycan can be used after being cleaved or isolated by use of hydrolase or transferred to the desired compound (acceptor compound) through transglycosylation using glycosyltransferase, in accordance with a method described in, for example, Patent Literature 1. For example, SG can be isolated by the hydrolytic cleavage of SGP through reaction with hydrolase (EndoM, etc.), or by transfer to the desired compound by use of endoglycosidase(EndoM N175Q mutant, etc.), according to a known method. Also, SGP treated with peptidase such as actinase and thereby degraded into (SG-)Asn or a peptide fragment containing (SG-)Asn, and the glycan-bonded fraction can be purified by a known separation method to obtain a glycan-attached amino acid. (SG-)Asn, (SG-)Gln or the peptide fragment containing the same, thus obtained can be bonded to the N terminus and/or C terminus of the hANP peptide through a peptide bond by the usual reactions using a protective group to produce the glycosylated hANP peptide.

<Fc-Containing Molecule>

In the conjugate of the present invention, the "Fc-containing molecule" is linked to the hANP peptide via a glycan attached to the side chain of asparagine (referred to as "Asn297"; which undergoes modification by a N-linked glycan) well conserved in the IgG heavy chain Fc region (this glycan is referred to as a "N297 glycan"), and functions as a carrier protein for sustaining the hANP peptide for a long period in the blood. Therefore, the Fc-containing molecule needs to have an amino acid sequence corresponding to a human IgG Fc region and to have no ability to bind specifically to a human biomolecule. Examples of the amino acid sequence corresponding to an IgG Fc region can include an amino acid sequence from amino acid positions 128 to 349 of SEQ ID NO: 7, an amino acid sequence from amino acid positions 128 to 349 of SEQ ID NO: 11, an amino acid sequence from amino acid positions 22 to 243 of SEQ ID NO: 15, an amino acid sequence from amino acid positions 26 to 247 of SEQ ID NO: 17, and amino acid sequences engineered from these sequences.

IgG consists of heavy and light chains. The heavy and light chains are linked through a disulfide bond, and the heavy chains are further linked at a hinge region to each other through a disulfide bond to form a homodimer. IgG also has a domain structure where Fab domains comprising variable regions and having the ability to bind to an antigen are linked via a hinge region to Fc domains binding to a Fc receptor. The Fc-containing molecule of the present invention is not particularly limited as long as the Fc-containing molecule comprises a Fc region. For example, a full-length IgG heavy chain, an antibody fragment containing a Fc region, or an engineered form derived from any of their amino acid sequences by partial engineering can be used. The Fc-containing molecule of the present invention may consist only of a heavy chain or may further have a light chain appropriate for the structure of the heavy chain. The subclass of IgG serving as an origin of the Fc-containing molecule is not particularly limited, and any subclass may be selected. The subclass is preferably IgG1, IgG2, IgG3 or IgG4, more preferably IgG1. The amino acid sequences of IgG constant regions are well conserved, and each amino acid is defined by the EU Index provided by Edelman et al. (Biochemistry, (1969) Vol. 63, pp. 78-85). For example, Asn297 to which a N-linked glycan is attached in the Fc region corresponds to the 297-position based on the EU Index. The amino acid is unambiguously identified by display according to the EU Index even if the actual amino acid position varies due to molecular fragmentation or regional deficiency.

In the case of adopting full-length IgG as the Fc-containing molecule, the full-length IgG is not particularly limited as long as the IgG has no ability to bind specifically to a substance usually present in the bodies of humans. IgG directed to a nonhuman animal protein as an antigen might exhibit cross reactivity with a corresponding or related human molecule, if any. Therefore, it is preferred to select a monoclonal antibody against an antigen free from corresponding or related human molecules. Even an antibody that might bind to a substance in the bodies of humans can be adopted as the Fc-containing molecule of the present invention as long as the molecule has been modified so it lacks binding activity against the human substance as a result of introducing a mutation to its variable region by a genetic engineering approach. The full-length IgG for use as the Fc-containing molecule of the present invention is more preferably IgG directed to a nonmammalian organism-derived molecule as an antigen, even more preferably IgG directed to a microbe-derived molecule as an antigen, further preferably IgG directed to lipopolysaccharide (LPS) as an antigen. Such a monoclonal antibody is described in, for example, WO2015/046505. Specific examples thereof include mAb-A consisting of a combination of a heavy chain consisting of an amino acid sequence from amino acid positions 20 to 474 of SEQ ID NO: 3 (amino acid positions 1 to 19 correspond to a signal peptide, and a nucleotide sequence encoding the heavy chain is shown in SEQ ID NO: 2), and a light chain consisting of an amino acid sequence from amino acid positions 21 to 234 of SEQ ID NO: 5 (amino acid positions 1 to 20 correspond to a signal peptide, and a nucleotide sequence encoding the light chain is shown in SEQ ID NO: 4).

In the case of adopting an antibody fragment or an engineered form as the Fc-containing molecule of the present invention, the antibody fragment or the engineered form is not particularly limited as long as the antibody fragment or the engineered form comprises a Fc region in a form that permits dimerization. Various sequences can be adopted. An engineered form that maintains a portion of or the whole of the variable regions may be adopted as long as the antibody serving as the source thereof has no ability to bind specifically to a human substance as mentioned above. A fragment or an engineered form lacking variable regions is preferred.

Examples of such an engineered form can include CH lacking a human IgG heavy chain variable region and consisting of a human IgG heavy chain constant region. In the case of adopting CH as the Fc-containing molecule of the present invention, the subclass of IgG serving as a source thereof is not particularly limited. The amino acid sequence of CH derived from human IgG1 (this CH is referred to as "CH-A") is shown in amino acid positions 20 to 349 of SEQ ID NO: 7 (the N terminal 1- to 19-positions correspond to a signal peptide, and a nucleotide sequence encoding CH-A is shown in SEQ ID NO: 6). In this sequence, the hinge region is EPKSCDKTHTCPPCP from Glu at the 118-position to Pro at the 132-position, the Fc region is from Ala at the 133-position to Lys at the 349-position, and Asn at the 199-position corresponds to Asn297 (the same holds true for SEQ ID NO: 11). In the case of selecting CH as the Fc-containing molecule, only CH may be adopted, or CLCH having CH in combination with CL consisting only of a light chain constant region may be adopted. The amino acid sequence of IgG1 light chain CL (referred to as "CL-A") is shown in amino acid positions 21 to 125 of SEQ ID NO: 9 (N terminal amino acids at the 1- to 20-positions correspond to a signal peptide, and a nucleotide sequence encoding CL-A is shown in SEQ ID NO: 8). Preferred examples of the Fc-containing molecule of the present invention can include CLCH. CLCH-A having CH-A and CL-A in combination is more preferred.

In the case of adopting a fragment or an engineered form composed mainly of a Fc region as the Fc-containing molecule of the present invention, for example, an antibody fragment consisting of the amino acid sequence of an IgG Fc region attached at its N terminus to the amino acid sequence CPPC, a portion of a hinge region can be adopted (an example of the sequence of IgG1 is a sequence from the 128- to 349-positions of SEQ ID NO: 7). The hinge region is a region that enhances the structural degree of freedom of the Fc-containing molecule and does not influence its function as a carrier protein as intended in the present invention. Therefore, the hinge region can be adopted with its length appropriately adjusted as long as the hinge region contains CPPC. Examples of such an antibody fragment composed mainly of Fc include an IgG1-derived Fc-containing molecule consisting of an amino acid sequence from Glu at the 118-position to Lys at the 349-position of SEQ ID NO: 7 or SEQ ID NO: 11 that may lack 1 to 10 amino acids consecutively from the N terminus of said amino acid sequence, and engineered forms engineered from its amino acid sequence. The antibody fragment composed mainly of Fc is preferably a Fc-containing molecule consisting of an amino acid sequence from Asp at the 123-position to Lys at the 349-position, Thr at the 127-position to Lys at the 349-position, or His at the 126-position to Lys at the 349-position of SEQ ID NO: 7. Examples of the molecules related to Fc-A and Fc-B can include a Fc-containing molecule consisting of an amino acid sequence from amino acid positions 22 to 243 of SEQ ID NO: 15 or an amino acid sequence from amino acid positions 26 to 247 of SEQ ID NO: 17, or an amino acid sequence thereof attached at its N terminus to amino acid residues T, HT, THT, KTHT or DKTHT, and engineered forms engineered from these amino acid sequences. The molecule is preferably a Fc-containing molecule consisting of an amino acid sequence from amino acid positions 21 to 243 of SEQ ID NO: 15, an amino acid sequence from amino acid positions 25 to 247 of SEQ ID NO: 17, or an amino acid sequence from amino acid positions 21 to 247 of SEQ ID NO: 17. Asn297 in these Fc fragments is Asn at the 93-position of SEQ ID NO: 15 or Asn at the 97-position of SEQ ID NO: 17.

In the case of designing an antibody fragment or an engineered form as the Fc-containing molecule of the present invention, an engineered form having the substitution, deletion, insertion and/or addition of 1 to several (preferably 20 or fewer, more preferably 15 or fewer, even more preferably 10 or fewer, further preferably 7, 6, 5, 4, 3, 2 or 1, per engineering site) amino acids at 1 to several sites (preferably 5 or fewer sites, more preferably 3, 2 or 1 site(s)) may be adopted without impairing functions as the carrier protein, as long as Cys for dimerization in the hinge region, Cys that contributes to an intramolecular disulfide bond in the Fc region, Asn297 for the attachment of the N297 glycan, and its neighboring amino acids are maintained. As for the engineering site in an amino acid sequence, the substitution, deletion and/or addition, etc. of N terminal and/or C terminal amino acid(s) is performed. Particularly, N terminal amino acids may influence the production of the Fc-containing molecule by a bioengineering approach and can be engineered into an amino acid sequence suitable for the desired production system. Amino acids Leu234 and Leu235 based on the EU Index are known as sites that influence the exhibition of effector activity by T cell activation through the binding of the antibody to a Fc receptor. Leu contained in this region may be replaced with Ala (the resulting mutant is referred to as a "LALA form") so that this effector activity can be eliminated so as to reduce the risk of adverse reaction (U.S. Pat. No. 5,885,573). Such engineering may be carried out, if necessary. In Examples of the present invention, CLCH-B and Fc-A were prepared as a LALA form of CLCH-A and a LALA form of Fc-B, respectively, and confirmed to function properly as the carrier molecule in the conjugate of the present invention.

A signal sequence, a peptidase recognition sequence, or a Tag sequence such as GST may be added thereto for the purpose of improving the expression or purification efficiency of the molecule of interest.

The Fc-containing molecule used in the present invention has a N297 glycan and the N297 glycan is remodeled into a SG type glycan having any of structures given below (SG type N297 glycan) from heterogeneous glycans originally attached to Asn297 of the Fc-containing molecule by post-translational modification in the course of production using animal cells. Usually, glycans are attached to Asn297 residues in both the monomers of a dimer during production from animal cells to produce a normal form having two N297 glycan moieties per dimeric Fc-containing molecule. However, depending on production conditions or the structure of the Fc-containing molecule, a glycan deletion mutant in which a N297 glycan is attached to only one of the monomers (molecule having one N297 glycan moiety per dimeric Fc-containing molecule) may be produced at a given rate. Even such a Fc-containing molecule comprising a glycan deletion mutant can be used in the present invention.

[Formula 24]

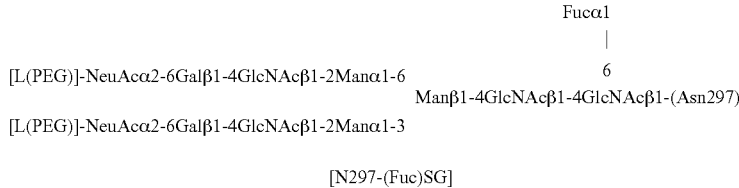

[N297-(Fuc)SG]

wherein [L(PEG)] represents L(PEG) being bound to carbonyl groups bonded to the 2-positions of sialic acid residues at the non-reducing ends of both the 1-3 and 1-6 branched chains of β-Man.

[Formula 25]

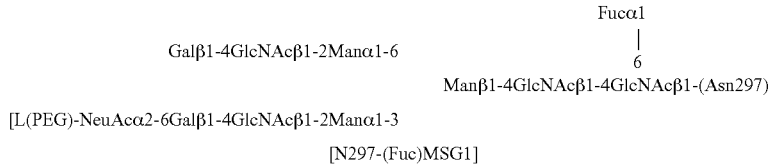

[N297-(Fuc)MSG1]

wherein [L(PEG)] represents L(PEG) being bound to a carbonyl group bonded to the 2-position of a sialic acid residue at the non-reducing end of the 1-3 branched chain of β-Man.

[Formula 26]

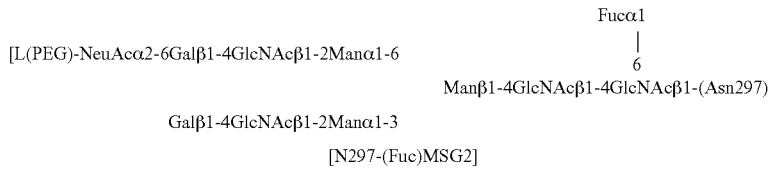

[N297-(Fuc)MSG2]

wherein [L(PEG)] represents L(PEG) being bound to a carbonyl group bonded to the 2-position of a sialic acid residue at the non-reducing end of the 1-6 branched chain of β-Man.

When the N297 glycan in the conjugate of the present invention is N297-(Fuc)MSG1 or N297-(Fuc)MSG2, the conjugate is a molecule having two PEG linker moieties and two hANP peptide moieties bonded thereto (divalent hANP peptide) because the Fc-containing molecule is a dimer usually having the N297 glycan in both the monomers (when the Fc-containing molecule is a glycan deletion mutant, N297-(Fuc)MSG1 or N297-(Fuc)MSG2 is attached to only one of the monomers to form a monovalent hANP peptide). On the other hand, when the N297 glycan is N297-(Fuc)SG, the conjugate is a molecule having four PEG linker moieties and four hANP peptide moieties bonded thereto (tetravalent hANP peptide) because the Fc-containing molecule is a dimer (when the Fc-containing molecule is a glycan deletion mutant, N297-(Fuc) SG is attached to only one of the monomers to form a conjugate with a divalent hANP peptide). The "conjugate" of the present invention may represent a molecule having these plural types of N297 glycans, or a mixture of molecules which are these normal forms together with molecules which are glycan deletion mutants (in the present invention, such a mixture is indicated as a conjugate in a normal form for the sake of convenience), or may be a molecule having a N297 glycan having any one structure. The conjugate of the present invention is preferably a molecule having a SG type N297 glycan having any one structure, more preferably conjugate having N297-(Fuc)SG as the N297 glycan and having a tetravalent hANP peptide (or a divalent hANP peptide for a glycan deletion mutant).

In these glycan structures, fucosylated GlcNAc (Fucα1, 6)GlcNAc) at the reducing end is derived from the Fc-containing molecule produced in an animal cell and thereby remodels a glycan on the non-reducing end side into a glycan structure similar to that of SG mentioned above. In any case, the glycan is bonded to the PEG linker through the use of carboxylic acid bonded to the 2-position of sialic acid at the non-reducing end.

Such a Fc-containing molecule having the SG type N297 glycan can be produced by a method as shown in FIGS. 3A and 3B in accordance with a method described in, for example, WO2013/120066. When the Fc-containing molecule is produced as a recombinant protein using animal cells in accordance with a known method, the N297 glycan has a fucosylated N-linked glycan structure as a basic structure. In this case, the Fc-containing molecule is obtained as a mixture of antibodies or fragments thereof having glycans having various structures where structures at non-reducing ends or constituent sugars are diversely modified (molecule (IV) of FIG. 3A). Such a Fc-containing molecule produced in an animal cell is treated with hydrolase such as EndoS so that the glycosidic bond between GlcNAcβ1and 4GlcNAc of a chitobiose structure at the reducing end is hydrolyzed to obtain a Fc-containing molecule having a single glycan structure having only (Fucα1, 6)GlcNAc as the N297 glycan (this Fc-containing molecule is referred to as a "(Fucα1,6)GlcNAc-Fc-containing molecule"; see FIG. 2A) (FIG. 3A).

For example, EndoS or a mutant enzyme thereof that maintains hydrolyzing activity can be used as such an enzyme for use in the hydrolysis reaction of the N297 glycan.

The (Fucα1,6)GlcNAc-Fc-containing molecule obtained by the hydrolysis reaction can be reacted as a glycan acceptor molecule with a SG type glycan donor molecule by use of endoglycosidase such as an EndoS D233Q mutant to obtain a Fc-containing molecule having a SG type N297 glycan having the structure mentioned above (see FIG. 2B) (FIG. 3B).

When the compound of interest is a conjugate having a tetravalent hANP peptide, a glycan donor molecule having SG(10) as a glycan is used in a transglycosylation reaction thereof. Such a SG(10) glycan used may be obtained by hydrolysis or the like from, for example, SGP or may be a SG(10) glycan alone such as a commercially available disialooctasaccharide (Tokyo Chemical Industry Co., Ltd.).

When the compound of interest is a conjugate having a divalent hANP peptide, a glycan donor molecule having MSG1(9) or MSG2(9) as a glycan is adopted. Such a glycan may be used by separation in accordance with a method described in Example 1-11 using commercially available monosialo-Asn free (1S2G/1G2S-10NC-Asn, GlyTech, Inc.) as a starting material, or may be used as a mixture without separation.

GlcNAc at the reducing end of the SG type glycan contained in the donor molecule is preferably used after being activated, for example, in the form of oxazoline by treatment with 2-chloro-1,3-dimethyl-1H-benzimidazol-3-ium-chloride, but does not have to be activated in the case of using two types of enzymes, as mentioned later, at the same time.

The SG type glycan contained in the donor molecule has a glycan with a PEG linker or a linker molecule having a partial structure thereof, bonded to carboxylic acid contained in sialic acid at the non-reducing end.

Various enzymes can be adopted as such an enzyme for use in the transglycosylation reaction as long as the enzyme has activity of transferring a complex glycan to the N297 glycan. EndoS D233Q is preferred which is an engineered form of EndoS that exhibits suppressed hydrolysis reactivity by the replacement of Asp at position 233 with Gln. The transglycosylation reaction using EndoS D233Q is described in WO2013/120066, etc. Alternatively, an engineered enzyme such as a further mutant of EndoS D233Q, i.e., EndoS D233Q/Q303L, EndoS D233Q/E350A, EndoS D233Q/E350Q, EndoS D233Q/E350D, EndoS D233Q/E350N, or EndoS D233Q/D405A may be utilized. A transglycosylation reaction using such an engineered form of EndoS D233Q is described in WO2017/010559.

The purification operation of the Fc-containing molecule after the glycan remodeling (sugar hydrolysis and transglycosylation reaction) of the Fc-containing molecule is aimed at separating the Fc-containing molecule from low-molecular weight compounds and the enzymes used in the reaction. Such purification usually employs gel filtration chromatography, ion exchange chromatography, affinity chromatography, or the like. The addition of further purification using a hydroxyapatite column was confirmed to improve transglycosylation reaction efficiency. Specifically, the present invention provides a method for producing the conjugate, further comprising a purification step using a hydroxyapatite column in the step of purifying an intermediate from a reaction solution after sugar hydrolysis of the Fc-containing molecule.

According to reported cases of glycan remodeling (J. Am. Chem. Soc. 2012, 134, 12308-12318; and Angew. Chem. Int. Ed. 2016, 55, 2361-2367), a reaction solution of a Fc-containing molecule treated with hydrolase is merely purified using a protein A column (affinity chromatography column). However, this purification method was found to fail to remove hydrolase (EndoS) completely and to influence the subsequent transglycosylation reaction due to the influence of the residual enzyme. As a result of studying the purification method herein, the reaction solution of the Fc-containing molecule treated with hydrolase was purified using a protein A column and a hydroxyapatite column (CHT column, Bio-Rad Laboratories, Inc.) in this order to thereby improve the reaction efficiency of the subsequent transglycosylation reaction without being influenced by the residual enzyme.

The present invention also provides a method for directly transglycosylating SGP, (SG-)Asn, or the like having an unactivated reducing end as a glycan donor to the N297 glycan of the Fc-containing molecule by use of two types of enzymes at the same time. Usual transglycosylation reactions require activating the reducing end of the glycan donor. The preparation of such an active donor is time consuming and costly. The method of the present invention can directly employ a naturally obtainable or commercially available glycopeptide or the like in the transglycosylation reaction and therefore enables efficient glycan remodeling.

For the two types of Endo enzymes used, it is important to combine properly enzyme A (EndoM-like enzyme) for a wide range of complex glycans as substrates and enzyme B (EndoS-like enzyme) for the N297 glycan of the Fc-containing molecule as a substrate.

Examples of enzyme A can include EndoM, EndoOm, and EndoCC, and EndoM mutants, EndoOm mutants, and EndoCC mutants that exhibit reduced hydrolyzing activity. Enzyme A is preferably EndoM N175Q, EndoCC N180H, or EndoOm N194Q.

Examples of enzyme B can include EndoS and EndoS2 (EndoS49), and EndoS mutants and EndoS2 (EndoS49) mutants that exhibit reduced hydrolyzing activity. Enzyme B is preferably EndoS D233Q, EndoS D233Q/Q303L, EndoS D233Q/E350A, EndoS D233Q/E350Q, EndoS D233Q/E350D, EndoS D233Q/E350N, EndoS D233Q/D405A, or the like.

The structure of the glycan donor is not particularly limited as long as the glycan donor has a glycan structure that is recognized by the enzyme A which is adopted. Various molecules, such as naturally obtained molecules and molecules synthesizable in a chemical reaction or enzymatic reaction, can be used. Any substituent other than R=H may be used as substituent R at the anomer site. In the case of a N-linked glycan structure (see the formulas given below; substituent R of the anomer is R at the reducing end of the uppermost structural formula), examples thereof can include amide structures and azide.

[Formula 27]

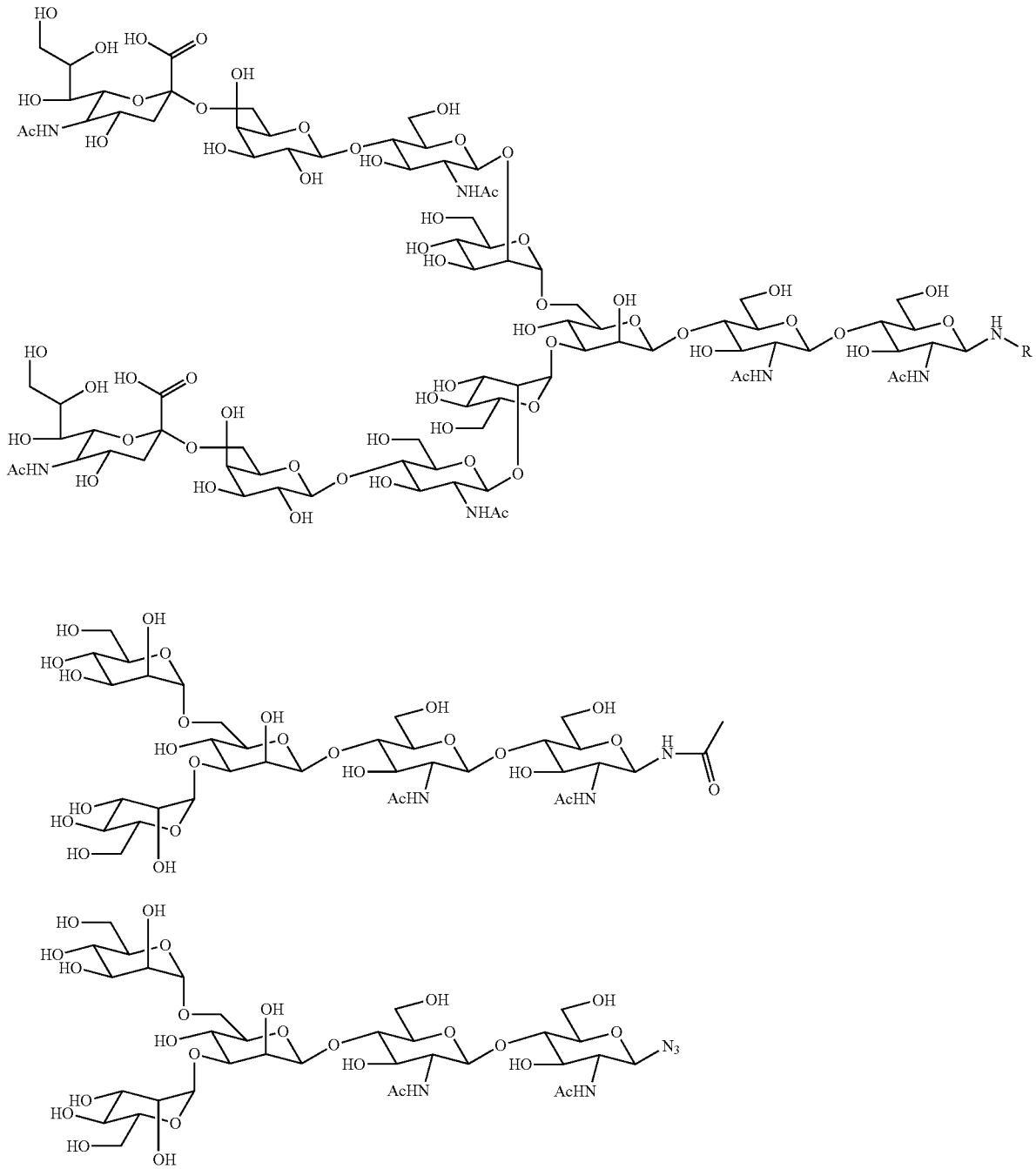

In the case of an O-linked glycan structure (see the formulas given below; substituent R of the anomer is R at the reducing end of the uppermost structural formula), examples thereof can include ethylene glycol structures, glycolic acid structures, and a benzyl group, an allyl group, and a p-nitrophenyl group for use as protective groups for the anomer hydroxy group. The structure at the non-reducing end of the glycan donor is not particularly limited as long as the structure is recognized by enzyme A. Various structures can be used such as natural glycan structures, non-reducing end glycan deletion mutants of natural glycan structures, structures where an arbitrary hydroxy group is modified with phosphoric acid, and structures chemically bonded to a linker structure. The glycan donor is preferably SGP, (SG-)Asn, ([$N_3$-PEG(3)]$_2$-SG)-Asn-PEG(3)-$N_3$, or the like.

[Formula 28]
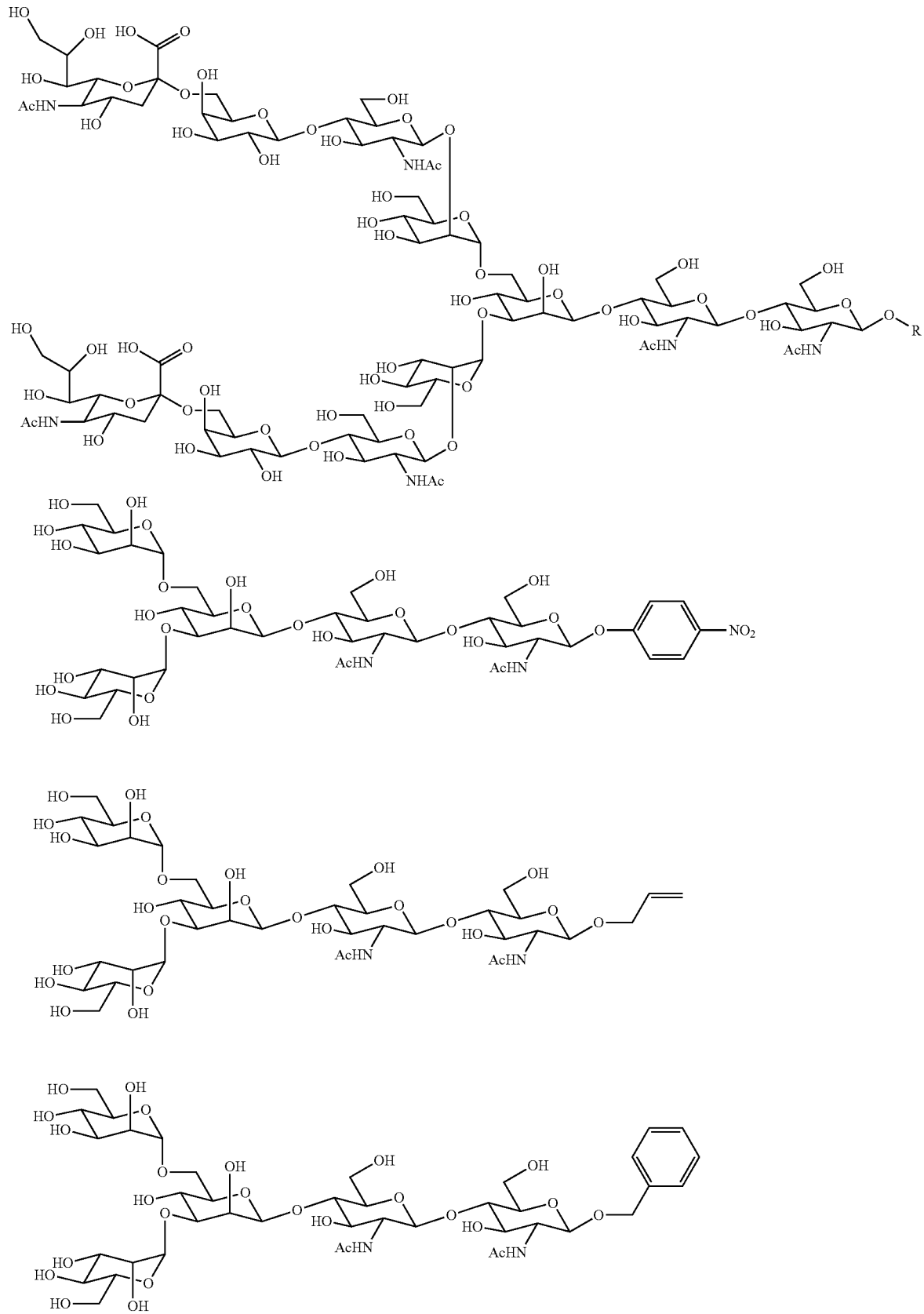

-continued

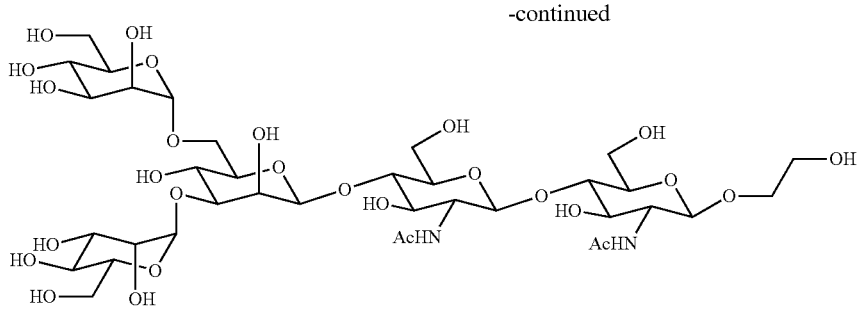

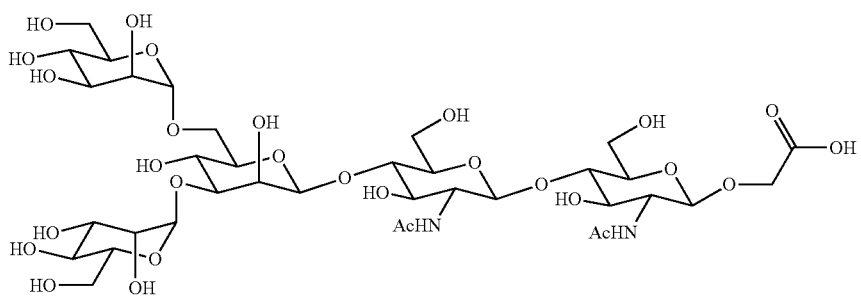

The acceptor molecule for use in the method of the present invention is not particularly limited as long as the acceptor molecule is a Fc-containing molecule having the N297 glycan. Various types such as mAb, CLCH, and Fc fragments can be appropriately selected and used.

The reaction temperature can be appropriately selected according to the optimum temperatures of the enzymes used and is usually 15 to 50° C., preferably 25 to 40° C. In the method of the present invention, which employs two types of enzymes, the transfer reaction may not properly proceed if one of the enzymes is deactivated at the optimum temperature of the other enzyme. Therefore, it is preferred to select a combination of enzymes similar in conditions such as the optimum reaction temperature.

<Peg Linker>

In the present invention, the PEG linker means a chemical structure that comprises a polyethylene glycol structure and mediates the linkage of the hANP peptide to the Fc-containing molecule in the conjugate of the present invention. The PEG linker structure usually consists of a linear structure free from any branched structure and binds at one end to the N terminal amino group or the C terminal carboxyl group of the hANP peptide and at the other end to carboxylic acid at the 2-position of sialic acid in the N297 glycan of the Fc-containing molecule.

The PEG linker contained in the conjugate of the present invention comprises approximately 10 or more ethylene glycol units in a linear form. This length is important for maintaining the activity of hANP exhibited by the conjugate. The upper limit of the number of ethylene glycol units (—CH2-CH2-O—) contained in the linker structure is approximately 50 or fewer, preferably approximately 40 or fewer, more preferably approximately 35 or fewer, even more preferably approximately 30 or fewer. The lower limit of the number of ethylene glycol units contained in the linker structure is preferably approximately 15 or more, more preferably approximately 20 or more, even more preferably approximately 25 or more.

Such a PEG linker may be derived from a single molecule or may consist of a plurality of partial structures where a plurality of molecules are bonded to each other. Such a molecule serving as a source of the linker structure is referred to as a "linker molecule".

When the PEG linker of the present invention is derived from one linker molecule, it is preferred to select a functional group contained in the linker molecule such that the PEG linker binds to the N terminus of the hANP peptide, for binding to carboxylic acid at the 2-position of sialic acid in the SG type N297 glycan of the Fc-containing molecule, and for securing the homogeneous structure of the conjugate.

When the PEG linker of the present invention is derived from a plurality of linker molecules, at least a compound containing a functional group binding to carboxylic acid at the 2-position of sialic acid in the N297 glycan, and a compound having a functional group capable of binding to the N terminus or C terminus of the hANP peptide are used as the linker molecules. These two types of linker molecules may be directly bonded to each other when they also have a functional group that permits their direct binding, or may be linked by the medium of an additional compound.

Each linker molecule used is appropriately selected as a compound having a proper functional group or structure, in consideration of conjugate production efficiency or convenience. Therefore, only one type of linker molecule may comprise PEG, or two or more linker molecules may comprise ethylene glycol units, as long as the finally constructed PEG linker structure comprises a predetermined number of ethylene glycol unit structures in total.

In the linker structure represented by "PEG(n)", n represents the number of consecutive ethylene glycol units contained therein. A linker structure having an insert of another chemical structure is represented by PEG(n)-PEG(m). For example, a linker structure comprising polyethylene glycol of 24 units is referred to as PEG(24), and a linker structure formed by the binding between a linker molecule comprising polyethylene glycol of 12 units and a linker molecule comprising polyethylene glycol of 6 units is referred to as PEG(12)-PEG(6). For example, the PEG(12)-PEG(12) moiety formed by the binding between identical linker molecules may also be simply referred to as PEG(12)$_2$. Such a PEG linker having the desired length can be formed as a linker having the desired PEG length, for example, by repeating deprotection and carboxylic acid activation using a Fmoc-PEG reagent, such as 3-[2-[2-[2-[2-[2-[2-[2-[2-[2-[2-[2-[2-(9H-fluoren-9-ylmethoxycarbonylamino)ethoxy]ethoxy]ethoxy]ethoxy]ethoxy]ethoxy]ethoxy]ethoxy]ethoxy]ethoxy]propanoic acid (Fmoc-PEG(12)-COOH), which has a Fmoc-protected amino group on one side and has carboxylic acid on the other side. Such a Fmoc-PEG reagent is commercially available as Fmoc-PEG(3)-COOH, Fmoc-PEG(6)-COOH, Fmoc-PEG(12)-COOH, Fmoc-PEG(24)-COOH, or the like from Novabiochem/Merck KGaA.

Various methods known in the field of organic synthetic chemistry can be applied to the binding between such linker molecules, without particular limitations. In general, this binding can be carried out with reference to a conjugation method applicable to antibody-drug conjugate synthesis (Bioconjugate Chem. 2015, 26, 2198-2215). Examples of a method for forming a ring through the Huisgen reaction of an azide group with an acetylene group can include a cycloaddition reaction to form a 1,2,3-triazole ring [Cu(I)-catalyzed azide-alkyne 1498711133922_0 (CuAAC)] and a cycloaddition reaction to form a 1,2,3-triazole ring from an azide group and dibenzylcyclooctene (DBCO) [strain-promoted azide-alkyne cycloaddition (SPARC)]. In this context, other compounds such as a compound having a twisted cyclooctyne structure, bicyclo[6.1.0]non-4-ene (BCN) (Angew. Chem. Int. Ed. 2010, 49, 9422-9425), and a cycloalkyne containing a heteroatom on a medium ring structure (Angew. Chem. Int. Ed. 2015, 54, 1190-1194) can also be similarly utilized. Other examples of the ring-forming reaction can include a Diels-Alder cycloaddition reaction of a 1,2,4,5-tetrazine ring with twisted alkene (Curr. Opin. Chem. Biol., 2014, 21, 89-95). Examples of cyclo-condensation based on a Pictet-Spengler reaction with an aldehyde group can include Hydrazino-Pictet-Spengler ligation (Bioconjugate Chem. 24, 846-851) and Oxyamin-based Pictet-Spengler ligation (Proc. Natl. Acad. Sci. U.S.A. 110, 46-51). Additional examples thereof can include an amide bond between an amino group and a carboxyl group, maleimide condensation of a SH group with a maleimide group, condensation of a SH group with a methylsulfonylphenyloxadiazole group (Angew. Chem., Int. Ed. 52, 12592-6), a bond between a SH group and an iodoacetyl group, a disulfide bond by condensation of a SH group with a 2-pyridyldithio group, hydrazone condensation of an aldehyde group with hydrazide, and oxime condensation of an aldehyde group with an aminooxy group. The linker molecule adopted in the present invention can be appropriately selected as a molecule having a functional group conforming to any of these binding patterns and used for the formation of the linker structure.

Such a binding reaction may form stereoisomers, optical isomers, geometric isomers, or the like, depending on the binding pattern. These isomers may be resolved by known methods or may be used as a mixture. Since the final conjugate is a macromolecule, the structural difference between the isomers of these partial structures is considered rarely to influence the conjugate.

Specific examples of such a PEG linker can include structures such as the following L(PEG) A1 to L(PEG) H1 and L(PEG) A2 to L(PEG) H2.

[Formula 29]

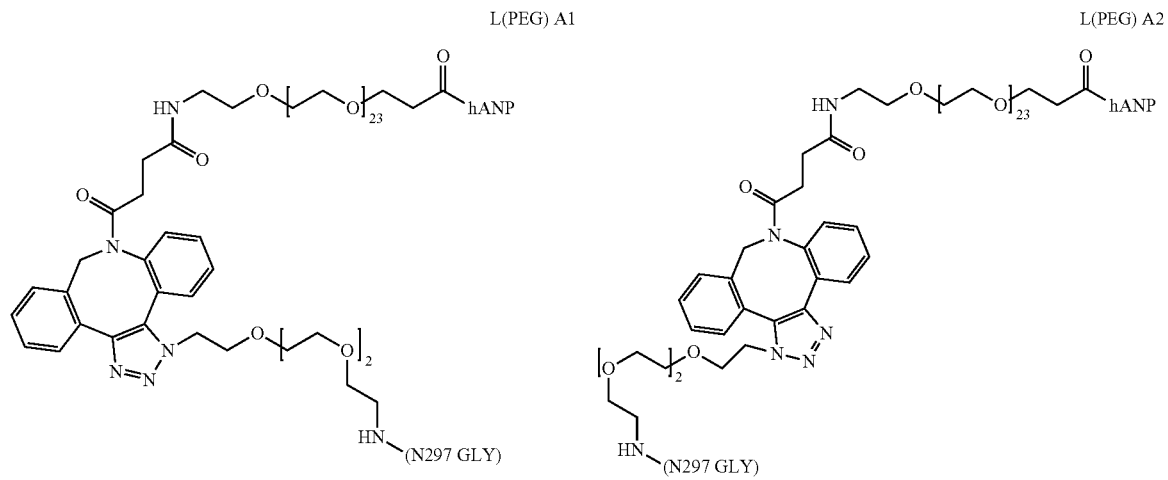

[Formula 30]
L(PEG) B1
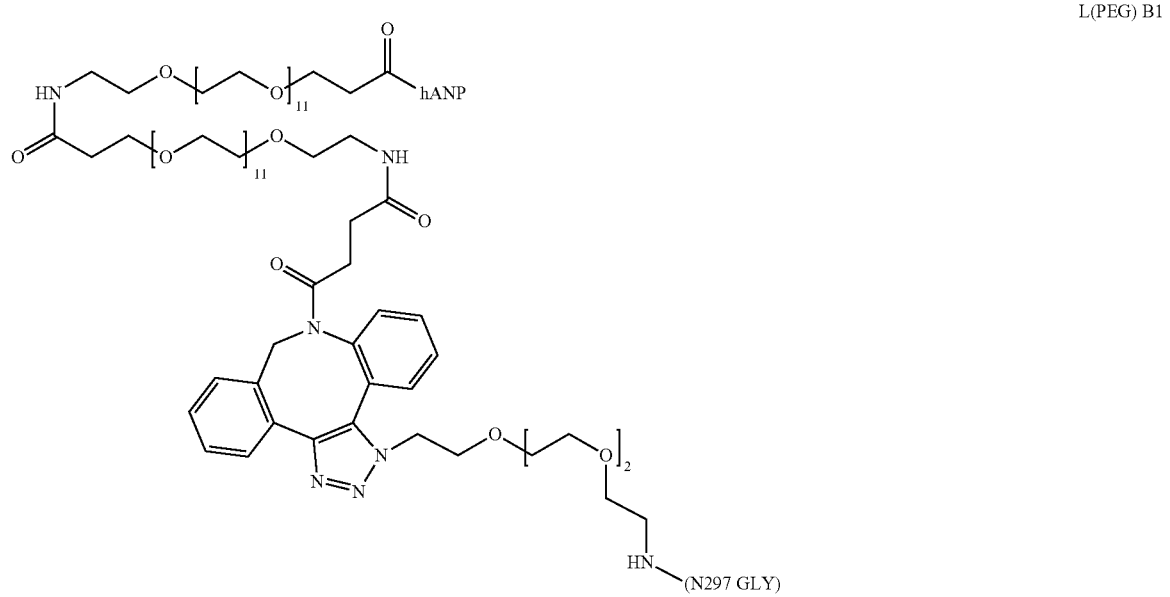
L(PEG) B2
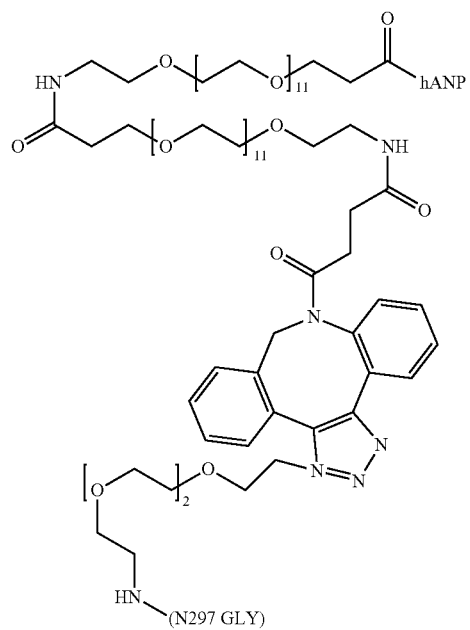

[Formula 31]
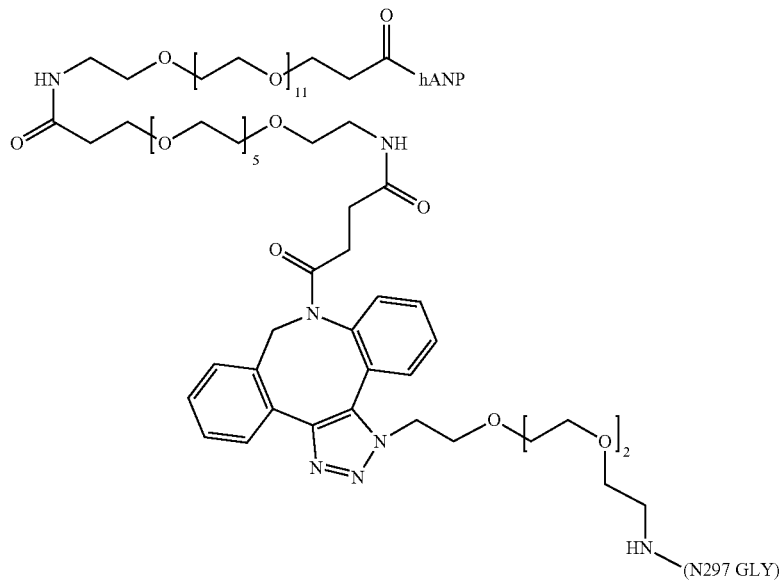
L(PEG) C1
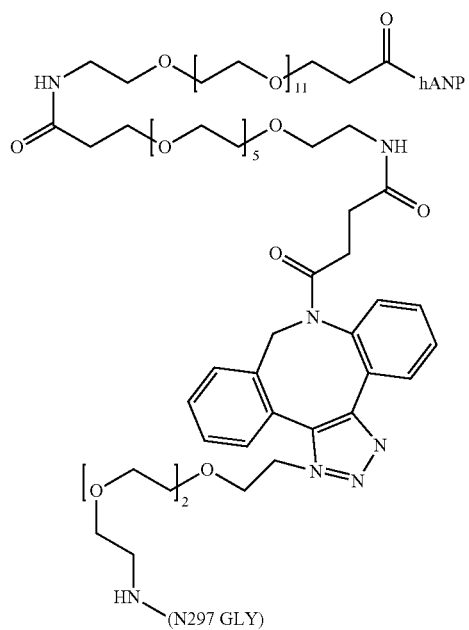
L(PEG) C2

[Formula 32]
L(PEG) D1
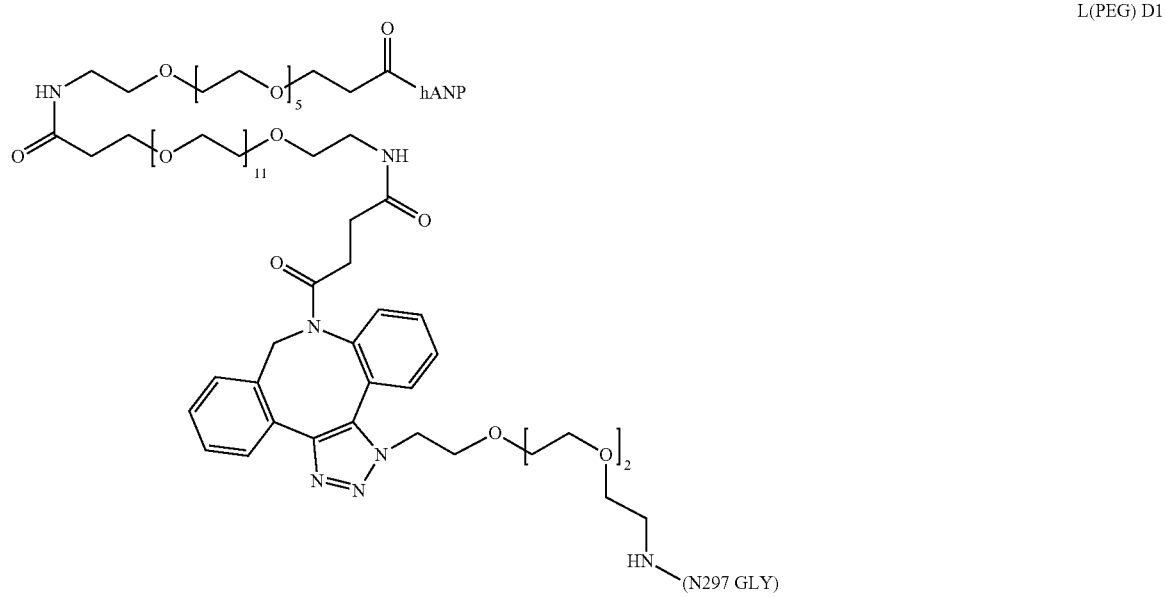
L(PEG) D2
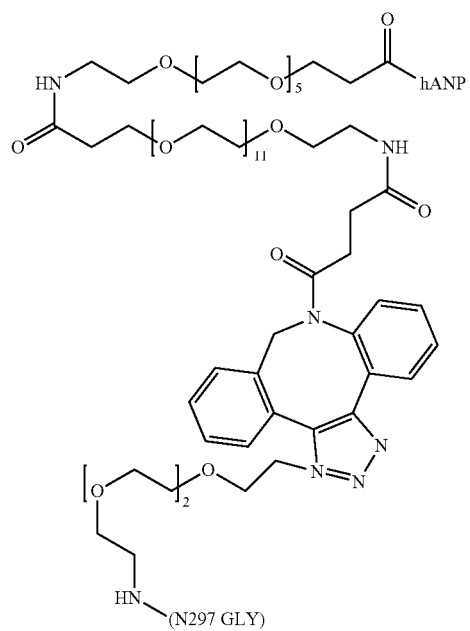

[Formula 33]
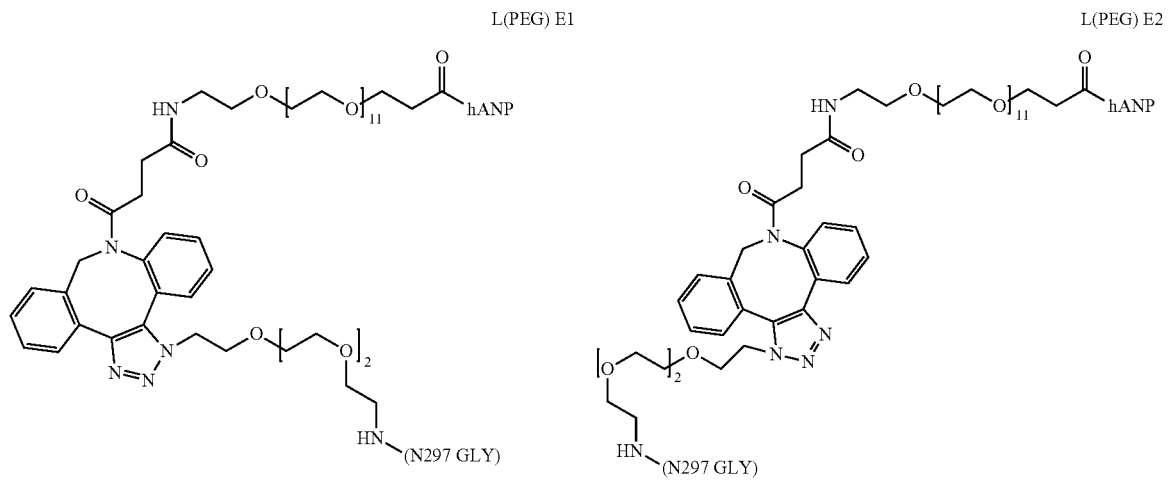
[Formula 34]
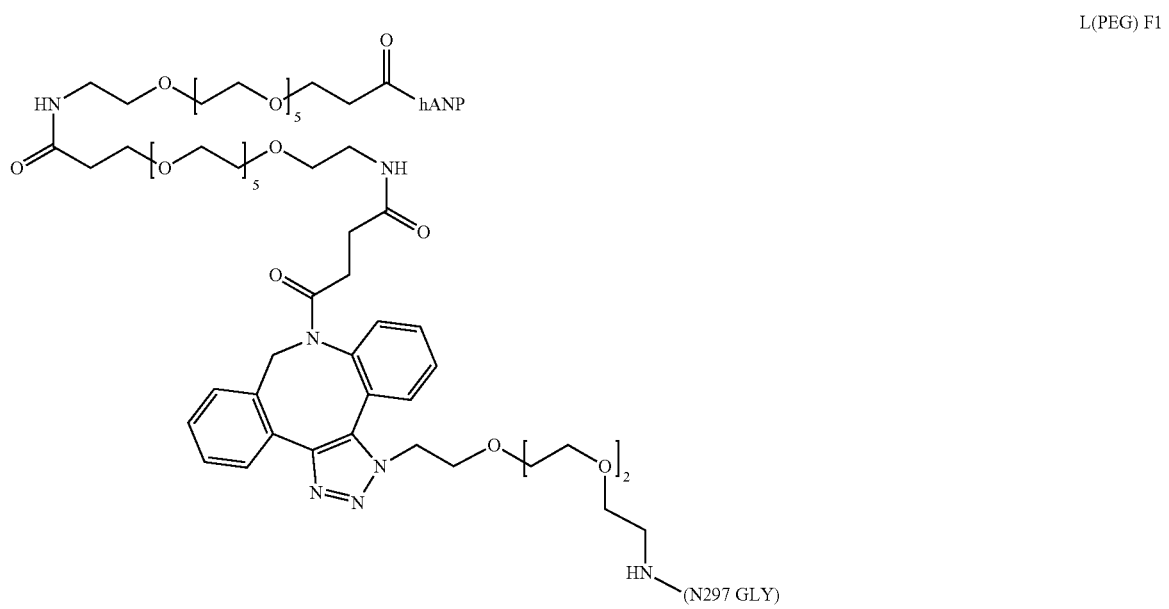

-continued
L(PEG) F2
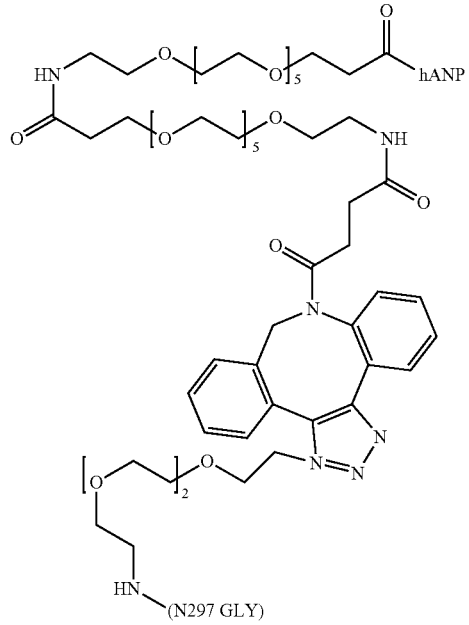
[Formula 35]
L(PEG) G1)     L(PEG) G2
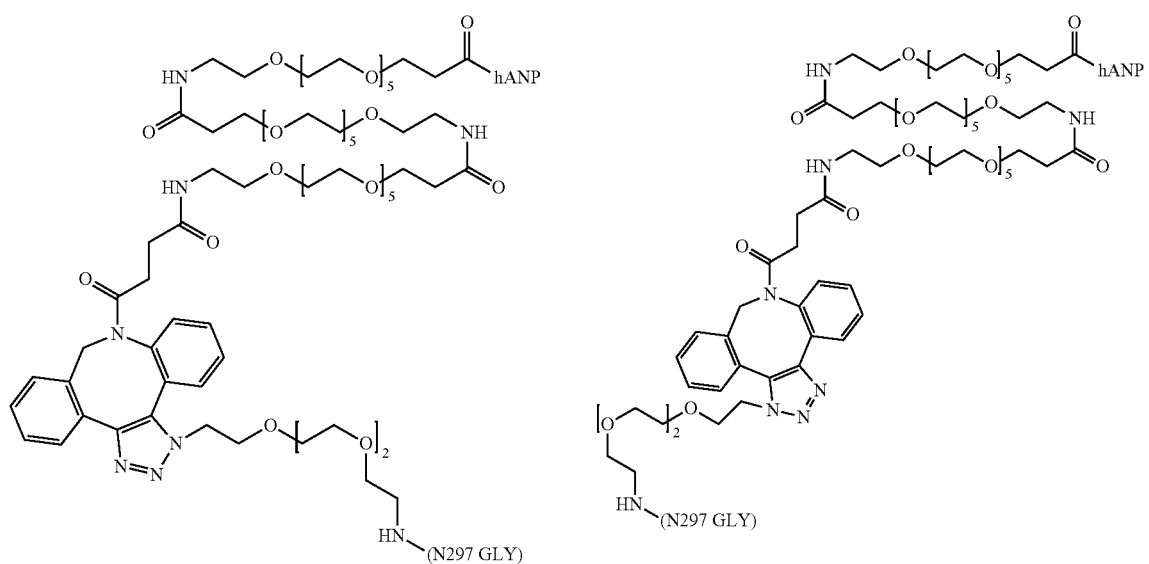

[Formula 36]

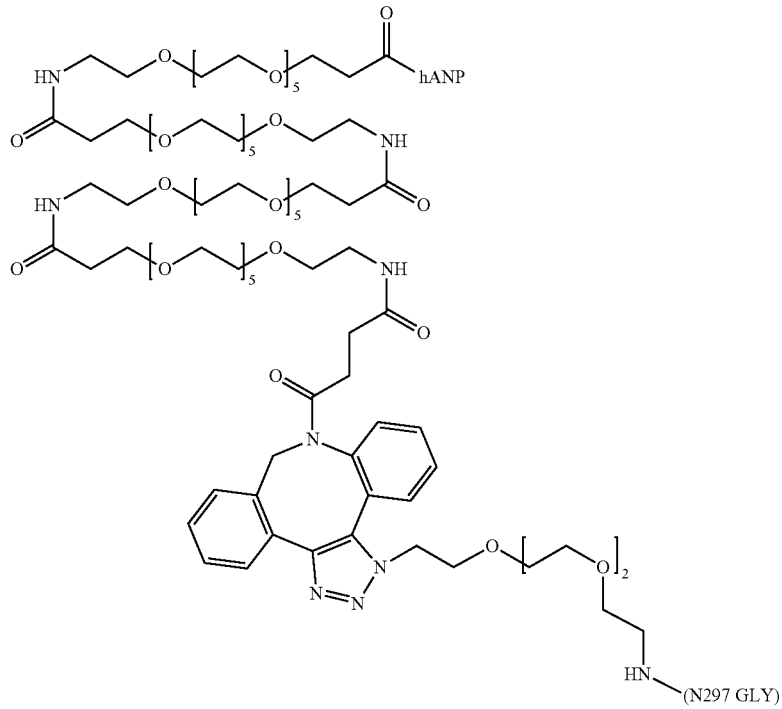

L(PEG)H1)

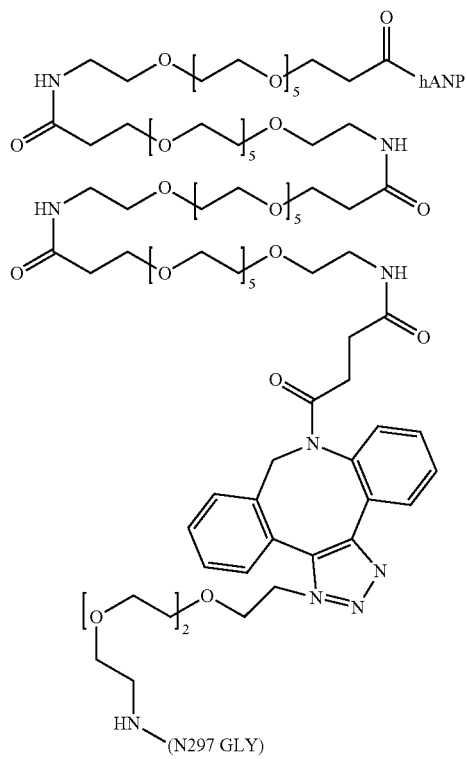

L(PEG)H2)

wherein "hANP" represents binding to the N terminus of the hANP peptide, and "N297 GLY" represents binding to the carbonyl group at the 2-position of sialic acid at the non-reducing end of the N297 glycan.

These linker structures have a 1,2,3-triazole ring formed through the Click reaction of an azide group introduced in the N297 glycan bonded to the Fc-containing molecule with a DBCO group bonded to the linker molecule comprising the hANP peptide. In this structure, geometric isomers are formed in which the linker structure bonded to the azide group is bonded to the 1- or 3-position of the triazole ring. Since the reaction occurs with two or four azide groups per Fc-containing molecule, geometric isomeric structures coexist in one molecule of the conjugate.

<Conjugate and Method for Producing Same>

The conjugate of the present invention can be produced by appropriately conjugating the intermediates such as the hANP peptide, the Fc-containing molecule, and the linker molecule mentioned above through the use of reactions known in the field of organic synthetic chemistry. The order of production thereof is not particularly limited, and various methods can be adopted by a common method according to the structures of the intermediates and the compound of interest.

The functional group carried by each intermediate is appropriately activated, inactivated, protected with a protective group, and deprotected, for example, by common methods according to the production steps.

The intermediate or the final product in each reaction step is appropriately separated and purified and subjected to the next reaction or utilized as a bulk pharmaceutical or a reagent.

The conjugate having any of the PEG linkers listed above can be produced, for example, as follows.

The linker molecule bonded to the N297 glycan is a molecule having a functional group (e.g., an azide group) at the non-reducing end of the N297 glycan and is synthesized by the glycan remodeling step for the Fc-containing molecule mentioned above. A linker molecule having an amino group on one side and another functional group (e.g., an azide group) on the other side is reacted with SG(10) to bond the linker molecule to carboxylic acid at the 2-position of sialic acid at the non-reducing end of the glycan. Subsequently, GlcNAc at the reducing end of this glycan molecule is activated to prepare a glycan donor molecule, which is then reacted with a (Fucα1,6)GlcNAc-Fc-containing molecule in the presence of endoglycosidase to introduce the functional group to the non-reducing end of the N297 glycan in the Fc-containing molecule.

The linker molecule bonded to the N terminus of the hANP peptide is a molecule having a carboxyl group on one side and another functional group (DBCO, a protective group-introduced amino group, etc.) on the other side. The hANP peptide can be reacted with the linker molecule to introduce the desired functional group to the N terminus of the hANP peptide.

The functional group-introduced Fc-containing molecule and hANP peptide thus obtained can be linked to each other directly or via another linker molecule to obtain the conjugate of the present invention.

Examples of the conjugate of the present invention can specifically include L(PEG)-A to L(PEG)-H described above in which the hANP peptide is hANP(1-28) or (SG-)Asn-hANP(1-28), the Fc-containing molecule is an antibody consisting of a combination of a heavy chain consisting of an amino acid sequence from amino acid positions 20 to 474 of SEQ ID NO: 3 and a light chain consisting of an amino acid sequence from amino acid positions 21 to 234 of SEQ ID NO: 5 (mAb-A), or CLCH consisting of a combination of a heavy chain consisting of an amino acid sequence from amino acid positions 20 to 349 of SEQ ID NO: 7 and a light chain consisting of an amino acid sequence from amino acid positions 21 to 125 of SEQ ID NO: 9 (CLCH-A), and the SG type N297 glycan is N297-(Fuc)SG or N297-(Fuc)MSG1, and can more specifically include compound 3-1 to compound 3-14 synthesized in Example 3. Compound 3-1 to compound 3-6 are preferred.

<Function and Activity>

The conjugate of the present invention exhibits a prolonged duration time in the blood and excellent physical properties as compared with unmodified hANP(1-28) and has the ability to migrate into the blood gradually, which is preferred for a hANP formulation, when subcutaneously administered. Native hANP(1-28) disappears rapidly from blood and therefore needs to be continuously administered by intravenous infusion or the like in clinical practice. By contrast, the conjugate of the present invention can exert a pharmacological effect for a long period even by usual subcutaneous administration. Furthermore, the conjugate of the present invention has the property of low aggregation even at a high concentration. Such characteristics of the conjugate of the present invention allow for adoption of administration methods, administration routes, and formulation techniques, which cannot be attained by conventional native hANP or existing hANP formulations, and also enable the conjugate to be used in the treatment of acute cardiovascular diseases as well as chronic cardiovascular diseases (hypertension, chronic heart diseases, etc.). Moreover, the conjugate of the present invention is also useful as a biological research tool. It is unclear how or whether native hANP migrates to a tissue, for example, when residing in the blood for a long period. By contrast, such localization or the influence of the long-term residence of hANP in the blood on living bodies can be examined by the administration of the conjugate of the present invention.

The duration time in the blood of the conjugate of the present invention can be tested in accordance with the method of Example 4-2 by administering the conjugate to an animal and then detecting a cGMP concentration in peripheral blood and/or the conjugate contained in a peripheral blood sample. The conjugate of the present invention maintains the effect of elevating the cGMP concentration in peripheral blood even approximately 24 hours after intracorporeal administration, more preferably maintains this effect even approximately 48 hours after the administration, even more preferably maintains this effect even approximately 72 hours after the administration, and further preferably maintains this effect even approximately 96, 120, 144 or 168 hours after the administration. Furthermore, the conjugate of the present invention gradually exhibits its activity after subcutaneous administration, and the activity often reaches a peak 24 to 48 hours later. Such kinetics in the blood are expected to be able to reduce or circumvent the risk of manifesting hypotension. As for the detection of the conjugate in peripheral blood after the administration of the conjugate, this conjugate is preferably detected even approximately 24 hours later, more preferably detected even approximately 48 hours later, even more preferably detected even approximately 72 hours later, and further preferably detected even approximately 96, 120, 144 or 168 hours later.

The conjugate of the present invention exhibits an excellent physical property of rarely aggregating even in an aqueous solution having a high concentration. The hANP peptide is prone to gelation due to the influence of a salt in a solution, etc. Thus, its formulation needs to be handled with caution. The conjugate of the present invention reduces problems associated with agglutination and can be applied to various forms of formulations in such a way that the concentration of the active ingredient is increased, or various additives can be adopted. Particularly, the conjugate comprising a glycosylated hANP peptide has been confirmed to exhibit very favorable non-agglutination.

The duration time of the conjugate of the present invention in the blood can be measured by administering the conjugate to an organism, sampling blood at certain intervals of time, and detecting the conjugate contained in the blood samples. Various methods, for example, detection by LC-MS and ELISA using an antibody specifically recognizing the ring structure of hANP, can be used as methods for detecting the conjugate. In the case of administering the conjugate of the present invention at a dose that produces its cGMP elevating activity, the cGMP levels of the blood samples can be measured using a commercially available measurement kit and compared with the cGMP level in the blood determined before the start of the administration to measure the duration time of the biological activity of the conjugate in blood. Alternatively, the conjugate may be labeled with a radioisotope and detected by separating the blood samples by SDS-PAGE or the like and detecting the radioactive signals.

In the present invention, "prolonged duration time in the blood" means that the time for which a test substance is detectable in the blood after administration is prolonged as compared with native hANP. Native hANP subcutaneously administered to a monkey has a concentration in the blood equal to or lower than the measurement limit at 30 minutes after the administration at 200 nmol/kg (data not shown), whereas the conjugate was detected from blood even 7 days after administration at 100 nmol/kg.

The conjugate of the present invention also has resistance to the degradation of the hANP peptide by NEP. This is probably responsible in part for the prolonged duration time. Such resistance to NEP degradation can be measured by known methods.

The cGMP elevating activity of the conjugate of the present invention is measured by stimulating GC-A receptor-expressing cells with a test substance adjusted to a concentration gradient up to a sufficient amount, then lysing the cells, measuring cGMP concentrations in the cell lysates, and identifying the maximum cGMP concentration (Emax). The phrase "maintaining cGMP elevating activity" described for the conjugate of the present invention means that the maximum cGMP concentration exhibited by the conjugate is approximately 30% or more compared with the maximum cGMP concentration of native hANP. The maximum cGMP concentration exhibited by the conjugate is preferably approximately 50% or more, more preferably approximately 70% or more. The conjugate of the present invention can be formulated at a high concentration as compared with native hANP and exhibits a prolonged duration time in blood. Therefore, it is not appropriate to define the activity of the conjugate of the present invention on the basis of an index such as a so-called EC50 value. Provided that the maximum activity of a conjugate at the elevated concentration can be equal to or greater than the given activity of native hANP, the conjugate can produce sufficient drug efficacy when administered continuously and/or at a high concentration in clinical practice.

The present invention provides a medicament comprising the conjugate of the present invention as an active ingredient.

<Medicament>

The substance that may be used as an active ingredient for the medicament according to the present invention may be a pharmaceutically acceptable salt of the conjugate mentioned above. Specifically, in the present invention, an acid (an inorganic acid, for example, hydrochloric acid, sulfuric acid, or phosphoric acid, or an organic acid, for example, formic acid, acetic acid, butyric acid, trifluoroacetic acid (TFA), succinic acid, or citric acid)-addition salt of the substance mentioned above may be used as the active ingredient. Alternatively, in the present invention, a metal (e.g., sodium, potassium, lithium, or calcium) salt of the substance mentioned above or a salt form based on an organic base thereof may be used as the active ingredient. Such a salt of the conjugate of the present invention may be a salt based on the hANP peptide moiety or may be a salt formed in the structure of the glycan. The salt of the conjugate of the present invention is preferably a pharmaceutically acceptable salt formed at the hANP peptide moiety. The pharmaceutical composition according to the present invention may contain a free form of the substance related to the active ingredient or a pharmaceutically acceptable salt thereof.

The substance that may be used as an active ingredient for the medicament according to the present invention, or the pharmaceutically acceptable salt thereof is preferably mixed with a known pharmaceutically acceptable carrier, excipient, diluent, or the like and administered to an individual by an administration method that is generally used for medicaments, i.e., an oral administration method or a parenteral administration method such as transmucosal administration, intravenous administration, intramuscular administration, or subcutaneous administration.

The dose of the substance that may be used as an active ingredient for the medicament according to the present invention differs depending on the type of disease, the age, body weight, and severity of a condition of the individual (patient), and the administration route, etc. In general, the upper limit of the daily dose is, for example, approximately 100 mg/kg or lower, preferably approximately 50 mg/kg or lower, more preferably 1 mg/kg or lower. The lower limit of the daily dose is, for example, approximately 0.1 µg/kg or higher, preferably 0.5 µg/kg or higher, more preferably 1 µg/kg or higher.

The dosing frequency of the medicament according to the present invention varies depending on the active ingredient used, the administration route, and the particular disease to be treated. In the case of orally administering, for example, a peptidic substance, this substance is preferably prescribed such that the number of doses per day is 4 or fewer. In the case of parenteral administration, for example, intravenous administration, the medicament may be injected using a normal syringe or may be continuously administered through the use of an infusion pump, a catheter, or the like. Alternatively, administration through a route such as subcutaneous injection or intramuscular injection is also preferred. In this case, various administration devices that are usually used can be adopted.

When the active ingredient for the medicament of the present invention is prepared in a solution, the conjugate of the present invention or the pharmaceutically acceptable salt thereof can be dissolved in an aqueous solvent and supplemented, if necessary, with a stabilizer, a pH adjuster, a surfactant, and the like to prepare the solution. In the case of preparing a freeze-dried formulation, the solution thus prepared can be freeze-dried and dissolved in physiological saline, injectable water, a glucose solution, or the like in use.

The medicament of the present invention is administered to a patient with a disease treatable by the activation of GC-A and the resulting elevation of the cGMP level, and is thereby effective for treating this disease. In this context, the "treatment" of the disease or its symptoms means that the progression of a pathological condition expected to be normalized by the activation of GC-A is delayed, alleviated, reduced, and/or suppressed, thereby making the condition closer to a normal state. The medicament of the present invention is expected to be effective for preventing the aggravation or onset of a disease by starting its administration at an early stage of the disease or by administering to an individual at a high risk of the disease. Although a patient who has developed the disease in the past is at risk of recurrence or chronicity, the medicament of the present invention can be expected to reduce the risk of recurrence or chronicity by continuous administration to such a patient. These effects are also included in the scope of the treatment.

Examples of such a disease include hypertension, acute heart failure (including the management of a medical condition after the onset of acute heart failure), chronic heart failure, ischemic heart diseases, acute nephritis (including the management of a medical condition after the onset of acute nephritis), chronic nephritis, acute renal failure (including the management of a medical condition after the onset of acute renal failure), chronic renal failure, ischemic heart diseases (myocardial infarction, etc.), metastasis of malignant tumor, hepatic fibrosis, hepatic cirrhosis, tissue adhesion caused by dialysis, and fibrosis.

EXAMPLES

Hereinafter, the present invention will be specifically described with reference to Examples. The embodiments of the present invention described in the Examples are given merely for illustrative purposes, and the present invention is not intended to be limited by these examples.

Example 1 is a production example of a hANP peptide and a linker molecule or a derivative thereof, which are intermediates for the production of the conjugate of the present invention. Example 2 is a preparation example of an antibody molecule. Example 3 is a synthesis example of a conjugate. Example 4 is a test example for confirming the characteristics or effect of the conjugate of the present invention.

The mass of each intermediate described in the present specification was confirmed by the following method: the apparatuses used were Q Exactive (manufactured by Thermo Fisher Scientific Inc.), Ultimate 3000 (manufactured by Thermo Fisher Scientific Inc.) and CORETECS UPLC C18 (manufactured by Waters Inc.) (1.6 µm, 2.1×50 mm). Acetonitrile was used in mobile phase A, and an aqueous solution supplemented with 0.1% formic acid was used in mobile phase B. The mobile phase A was used on a gradient changed from 2% to 95% in 4 minutes. The analysis was conducted at 40° C. at a flow rate of 0.4 mL/min.

Protein concentrations described herein were determined using a micro volume spectrophotometer Xpose (manufactured by Trinean NV). The masses of a glycan-remodeled antibody molecule and a conjugate were confirmed by the following method: the glycan-remodeled antibody molecule or the conjugate was fragmented into heavy and light chains. Then, their respective peaks were separated using an analytical column, followed by mass spectrometry. The apparatuses used were Q Exactive (manufactured by Thermo Fisher Scientific Inc.), Ultimate 3000 (manufactured by Thermo Fisher Scientific Inc.) and MAbPac RP (manufactured by Thermo Fisher Scientific Inc.) (4.0 µm, 2.1×50 mm). Acetonitrile was used in mobile phase A, and an aqueous solution supplemented with 0.1% formic acid/0.02% trifluoroacetic acid was used in mobile phase B. The mobile phase A was used on a gradient changed from 20% to 50% in 4 minutes. The analysis was conducted at 80° C. at a flow rate of 0.6 mL/min.

[Example 1] Synthesis of Various Intermediates

The simple term "hANP" in each structural formula given below represents that the hANP peptide in a modified peptide was hANP(1-28) (SEQ ID NO: 1). This peptide was bonded at its N terminal Ser to a linker molecule or glycosylated.

<Example 1-1> Synthesis of
DBCO-PEG(12)$_2$-hANP(1-28) FIG. 10

(1-1A) Synthesis of Fmoc-PEG(12)-hANP(1-28)

To a solution of a Fmoc-PEG reagent Fmoc-PEG(12)-COOH; 3-[2-[2-[2-[2-[2-[2-[2-[2-[2-[2-[2-(9H-fluoren-9-ylmethoxycarbonylamino)ethoxy]ethoxy]ethoxy]ethoxy]ethoxy]ethoxy]ethoxy]ethoxy]ethoxy]ethoxy]ethoxy]propano is acid (manufactured by Novabiochem/Merck KGaA, 304 mg, 0.36 mmol) in N,N-dimethylformamide (4.6 ml), a solution of N,N,N',N'-tetramethyl-O—(N-succinimidyl)uronium tetrafluoroborate (manufactured by Tokyo Chemical Industry Co., Ltd., 109 mg, 0.36 mmol) in N,N-dimethylformamide (1.0 ml) and diisopropylethylamine (131 µl, 0.75 mmol) were added, and the mixture was stirred at room temperature for 1 hour.

hANP(1-28) acetate (1000 mg) was dissolved in N,N-dimethylformamide (11 ml) and distilled water (3 ml). To the solution, diisopropylethylamine (315 µl, 1.81 mmol) was added. The preliminarily prepared N,N-dimethylformamide solution (5.6 m) containing active ester was added to the resulting solution, and the mixture was stirred at room temperature for 1 hour.

After the completion of the reaction, trifluoroacetic acid (186 µl, 2.41 mmol) was added to the reaction solution, and the mixture was transferred to a 20 mL scintillation vial (manufactured by Biotage Japan Ltd.). The solvent was removed using a high-speed concentration apparatus V-10 (Biotage Japan Ltd.). An appropriate amount of acetonitrile was added to the vial, and the solvent was removed using high-speed concentration apparatus V-10 (Biotage Japan Ltd.) to obtain solid matter. An appropriate amount of diethyl ether was added to the solid matter, and the mixture was decanted. Then, an appropriate amount of acetonitrile/diethyl ether (½) was added thereto, and the mixture was decanted again. The obtained solid matter was dried under reduced pressure to obtain a crude product containing the title compound. The obtained crude product was used directly in the next reaction without being further purified.

(1-1B) Synthesis of H2N-PEG(12)-hANP(1-28)

The crude product (whole amount) synthesized in step (1-1A) was dissolved in a mixed solution of N,N-dimethylformamide (16 ml) and distilled water (3.2 ml). To the solution, piperidine (518 µl, 5.23 mmol) was added, and the mixture was stirred at room temperature for 1 hour. After the completion of the reaction, acetic acid (451 µl, 7.88 mmol) was added to the reaction solution, and the mixture was transferred to a 20 mL scintillation vial (Biotage Japan Ltd.). The solvent was removed using high-speed concentration apparatus V-10 (Biotage Japan Ltd.). An appropriate amount of acetonitrile was added to the vial, and the solvent was removed using high-speed concentration apparatus V-10 (Biotage Japan Ltd.) to obtain solid matter. An appropriate amount of diethyl ether was added to the solid matter, and the mixture was decanted. Then, an appropriate amount of acetonitrile/diethyl ether (½) was added thereto, and the mixture was decanted again. The obtained solid matter was dissolved by the addition of an appropriate amount of a 0.1% aqueous trifluoroacetic acid solution and acetic acid, and the solution was separated and purified in several portions by reverse phase HPLC. A 0.1% aqueous trifluoroacetic acid solution and a 0.1% solution of trifluoroacetic acid in acetonitrile were used as eluents. The apparatus used was Purif-Rp2 (manufactured by Shoko Scientific Co., Ltd.). The column used was Inertsil ODS-3 (manufactured by GL Sciences Inc.). Fractions containing the compound of interest detected by UV (220 nm) during elution were unified and freeze-dried. The title compound (826 mg) was obtained as a colorless solid.

(1-1C) Synthesis of Fmoc-PEG(12)$_2$-hANP

To a solution of a Fmoc-PEG reagent Fmoc-PEG(12)-COOH; 3-[2-[2-[2-[2-[2-[2-[2-[2-[2-[2-[2-[2-(9H-fluoren-9-ylmethoxycarbonylamino)ethoxy]ethoxy]ethoxy]ethoxy]ethoxy]ethoxy]ethoxy]ethoxy]ethoxy]ethoxy]ethoxy]propano is acid (manufactured by Novabiochem/Merck KGaA, 251 mg, 0.30 mmol) in N,N-dimethylformamide (3.8 ml), a solution of N,N,N',N'-tetramethyl-O—(N-succinimidyl)uronium tetrafluoroborate (manufactured by Tokyo Chemical Industry Co., Ltd., 90 mg, 0.30 mmol) in N,N-dimethylformamide (0.8 ml) and diisopropylethylamine (87 μl, 0.50 mmol) were added, and the mixture was stirred at room temperature for 1 hour.

The compound (826 mg) synthesized in step (1-1B) was dissolved by the addition of N,N-dimethylformamide (10 ml) and distilled water (3.5 ml). To the solution, diisopropylethylamine (160 μl, 0.92 mmol) was added. The preliminarily prepared N,N-dimethylformamide solution (4.6 m) containing active ester was added to the resulting solution, and the mixture was stirred at room temperature for 1 hour. After completion of the reaction, trifluoroacetic acid (77 μl, 1.00 mmol) was added to the reaction solution, and the mixture was transferred to a 20 mL scintillation vial (manufactured by Biotage Japan Ltd.). The solvent was removed using high-speed concentration apparatus V-10 (Biotage Japan Ltd.). An appropriate amount of acetonitrile was added to the vial, and the solvent was removed using high-speed concentration apparatus V-10 (Biotage Japan Ltd.) to obtain solid matter. Diethyl ether was added to the solid matter, and the mixture was decanted. Then, an appropriate amount of acetonitrile/diethyl ether (½) was added thereto, and the mixture was decanted again. The obtained solid matter was dried under reduced pressure to obtain a crude product containing the title compound. The obtained crude product was used directly in the next reaction without being further purified.

(1-1D) Synthesis of H2N-PEG(12)$_2$-hANP(1-28)

The crude product (whole amount) synthesized in step (1-1C) was dissolved by the addition of N,N-dimethylformamide (14 ml) and distilled water (1.4 ml). To the solution, piperidine (395 μl, 3.99 mmol) was added, and the mixture was stirred at room temperature for 30 minutes. Distilled water (1.0 ml) was added to the reaction solution, and the mixture was further stirred for 30 minutes. After completion of the reaction, acetic acid (343 μl, 5.99 mmol) was added to the reaction solution, and the mixture was transferred to a 20 mL scintillation vial (manufactured by Biotage Japan Ltd.). The solvent was removed using high-speed concentration apparatus V-10 (Biotage Japan Ltd.). Acetonitrile was added to the vial, and the solvent was removed using high-speed concentration apparatus V-10 (Biotage Japan Ltd.) to obtain solid matter. An appropriate amount of diethyl ether was added to the solid matter, and the mixture was decanted. Then, an appropriate amount of acetonitrile/diethyl ether (½) was added thereto, and the mixture was decanted again. The obtained solid matter was dissolved by the addition of an appropriate amount of a 0.2% aqueous trifluoroacetic acid solution and acetic acid, and the solution was separated and purified in several portions by reverse phase HPLC. A 0.1% aqueous trifluoroacetic acid solution and a 0.1% solution of trifluoroacetic acid in acetonitrile were used as eluents. The apparatus used was Purif-Rp2 (manufactured by Shoko Scientific Co., Ltd.). The column used was Inertsil ODS-3 (manufactured by GL Sciences Inc.). Fractions containing the compound of interest detected by UV (220 nm) during elution were unified and freeze-dried. The title compound (694 mg) was obtained as a colorless solid.

(1-1E) Synthesis of DBCO-PEG(12)$_2$-hANP(1-28)

The compound (520 mg) synthesized in step (1-1D) was dissolved by the addition of N,N-dimethylformamide (5.5 ml) and distilled water (1.5 ml). To the solution, diisopropylethylamine (77 μl, 0.44 mmol) was added. A solution of DBCO-NHS ester (manufactured by Click Chemistry Tools LLC, 53 mg, 132 mmol) in N,N-dimethylformamide (0.2 m) was added to the resulting solution, and the mixture was stirred at room temperature for 1 hour. After the completion of reaction, the reaction solution was transferred to a 20 mL scintillation vial (manufactured by Biotage Japan Ltd.). The solvent was removed using high-speed concentration apparatus V-10 (Biotage Japan Ltd.). Diethyl ether was added to the solid matter, and the mixture was decanted. Then, acetonitrile/diethyl ether (½) was added thereto, and the mixture was decanted again. The obtained solid matter was dissolved by the addition of an appropriate amount of a 0.1% aqueous trifluoroacetic acid solution and acetic acid, and the solution was separated and purified in several portions by reverse phase HPLC. A 0.1% aqueous trifluoroacetic acid solution and a 0.1% solution of trifluoroacetic acid in acetonitrile were used as eluents. The apparatus used was Purif-Rp2 (manufactured by Shoko Scientific Co., Ltd.). The column used was Inertsil ODS-3 (manufactured by GL Sciences Inc.). Fractions containing the compound of interest detected by UV (220 nm) during elution were unified and freeze-dried to obtain the title compound (compound 1-1) (283 mg) as a colorless solid.

ESI-MS: Calcd for $C_{200}H_{322}N_{48}O_{67}S_3$: $[M+4H]^{4+}$ 1142.8 (ave.), Found 1142.6; $[M+5H]^{5+}$ 914.4 (ave.), Found 914.3; $[M+6H]^{6+}$ 762.2 (ave.), Found 762.0.

Figure 11:
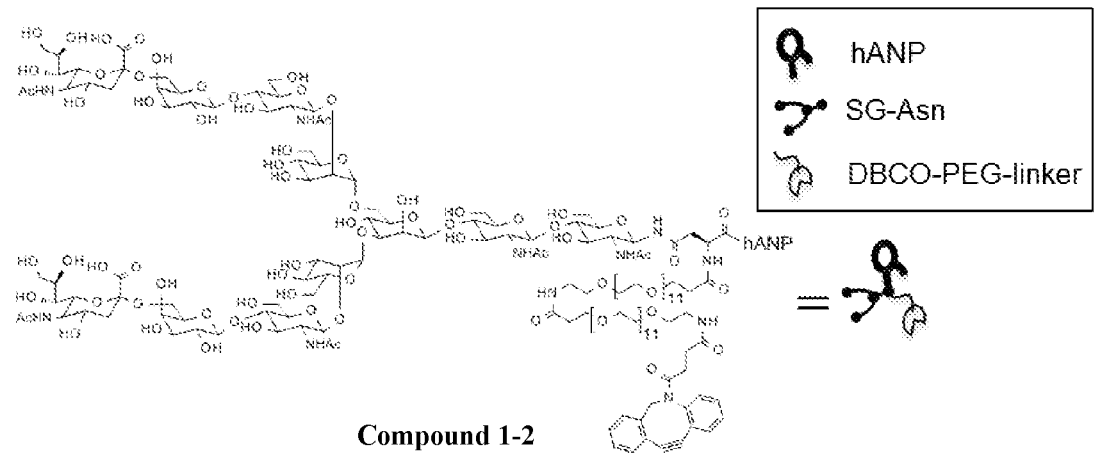
FIG. 11 shows Formula 38 (i.e., Compound 1-2), wherein the schematic diagram on the right of the structural formula shows the corresponding structure in the schematic diagram of the conjugate or the intermediate shown in the reaction schemes of FIGS. 1 to 3 and Example 3.

<Example 1-2> Synthesis of DBCO-PEG(12)$_2$-(SG-)Asn-hANP(1-28) FIG. 11

(1-2A) Preparation of Fmoc-(SG-)Asn in Free Form

Fmoc-(SG-)Asn (1S2S-11NC-Asn-Fmoc, manufactured by GlyTech, Inc., 2 g) was dissolved in an appropriate amount of a 0.1% aqueous trifluoroacetic acid solution. The solution was separated and purified in several portions by reverse phase HPLC. A 0.1% aqueous trifluoroacetic acid solution and a 0.1% solution of trifluoroacetic acid in acetonitrile were used as eluents. The apparatus used was Purif-Rp2 (manufactured by Shoko Scientific Co., Ltd.). The column used was Inertsil ODS-3 (manufactured by GL Sciences Inc.). Fractions containing the compound of interest detected by UV (220 nm) during elution were unified and freeze-dried. A colorless solid (1.8 g) was obtained.

(1-2B) Preparation of hANP(1-28) TFA Salt (Trifluoroacetate)

Carperitide acetate (hANP(1-28) acetate) (2.7 g) was dissolved in distilled water (200 ml). To the solution, trifluoroacetic acid (4 ml, 52.3 mmol) was added, and the mixture was left for 10 minutes and then freeze-dried. After the completion of freeze drying, the residue was dissolved in distilled water (200 ml). The solution was freeze-dried again. A colorless solid (2.7 g) was obtained.

(1-2C) Synthesis of (SG-)Asn-hANP(1-28)

To a solution of Fmoc-(SG-)Asn in a free form (436 mg) prepared in the step (1-2A) in N,N-dimethylformamide (7.2 ml), a solution of HATU (65 mg, 0.17 mmol) in N,N-dimethylformamide (0.8 ml) and diisopropylethylamine (118 µl, 0.68 mmol) were added under ice cooling, and the mixture was stirred for 2.5 minutes and immediately used in the next reaction (solution 1-2C).

hANP(1-28) TFA salt (400 mg) prepared in the step (1-2B) was dissolved by the addition of a N,N-dimethylformamide solution (4.8 ml) and distilled water (1.2 ml). To the solution, diisopropylethylamine (118 µl, 0.68 mmol) was added. The preliminarily prepared N,N-dimethylformamide solution 1-2C (8.0 m) containing active ester was added to the resulting solution, and the mixture was stirred at room temperature for 30 minutes. After completion of the reaction, acetic acid (82 µl, 1.36 mmol) was added thereto. Approximately 5 ml/tube of the reaction solution was transferred to three centrifuge tubes (50 ml) supplemented in advance with acetonitrile (35 ml). Solid matter was precipitated using a small centrifuge (Hitachi Koki Sales Co., Ltd., CF16RX), and the supernatant was removed. The solid matter in the three centrifuge tubes was unified into one centrifuge tube, washed with acetonitrile (30 mL), then washed twice with diethyl ether (30 mL), and then dried under reduced pressure to obtain a crude product.

The obtained crude product (whole amount) was dissolved in a N,N-dimethylformamide solution (8.4 ml) and distilled water (1.4 ml). To the solution, piperidine (224 µl, 2.26 mmol) was added, and the mixture was stirred at room temperature for 30 minutes. After completion of the reaction, acetic acid (194 µl, 3.39 mmol) was added thereto. Approximately 5 ml/tube of the reaction solution was transferred to two centrifuge tubes (50 ml) supplemented in advance with acetonitrile (35 ml). Solid matter was precipitated using a small centrifuge (Hitachi Koki Sales Co., Ltd., CF16RX), and the supernatant was removed. The solid matter in the two centrifuge tubes was unified into one centrifuge tube, washed with acetonitrile (30 mL), washed with diethyl ether (30 mL)×2, and then dried under reduced pressure to obtain a crude product.

The operation described above was performed for 3 lots. The crude products in the 3 lots were unified. The obtained solid matter was dissolved by the addition of an appropriate amount of a 0.1% aqueous trifluoroacetic acid solution and acetic acid, and the solution was separated and purified in several portions by reverse phase HPLC. A 0.1% aqueous trifluoroacetic acid solution and a 0.1% solution of trifluoroacetic acid in acetonitrile were used as eluents. The apparatus used was Purif-Rp2 (manufactured by Shoko Scientific Co., Ltd.). The column used was Inertsil ODS-3 (manufactured by GL Sciences Inc.). Fractions containing the compound of interest detected by UV (220 nm) during elution were unified and freeze-dried. The title compound (SG-)Asn-hANP(1-28) (1.49 g) was obtained as a colorless solid. ESI-MS: Calcd for $C_{215}H_{345}N_{53}O_{102}S_3$: $[M+4H]^{4+}$ 1351.1 (ave.), Found 1351.1; $[M+5H]^{5+}$ 1081.1 (ave.), Found 1080.9.

(1-2D) Synthesis of Fmoc-PEG(12)$_2$-(SG-)Asn-hANP

To a solution of Fmoc-NH-PEG(12)$_2$-COOH (122 mg, 0.085 mmol) synthesized according to the method described in WO2014115797A1 (Example 2-28A) in N,N-dimethylformamide (1.0 ml), a solution of N,N,N',N'-tetramethyl-O—(N-succinimidyl)uronium tetrafluoroborate (Tokyo Chemical Industry Co., Ltd., 23 mg, 0.077 mmol) in N,N-dimethylformamide (1.0 ml) and diisopropylethylamine (54 µl, 0.31 mmol) were added, and the mixture was stirred at room temperature for 1 hour (solution 1-2D).

The compound (300 mg) synthesized in the (1-2C) was dissolved in N,N-dimethylformamide (3 ml) and distilled water (1.4 ml). To the solution, diisopropylethylamine (54 µl, 0.31 mmol) was added. The preliminarily prepared N,N-dimethylformamide solution 1-2D (2.0 m) containing active ester was added to the resulting solution, and the mixture was stirred at room temperature for 22 hours.

After the completion of reaction, trifluoroacetic acid (47 µl, 0.61 mmol) was added to the reaction solution, and approximately 3.2 ml/tube of the reaction solution was transferred to two centrifuge tubes (50 ml) supplemented in advance with diethyl ether/acetonitrile (30 ml/10 ml). Solid matter was precipitated using a small centrifuge (Hitachi Koki Sales Co., Ltd., CF16RX), and the supernatant was removed. The solid matter in the two centrifuge tubes was unified into one centrifuge tube, washed with an appropriate amount of diethyl ether/acetonitrile (1/1), and then dried under reduced pressure to obtain a crude product. The obtained crude product was used directly without being further purified. The operation described above was performed for 4 lots to obtain 1.47 g in total of a crude product containing the title compound.

(1-2E) Synthesis of H2N-PEG(12)$_2$-(SG-)Asn-hANP(1-28)

The crude product (0.734 g) synthesized in step (1-2D) was dissolved in N,N-dimethylformamide (7.2 ml) and distilled water (1.2 ml). To the solution, piperidine (200 µl, 2.05 mmol) was added, and the mixture was stirred at room temperature for 45 minutes. After completion of the reaction, acetic acid (176 µl, 3.07 mmol) was added to the reaction solution, and approximately 2.1 ml/tube of the reaction solution was transferred to four centrifuge tubes (50 ml) supplemented in advance with diethyl ether/acetonitrile (30 ml/10 ml). Solid matter was precipitated using a small centrifuge (Hitachi Koki Sales Co., Ltd., CF16RX), and the supernatant was removed. The solid matter in the four centrifuge tubes was unified into one centrifuge tube, washed with an appropriate amount of diethyl ether/acetonitrile (1/1) and an appropriate amount of diethyl ether, and then dried under reduced pressure to obtain a crude product. The obtained solid matter was dissolved by the addition of an appropriate amount of a 0.2% aqueous trifluoroacetic acid solution and acetic acid, and the solution was separated and purified in several portions by reverse phase HPLC. A 0.1% aqueous trifluoroacetic acid solution and a 0.1% solution of trifluoroacetic acid in acetonitrile were used as eluents. The apparatus used was Purif-Rp2 (manufactured by Shoko Scientific Co., Ltd.). The column used was Inertsil ODS-3 (manufactured by GL Sciences Inc.). Fractions containing the compound of interest detected by UV (220 nm) during elution were unified and freeze-dried. The title compound (416 mg) was obtained as a colorless solid.

(1-2F) Synthesis of DBCO-PEG(12)$_2$-(SG-)Asn-hANP

The compound (832 mg) synthesized in step (1-2E) was dissolved in N,N-dimethylformamide (12 ml) and distilled water (2.4 ml). To the solution, diisopropylethylamine (123 µl, 0.71 mmol) was added. A solution of DBCO-NHS ester (manufactured by Click Chemistry Tools LLC, 57 mg, 142 mmol) in N,N-dimethylformamide (0.4 m) was added to the resulting solution, and the mixture was stirred at room temperature for 1 hour. After completion of the reaction, trifluoroacetic acid (109 µl, 1.42 mmol) was added to the reaction solution, and approximately 2.5 ml/tube of the reaction solution was transferred to six centrifuge tubes (50 ml) supplemented in advance with diethyl ether/acetonitrile (30 ml/5 ml). Solid matter was precipitated using a small centrifuge (Hitachi Koki Sales Co., Ltd., CF16RX), and the supernatant was removed. The solid matter in the six centrifuge tubes was unified into one centrifuge tube, washed with an appropriate amount of diethyl ether/acetonitrile (1/1), and then dried under reduced pressure to obtain a crude product. The obtained solid matter was dissolved by the addition of an appropriate amount of a 0.2% aqueous trifluoroacetic acid solution and acetic acid, and the solution was separated and purified by reverse phase HPLC. A 0.1% aqueous trifluoroacetic acid solution and a 0.1% solution of trifluoroacetic acid in acetonitrile were used as eluents. The apparatus used was Purif-Rp2 (manufactured by Shoko Scientific Co., Ltd.). The column used was Inertsil ODS-3 (manufactured by GL Sciences Inc.). Fractions containing the compound of interest detected by UV (220 nm) during elution were unified and freeze-dried. The title compound (620 mg) was obtained as a colorless solid.

ESI-MS: Calcd for $C_{288}H_{464}N_{56}O_{130}S_3$: $[M+5H]^{5+}$ 1378.4 (ave.), Found 1378.2; $[M+6H]^{6+}$ 1148.9 (ave.), Found 1148.7; $[M+7H]^{7+}$ 984.9 (ave.), Found 984.9.

The PEG length or the number of condensed PEG of a PEG linker is controllable by the selection of the Fmoc-PEG reagent used, the order of condensation and Fmoc deprotection, and the number of repeats. Thus, DBCO-L(PEG)-hANP can be synthesized as demanded by integrating the selection of these factors into the method of Example 1-1 or 1-2. Hereinafter, compounds will be given which were synthesized by changing the Fmoc-PEG reagent, the order of condensation and Fmoc deprotection, and the number of repeats according to a method similar to the method described in Example 1-1.

Figure 12:
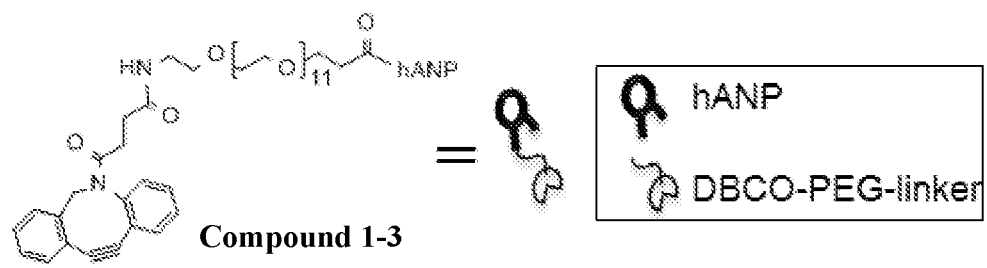
FIG. 12 shows Formula 39 (i.e., Compound 1-3), wherein the schematic diagram on the right of the structural formula shows the corresponding structure in the schematic diagram of the conjugate or the intermediate shown in the reaction schemes of FIGS. 1 to 3 and Example 3.

<Example 1-3> Synthesis of DBCO-PEG(12)-hANP(1-28) (FIG. 12)

The title compound 1-3 was obtained through synthesis using the starting material replaced with H2N-PEG(12)-hANP(1-28) synthesized in the step (1-1B) in the step (1-1E) of Example 1-1.

ESI-MS: Calcd for $CC_{173}H_{269}N_{47}O_{54}S_3$: $[M+2H]^{3+}$ 1323.5(ave.), Found 1323.2; $[M+5H]^{5+}$794.5(ave.), Found 794.4.

Figure 13:
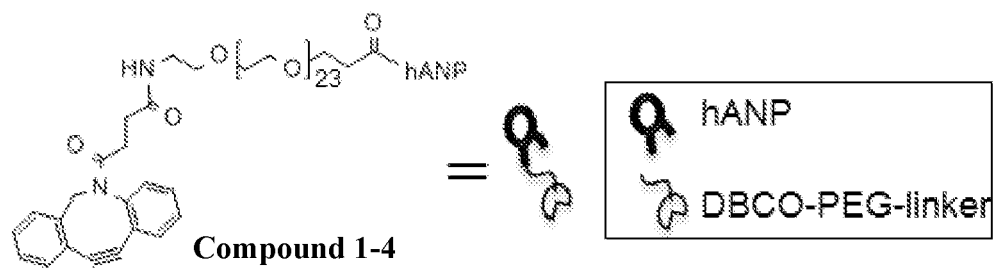
FIG. 13 shows Formula 40 (i.e., Compound 1-4), wherein the schematic diagram on the right of the structural formula shows the corresponding structure in the schematic diagram of the conjugate or the intermediate shown in the reaction schemes of FIGS. 1 to 3 and Example 3.

<Example 1-4> Synthesis of DBCO-PEG(24)-hANP(1-28) (FIG. 13)

The title compound 1-4 was obtained through synthesis using Fmoc-PEG(24)-COOH as the Fmoc-PEG reagent in the step (1-1A) of Example 1-1 and using the starting material of step (1-1E) replaced with H2N-PEG(24)-hANP(1-28) obtained in the step (1-1B) by the method.

ESI-MS: Calcd for $C_{197}H_{317}N_{47}O_{66}S_3$: $[M+4H]^{4+}$1125.0 (ave), Found 1124.8, $[M+5H]^{5+}$900.2(ave.), Found 900.0; $[M+6H]^{6+}$750.4 (ave.), Found 750.2.

Figure 14:
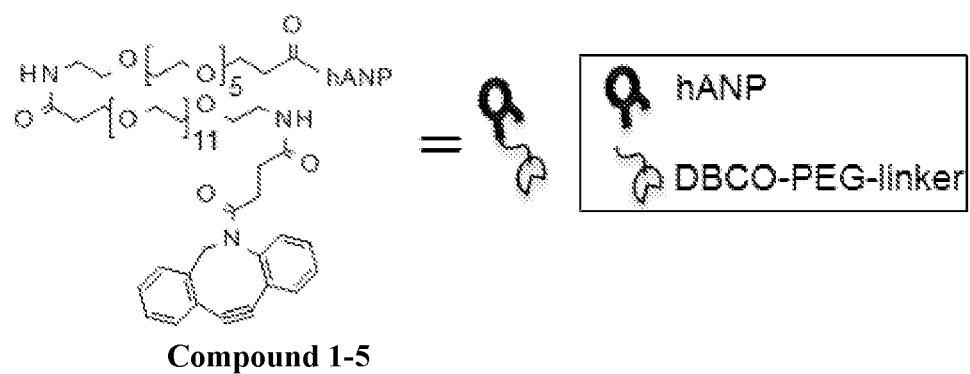
FIG. 14 shows Formula 41 (i.e., Compound 1-5), wherein the schematic diagram on the right of the structural formula shows the corresponding structure in the schematic diagram of the conjugate or the intermediate shown in the reaction schemes of FIGS. 1 to 3 and Example 3.

<Example 1-5> Synthesis of DBCO-PEG(12)-PEG(6)-hANP(1-28) FIG. 14

The title compound 1-5 was obtained through synthesis using the Fmoc-PEG reagent replaced with Fmoc-PEG(6)-COOH in the step (1-1A) of Example 1-1.

ESI-MS: Calcd for $C_{288}H_{464}N_{56}O_{130}S_3$: $[M+5H]^{5+}$ 1378.4 (ave.), Found 1378.2; $[M+6H]^{6+}$1148.9 (ave.), Found 1148.7; $[M+7H]^{7+}$984.9 (ave.), Found 984.9.

Figure 15:
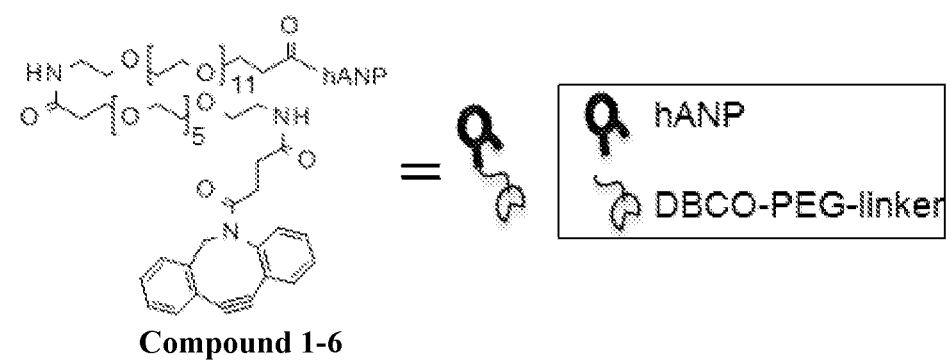
FIG. 15 shows Formula 42 (i.e., Compound 1-6), wherein the schematic diagram on the right of the structural formula shows the corresponding structure in the schematic diagram of the conjugate or the intermediate shown in the reaction schemes of FIGS. 1 to 3 and Example 3.

<Example 1-6> Synthesis of DBCO-PEG(6)-PEG(12)-hANP(1-28)(FIG. 15)

The title compound 1-6 was obtained through synthesis using the Fmoc-PEG reagent replaced with Fmoc-PEG(6)-COOH in the step (1-1C) of Example 1-1.

ESI-MS: Calcd for $C_{188}H_{298}N_{48}O_{61}S_3$: $[M+3H]^{3+}$1435.3 (ave.), Found 1435.0; $[M+4H]^{4+}$1076.7 (ave.), Found 1076.5; $[M+5H]^{5+}$861.6 (ave.), Found 861.4.

Figure 16:
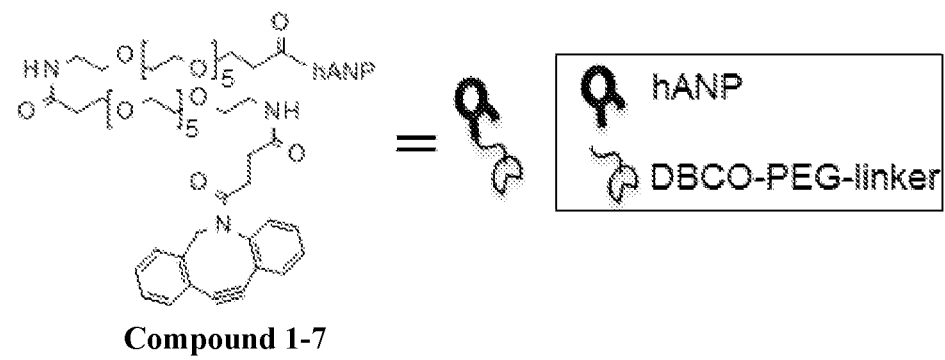
FIG. 16 shows Formula 43 (i.e., Compound 1-7), wherein the schematic diagram on the right of the structural formula shows the corresponding structure in the schematic diagram of the conjugate or the intermediate shown in the reaction schemes of FIGS. 1 to 3 and Example 3.

<Example 1-7> Synthesis of DBCO-PEG(6)$_2$-hANP(1-28)(FIG. 16)

The title compound 1-7 was obtained through synthesis using the Fmoc-PEG reagent replaced with Fmoc-PEG(6)-COOH in the steps (1-1A) and (1-1C) of Example 1-1.

ESI-MS: Calcd for $C_{176}H_{274}N_{48}O_{55}S_3$: $[M+3H]^{3+}$1347.2 (ave.), Found 1347.0; $[M+4H]^{4+}$1010.6 (ave.), Found 1010.5; $[M+5H]^{5+}$808.7 (ave.), Found 808.6.

Figure 17:
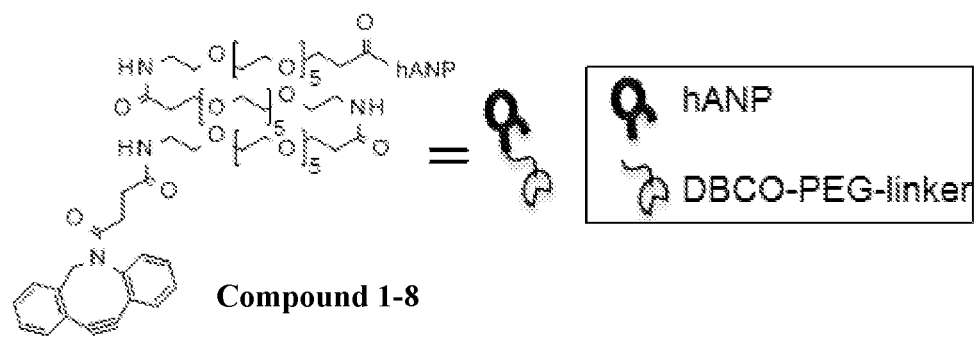
FIG. 17 shows Formula 44 (i.e., Compound 1-8), wherein the schematic diagram on the right of the structural formula shows the corresponding structure in the schematic diagram of the conjugate or the intermediate shown in the reaction schemes of FIGS. 1 to 3 and Example 3.

<Example 1-8> Synthesis of DBCO-PEG(6)$_3$-hANP(1-28)(FIG. 17)

The title compound 1-8 was obtained through synthesis by replacing the Fmoc-PEG reagent with Fmoc-PEG(6)-COOH in the steps (1-1A) and (1-1C) of Example 1-1 and further repeating the steps (1-1C) and (1-1D) between the steps (1-1D) and (1-1E).

ESI-MS: Calcd for $C_{191}H_{303}N_{49}O_{62}S_3$: $[M+3H]^{3+}$1459.0 (ave.), Found 1458.7; $[M+4H]^{4+}$1094.5 (ave.), Found 1094.3; $[M+5H]^{5+}$875.8 (ave.), Found 875.6.

Figure 18:
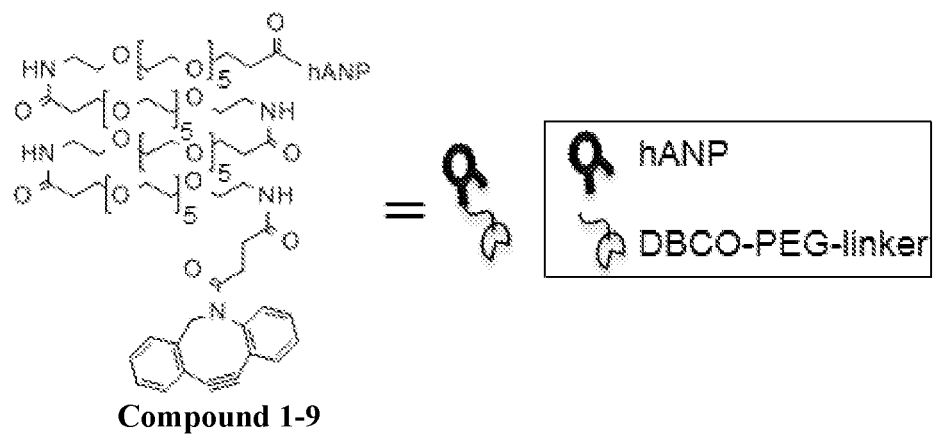
FIG. 18 shows Formula 45 (i.e., Compound 1-9), wherein the schematic diagram on the right of the structural formula shows the corresponding structure in the schematic diagram of the conjugate or the intermediate shown in the reaction schemes of FIGS. 1 to 3 and Example 3.

<Example 1-9> Synthesis of DBCO-PEG(6)$_4$-hANP(1-28)(FIG. 18)

The title compound 1-9 (FIG. 18) was obtained through synthesis by replacing the Fmoc-PEG reagent with Fmoc-PEG(6)-COOH in the steps (1-1A) and (1-1C) of Example 1-1 and further repeating the steps (1-1C) and (1-1D) twice between the steps (1-1D) and (1-1E).

ESI-MS: Calcd for $C_{206}H_{332}N_{50}O_{69}S_3$: $[M+4H]^{4+}$1178.3 (ave.), Found 1178.3; $[M+5H]^{5+}$942.9 (ave.), Found 942.7; $[M+6H]^{6+}$785.9 (ave.), Found 785.7.

Figure 19:
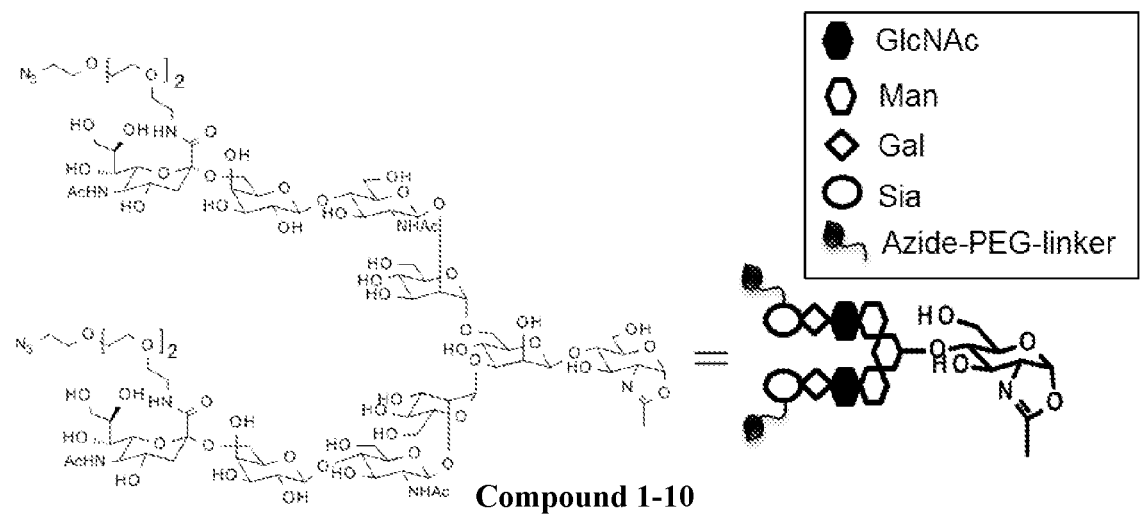
FIG. 19 shows Formula 46 (i.e., Compound 1-10), wherein the schematic diagram on the right of the structural formula shows the corresponding structure in the schematic diagram of the conjugate or the intermediate shown in the reaction schemes of FIGS. 1 to 3 and Example 3.

<Example 1-10> Synthesis of [N$_3$-PEG(3)]$_2$-SG(10)-Ox(FIG. 19)

(1-10A) Synthesis of [N$_3$-PEG(3)]$_2$-SG(10)

To a 5 ml sampling tube (Ina Optika Co., Ltd.), 11-azido-3,6,9-trioxaundecan-1-amine (Sigma-Aldrich Co. LLC, 96

μl, 0.485 mmol) and an aqueous disialooctasaccharide (Tokyo Chemical Industry Co., Ltd., 50 mg, 0.24 mmol) solution (0.5 ml) were added, and the mixture was stirred for 1 hour and then freeze-dried. To the 5 ml sampling tube thus freeze-dried, a solution of HATU (92 mg, 0.24 mmol) in N,N-dimethylformamide (0.6 ml) and diisopropylethylamine (42 μl, 0.24 mmol) were added, and the mixture was stirred at 37° C. for 4 hours.

After completion of the reaction, the reaction solution was transferred to a centrifuge tube (50 ml) supplemented in advance with diethyl ether (20 ml). Solid matter was precipitated using a small centrifuge (Hitachi Koki Sales Co., Ltd., CF16RX), and the supernatant was removed. Diethyl ether (20 ml) was added to the residue, and the mixture was decanted. Subsequently, acetonitrile (20 ml) was added thereto, and the mixture was decanted and then dried under reduced pressure to obtain a crude product. The obtained solid matter was dissolved in an appropriate amount of a 0.2% aqueous trifluoroacetic acid solution, and the solution was separated and purified by reverse phase HPLC. A 0.1% aqueous trifluoroacetic acid solution and a 0.1% solution of trifluoroacetic acid in acetonitrile were used as eluents. The apparatus used was Purif-Rp2 (manufactured by Shoko Scientific Co., Ltd.). The column used was Inertsil ODS-3 (manufactured by GL Sciences Inc.). Fractions containing the compound of interest detected by UV (220 nm) during elution were unified and freeze-dried to obtain the title compound (42 mg) as a colorless solid. ESI-MS: Calcd for $C_{92}H_{157}N_{13}O_{61}$: $[M+2H]^{2+}1211.7$ (ave.), Found 1211.5; $[M-2H]^{2-}$ 1209.6 (ave.), Found 1209.5.

(1-10B) Synthesis of $[N_3\text{-PEG(3)}]_2\text{-SG(10)-Ox}$

To a 5 ml sampling tube (manufactured by Ina Optika Co., Ltd.), the compound (40 mg) synthesized in step (1-10A) and an aqueous 2-chloro-1,3-dimethyl-1H-benzimidazol-3-ium-chloride (CDMBI) (manufactured by Fushimi Pharmaceutical Co., Ltd., 17.9 mg, 0.083 mmol) solution (200 μl) were added. An aqueous tripotassium phosphate (52.6 mg, 0.25 mmol) solution (200 μl) was added to the reaction solution after ice cooling, and the mixture was stirred for 2 hours under ice cooling. The obtained reaction solution was ultrafiltered using Amicon Ultra (Ultracel 30K, manufactured by Merck Millipore/Merck KGaA) to remove solid matter. The flow through solution was purified by gel filtration chromatography. The apparatus used was Purif-Rp2 (manufactured by Shoko Scientific Co., Ltd.). The column used was HiPrep 26/10 Desalting (manufactured by GE Healthcare Japan Corp.). A 0.03% aqueous $NH_3$ solution was used in a mobile phase. The flow rate was set to 10 ml/min, and the fraction capacity was set to 10 ml. Fractions containing the compound of interest detected by UV (220 nm) during elution were unified. A 1 N aqueous sodium hydroxide solution (33 μl, 0.033 mmol) was added thereto, and the mixture was freeze-dried. The title compound (34 mg) was obtained as a colorless solid. NMR (in D2O) (chart of FIG. 4).

Figure 20:
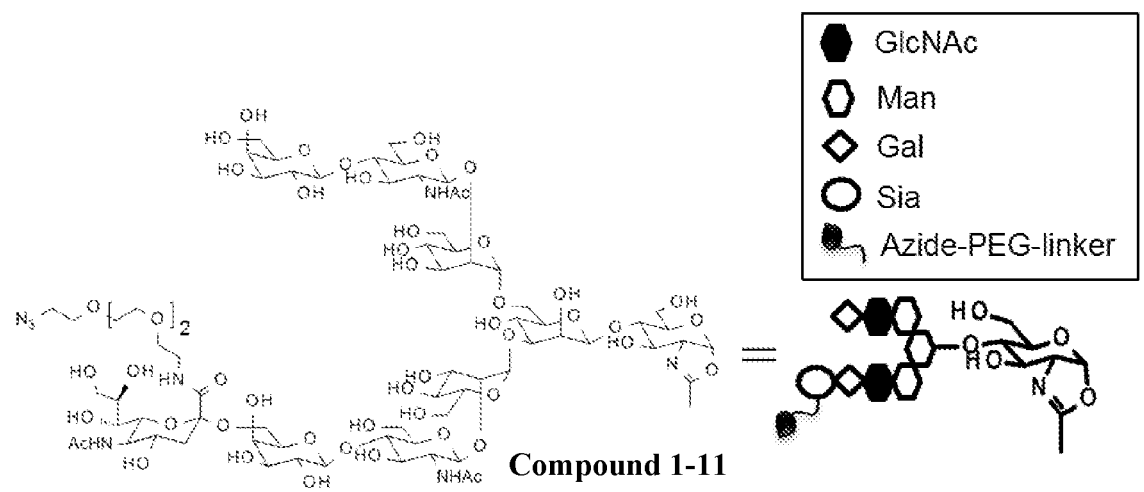
FIG. 20 shows Formula 47 (i.e., Compound 1-11), wherein the schematic diagram on the right of the structural formula shows the conjugate or the intermediate shown in the reaction schemes of FIGS. 1 to 3 and Example 3, or the corresponding structure in the schematic diagram in the reaction schemes.

<Example 1-11> Synthesis of $[N_3\text{-PEG(3)}]\text{-MSG1}$ (9)-Ox(FIG. 20)

(1-11A) Preparation of (MSG1-)Asn

A commercially available product monosialo-Asn free form (1S2G/1G2S-10NC-Asn, manufactured by GlyTech, Inc.) (referred to as "(MSG-)Asn") (500 mg) was separated and purified by reverse phase HPLC under conditions given below to separate (MSG1-)Asn (retention time: around 15 to 19 min) eluted as the 1st main peak and (MSG2-)Asn (retention time: around 21 to 26 min) eluted as the 2nd main peak. The eluent used was a 0.1% aqueous formic acid solution. The apparatus used was ELS-PDA trigger preparative system (manufactured by JASCO Corp.). The column used was Inertsil ODS-3 (10 um, 304)×250 mm, manufactured by GL Sciences Inc.). The flow rate was set to 30 ml/min. Fractions belonging to the 1st peak detected by UV (210 nm) during elution were unified and freeze-dried to obtain the title compound (238 mg) as a colorless solid. Fractions belonging to the 2nd peak detected by UV in the elution operation described above can be collected to obtain (MSG2-)Asn.

(1-11B) Synthesis of MSG1(9)

The compound (229 mg) obtained in step (1-11A) was dissolved in a 200 mM phosphate buffer solution (pH 6.25) (1145 μL). To the solution, an aqueous EndoM (manufactured by Tokyo Chemical Industry Co., Ltd., 1 U/mL)) solution (100 μL) was added, and the mixture was incubated at 35° C. for 6 days. After completion of the reaction, the reaction solution was ultrafiltered using VIVASPIN 15R (Hydrosart membrane, 30K, 6,000 g), and the obtained flow through solution was separated and purified by reverse phase HPLC. The eluent used was a 0.1% aqueous trifluoroacetic acid solution. The apparatus used was a ELS-PDA trigger preparative system (manufactured by JASCO Corp.). The column used was Inertsil ODS-3 (manufactured by GL Sciences Inc.). Fractions containing the compound of interest detected by UV (210 nm) during elution were unified and freeze-dried to obtain the title compound (117 mg) as a colorless solid.

(1-1 IC) Synthesis of $[N_3\text{-PEG(3)}]\text{-MSG1(9)}$

The title compound (94.2 mg) was obtained according to the same approach as in the step (1-10A) using the compound (169 mg) synthesized in the step (1-11B).
ESI-MS: Calcd for $C_{73}H_{124}N_8O_{51}$: $[M+H]^+1929.9$ (ave.), Found 1929.7.

(1-11D) Synthesis of $[N_3\text{-PEG(3)}]\text{-MSG1(9)-Ox}$

The title compound (89 mg) was obtained according to the same approach as in the step (1-10B) using the compound (100 mg) synthesized in the step (1-11 C).
NMR (in D2O) (chart of FIG. 5).

Figure 21:
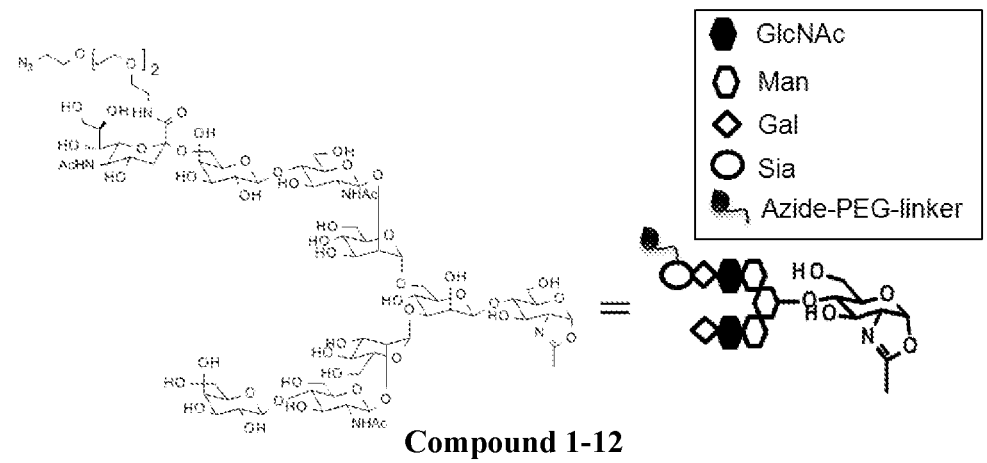
FIG. 21 shows Formula 48 (i.e., Compound 1-12), <Example 1-12> Synthesis of $[N_3\text{-PEG(3)}]_2\text{-SG(10)-2}$ $[N_3\text{-PEG(3)}]_2\text{-SG(10)}$ synthesized in the step (1-10A) was also synthesized by the method given below. Compound 1-10 (FIG. 19) can be synthesized by the step (1-10B) using the compound obtained by this method.

[N3-PEG(3)]-MSG2(9)-Ox (compound 1-12 of FIG. 21 in which a linker is bonded to sialic acid in the 1-6 branched chain of β-Man in compound 1-11 of FIG. 20) can be synthesized by using (MSG2-)Asn obtained as the 2nd peak in the step (1-11A) as the starting material of the step (1-11B) and subsequently performing the same operation as in this step. A conjugate comprising two hANP peptide moieties linked to different branched chains can be synthesized by replacing compound 1-11 of FIG. 20 with compound 1-12 of FIG. 21 in Examples 3-5 and 3-6.

<Example 1-12> Synthesis of $[N_3\text{-PEG(3)}]_2\text{-SG}$ (10)-2

$[N_3\text{-PEG(3)}]_2\text{-SG(10)}$ synthesized in the step (1-10A) was also synthesized by the method given below. Compound 1-10 of FIG. 19 can be synthesized by the step (1-10B) using the compound obtained by this method.

Figure 22:
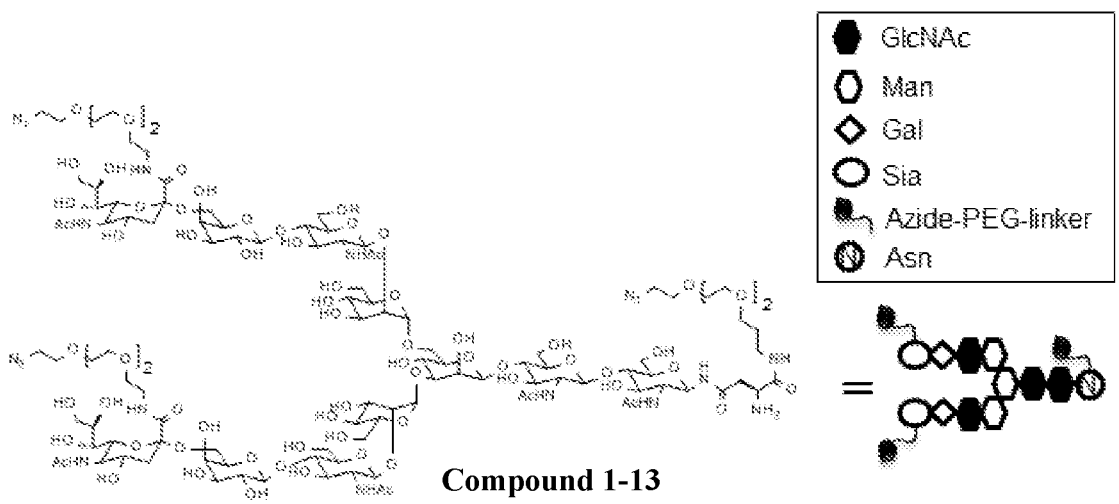
FIG. 22 shows Formula 49 (i.e., Compound 1-13), (1-12A) Synthesis of $([N_3\text{-PEG(3)}]_2\text{-SG})\text{-Asn-PEG(3)-N}_3$.

(1-12A) Synthesis of ([N$_3$-PEG(3)]$_2$-SG)-Asn-PEG(3)-N$_3$ (FIG. 22)

To a solution of Fmoc-(SG-)Asn in a free form (1000 mg) prepared in the step (1-2A) in N,N-dimethylformamide (10 ml), a solution of HATU (891 mg, 2.34 mmol) in N,N-dimethylformamide (3 ml) and a solution of 11-azido-3,6,9-trioxaundecan-1-amine (Tokyo Chemical Industry Co., Ltd., 511 mg, 2.34 mmol) and diisopropylethylamine (816 µl, 4.69 mmol) in N,N-dimethylformamide (3 ml) were added thereto, and the mixture was stirred at 37° C. for 3 hours. A solution of HATU (148 mg, 0.39 mmol) in N,N-dimethylformamide (500 µl) was further added, and the mixture was stirred at 37° C. for 1 hour. Then, piperidine (386 µl, 3.91 mmol) was added thereto, and the mixture was stirred at 37° C. for 1 hour. After the completion of reaction, acetic acid (469 µl) was added thereto.

The reaction solution was transferred in half to two jumbo conical tubes (175 ml) supplemented in advance with diethyl ether (100 ml). Solid matter was precipitated using a small centrifuge (Hitachi Koki Sales Co., Ltd., CF16RX), and the supernatant was removed. Gum-like solid matter was transferred to a centrifuge tube (50 ml). Diethyl ether (30 ml) and acetonitrile (10 ml) were added thereto, and the mixture was decanted. This operation was repeated twice. Similarly, an appropriate amount of acetonitrile or an appropriate amount of diethyl ether was added thereto, and the mixture was decanted and then dried under reduced pressure to obtain a crude product. The obtained solid matter was dissolved in an appropriate amount of a 0.2% aqueous trifluoroacetic acid solution, and the solution was separated and purified by reverse phase HPLC. A 0.1% aqueous trifluoroacetic acid solution and a 0.1% solution of trifluoroacetic acid in acetonitrile were used as eluents. The apparatus used was Purif-Rp2 (manufactured by Shoko Scientific Co., Ltd.). The column used was Inertsil ODS-3 (manufactured by GL Sciences Inc.). Fractions containing the compound of interest detected by UV (220 nm) during elution were unified and freeze-dried to obtain the title compound (637 mg) as a colorless solid.

ESI-MS: Calcd for $C_{112}H_{192}N_{20}O_{70}$: $[M+3H]^{3+}$ 980.6 (ave.), Found 980.4.

(1-12B) Synthesis of [N$_3$-PEG(3)]$_2$-SG(10) (Compound of Step (1-10A))

Figure 23:
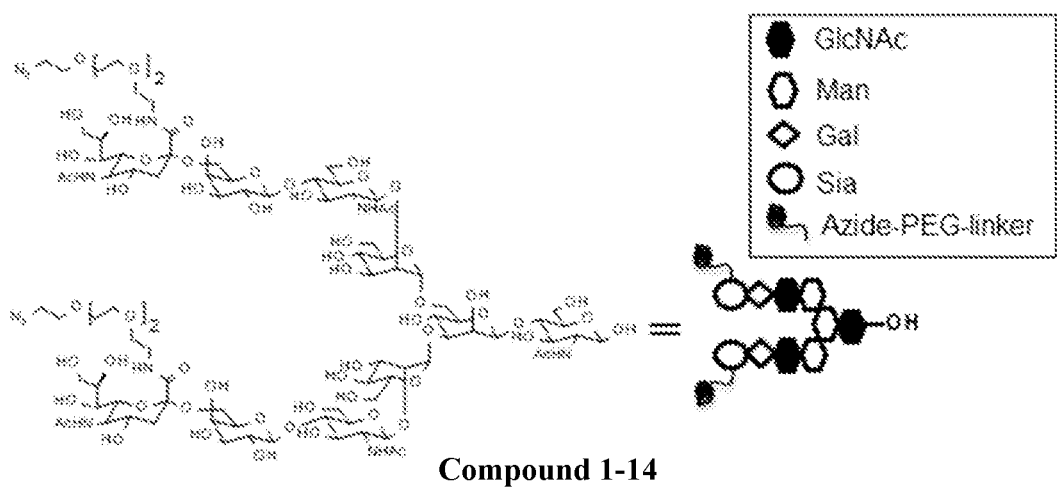
FIG. 23 shows Formula 50 (i.e., Compound 1-14) (1-12B) Synthesis of $[N_3\text{-PEG(3)}]_2\text{-SG(10)}$.

As listed in FIG. 23, in a 2 ml tube, ([N$_3$-PEG(3)]$_2$-SG)-Asn-PEG(3)-N$_3$ (78.6 mg) synthesized in the step (1-12A) was dissolved in a 100 mM phosphate buffer, pH 6.0 (Nacalai Tesque, Inc., 465 µl). To this solution, 1 U/mL EndoM (Tokyo Chemical Industry Co., Ltd., 70 µl) was added, and the mixture was shaken at 28° C. for 5 hours and then left standing at room temperature for 4 days. After the completion of reaction, an appropriate amount of a 0.2% aqueous trifluoroacetic acid solution was added thereto, and the mixture was separated and purified by reverse phase HPLC. A 0.1% aqueous trifluoroacetic acid solution and a 0.1% solution of trifluoroacetic acid in acetonitrile were used as eluents. The apparatus used was Purif-Rp2 (manufactured by Shoko Scientific Co., Ltd.). The column used was Inertsil ODS-3 (manufactured by GL Sciences Inc.). Fractions containing the compound of interest detected by UV (220 nm) during elution were unified and freeze-dried to obtain the title compound (40 mg) as a colorless solid.

ESI-MS: Calcd for $C_{92}H_{157}N_{13}O_{61}$: $[M+2H]^{2+}$ 1211.7 (ave.), Found 1211.5.

[Example 2] Preparation of Carrier Protein

<Example 2-1> Preparation of Full-Length Antibody (mAb-A) for Carrier

Anti-LPS antibody A (hereinafter, referred to as "mAb-A") (h #1G5-H1/L1 in WO2015/046505) recognizing an antigen absent in the bodies of humans was selected as a full-length antibody for a carrier. The antibody was prepared in the same way as the method described in Examples 2, 5 and 7, etc. of WO2015/046505. The final preservation sample was 19.4 mg/ml of a mAb-A solution (HBSor (25 mM histidine/5% sorbitol, pH 6.0)).

<Example 2-2> Preparation of CLCH-A

A partial antibody molecule CLCH-A lacking IgG1 variable regions was prepared as a molecule for a carrier as follows.

(2-2A) Construction of CH-A Expression Vector

A DNA fragment (SEQ ID NO: 6) was synthesized which comprised a DNA sequence encoding the amino acids of a CH type heavy chain (CH-A) containing a human IgG1 constant region connected to a human heavy chain secretion signal. The synthesized DNA fragment was amplified by PCR and ligated with a DNA fragment of pCMA-LK described in WO2015/046505 from which DNA sequences encoding a κ chain secretion signal and a human κ chain constant region were removed by digestion with XbaI and PmeI, using an InFusion HD PCR cloning kit (Clontech Laboratories, Inc.) to construct a CH-A expression vector. The obtained expression vector was designated as "pCMA/CH". The amino acid sequence of CH-A is shown in amino acid positions 20 to 349 of SEQ ID NO: 7 (amino acid positions 1 to 19 correspond to a signal sequence).

(2-2B) Construction of CL-A Expression Vector

A DNA fragment (SEQ ID NO: 8) was synthesized which comprised a DNA sequence encoding the amino acids of a CL type light chain (CL-A) containing a human κ chain constant region connected to a human light chain secretion signal. A CL expression vector was constructed in the same way as in step (2-2A). The obtained expression vector was designated as "pCMA/CL". The amino acid sequence of CL-A is shown in amino acid positions 21 to 125 of SEQ ID NO: 9 (amino acid positions 1 to 20 correspond to a signal sequence).

(2-2C) Production of CLCH-A

A culture supernatant containing a partial antibody molecule of CH-A combined with CL-A was obtained in the same way as the method described in Example 2 of WO2015/046505 using the constructed pCMA/CH and pCMA/CL in combination and FreeStyle 293F cells (manufactured by Invitrogen Corp.). The obtained partial antibody molecule was designated as "CLCH-A".

(2-2D) Purification of CLCH-A

From the culture supernatant obtained in step (2-2C), CLCH-A was purified by two steps of recombinant protein A affinity chromatography and cation exchange chromatography. Buffer replacement in the purification steps and after the purification, and a concentration step were carried out at 4 to 6° C. First, the culture supernatant was applied to a column packed with MabSelect SuRe (manufactured by GE Healthcare Biosciences Corp.) equilibrated with PBS. After placement of the whole culture solution in the column, the column was washed with PBS in an amount of twice or more the volume of the column. Subsequently, elution was performed with a 2 M arginine hydrochloride solution (pH 4.0). The eluate was fractionated, and fractions containing CLCH-A were collected on the basis of absorbance. The recovered liquid was buffer-replaced with 50 mM MES/20 mM NaCl, pH 6.0 by dialysis (Thermo Fisher Scientific Inc., Slide-A-Lyzer Dialysis Cassette). The recovered solution was applied to HiTrap SP HP (manufactured by GE Healthcare Biosciences Corp.) equilibrated with 50 mM MES/20 mM NaCl, pH 6.0. The column was washed with 50 mM MES/20 mM NaCl, pH 6.0. Then, linear concentration gradient elution (10 times the volume of the column) was carried out with 0 to 200 mM sodium chloride, and fractions containing CLCH-A were collected from the eluate in the same way as above. The recovered liquid was buffer-replaced with HBSor (25 mM histidine/5% sorbitol, pH 6.0) by dialysis (Thermo Fisher Scientific Inc., Slide-A-Lyzer Dialysis Cassette). Finally, the recovered solution was concentrated using Centrifugal UF Filter Device VIVASPIN 20 (molecular weight cut off: UF10K, Sartorius AG, at 4° C.). The concentration was adjusted to 20 mg/ml or higher to prepare a purified CLCH-A sample.

<Example 2-3> Preparation of CLCH-B

CLCH-B which was a partial antibody molecule with a LALA mutation introduced in the heavy chain of CLCH-A was prepared as a molecule for a carrier as follows.

(2-3A) Construction of CH-B Expression Vector

A mutation to substitute Leu-Leu at amino acid positions 136 and 137 of SEQ ID NO: 9 (corresponding to Leu234-Leu235 based on the EU Index) with Ala-Ala was introduced to pCMA/CH as a template using the primer set described below (CHLALA-F and CHLALA-R) and KOD-Plus-Mutagenesis Kit (Toyobo Co., Ltd.) to construct a CH-B expression vector. The constructed expression vector was designated as "pCMA/CH-B". The nucleotide sequence of DNA encoding CH-B is shown in nucleotide positions 58 to 1047 of SEQ ID NO: 10 (nucleotide positions 1 to 57 correspond to a signal sequence). The amino acid sequence thereof is shown in amino acid positions 20 to 349 of SEQ ID NO: 11 (amino acid positions 1 to 19 correspond to a signal sequence).

```
Primer set
CHLALA-F;
                                    (SEQ ID NO: 12)
5'-GCGGGAGGCCCTTCCGTGTTCCTGTTCCCC-3'

CHLALA-R;
                                    (SEQ ID NO: 13)
5'-GGCTTCGGGGGCAGGACAAGGGGGACAGGTG-3'.
```

(2-3B) Production and Purification of CLCH-B

A culture supernatant containing a partial antibody molecule of CH-B combined with CL-A (the resulting partial antibody molecule was designated as "CLCH-B") was obtained in the same way as in step (2-2C) using pCMA/CH-B and pCMA/CL prepared in step (2-2B) in combination. From the obtained culture supernatant, the partial antibody molecule was purified in the same way as in step 2-2D and used as a purified CLCH-B sample.

<Example 2-4> Preparation of Fc-B (Wild Type Fc)

Fc-B which was a partial antibody molecule consisting of an IgG1 Fc fragment was prepared as a molecule for a carrier as follows.

(2-4A) Construction of Fc-B Expression Vector

A DNA fragment (SEQ ID NO: 14) was synthesized which comprised a DNA sequence encoding the amino acid sequence of Fc-B containing a human Fc region connected to a human light chain secretion signal. A Fc-B expression vector was constructed in the same way as in step (2-2A). The obtained expression vector was designated as "pCMA/Fc-B". The amino acid sequence of Fc-B is shown in amino acid positions 21 to 243 of SEQ ID NO: 15 (amino acid positions 1 to 20 correspond to a signal sequence).

(2-4B) Production of Fc-B

A culture supernatant containing Fc-B as a partial antibody molecule was obtained in the same way as in Example (2-2C) using pCMA/Fc-B.

(2-4C) Purification of Fc-B

From the culture supernatant obtained in step (2-4B), the Fc fragment was purified by two steps of recombinant protein A affinity chromatography (at 4 to 6° C.) and ceramic hydroxyapatite (at room temperature). Buffer replacement steps after the purification by recombinant protein A affinity chromatography and after the purification using ceramic hydroxyapatite were carried out at 4 to 6° C. First, the culture supernatant was applied to MabSelect SuRe (manufactured by GE Healthcare Biosciences Corp., HiTrap column) equilibrated with PBS. After placement of the whole culture supernatant in the column, the column was washed with PBS in an amount of twice or more the volume of column. Subsequently, elution was performed with a 2 M arginine hydrochloride solution (pH 4.0), and fractions containing the Fc fragment were collected. The buffer in the fractions was replaced with PBS by dialysis (Thermo Fisher Scientific Inc., Slide-A-Lyzer Dialysis Cassette) and then diluted 5-fold with a buffer of 5 mM sodium phosphate/50 mM MES, pH 7.0. The Fc fragment solution was applied to a ceramic hydroxyapatite column (Bio-Rad Laboratories, Inc., Bio-Scale CHT Type-1 Hydroxyapatite Column) equilibrated with a buffer of 5 mM NaPi/50 mM MES/30 mM NaCl, pH 7.0. Linear concentration gradient elution was carried out with 0 to 2 M sodium chloride, and fractions containing Fc-B were collected. The buffer in the fractions was replaced with HBSor (25 mM histidine/5% sorbitol, pH 6.0) by dialysis (Thermo Fisher Scientific Inc., Slide-A-Lyzer Dialysis Cassette). Finally, the recovered solution was concentrated using Centrifugal UF Filter Device VIVASPIN 20 (molecular weight cut off: UF10K, Sartorius AG, at 4° C.). The concentration was adjusted to 10 mg/ml to prepare a purified Fc-B sample.

<Example 2-5> Preparation of Fc-A (LALA Form)

Fc-A which was a LALA form of Fc-B having an extended N terminus was prepared as a molecule for a carrier as follows.

(2-5A) Construction of Fc-A Expression Vector

Mutations to substitute Leu-Leu at amino acid positions 30 and 31 of SEQ ID NO: 15 (corresponding to Leu234-Leu235 based on the EU Index) with Ala-Ala and to add 4 amino acids (DKTH) to the N terminus were introduced to pCMA/Fc-B as a template using the primer set described below (FcLALA-F and Fc05-R) and a KOD-Plus-Mutagenesis Kit (Toyobo Co., Ltd.) to construct a Fc-A expression vector. The constructed expression vector was designated as "pCMA/Fc-A". The nucleotide sequence of DNA encoding Fc-A is shown in nucleotide positions 61 to 741 of SEQ ID NO: 16 (nucleotide positions 1 to 60 correspond to a signal sequence). The amino acid sequence thereof is shown in amino acid positions 21 to 247 of SEQ ID NO: 17 (amino acid positions 1 to 20 correspond to a signal sequence).

```
Primer set
FcLALA-F;
                                          (SEQ ID NO: 18)
5'-TGTCCTGCTCCAGAGGCCGCGGGCGGACCTAGCGTGTTCCT
GTTCCCC-3'

Fc05-R;
                                          (SEQ ID NO: 19)
5'-TGGAGGACAGGTGTGAGTTTTGTCGCCGTAGGCGCCGCTGA
TCCACAGCAG-3'
```

(2-5B) Production and Purification of Fc-A

A culture supernatant containing Fc-A as a partial antibody molecule was obtained in the same way as in step (2-2C) using pCMA/Fc-A. From the obtained culture supernatant, the partial antibody molecule was purified in the same way as in Example 2-4C and used as a purified Fc-A sample.

[Example 3] Preparation of Conjugate

Each conjugate produced in this Example was named to indicate its structural feature. Although this name adopted the nomenclature described above in the specification as a rule, the complete structure is identified with reference to a drawing or a structural formula. In a PEG linker, the symbol "//" represents a 1,2,3-triazole ring formed through the reaction of an azide group with DBCO, and the symbol "-" represents an amide bond.

Figure 27:
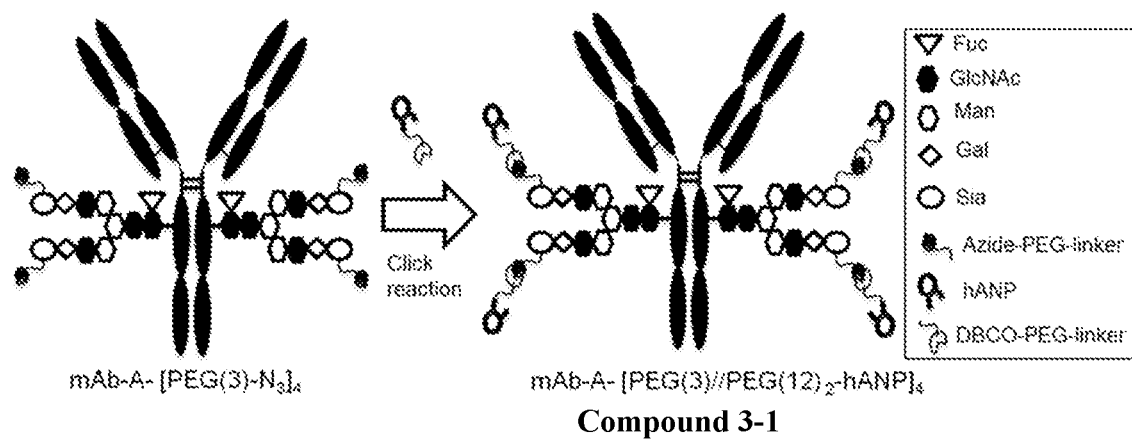
FIG. 27 shows Formula 54 (i.e., Compound 3-1), the preparation of mAb-A-$[\text{PEG(3)//PEG(12)}_2\text{-hANP(1-28)}]_4$.

<Example 3-1> Synthesis of mAb-A-[PEG(3)//PEG(12)$_2$-hANP(1-28)]$_4$(FIG. 27)

Figure 24:
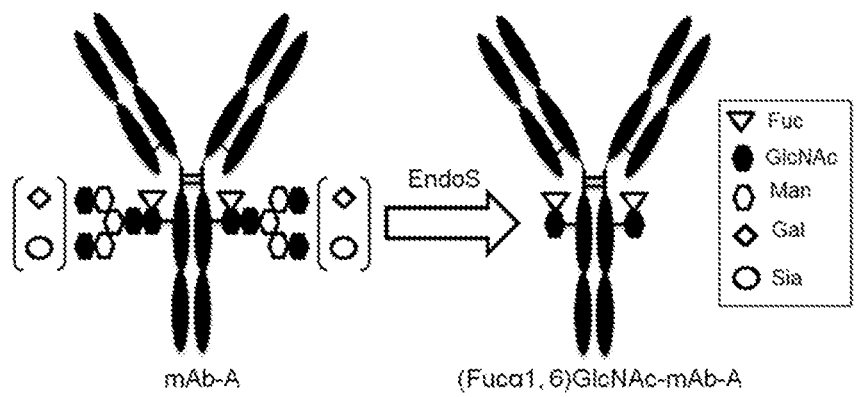
FIG. 24 shows Formula 51, the preparation of (Fucα1,6)GlcNAc-mAb-A.

(3-1A) Preparation of (Fucα1,6)GlcNAc-mAb-A (FIG. 24)

19.4 mg/ml of the mAb-A solution (5% sorbitol/25 mM histidine solution (pH 6.0)) (26.0 ml) prepared in Example 2-1 was buffer-replaced with a 50 mM phosphate buffer solution (pH 6.0) using Amicon Ultra (Ultracel 30K, manufactured by Merck Millipore/Merck KGaA). 2.00 mg/ml of a wild type EndoS solution (PBS) (1.26 ml) was added to 24.5 mg/ml of the obtained mAb1 solution (50 mM phosphate buffer solution (pH 6.0)) (20.0 ml), and the mixture was incubated at 37° C. for 3 hours. The degree of progression of the reaction was confirmed using Experion electrophoresis station (manufactured by Bio-Rad Laboratories, Inc.). After the completion of reaction, purification by affinity chromatography and purification using a hydroxyapatite column were performed according to the following method.

(1) Purification by Affinity Chromatography
Purification apparatus: AKTA pure 150 (manufactured by GE Healthcare Japan Corp.)
Column: HiTrap rProtein A FF (5 ml) (manufactured by GE Healthcare Japan Corp.)
Flow rate: 5 ml/min (1.25 ml/min during charging)

The obtained reaction solution was purified in five portions. For binding to the column, the reaction solution was added to the upper part of the column, and a binding buffer (20 mM phosphate buffer solution (pH 7.0)) was injected into the column in 2 CV at 1.25 ml/min and further injected thereinto in 5 CV at 5 ml/min. For intermediate washing, a washing solution (20 mM phosphate buffer solution (pH 7.0) and 0.5 M sodium chloride solution) was injected to the column in 15 CV. For elution, an elution buffer (ImmunoPure IgG Elution buffer, manufactured by Pierce/Thermo Fisher Scientific Inc.) was injected to the column in 6 CV. The eluate was immediately neutralized with a 1 M Tris buffer solution (pH 9.0). Fractions detected by UV (280 nm) during elution were confirmed using a micro volume spectrophotometer Xpose (manufactured by Trinean NV) and Experion electrophoresis station (manufactured by Bio-Rad Laboratories, Inc.).

Fractions containing the compound of interest were concentrated using Amicon Ultra (Ultracel 30K, manufactured by Merck Millipore/Merck KGaA) and buffer-replaced with a buffer solution (5 mM phosphate buffer solution and 50 mM 2-morpholinoethanesulfonic acid (MES) solution (pH 6.8)).

(2) Purification by Hydroxyapatite Chromatography
Purification apparatus: AKTA pure 150 (manufactured by GE Healthcare Japan Corp.)
Column: Bio-Scale Mini CHT Type I cartridge (5 ml) (manufactured by Bio-Rad Laboratories, Inc.)
Flow rate: 5 ml/min (1.25 ml/min during charging)

Two columns were connected, and the solution obtained in the preceding step (1) was purified in two portions. The solution was added to the upper part of the column, and solution A (5 mM phosphate buffer solution and 50 mM 2-morpholinoethanesulfonic acid (MES) solution (pH 6.8)) was injected into the column in 2 CV at 1.25 ml/min and further injected thereinto in 3 CV at 5 ml/min. Then, elution was performed using solution A and solution B (5 mM phosphate buffer solution, 50 mM 2-morpholinoethanesulfonic acid (MES) solution (pH 6.8), and 2 M sodium chloride solution). The elution conditions involved solution A:solution B=100:0 to 0:100 (15 CV). Further, a washing solution (500 mM phosphate buffer solution (pH 6.5)) was injected into the column in 5 CV.

Fractions detected by UV (280 nm) during elution were confirmed using a micro volume spectrophotometer Xpose (manufactured by Trinean NV) and an Experion electrophoresis station (manufactured by Bio-Rad Laboratories, Inc.).

Fractions containing the compound of interest were concentrated using Amicon Ultra (Ultracel 30K, manufactured by Merck Millipore/Merck KGaA) and buffer-replaced with a 50 mM phosphate buffer solution (pH 6.0) to obtain 23.7 mg/ml of a (Fucα1,6)GlcNAc-mAb-A solution (50 mM phosphate buffer solution (pH 6.0)) (19.9 ml).

ESI-MS:

calculated for the heavy chain of (Fucα1, 6)GlcNAc-mAb-A(-Lys, pyrGlu), M=50166.6 found (m/z), 50165.3 (deconvolution data).

calculated for the light chain of (Fucα1, 6)GlcNAc-mAb-A, M=23292.9 found (m/z), 23292.0 (deconvolution data).

Figure 25:
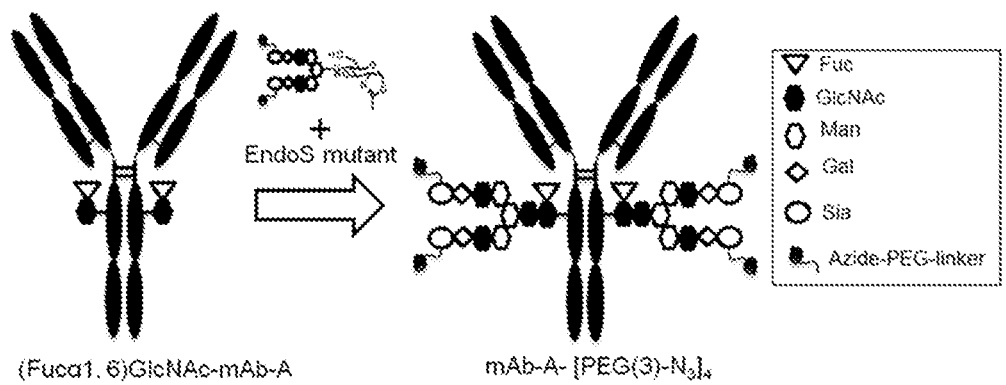
FIG. 25 shows Formula 52, the preparation of mAb-A-$[\text{PEG(3)-N}_3]_4$.

(3-I B) Preparation of mAb-A-[PEG(3)-N$_3$]$_4$ (FIG. 25)

Figure 26:
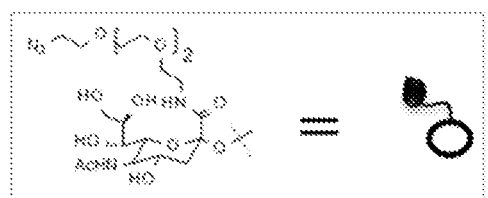
FIG. 26 shows Formula 53 which represents a linker structure with an azide group introduced in sialic acid at the non-reducing end of a SG type N297 glycan, and in Example 3, all intermediate linker structures with an azide group introduced in a N297 glycan are the same structures as in the formula.

Formula 53 of FIG. 26 represents a linker structure with an azide group introduced in sialic acid at the non-reducing end of a SG type N297 glycan, and in Example 3, all intermediate linker structures with an azide group introduced in a N297 glycan are the same structures as in the formula 53 FIG. 26.

To 23.7 mg/ml of the (Fucα1,6)GlcNAc-mAb-A solution (50 mM phosphate buffer solution (pH 6.0)) (8.90 ml) obtained in the step (3-IA), a 50 mM phosphate buffer solution (pH 6.0) (1.65 ml), a solution of [N$_3$-PEG(3)]$_2$-SG (10)-Ox (33.8 mg) synthesized in Example 1-10 in a 50 mM phosphate buffer solution (pH 6.0) (0.676 ml), and 2.10 mg/ml of an EndoS D233Q/Q303L solution (PBS) (1.98 ml) were added, and the mixture was incubated at 30° C. for 3.5 hours. The operation described above was performed for 2 lots. The degree of progression of the reaction was confirmed using Experion electrophoresis station (manufactured by Bio-Rad Laboratories, Inc.). After the completion of reaction, the binding buffer used in the purification by affinity chromatography was changed from the 20 mM phosphate buffer solution (pH 7.0) to a 20 mM phosphate buffer solution (pH 6.0), and purification by affinity chromatography and purification by hydroxyapatite chromatography were performed according to the same method as in the step (3-1A). Then, fractions containing the compound of interest were concentrated using Amicon Ultra (Ultracel 30K, manufactured by Merck Millipore/Merck KGaA) and subsequently buffer-replaced with a 20 mM phosphate buffer solution (pH 6.0) to obtain 20.5 mg/ml of a mAb-A-[PEG(3)-N$_3$]$_4$ solution (20 mM phosphate buffer solution (pH 6.0)) (19.0 ml).

ESI-MS:

calculated for the heavy chain of mAb-A-[PEG(3)-N$_3$]$_4$ (-Lys, pyrGlu), M=52569.9 found (m/z), 52569.4 (deconvolution data).

calculated for the light chain of mAb-A-[PEG(3)-N$_3$]$_4$, M=23292.9 found (m/z), 23292.1 (deconvolution data).

(3-1C) Preparation of mAb-A4PEG(3)//PEG(12)$_2$-hANP (1-28)$_4$(compound of interest of the following formula: compound 3-1 (FIG. 27)).

Figure 28:
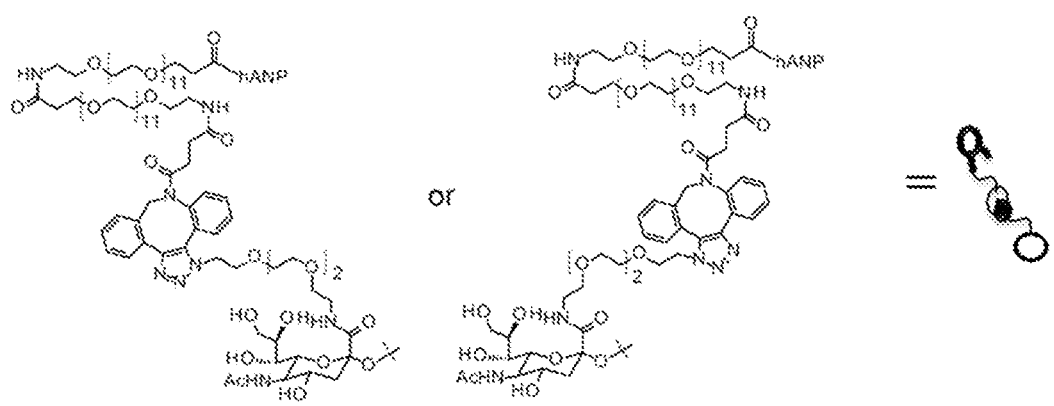
FIG. 28 shows Formula 55 which represents the structures of sialic acid in a N297 glycan, a PEG linker and a hANP peptide in compound 3-1 (FIG. 27).

The formulas given in FIGS. 27 and 28 represent the structures of sialic acid in a N297 glycan, a PEG linker and a hANP peptide in compound 3-1 of FIG. 27; the triazole ring formed through Click reaction in the formulas has geometric isomerism, and compound 3-1 of FIG. 27 maintains a mixture of linkers having the right and left structures of the formulas; and since sialic acid residues at the non-reducing ends of all the N297 glycan moieties in compound 3-1 of FIG. 27 are modified with the linker moieties of the formula given above, four hANP(1-28) molecules are linked per conjugate molecule.

To 20.5 mg/ml of the mAb-A-[PEG(3)-N$_3$]$_4$ solution (20 mM phosphate buffer solution (pH 6.0)) (2.44 ml) obtained in the step (3-1B), a 20 mM phosphate buffer solution (pH 6.0) (1.56 ml), dimethyl sulfoxide (0.736 ml), and a solution of DBCO-PEG(12)$_2$-hANP(1-28) (12.9 mg) synthesized in Example 1-1 in dimethyl sulfoxide (0.264 ml) as a DBCO compound were added, and the mixture was incubated at 30° C. for 16 hours (Click reaction). The reaction solution was partially purified with NAP25 (manufactured by GE Healthcare Japan Corp.) and a 20 mM phosphate buffer solution (pH 6.0). The degree of progression of the reaction was confirmed by hydrophobic interaction chromatography under the conditions given below, followed by purification by affinity chromatography given below.

(1) Analysis Conditions for Hydrophobic Interaction Chromatography

Analysis apparatus: Hitachi D-7000 (manufactured by Hitachi, Ltd.)
Column: TSKgel Butyl-NPR (4.6×100 mm) (manufactured by Tosoh Corp.)
Mobile phase: solution A: 20 mM phosphate buffer solution (pH 7.0) and 2 M ammonium sulfate solution
solution B: 20 mM phosphate buffer solution (pH 7.0)
Gradient: A:B=75:25 to 0:100 (0 to 25 min)-0:100 (25 to 30 min)
Temperature: 25° C.
Wavelength: 214 nm
Flow rate: 1 ml/min (2) Purification by Affinity Chromatography
Purification apparatus: AKTA pure 150 (manufactured by GE Healthcare Japan Corp.)
Column: HiTrap rProtein A FF (5 ml) (manufactured by GE Healthcare Japan Corp.)
Flow rate: 5 ml/min (1.25 ml/min during charging)

For binding to the column, the obtained reaction solution was added to the upper part of the column, and a binding buffer (20 mM phosphate buffer solution (pH 6.0)) was injected into the column in 2 CV at 1.25 ml/min and further injected thereinto in 5 CV at 5 ml/min. For intermediate washing, a washing solution (20 mM phosphate buffer solution (pH 7.0) and 0.5 M sodium chloride solution) was injected into the column in 10 CV. For elution, an elution buffer (ImmunoPure IgG Elution buffer, manufactured by Pierce/Thermo Fisher Scientific Inc.) was injected into the column in 6 CV. The eluate was immediately neutralized with a 1 M Tris buffer solution (pH 9.0). Fractions detected by UV (280 nm) during elution were confirmed using a micro volume spectrophotometer Xpose (manufactured by Trinean NV) and hydrophobic interaction chromatography.

Fractions containing the compound of interest were concentrated using Amicon Ultra (Ultracel 30K, manufactured by Merck Millipore/Merck KGaA), buffer-replaced with a 5% sorbitol/10 mM acetate buffer solution (pH 5.5), and filtered through a filter (Millex-GV, 0.22 μm, PVDF, already sterilized, manufactured by Merck Millipore/Merck KGaA) to obtain 19.4 mg/ml of a mAb-A-[PEG(3)//PEG(12)$_2$-hANP]$_4$ solution (5% sorbitol/10 mM acetate buffer solution (pH 5.5)) (2.14 ml).

ESI-MS:

calculated for the heavy chain of mAb-A-[PEG(3)//PEG (12)$_2$-hANP]$_4$(-Lys, pyr-Glu), M=61708.2 found (m/z), 61706.4 (deconvolution data).

calculated for the light chain of mAb-A-[PEG(3)//PEG (12)$_2$-hANP]$_4$, M=23292.9 found (m/z), 23291.7 (deconvolution data).

<Example 3-2> Synthesis of mAb-A-[PEG(3)//PEG (12)$_2$-(SG-)Asn-hANP(1-28)]$_4$ (Compound of Interest of the Following Formula: Compound 3-2 (FIG. 29))

Figure 29:
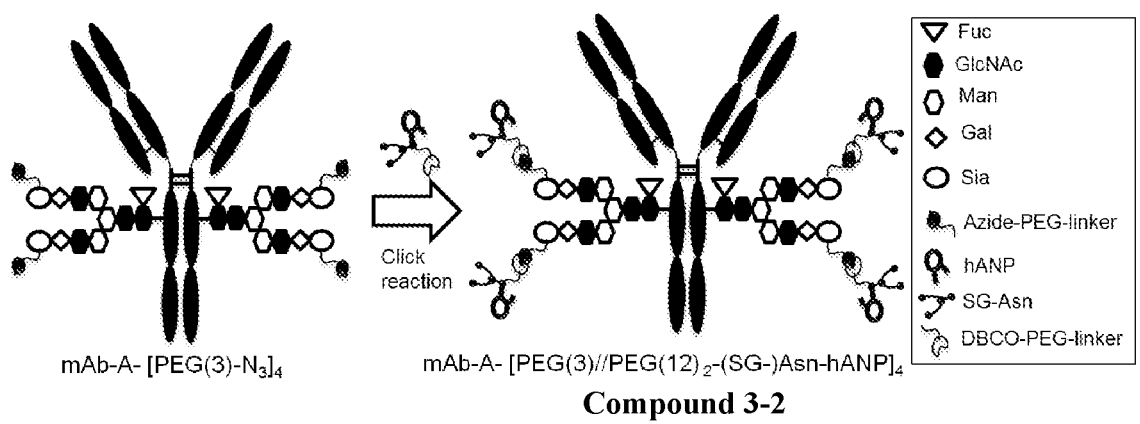
FIG. 29 shows Formula 56 (i.e., Compound 3-2), <Example 3-2> Synthesis of mAb-A-$[\text{PEG(3)//PEG(12)}_2\text{-(SG-)Asn-hANP(1-28)}]_4$.
Figure 30:
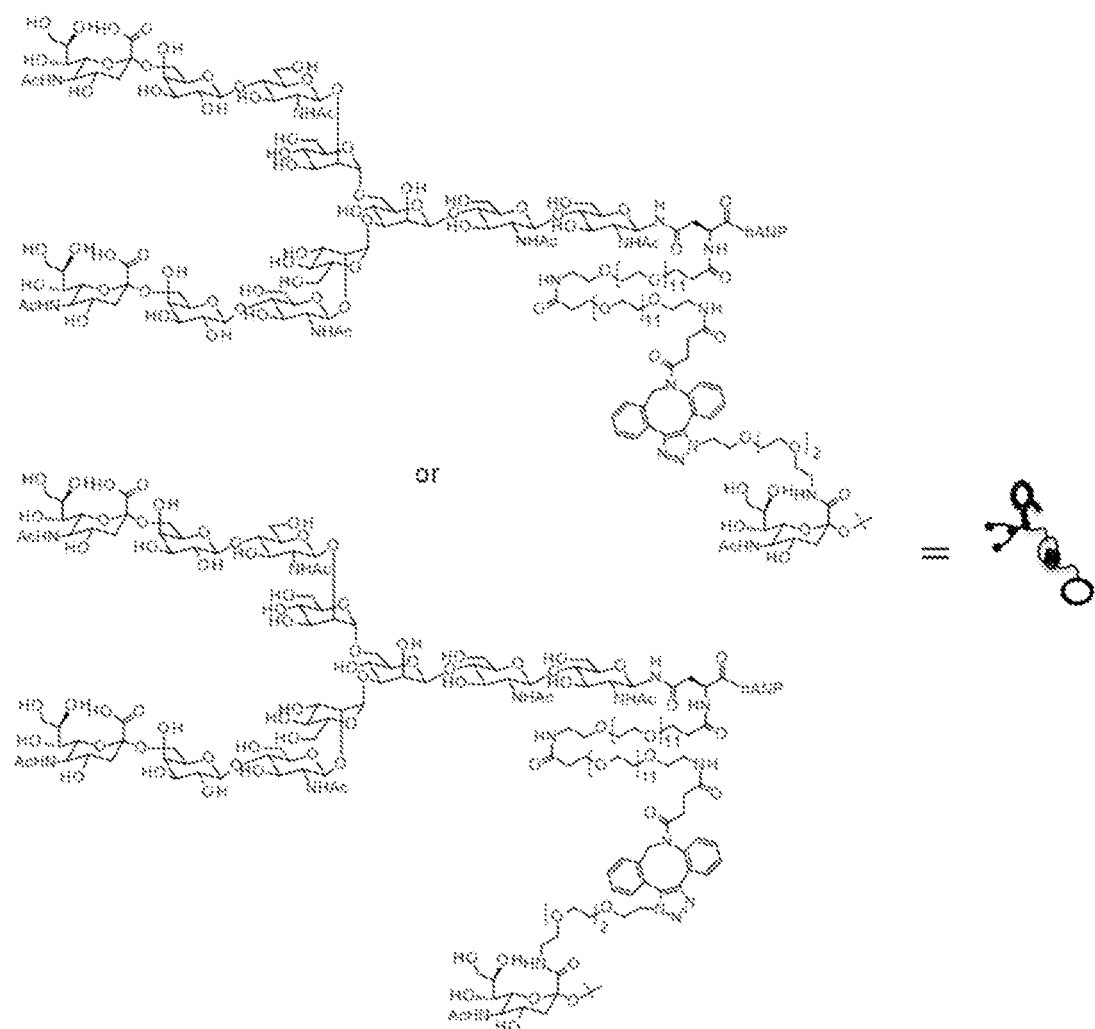
FIG. 30 shows Formula 57 which represents the structures of sialic acid in a N297 glycan, a PEG linker and a hANP peptide in compound 3-2 (FIG. 29).

The formulas given in FIGS. 29 and 30 represent the structures of sialic acid in a N297 glycan, a PEG linker and a hANP peptide in compound 3-2 of FIG. 29; the triazole ring formed through Click reaction in the formulas has geometric isomerism, and compound 3-2 of FIG. 29 maintains a mixture of linkers having the right and left structures of the formulas; and since sialic acid residues at the non-reducing ends of all the N297 glycan moieties in compound 3-2 of FIG. 29 are modified with the linker moieties of the formula given above, four hANP(1-28) molecules are linked per conjugate molecule.

20.5 mg/ml of the mAb-A-[PEG(3)-$N_3$]$_4$ solution (20 mM phosphate buffer solution (pH 6.0)) (5.51 ml) obtained in the step (3-1B), a 20 mM phosphate buffer solution (pH 6.0) (2.49 ml), dimethyl sulfoxide (1.40 ml), and a solution of DBCO-PEG(12)$_2$-(SG-)Asn-hANP(1-28) (43.1 mg) synthesized in the step (1-2F) in dimethyl sulfoxide (0.596 ml) were incubated at 30° C. for 16 hours. The operation described above was performed for 2 lots. The subsequent procedures were performed in the same way as in the step (3-1C) to obtain 21.6 mg/ml of a mAb-A-[PEG(3)//PEG(12)$_2$-(SG-)Asn-hANP(1-28)]$_4$ solution (5% sorbitol/10 mM acetate buffer solution (pH 5.5)) (10.2 ml).

ESI-MS:
calculated for the heavy chain of mAb-A-[PEG(3)//PEG(12)$_2$-(SG-)Asn-hANP]$_4$(-Lys, pyrGlu), M=66348.4 found (m/z), 66347.5 (deconvolution data).

calculated for the light chain of mAb-A-[PEG(3)//PEG(12)$_2$-(SG-)Asn-hANP]$_4$, M=23292.9 found (m/z), 23291.9 (deconvolution data).

Figure 33:
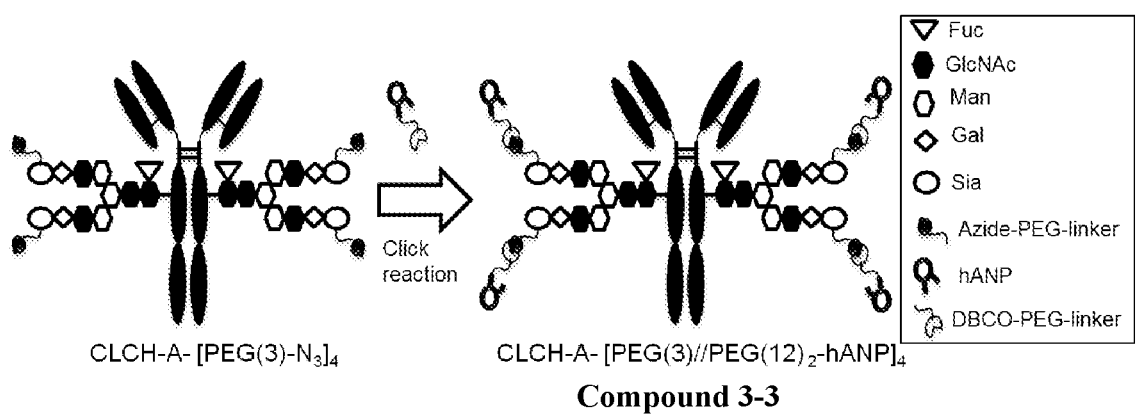
FIG. 33 shows Formula 60 (i.e., Compound 3-3), which is a preparation of CLCH-A-$[\text{PEG(3)//PEG(12)}_2\text{-hANP(1-28)}]_4$.

<Example 3-3> Synthesis of CLCH-A-[PEG(3)//PEG(12)$_2$-hANP(1-28)]$_4$ (FIG. 33)

(3-3A) Preparation of (Fucα1,6)GlcNAc-CLCH-A

Figure 31:
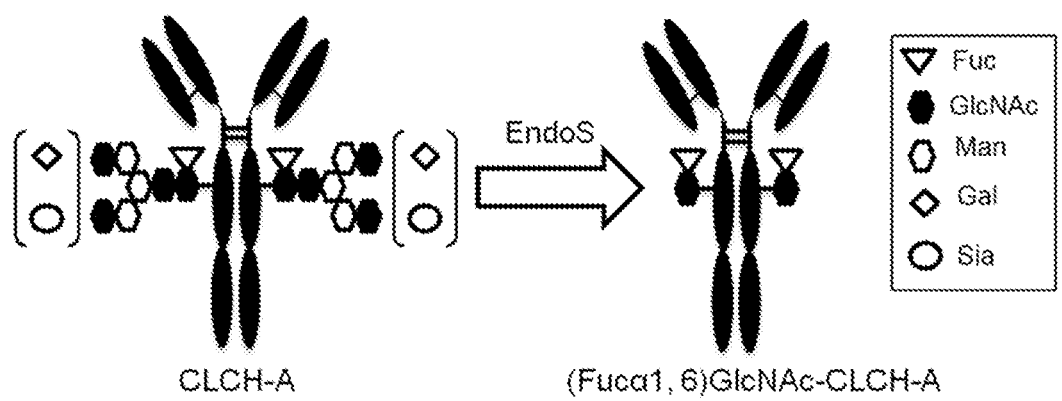
FIG. 31 shows Formula 58 which is a preparation of (Fucα1,6)GlcNAc-CLCH-A.

In FIG. 31, 21.6 mg/ml of the CLCH-A solution (5% sorbitol/25 mM histidine solution (pH 6.0)) (21.0 ml) prepared in Example 2-2 was buffer-replaced with a 50 mM phosphate buffer solution (pH 6.0) using Amicon Ultra (Ultracel 10K, manufactured by Merck Millipore/Merck KGaA). 2.00 mg/ml of a wild type EndoS solution (PBS) (2.27 ml) was added to 22.0 mg/ml of the obtained CLCH-A solution (50 mM phosphate buffer solution (pH 6.0)) (20.0 ml), and the mixture was incubated at 37° C. for 6 hours. The degree of progression of the reaction was confirmed using Experion electrophoresis station (manufactured by Bio-Rad Laboratories, Inc.). After the completion of reaction, purification by affinity chromatography and purification using a hydroxyapatite column were performed according to the same method as in the step (3-1A). Then, fractions containing the compound of interest were concentrated using Amicon Ultra (Ultracel 10K, manufactured by Merck Millipore/ Merck KGaA) and subsequently buffer-replaced with a 50 mM phosphate buffer solution (pH 6.0) to obtain 21.1 mg/ml of a (Fucα1,6)GlcNAc-CLCH-A solution (50 mM phosphate buffer solution (pH 6.0)) (20.4 ml).

ESI-MS:
calculated for the heavy chain of (Fucα1,6)GlcNAc-CLCH-A(-Lys), M=36386.4 found (m/z), 36386.1 (deconvolution data).

calculated for the light chain of (Fucα1,6)GlcNAc-CLCH-A, M=11507.6 found (m/z), 11506.8 (deconvolution data).

Figure 32:
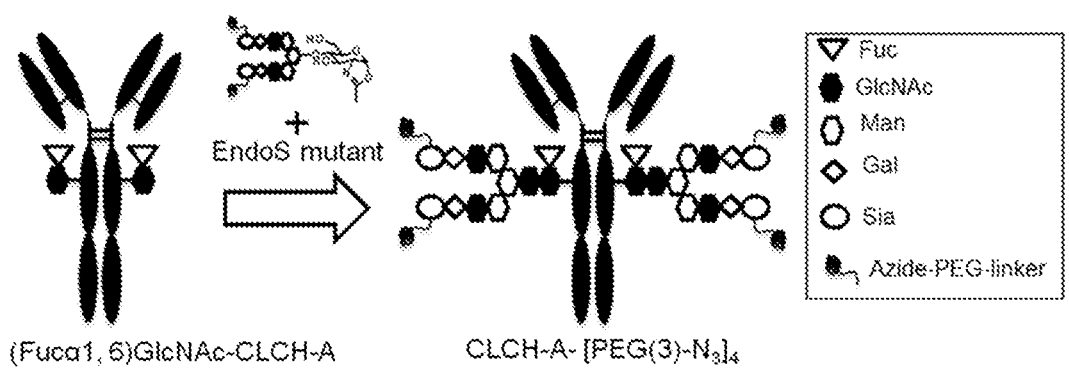
FIG. 32 shows Formula 59 which is a preparation of CLCH-A-$[\text{PEG(3)-N}_3]_4$.

(3-3B) Preparation of CLCH-A-[PEG(3)-$N_3$]$_4$ (FIG. 32)

To 21.1 mg/ml of the (Fucα1,6)GlcNAc-CLCH-A solution (50 mM phosphate buffer solution (pH 6.0)) (4.65 ml) obtained in the step (3-3A), a 50 mM phosphate buffer solution (pH 6.0) (2.66 ml), a solution of [$N_3$-PEG(3)]$_2$-SG(10)-Ox (23.5 mg) synthesized in Example 1-10 in a 50 mM phosphate buffer solution (pH 6.0) (0.470 ml), and 2.10 mg/ml of an EndoS D233Q/Q303L solution (PBS) (1.40 ml) were added, and the mixture was incubated at 30° C. for 3 hours. Further, a solution of [$N_3$-PEG(3)]$_2$-SG(10)-Ox (11.8 mg) synthesized in the step (1-10B) in a 50 mM phosphate buffer solution (pH 6.0) (0.236 ml) was added thereto, and the mixture was incubated at 30° C. for 1 hour. The operation described above was performed for 3 lots. The degree of progression of the reaction was confirmed using Experion electrophoresis station (manufactured by Bio-Rad Laboratories, Inc.). After the completion of reaction, the binding buffer used in the purification using an affinity column was changed from the 20 mM phosphate buffer solution (pH 7.0) to a 20 mM phosphate buffer solution (pH 6.0), and purification by affinity chromatography and purification using a hydroxyapatite column were performed according to the same method as in the step (3-1A). Then, fractions containing the compound of interest were concentrated using Amicon Ultra (Ultracel 10K, manufactured by Merck Millipore/Merck KGaA) and subsequently buffer-replaced with a 5% sorbitol/10 mM acetate buffer solution (pH 5.5) to obtain 19.3 mg/ml of a CLCH-A-[PEG(3)-$N_3$]$_4$ solution (5% sorbitol/10 mM acetate buffer solution (pH 5.5)) (13.8 ml).

ESI-MS:
calculated for the heavy chain of CLCH-A-[PEG(3)-$N_3$]$_4$(-Lys), M=38789.6 found (m/z), 38789.4 (deconvolution data).

calculated for the light chain of CLCH-A-[PEG(3)-$N_3$]$_4$, M=11507.6 found (m/z), 11506.7 (deconvolution data).

(3-3C) Preparation of CLCH-A-[PEG(3)//PEG(12)$_2$-hANP(1-28)]$_4$(FIG. 33)

Figure 34:
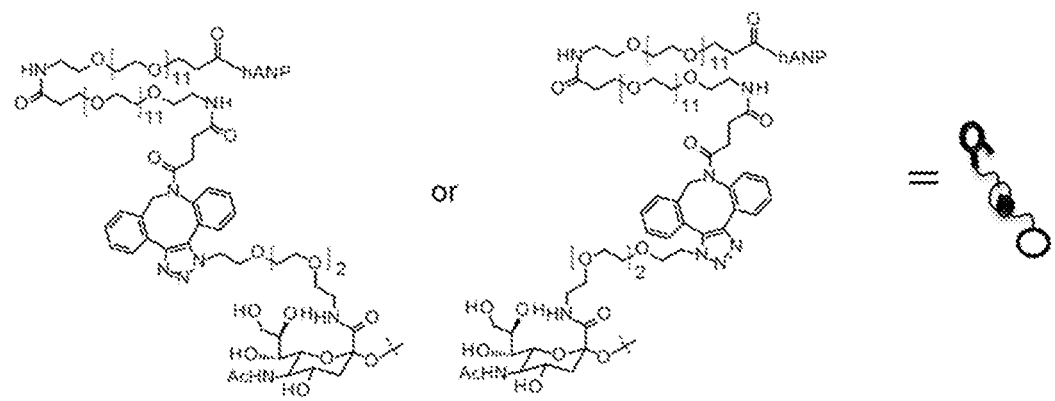
FIG. 34 shows Formula 61 which represents the structures of sialic acid in a N297 glycan, a PEG linker and a hANP peptide in compound 3-3 (FIG. 33).

The formulas given in FIGS. 33 and 34 represent the structures of sialic acid in a N297 glycan, a PEG linker and a hANP peptide in compound 3-3 of FIG. 33; the triazole ring formed through Click reaction in the formulas has geometric isomerism, and compound 3-3 of FIG. 33 maintains a mixture of linkers having the right and left structures of the formulas; and since sialic acid residues at the non-reducing ends of all the N297 glycan moieties in compound 3-3 of FIG. 33 are modified with the linker moieties of the formula given above, four hANP(1-28) molecules are linked per conjugate molecule.

To 19.3 mg/ml of the CLCH-A-[PEG(3)-$N_3$]$_4$ solution (5% sorbitol/10 mM acetate buffer solution (pH 5.5)) (5.18 ml) obtained in the step (3-3B), a 5% sorbitol/10 mM acetate buffer solution (pH 5.5) (2.82 ml), dimethyl sulfoxide (1.18 ml), and a solution of DBCO-PEG(12)$_2$-hANP(1-28) (40.1 mg) synthesized in Example 1-1 in dimethyl sulfoxide (0.816 ml) were added, and the mixture was incubated at 30° C. for 16 hours. The operation described above was performed for 2 lots. The reaction solution was partially purified with NAP25 (manufactured by GE Healthcare Japan Corp.) and a 20 mM phosphate buffer solution (pH 6.0). The degree of progression of the reaction was confirmed by hydrophobic interaction chromatography under the conditions given below, followed by purification by affinity chromatography given below.

(1) Analysis Conditions for Hydrophobic Interaction Chromatography

Analysis apparatus: Hitachi D-7000 (manufactured by Hitachi, Ltd.)

Column: TSKgel Butyl-NPR (4.6×100 mm) (manufactured by Tosoh Corp.)

Mobile phase: solution A: 20 mM phosphate buffer solution (pH 7.0) and 2 M ammonium sulfate solution solution B: 20 mM phosphate buffer solution (pH 7.0)

Gradient: A:B=75:25 to 0:100 (0 to 25 min)-0:100 (25 to 30 min)
Temperature: 25° C.
Wavelength: 214 nm
Flow rate: 1 ml/min
(2) Purification by Affinity Chromatography
Purification apparatus: AKTA pure 150 (manufactured by GE Healthcare Japan Corp.)
Column: HiTrap rProtein A FF (5 ml) (manufactured by GE Healthcare Japan Corp.)
Flow rate: 5 ml/min (1.25 ml/min during charging)

The obtained reaction solutions of 2 lots were purified in three portions. For binding to the column, the reaction solution was added to the upper part of the column, and a binding buffer (20 mM phosphate buffer solution (pH 6.0)) was injected into the column in 4 CV at 1.25 ml/min and further injected thereinto in 5 CV at 5 ml/min. For intermediate washing, a washing solution (20 mM phosphate buffer solution (pH 7.0) and 0.5 M sodium chloride solution) was injected into the column in 10 CV. For elution, an elution buffer (ImmunoPure IgG Elution buffer, manufactured by Pierce/Thermo Fisher Scientific Inc.) was injected into the column in 6 CV. The eluate was immediately neutralized with a 1 M Tris buffer solution (pH 9.0). Fractions detected by UV (280 nm) during elution were confirmed using a micro volume spectrophotometer Xpose (manufactured by Trinean NV) and hydrophobic interaction chromatography.

Fractions containing the compound of interest were concentrated using Amicon Ultra (Ultracel 10K, manufactured by Merck Millipore/Merck KGaA), buffer-replaced with a 5% sorbitol/10 mM acetate buffer solution (pH 5.5), and filtered through a filter (Millex-GV, 0.22 μm, PVDF, already sterilized, manufactured by Merck Millipore/Merck KGaA) to obtain 21.3 mg/ml of a CLCH-A-[PEG(3)//PEG(12)$_2$-hANP(1-28)]$_4$ solution (5% sorbitol/10 mM acetate buffer solution (pH 5.5)) (9.60 ml).
ESI-MS:
calculated for the heavy chain of CLCH-A-[PEG(3)//PEG(12)$_2$-hANP]$_4$(-Lys), M=47928.0 found (m/z), 47928.4 (deconvolution data).
calculated for the light chain of CLCH-A-[PEG(3)//PEG(12)$_2$-hANP]$_4$, M=11507.6 found (m/z), 11506.7 (deconvolution data).

<Example 3-4> Synthesis of CLCH-A-[PEG(3)//PEG(12)$_2$-(SG-)Asn-hANP(1-28)]$_4$ (Compound of Interest of the Following Formula: Compound 3-4 (FIG. 35))

Figure 35:
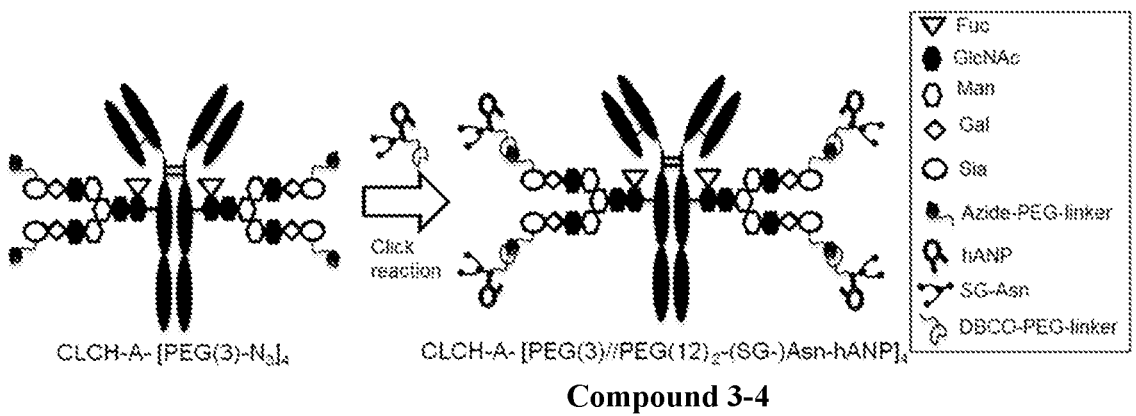
FIG. 35 shows Formula 62 (i.e., Compound 3-4), <Example 3-4> Synthesis of CLCH-A1PEG(3)//PEG(12)$_2$-(SG-)Asn-hANP(I-28)$_4$.
Figure 36:
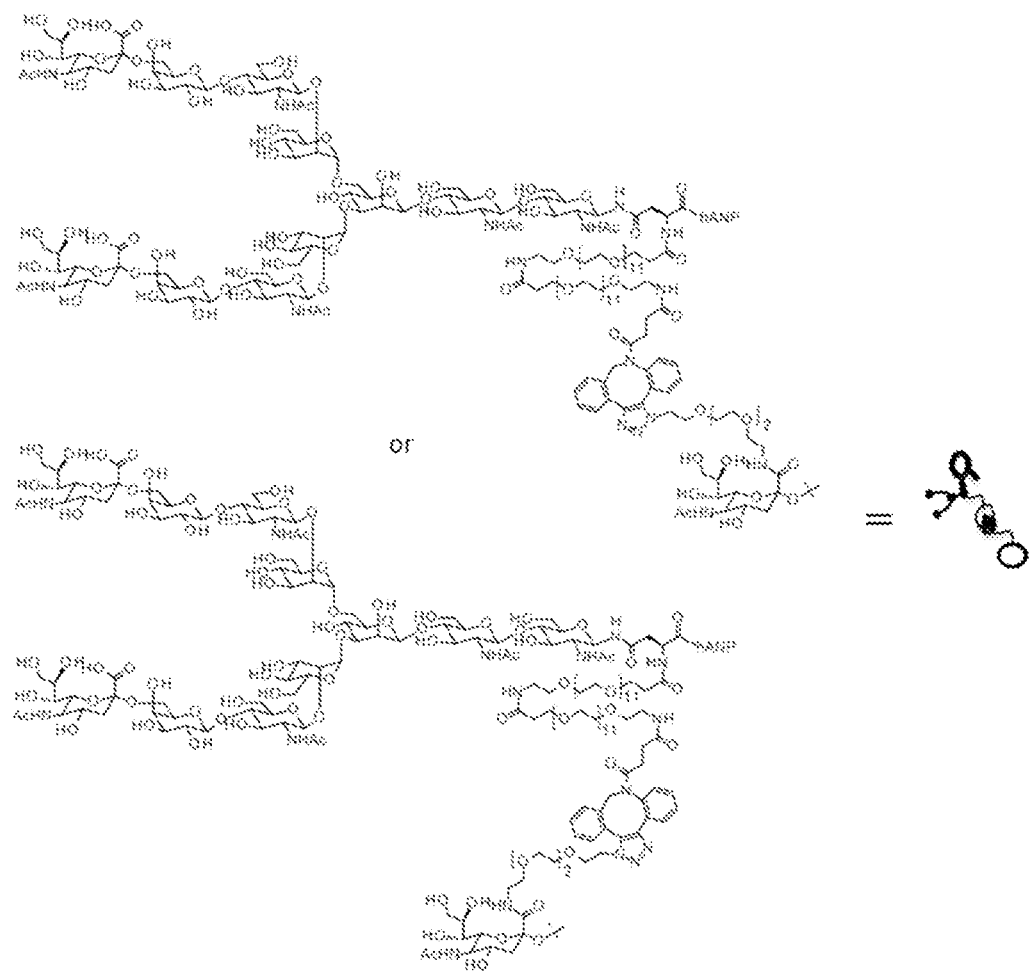
FIG. 36 shows Formula 63 represents the structures of sialic acid in a N297 glycan, a PEG linker and a hANP peptide in compound 3-4 (FIG. 35).

The formulas given in FIGS. 35 and 36 represent the structures of sialic acid in a N297 glycan, a PEG linker and a hANP peptide in compound 3-4 of FIG. 35; the triazole ring formed through Click reaction in the formulas has geometric isomerism, and compound 3-4 of FIG. 35 maintains a mixture of linkers having the right and left structures of the formulas; and since sialic acid residues at the non-reducing ends of all the N297 glycan moieties in compound 3-4 of FIG. 35 are modified with the linker moieties of the formula given above, four hANP(1-28) molecules are linked per conjugate molecule.

19.3 mg/ml of the CLCH-A-[PEG(3)-N$_3$]$_4$ solution (5% sorbitol/10 mM acetate buffer solution (pH 5.5)) (2.59 ml) obtained in the step (3-3B), a 5% sorbitol/10 mM acetate buffer solution (pH 5.5) (1.41 ml), dimethyl sulfoxide (0.602 ml), and a solution of DBCO-PEG(12)$_2$-(SG-)Asn-hANP(1-28) (28.7 mg) synthesized in Example 1-2 in dimethyl sulfoxide (0.398 ml) were incubated at 30° C. for 16 hours.

The subsequent procedures were performed in the same way as in the step (3-3C) to obtain 20.0 mg/ml of a CLCH-A-[PEG(3)//PEG(12)$_2$-(SG-)Asn-hANP(1-28)]$_4$ solution (5% sorbitol/10 mM acetate buffer solution (pH 5.5)) (2.46 ml).
ESI-MS:
calculated for the heavy chain of CLCH-A-[PEG(3)//PEG(12)$_2$-(SG-)Asn-hANP]$_4$(-Lys), M=52568.2 found (m/z), 52568.4 (deconvolution data).
calculated for the light chain of CLCH-A-[PEG(3)//PEG(12)$_2$-(SG-)Asn-hANP]$_4$, M=11507.6 found (m/z), 11506.7 (deconvolution data).

<Example 3-5> Synthesis of mAb-A-[PEG(3)//PEG(12)$_2$-(SG-)Asn-hANP]$_2$(compound 3-5 (FIG. 38))

Figure 37:
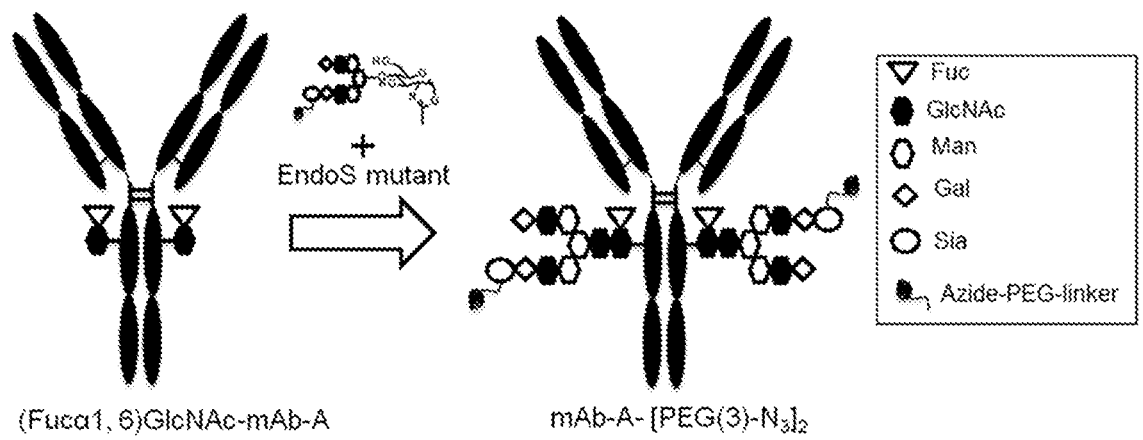
FIG. 37 shows Formula 64, which is a preparation of mAb-A-$[\text{PEG(3)-N}_3]_2$ and mAb-A-$[\text{PEG(3)//PEG(12)2-(SG-)Asn-hANP(1-28)}]_2$ (compound of interest of the following formula: compound 3-5 (FIG. 38)).

(3-5A) Preparation of mAb-A-[PEG(3)-N$_3$]$_2$
In FIG. 37, the compound synthesized in the step (3-1A) was incubated at 30° C. for 3 hours using [N$_3$-PEG(3)]-MSG1(9)-Ox synthesized in Example 1-11 as a glycan donor. The same operation as in the step (3-1B) was performed to obtain 14.1 mg/ml of a mAb-A4PEG(3)-N$_3$]$_2$ solution (20 mM phosphate buffer solution (pH 6.0)) (5.90 ml).
ESI-MS:
calculated for the heavy chain of mAb-A-[PEG(3)-N$_3$]$_2$ (-Lys, pyrGlu), M=52078.4 found (m/z), 52077.0 (deconvolution data).
calculated for the light chain of mAb-A-[PEG(3)-N$_3$]$_2$, M=23292.9 found (m/z), 23291.7 (deconvolution data).

(3-5B) Preparation of mAb-A-[PEG(3)//PEG(12)$_2$-(SG-)Asn-hANP(1-28)]$_2$ (compound of interest of the following formula: compound 3-5 (FIG. 38)).

Figure 38:
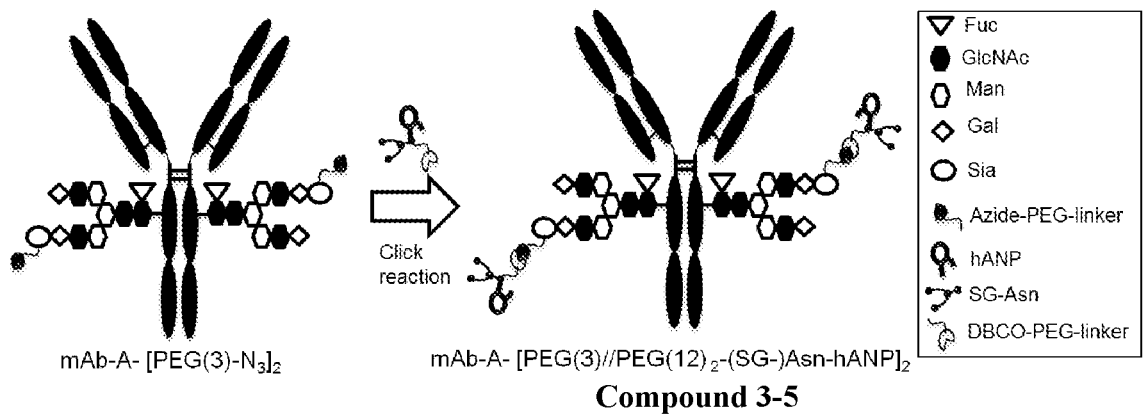
FIG. 38 shows Formula 65 (i.e., Compound 3-5).
Figure 39:
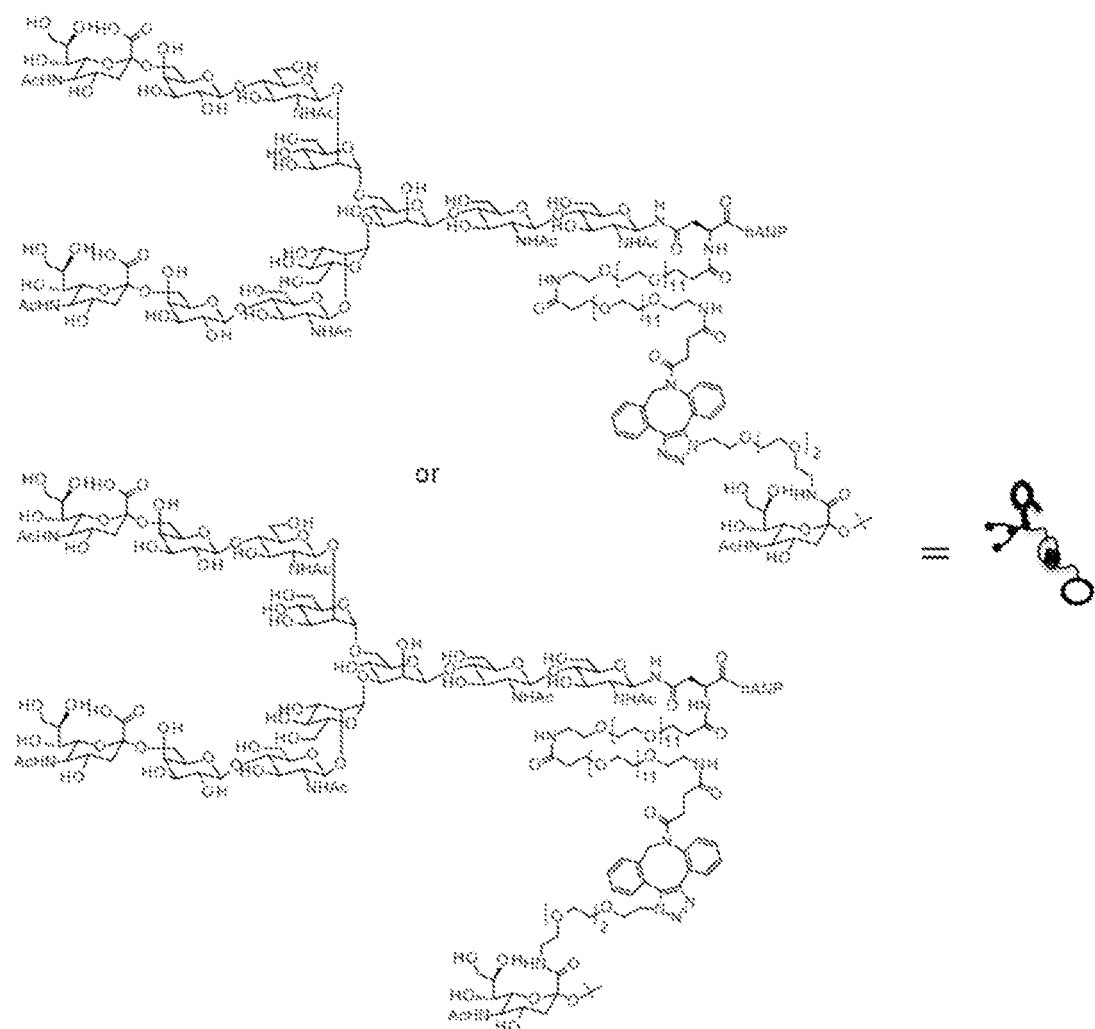
FIG. 39 shows Formula 66 represents the structures of sialic acid in a N297 glycan, a PEG linker and a hANP peptide in compound 3-5 (FIG. 38).

The structural formulas given in FIGS. 38 and 39 represent the structures of sialic acid in a N297 glycan, a PEG linker and a hANP peptide in compound 3-5 of FIG. 38; the triazole ring formed through Click reaction in the formulas has geometric isomerism, and compound 3-5 of FIG. 38 maintains a mixture of linkers having the right and left structures of the formulas; and since sialic acid residues at the non-reducing ends of all the N297 glycan moieties in compound 3-5 of FIG. 38 are modified with the linker moieties of the formula given above, two hANP(1-28) molecules are linked per conjugate molecule.

The compound synthesized in the step (3-5A) was subjected to the same operation as in Example 3-2 using 4 equivalents of DBCO-PEG(12)$_2$-(SG-)Asn-hANP(1-28) synthesized in Example 1-2 to obtain 17.9 mg/ml of a mAb-A-[PEG(3)//PEG(12)$_2$-hANP(1-28)]$_2$ solution (5% sorbitol/10 mM acetate buffer solution (pH 5.5)) (2.55 ml).
ESI-MS:
calculated for the heavy chain of mAb-A-[PEG(3)//PEG(12)$_2$-hANP]$_2$(-Lys, pyrGlu), M=58967.7 found (m/z), 58968.1 (deconvolution data).
calculated for the light chain of mAb-A-[PEG(3)//PEG(12)$_2$-hANP]$_2$, M=23292.9 found (m/z), 23291.8 (deconvolution data).

<Example 3-6> Synthesis of CLCH-A-[PEG(3)//PEG(12)$_2$-(SG-)Asn-hANP(1-28)]$_2$ (compound 3-6 (FIG. 41))

Figure 40:
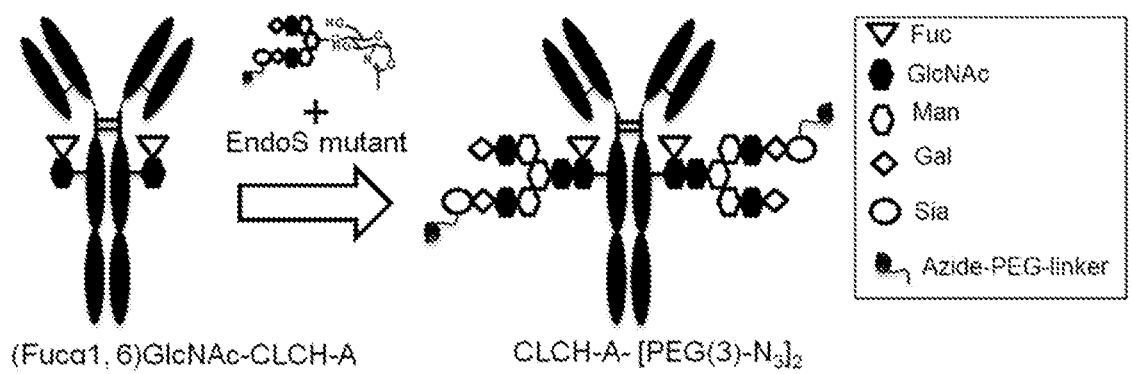
FIG. 40 shows Formula 67, which is a preparation of CLCH-A-$[\text{PEG(3)-[N}_3]_2$.

(3-6A) Preparation of CLCH-A-[PEG(3)-N$_3$]$_2$
The compound synthesized in the step (3-3A) of FIG. 40 was incubated at 30° C. for 3 hours using [N$_3$-PEG(3)]-MSG1(9)-Ox synthesized in Example 1-11 as a glycan donor. The same operation as in the step (3-3B) was performed to obtain 14.6 mg/ml of a CLCH-A-[PEG(3)-N$_3$]$_2$ solution (5% sorbitol/10 mM acetate buffer solution (pH 5.5)) (3.98 ml).

ESI-MS:

calculated for the heavy chain of N$_3$-MSG-CLCH-A(-Lys), M=38298.1 found (m/z), 38297.7 (deconvolution data).

calculated for the light chain of N$_3$-MSG-CLCH-A, M=11507.6 found (m/z), 11506.8 (deconvolution data).

Figure 41:
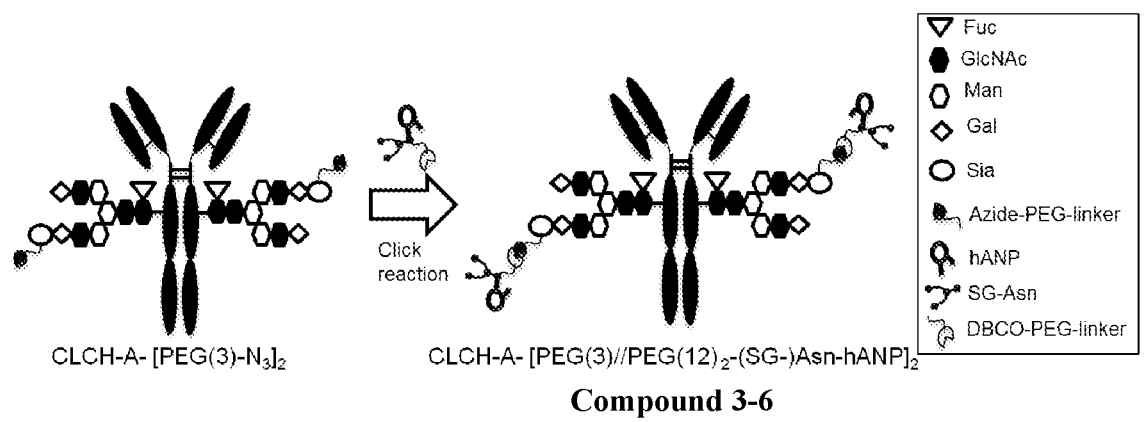
FIG. 41 shows Formula 68 (i.e., Compound 3-6), which is a preparation of CLCH-A-$[\text{PEG(3)//PEG(12)}_2\text{-(SG-)Asn-ANP(1-28)}]_2$.

(3-6B) Preparation of CLCH-A-[PEG(3)//PEG(12)$_2$-(SG-)Asn-ANP(1-28)]$_2$(FIG. 41)

Figure 42:
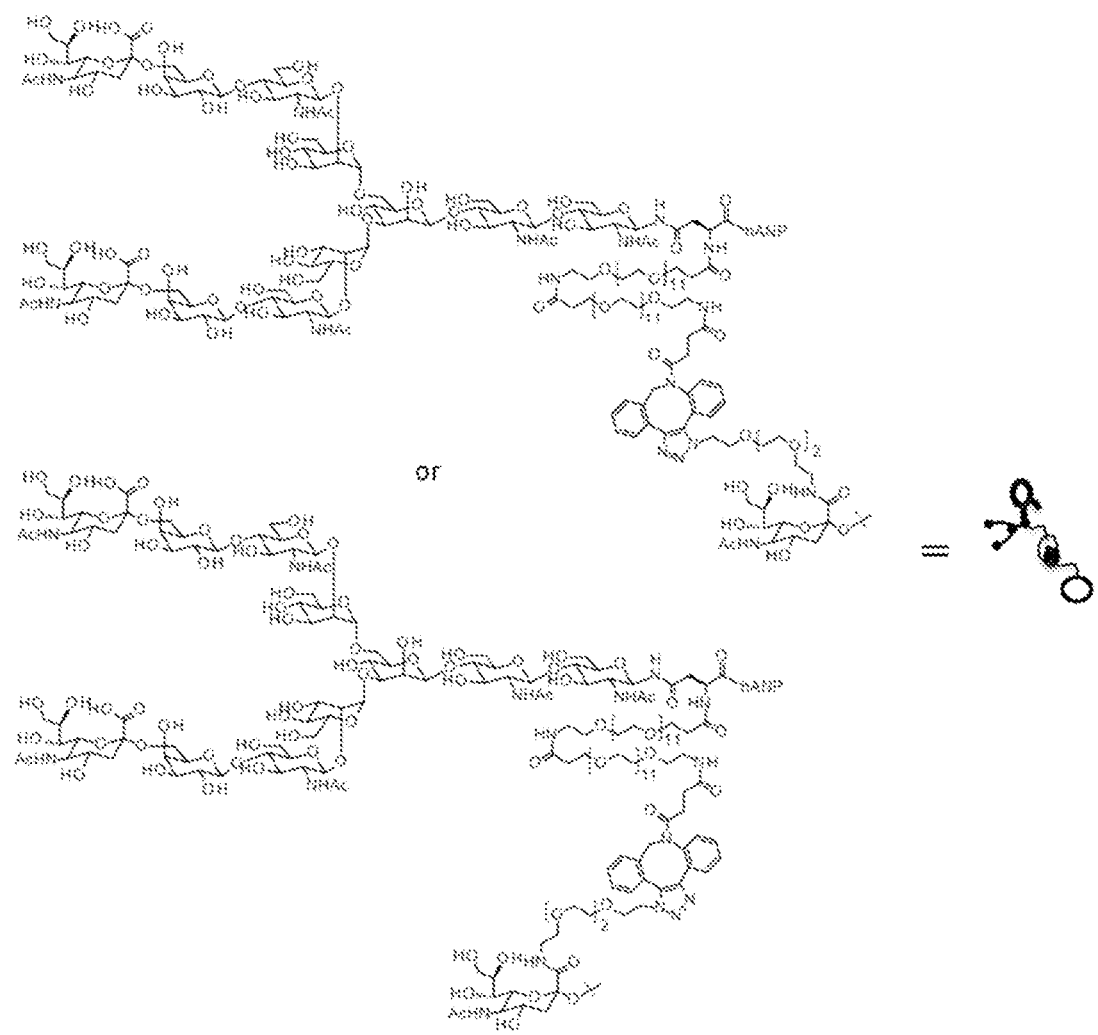
FIG. 42 shows Formula 69 represents the structures of sialic acid in a N297 glycan, a PEG linker and a hANP peptide in compound 3-6 (FIG. 41).

The formulas given in FIGS. 41 and 42 represent the structures of sialic acid in a N297 glycan, a PEG linker and a hANP peptide in compound 3-6 of FIG. 41; the triazole ring formed through Click reaction in the formulas has geometric isomerism, and compound 3-6 of FIG. 41 maintains a mixture of linkers having the right and left structures of the formulas; and since sialic acid residues at the non-reducing ends of all the N297 glycan moieties in compound 3-6 of FIG. 41 are modified with the linker moieties of the formula given above, two hANP(1-28) molecules are linked per conjugate molecule.

The compound synthesized in the step (3-6A) was subjected to the same operation as in Example 3-4 using 4 equivalents of DBCO-PEG(12)$_2$-(SG-)Asn-hANP(1-28) synthesized in Example 1-2 to obtain 19.2 mg/ml of a CLCH-A-[PEG(3)//PEG(12)$_2$-(SG-)Asn-ANP(1-28)]$_2$ solution (5% sorbitol/10 mM acetate buffer solution (pH 5.5)) (2.62 ml).

ESI-MS:

calculated for the heavy chain of CLCH-A-[PEG(3)//PEG(12)$_2$-(SG-)Asn-ANP]$_2$(-Lys), M=45187.4 found (m/z), 45188.0 (deconvolution data).

calculated for the light chain of CLCH-A-[PEG(3)//PEG(12)$_2$-(SG-)Asn-ANP]$_2$, M=11507.6 found (m/z), 11506.8 (deconvolution data).

<Example 3-7> Synthesis of Conjugates Having Diverse Linker Structures (Compounds 3-7 to 3-14)

Figure 43:
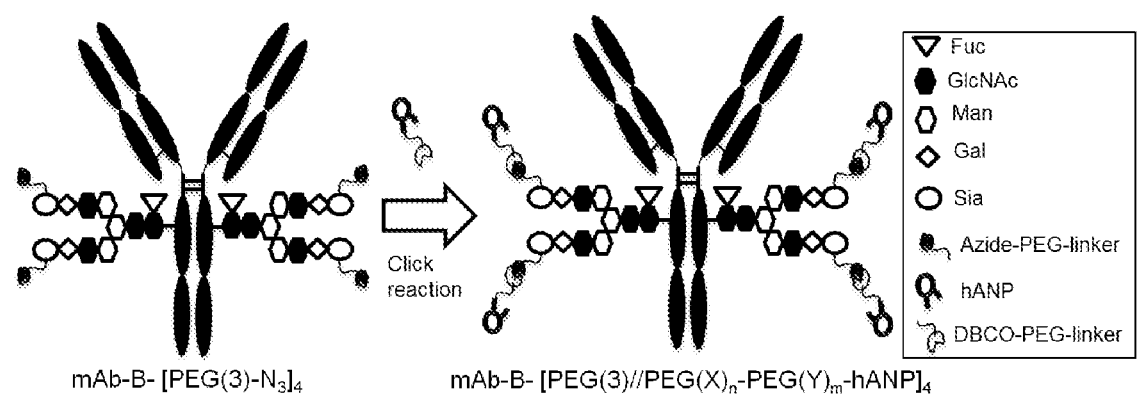
FIG. 43 shows Formula 70, <Example 3-7> Synthesis of conjugates having diverse linker structures (compounds 3-7 to 3-14).

In FIG. 43, mAb-B-[PEG(3)-N$_3$]$_4$ was synthesized from a monoclonal antibody (mAb-B) by use of the method described in Example 3-1. Subsequently, mAb-B-[L(PEG)-hANP(1-28)]$_4$ molecules differing in the structure of the PEG linker moiety were synthesized by differently using the compounds 1-1, 1-3, 1-4, 1-5, 1-6, 1-7, 1-8 and 1-9 (FIGS. 10-18)) synthesized in Example 1 as a DBCO compound for use in Click reaction. Table 1 shows the correspondence between the DBCO compounds used and the structures of the conjugates of interest (L(PEG) corresponding to each compound is compound 3-7: L(PEG) B, compound 3-8: L(PEG)E, compound 3-9: L(PEG)A, compound 3-10: L(PEG)D, compound 3-11: L(PEG)C, compound 3-12: L(PEG)F, compound 3-13: L(PEG)G, or compound 3-14: L(PEG)H); in all the compounds, as in compounds 3-1 to 3-6 (FIGS. 27, 29, 33, 35, 38, and 41), the triazole ring formed through Click reaction in the formulas has geometric isomerism, and the compounds maintain a mixture of linkers having geometric isomeric structures; and four hANP(1-28) molecules are linked per conjugate molecule).

TABLE 1

Type of PEG linker used in mAb-B

| Compound No. | Type of PEG linker | DBCO compound |
|---|---|---|
| 3-7 | mAb-B-[PEG(3)//PEG(12)-PEG(12)-hANP(1-28)]$_4$ | Compound 1-1 |
| 3-8 | mAb-B-[PEG(3)//PEG(12)-hANP(1-28)]$_4$ | Compound 1-3 |
| 3-9 | mAb-B-[PEG(3)//PEG(24)-hANP(1-28)]$_4$ | Compound 1-4 |
| 3-10 | mAb-B-[PEG(3)//PEG(12)-PEG(6)-hANP(1-28)]$_4$ | Compound 1-5 |
| 3-11 | mAb-B-[PEG(3)//PEG(6)-PEG(12)-hANP(1-28)]$_4$ | Compound 1-6 |
| 3-12 | mAb-B-[PEG(3)//PEG(6)-PEG(6)-hANP(1-28)]$_4$ | Compound 1-7 |
| 3-13 | mAb-B-[PEG(3)//PEG(6)-PEG(6)-PEG(6)-hANP(1-28)]$_4$ | Compound 1-8 |
| 3-14 | mAb-B-[PEG(3)//PEG(6)-PEG(6)-PEG(6)-PEG(6)-hANP(1-28)]$_4$ | Compound 1-9 |

<Example 3-8> Synthesis of CLCH-B-[(3)//PEG(12)$_2$-(SG-)Asn-hANP(1-28)]$_4$ (Compound of Interest in Which CLCH-A in the Structure of Compound 3-2 of FIG. 29 Described Above was Replaced with CLCH-B: Compound 3-15)

The reaction scheme and the structure of a substance in each step of this Example correspond to those in which CLCH-A in the corresponding scheme of Example 3-2 was replaced with CLCH-B.

(3-8A) Preparation of (Fucα1,6)GlcNAc-CLCH-B 19.8 mg/ml of a (Fucα1,6)GlcNAc-CLCH-B solution (50 mM phosphate buffer solution (pH 6.0)) (16 ml) was obtained in accordance with the method described in the step (3-3A) by replacing the CLCH-A solution described in the step (3-3A) with 20.6 mg/mL of the CLCH-B solution (5% sorbitol/25 mM histidine solution (pH 6.0)) prepared in Example 2-3.

ESI-MS:

calculated for the heavy chain of (Fucα1,6)GlcNAc-CLCH-B(-Lys), M=36303.1; found 36302.6 (deconvolution data).

calculated for the light chain of (Fucα1,6)GlcNAc-CLCH-B, M=11507.8; found 11506.7 (deconvolution data).

(3-8B) Preparation of CLCH-B-[PEG(3)-N$_3$]$_4$ 19.3 mg/ml of a CLCH-B-[PEG(3)-N$_3$]$_4$ solution (5% sorbitol/10 mM acetate buffer solution (pH 5.5)) (15.7 ml) was obtained in accordance with the method described in step (3-3B) by replacing the (Fucα1,6)GlcNAc-CLCH-A solution described in step (3-3B) with 19.8 mg/ml of the (Fucα1,6)GlcNAc-CLCH-B solution (50 mM phosphate buffer solution (pH 6.0)) obtained in step (3-8A).

ESI-MS:

calculated for the heavy chain of CLCH-B-[PEG(3)-N$_3$]$_4$(-Lys), M=38706.3; found 38704.7 (deconvolution data).

calculated for the light chain of CLCH-B-[PEG(3)-N$_3$]$_4$, M=11507.8; found 11506.8 (deconvolution data).

(3-8C) Preparation of CLCH-B-[PEG(3)//PEG(12)$_2$-(SG-) Asn-hANP(1-28)]$_4$ (Compound 3-15)

19.3 mg/ml of the CLCH-B-[PEG(3)-N$_3$]$_4$ solution (5% sorbitol/10 mM acetate buffer solution (pH 5.5)) (3.90 ml) obtained in step (3-8B), a 5% sorbitol/10 mM acetate buffer solution (pH 5.5) (4.1 ml), dimethyl sulfoxide (1.4 ml), and a solution of DBCO-PEG(12)2-(SG-)Asn-hANP(1-28) (43.4 mg) synthesized in Example 1-2 in dimethyl sulfoxide (0.6 ml) were mixed and incubated at 30° C. for 16 hours. The operation described above was carried out for 4 lots. The subsequent procedures were performed in the same way as in the (3-3C) to obtain 27.1 mg/ml of a CLCH-B-[PEG(3)//PEG(12)$_2$-(SG-)Asn-hANP(1-28)]$_4$ solution (5% sorbitol/10 mM acetate buffer solution (pH 5.5)) (11.5 ml).

ESI-MS:

calculated for the heavy chain of CLCH-B-[PEG(3)//PEG(12)$_2$-(SG-)Asn-hANP]$_4$(-Lys), M=52484.9; found 52484.4 (deconvolution data).

calculated for the light chain of CLCH-B-[PEG(3)//PEG(12)$_2$-(SG-)Asn-hANP]$_4$, M=11507.8; found 11506.7 (deconvolution data).

Figure 44:
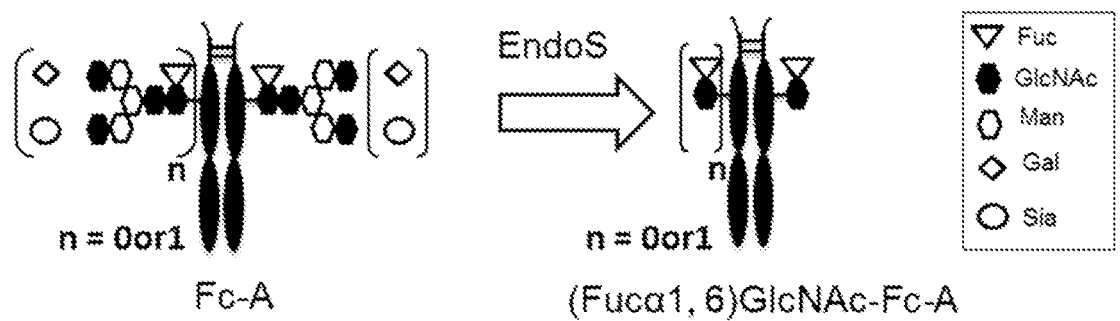
FIG. 44 shows Formula 71 which represents a mixture derived from a glycan structure deletion mutant contained in a prepared carrier protein.

(3-9A) Preparation of (Fucα1,6)GlceNAc-Fc-A (FIG. 44)

The formulas given in FIG. 44 represent a mixture derived from a glycan structure deletion mutant contained in a prepared carrier protein; and in addition to n=1, n=0 may be included.

10.4 mg/ml of the Fc-A solution (5% sorbitol/25 mM histidine solution (pH 6.0)) (80.0 ml) prepared in Example 2-5 was buffer-replaced with a 50 mM phosphate buffer solution (pH 6.0) using VIVASPIN 20 (10,000 MWCO, manufactured by Sartorius AG) and adjusted to approximately 50 mL. The obtained Fc-A solution (50 mM phosphate buffer solution (pH 6.0)) was divided to two Violamo centrifuge tubes (VIO-50B). 7.70 mg/ml of a wild type EndoS solution (PBS) (0.8 ml) was added thereto, and the mixture was incubated at 37° C. for 2 hours. The degree of progression of the reaction was confirmed using Experion electrophoresis station (manufactured by Bio-Rad Laboratories, Inc.). After the completion of reaction, purification by affinity chromatography and purification using a hydroxyapatite column were performed according to the following method.

(1) Purification by Affinity Chromatography Purification
Apparatus: AKTA Pure 150 (Manufactured by GE Healthcare Japan Corp.)
Column: MediaScout ValiChrom 25 mm ID×100 mm H; V=50.0 mL
column packings: KANEKA KanCapA
Flow rate: 40 mL/min (10 mL/min during sample addition)

The obtained reaction solution (×2 tubes) was filtered through a 0.45 μm PVDF filter, adjusted to approximately 40 mL (×2), and purified in two portions. For binding to the column, the reaction solution was added to the upper part of the column, and a binding buffer (20 mM phosphate buffer solution (pH 7.0)) was injected into the column in 4.4 CV at 10 ml/min and further injected thereinto in 5 CV at 40 ml/min. For intermediate washing, a washing solution (20 mM phosphate buffer solution (pH 7.0) and 0.5 M sodium chloride solution) was injected into the column in 10 CV. For elution, an elution buffer (ImmunoPure IgG Elution buffer, manufactured by Pierce/Thermo Fisher Scientific Inc.) was injected into the column in 6 CV. The eluate was immediately neutralized with a 1 M Tris buffer solution (pH 9.0). Fractions detected by UV (280 nm) during elution were confirmed using, according to need, a micro volume spectrophotometer Xpose (manufactured by Trinean NV) and an Experion electrophoresis station (manufactured by Bio-Rad Laboratories, Inc.). Fractions containing the compound of interest were concentrated using VIVASPIN 20 (10,000 MWCO, manufactured by Sartorius AG) and buffer-replaced with a buffer solution (5 mM phosphate buffer solution and 50 mM 2-morpholinoethanesulfonic acid (MES) solution (pH 7.0)).

(2) Purification by Hydroxyapatite Chromatography Purification Apparatus: AKTA Pure 150 (Manufactured by GE Healthcare Japan Corp.)
Column: MediaScout ValiChrom 25 mm ID×100 mm H; V=50.0 mL
column packings: BIO-RAD CHT Type I 40 um
Flow rate: 20 mL/min (10 mL/min during sample addition)

The solution obtained in the preceding step (1) was filtered through a 0.45 μm PVDF filter and divided into two portions (approximately 40 mL each). These portions were purified in the two portions by the following steps: the solution was added to the upper part of the column, and solution A (5 mM phosphate buffer solution and 50 mM 2-morpholinoethanesulfonic acid (MES) solution (pH 7.0)) was injected into the column in 4.2 CV at 10 ml/min and further injected thereinto in 2 CV at 20 ml/min. Then, elution was performed using solution A and solution B (5 mM phosphate buffer solution, 50 mM 2-morpholinoethanesulfonic acid (MES) solution (pH 7.0), and 2 M sodium chloride solution). The elution conditions involved solution A:solution B=100:0 to 0:100 (15 CV). Further, a washing solution (500 mM phosphate buffer solution (pH 6.5)) was injected into the column in 5 CV.

Fractions detected by UV (280 nm) during elution were confirmed using, according to need, a micro volume spectrophotometer Xpose (manufactured by Trinean NV) and an Experion electrophoresis station (manufactured by Bio-Rad Laboratories, Inc.).

Fractions containing the compound of interest were concentrated using VIVASPIN 20 (10,000 MWCO, manufactured by Sartorius AG) and buffer-replaced with a 50 mM phosphate buffer solution (pH 6.0). The obtained solution was divided to 4 containers (24 mL each) and used as the following solutions a to d.

Solution a: 7.24 mg/mL of the (Fucα1,6)GlcNAc-Fc-A solution (50 mM phosphate buffer solution (pH 6.0)) (24 ml) (173.8 mg)

Solution b: 7.42 mg/mL of the (Fucα1,6)GlcNAc-Fc-A solution (50 mM phosphate buffer solution (pH 6.0)) (24 ml) (178.1 mg)

Solution c: 7.18 mg/mL of the (Fucα1,6)GlcNAc-Fc-A solution (50 mM phosphate buffer solution (pH 6.0)) (24 ml) (172.3 mg)

Solution d: 7.19 mg/mL of the (Fucα1,6)GlcNAc-Fc-A solution (50 mM phosphate buffer solution (pH 6.0)) (24 ml) (172.6 mg)

ESI-MS:
calculated for the chain of (Fucα1,6)GlcNAc-Fc-A(-Lys), M=25685.0, found 25681.9 (deconvolution data).

Figure 45:
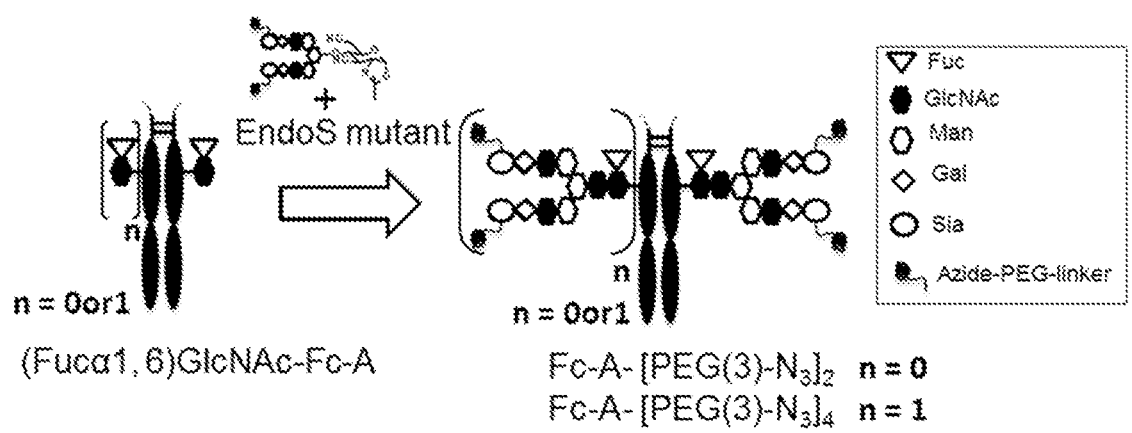
FIG. 45 shows Formula 72 which represents a mixture derived from a glycan structure deletion mutant contained in a prepared carrier protein.

(3-9B) Preparation of Fc-A-[PEG(3)-N$_3$]$_4$(FIG. 45)

The formulas given in FIGS. 44 and 45 represent a mixture derived from a glycan structure deletion mutant contained in a prepared carrier protein; and in addition to n=1, n=0 may be included.

The four (Fucα1,6)GlcNAc-Fc-A solutions (50 mM phosphate buffer solution (pH 6.0)) (24 ml) obtained in the step (3-8A) were each divided into two portions to prepare a total of eight 50 mL centrifuge tubes.

To one (Fucα1,6)GlcNAc-Fc-A solution (50 mM phosphate buffer solution (pH 6.0)) (12 ml), a 50 mM phosphate buffer solution (pH 6.0) (1.65 ml), a solution of [N3-PEG(3)]$_2$-SG(10)-Ox (56.0 mg) synthesized in Example 1-10 in a 50 mM phosphate buffer solution (pH 6.0) (1.0 ml), and 4.3 mg/ml of an EndoS D233Q/Q303L solution (PBS) (1.16 ml) were added, and the mixture was incubated at 30° C. for 4 hours. The operation described above was performed for 8 lots. The degree of progression of the reaction was confirmed using Experion electrophoresis station (manufactured by Bio-Rad Laboratories, Inc.). After the completion of reaction, the binding buffer used in the purification by affinity chromatography was changed from the 20 mM phosphate buffer solution (pH 7.0) to a 20 mM phosphate buffer solution (pH 6.0), and purification by affinity chromatography and purification by hydroxyapatite chromatography were performed according to the same method as in the step (3-9A). All fractions containing the compound of interest were combined and then concentrated into approximately 100 mL using an ultrafiltration apparatus (Cogent µScale TFF System) equipped with ultrafiltration membranes (Pellicon XL50 Cassette Ultracel 10 kDa (two membranes were used)). The concentrate was buffer-replaced with a 5% sorbitol/10 mM acetate buffer solution (pH 5.5) using VIVASPIN 20 (10,000 MWCO, manufactured by Sartorius AG). The obtained solutions were divided to two containers and used as the following solutions a and b.

Solution a: 12.45 mg/mL of the Fc-A4PEG(3)-$N_3]_4$ solution (5% sorbitol/10 mM acetate buffer solution (pH 5.5)) (19.7 ml) (245.3 mg)

Solution b: 14.95 mg/mL of the Fc-A-[PEG(3)-$N_3]_4$ solution (5% sorbitol/10 mM acetate buffer solution (pH 5.5)) (19.5 ml) (291.5 mg)

ESI-MS:

calculated for the chain of Fc-A-[PEG(3)-$N_3]_4$(-Lys), M=28088.3; found 28086.4 (deconvolution data).

Figure 46:
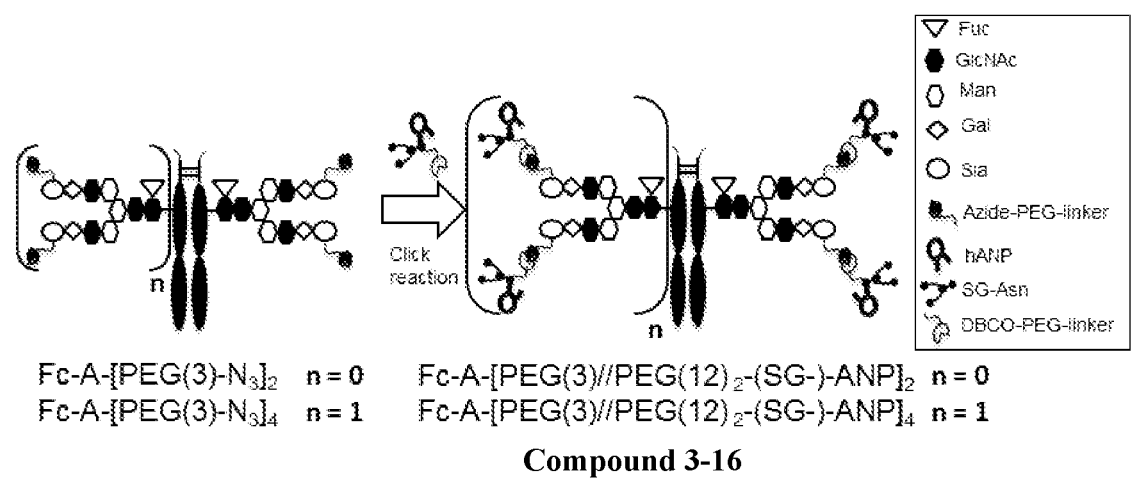
FIG. 46 shows Formula 73 (i.e., Compound 3-16) which represents a mixture derived from a glycan structure deletion mutant contained in a prepared carrier protein.

(3-9C) Preparation of Fc-A-[PEG(3)//PEG(12)$_2$-(SG-)Asn-hANP(1-28)]$_4$(FIG. 46)

The formulas given in FIG. 46 represent a mixture derived from a glycan structure deletion mutant contained in a prepared carrier protein; and in addition to n=1, n=0 may be included.

Figure 47:
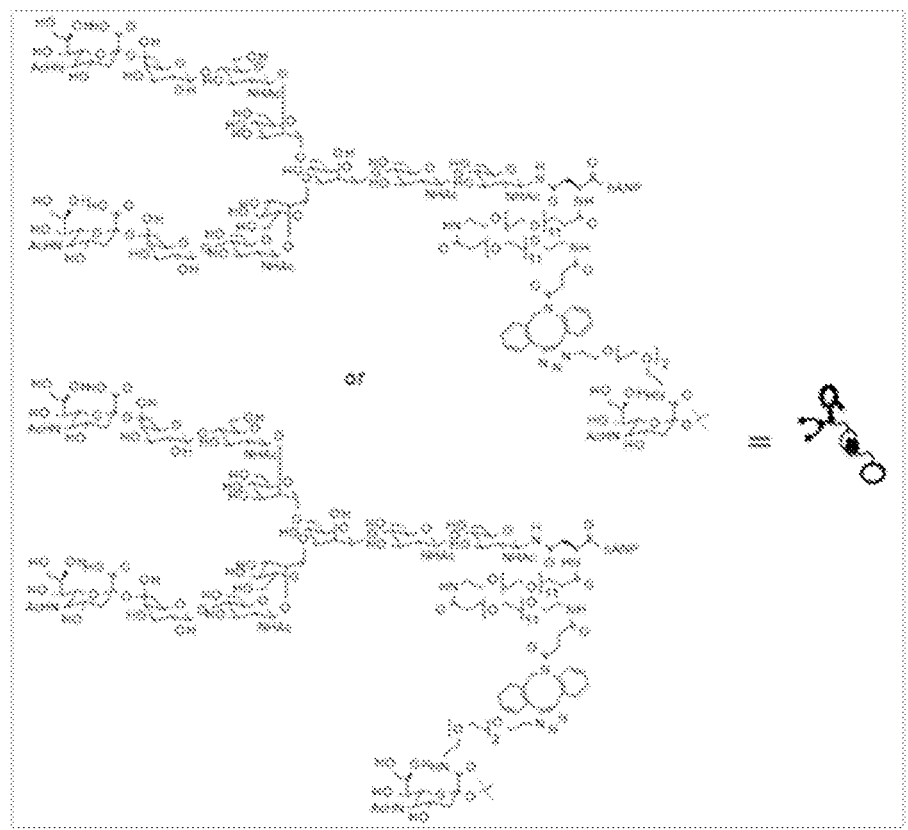
FIG. 47 shows Formula 74 which represents the structures of sialic acid in a N297 glycan, a PEG linker and a hANP peptide in compound 3-16 (FIG. 46).
Figure 48:
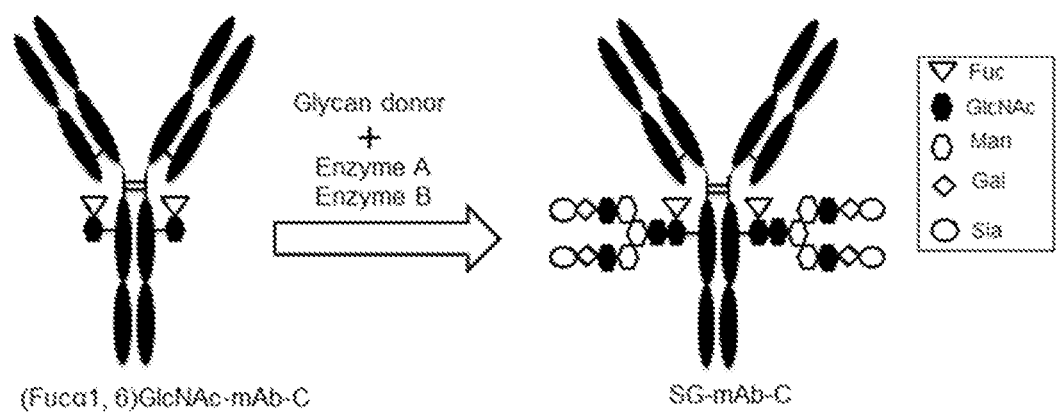
FIG. 48 shows Formula 75.
Figure 49:
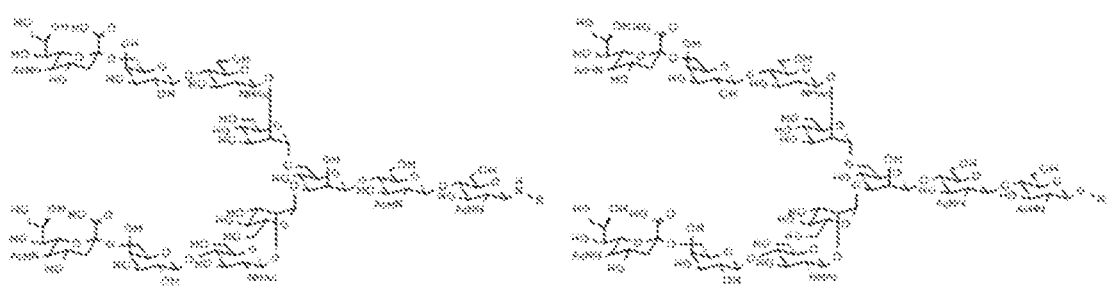
FIG. 49 shows Formula 76.

The formulas given in FIGS. 46 and 47 represent the structures of sialic acid in a N297 glycan, a PEG linker and a hANP peptide in compound 3-16 of FIG. 46; the triazole ring formed through Click reaction in the formulas has geometric isomerism, and compound 3-16 of FIG. 46 maintains a mixture of linkers having the right and left structures of the formulas; and since sialic acid residues at the non-reducing ends of all the N297 glycan moieties in compound 3-16 of FIG. 46 are modified with the linker moieties of the formula given above, four hANP(1-28) molecules for normal form Fc-A and two hANP(1-28) molecules for glycan deletion mutant Fc-A are linked per conjugate molecule.

12.45 mg/mL of the Fc-A-[PEG(3)-$N_3]_4$ solution (5% sorbitol/10 mM acetate buffer solution (pH 5.5)) (4.0 ml) which was solution a prepared in the step (3-9B), a 5% sorbitol/10 mM acetate buffer solution (pH 5.5) (6.0 ml), dimethyl sulfoxide (1.9 ml), and a solution of DBCO-PEG (12)2-(SG-)Asn-hANP(1-28) (45.1 mg) synthesized in Example 1-2 in dimethyl sulfoxide (0.62 ml) were mixed and incubated at 30° C. for 16 hours. The operation described above was carried out for 4 lots as to solution a. Also, 14.95 mg/mL of the Fc-A-[PEG(3)-$N_3]_4$ solution (5% sorbitol/10 mM acetate buffer solution (pH 5.5)) (3.3 ml) which was solution b prepared in the step (3-9B), a 5% sorbitol/10 mM acetate buffer solution (pH 5.5) (6.7 ml), dimethyl sulfoxide (1.9 ml), and a solution of DBCO-PEG (12)$_2$-(SG-)Asn-hANP(1-28) (45.1 mg) synthesized in Example 1-2 in dimethyl sulfoxide (0.62 ml) were mixed and incubated at 30° C. for 16 hours. The operation described above was carried out for 4 lots as to solution b. The reaction solutions in a total of 8 lots thus obtained were partially purified with NAP25 (manufactured by GE Healthcare Japan Corp.) and a 20 mM phosphate buffer solution (pH 6.0). The degree of progression of the reaction was confirmed by hydrophobic interaction chromatography under the conditions given below, followed by purification by affinity chromatography given below.

(1) Analysis Conditions for Hydrophobic Interaction Chromatography

Analysis apparatus: Hitachi D-7000 (manufactured by Hitachi, Ltd.)
Column: TSKgel Butyl-NPR (4.6×100 mm) (manufactured by Tosoh Corp.)
Mobile phase: solution A: 20 mM phosphate buffer solution (pH 7.0) and 2 M ammonium sulfate solution
solution B: 20 mM phosphate buffer solution (pH 7.0)
Gradient: A:B=75:25 to 0:100 (0 to 25 min)-0:100 (25 to 30 min)
Temperature: 25° C.
Wavelength: 214 nm
Flow rate: 1 ml/min (2) Purification by Affinity Chromatography Purification Apparatus: AKTA Pure 150 (Manufactured by GE Healthcare Japan Corp.)
Column: MediaScout ValiChrom 25 mm ID×100 mm H; V=50.0 mL
column packings: KANEKA KanCapA
Flow rate: 40 mL/min (10 mL/min during sample addition)

The obtained solution was filtered through a 0.45 µm PVDF filter, divided into two portions (approximately 80 mL each), and purified in the two portions by the following operation: for binding to the column, the reaction solution was added to the upper part of the column, and a binding buffer (20 mM phosphate buffer solution (pH 6.0)) was injected into the column in 5 CV at 10 ml/min and further injected thereinto in 5 CV at 40 ml/min. For intermediate washing, a washing solution (20 mM phosphate buffer solution (pH 7.0) and 0.5 M sodium chloride solution) was injected into the column in 10 CV. For elution, an elution buffer (ImmunoPure IgG Elution buffer, manufactured by Pierce/Thermo Fisher Scientific Inc.) was injected into the column in 6 CV. The eluate was immediately neutralized with a 1 M Tris buffer solution (pH 9.0). Fractions detected by UV (280 nm) during elution were confirmed using, according to need, a micro volume spectrophotometer Xpose (manufactured by Trinean NV) and hydrophobic interaction chromatography.

All fractions containing the compound of interest from the two portions were combined, then concentrated into approximately 40 mL using an ultrafiltration apparatus (Cogent µScale TFF System) equipped with ultrafiltration membranes (Pellicon XL50 Cassette Ultracel 10 kDa (two membranes were used)), and then buffer-replaced with a 5% sorbitol/10 mM acetate buffer solution (pH 5.5). Finally, the solution was filtered through a filter (Millex-GV, 0.22 µm, PVDF, already sterilized, manufactured by Merck Millipore/Merck KGaA) to obtain 7.81 mg/ml of a Fc-A-[PEG(3)//PEG(12)$_2$-hANP(1-28)]$_4$ solution (5% sorbitol/10 mM acetate buffer solution (pH 5.5)) (56 ml).

calculated for the chain of Fc-A-[PEG(3)//PEG(12)$_2$-hANP(1-28)]$_4$(-Lys), M=41866.8; found 41863.8 (deconvolution data).

Results of analyzing the conjugate by mass spectrometry without fragmentation will be given below.

calculated for Fc-A-[PEG(3)//PEG(12)$_2$-hANP(1-28)]$_4$(-Lys), M=83713.5; found 83712.6 (deconvolution data).

calculated for Fc-A-[PEG(3)//PEG(12)$_2$-hANP(1-28)]$_2$(-Lys), M=67186.4; found 67184.8 (deconvolution data).

<Example 3-10> Synthesis of Fc-B-[PEG(3)//PEG(12)$_2$-(SG-)Asn-hANP(1-28)]$_4$ (compound having a structure where Fc-A in the structure of compound 3-16 of FIG. 46 was replaced with Fc-B: compound 3-17)

The reaction scheme and the structure of a substance in each step of this Example correspond to those in which Fc-A in the corresponding scheme of Example 3-9 was replaced with Fc-B.

(3-10A) Preparation of (Fucα1,6)GlcNAc-Fc-B 13.0 mg/ml of the Fc-B solution (5% sorbitol/25 mM histidine solution (pH 6.0)) (20.0 ml) prepared in Example 2-4 was buffer-replaced with a 50 mM phosphate buffer solution (pH 6.0) using VIVASPIN 20 (10,000 MWCO, manufactured by Sartorius AG). To 20.0 mg/ml of the obtained Fc-B solution (50 mM phosphate buffer solution (pH 6.0)) (13.0 ml), a 50 mM phosphate buffer solution (pH 6.0) (7.0 ml) was added, then 2.00 mg/ml of a wild type EndoS solution (PBS) (1.92 ml) was added, and the mixture was incubated at 37° C. for 2 hours. The degree of progression of the reaction was confirmed using an Experion electrophoresis station (manufactured by Bio-Rad Laboratories, Inc.). After completion of the reaction, purification by affinity chromatography and purification using a hydroxyapatite column were performed according to the following method.

(1) Purification by Affinity Chromatography
Purification apparatus: AKTA pure 150 (manufactured by GE Healthcare Japan Corp.)
Column: HiTrap rProtein A FF (5 ml) (manufactured by GE Healthcare Japan Corp.)
Flow rate: 5 ml/min (1.25 ml/min during charging)

The obtained reaction solution was divided into five portions and purified in the five portions by the following method: for binding to the column, the reaction solution was added to the upper part of the column, and a binding buffer (20 mM phosphate buffer solution (pH 7.0)) was injected into the column in 2 CV at 1.25 ml/min and further injected thereinto in 5 CV at 5 ml/min. For intermediate washing, a washing solution (20 mM phosphate buffer solution (pH 7.0) and 0.5 M sodium chloride solution) was injected into the column in 10 CV. For elution, an elution buffer (ImmunoPure IgG Elution buffer, manufactured by Pierce/Thermo Fisher Scientific Inc.) was injected into the column in 6 CV. The eluate was immediately neutralized with a 1 M Tris buffer solution (pH 9.0). Fractions detected by UV (280 nm) during elution were confirmed using, according to need, a micro volume spectrophotometer Xpose (manufactured by Trinean NV) and an Experion electrophoresis station (manufactured by Bio-Rad Laboratories, Inc.).

All fractions containing the compound of interest from the five portions were combined, then concentrated using VIVASPIN 20 (10,000 MWCO, manufactured by Sartorius AG), buffer-replaced with a buffer solution (5 mM phosphate buffer solution and 50 mM 2-morpholinoethanesulfonic acid (MES) solution (pH 6.5)), and adjusted to 12 mL.

(2) Purification by Hydroxyapatite Chromatography Purification Apparatus: AKTA Pure 150 (Manufactured by GE Healthcare Japan Corp.)
Column: Bio-Scale Mini CHT Type I cartridge (5 ml) (manufactured by Bio-Rad Laboratories, Inc.)
Flow rate: 5 ml/min (1.25 ml/min during charging)

Two columns were connected, and the solution obtained in the preceding step (1) was divided into three portions and purified in the three portions by the following method: the solution was added to the upper part of the column, and solution A (5 mM phosphate buffer solution and 50 mM 2-morpholinoethanesulfonic acid (MES) solution (pH 6.5)) was injected into the column in 2 CV at 1.25 ml/min and further injected thereinto in 3 CV at 5 ml/min. Then, elution was performed using solution A and solution B (5 mM phosphate buffer solution, 50 mM 2-morpholinoethanesulfonic acid (MES) solution (pH 6.5), and 2 M sodium chloride solution). The elution conditions involved solution A:solution B=100:0 to 0:100 (15 CV). Further, a washing solution (500 mM phosphate buffer solution (pH 6.5)) was injected into the column in 5 CV.

Fractions detected by UV (280 nm) during elution were confirmed using, according to need, a micro volume spectrophotometer Xpose (manufactured by Trinean NV) and an Experion electrophoresis station (manufactured by Bio-Rad Laboratories, Inc.).

All fractions containing the compound of interest from the three portions were combined, then concentrated using VIVASPIN 20 (10,000 MWCO, manufactured by Sartorius AG), and buffer-replaced with a 50 mM phosphate buffer solution (pH 6.0) to obtain 7.17 mg/ml of a (Fucα1,6)GlcNAc-Fc-B solution (50 mM phosphate buffer solution (pH 6.0)) (35.4 ml).

ESI-MS:
calculated for the chain of (Fucα1,6)GlcNAc-Fc-B(-Lys), M=25287.7; found 25286.8 (deconvolution data).

(3-10B) Preparation of Fc-B-[PEG(3)-N$_3$]$_4$

To 7.17 mg/ml of the (Fucα1,6)GlcNAc-Fc-B solution (50 mM phosphate buffer solution (pH 6.0)) (6.0 ml) obtained in step (3-10A), the [N3-PEG(3)]$_2$-SG(10)-Ox (28.6 mg) solution (50 mM phosphate buffer solution (pH 6.0)) (0.50 ml) synthesized in Example 1-10 and 2.10 mg/ml of an EndoS D233Q/Q303L solution (PBS) (1.2 ml) were added, and the mixture was incubated at 30° C. for 3.5 hours. To this reaction solution, the [N3-PEG(3)]2-SG(10)-Ox (6.1 mg) solution (50 mM phosphate buffer solution (pH 6.0)) (0.10 ml) synthesized in Example 1-10 was further added, and the mixture was incubated at 30° C. for 0.5 hours. The operation described above was performed for 5 lots. The degree of progression of the reaction was confirmed using an Experion electrophoresis station (manufactured by Bio-Rad Laboratories, Inc.). After completion of the reaction, the binding buffer used in the purification by affinity chromatography was changed from the 20 mM phosphate buffer solution (pH 7.0) to a 20 mM phosphate buffer solution (pH 6.0), and purification by affinity chromatography and purification by hydroxyapatite chromatography were performed according to the same method as in step (3-10A). The portions obtained in the division operation were combined, and all fractions containing the compound of interest were concentrated using VIVASPIN 20 (10,000 MWCO, manufactured by Sartorius AG) and then buffer-replaced with a 5% sorbitol/10 mM acetate buffer solution (pH 5.5) using NAP25 (manufactured by GE Healthcare Japan Corp.) to obtain 13.06 mg/mL of a Fc-B-[PEG(3)-N$_3$]$_4$ solution (5% sorbitol/10 mM acetate buffer solution (pH 5.5)) (13.7 ml).

ESI-MS:
calculated for the chain of Fc-B-[PEG(3)-N$_3$]$_4$(-Lys), M=27691.0; found 27690.4 (deconvolution data).

(3-10C) Preparation of Fc-B-[PEG(3)//PEG(12)$_2$-(SG-) Asn-hANP(1-28)]$_4$ (Compound 3-17)

13.06 mg/mL of the Fc-B-[PEG(3)-N$_3$]$_4$ solution (5% sorbitol/10 mM acetate buffer solution (pH 5.5)) (3.1 ml)

prepared in step (3-10B), a 5% sorbitol/10 mM acetate buffer solution (pH 5.5) (4.9 ml), dimethyl sulfoxide (1.5 ml), and a solution of DBCO-PEG(12)2-(SG-)Asn-hANP (1-28) (36.6 mg) synthesized in Example 1-2 in dimethyl sulfoxide (0.51 ml) were mixed and incubated at 30° C. for 16 hours. The operation described above was carried out for 4 lots. The reaction solution was partially purified with NAP25 (manufactured by GE Healthcare Japan Corp.) and a 20 mM phosphate buffer solution (pH 6.0). The degree of progression of the reaction was confirmed by hydrophobic interaction chromatography under the conditions given below, followed by purification by affinity chromatography given below.

(1) Analysis Conditions for Hydrophobic Interaction Chromatography
Analysis apparatus: Hitachi D-7000 (manufactured by Hitachi, Ltd.)
Column: TSKgel Butyl-NPR (4.6×100 mm) (manufactured by Tosoh Corp.)
Mobile phase: solution A: 20 mM phosphate buffer solution (pH 7.0) and 2 M ammonium sulfate solution
solution B: 20 mM phosphate buffer solution (pH 7.0)
Gradient: A:B=75:25 to 0:100 (0 to 25 min)-0:100 (25 to 30 min)
Temperature: 25° C.
Wavelength: 214 nm
Flow rate: 1 ml/min (2) Purification by Affinity Chromatography
Purification apparatus: AKTA pure 150 (manufactured by GE Healthcare Japan Corp.)
Column: HiTrap rProtein A FF, 5 mL
Flow rate: 5 mL/min (1.25 mL/min during sample addition)

The obtained solution was divided into six portions and purified in the six portions by the following method: for binding to the column, the reaction solution was added to the upper part of the column, and a binding buffer (20 mM phosphate buffer solution (pH 6.0)) was injected into the column in 4 CV at 1.25 ml/min and further injected thereinto in 5 CV at 5 ml/min. For intermediate washing, a washing solution (20 mM phosphate buffer solution (pH 7.0) and 0.5 M sodium chloride solution) was injected into the column in 10 CV. For elution, an elution buffer (ImmunoPure IgG Elution buffer, manufactured by Pierce/Thermo Fisher Scientific Inc.) was injected into the column in 6 CV. The eluate was immediately neutralized with a 1 M Tris buffer solution (pH 9.0). Fractions detected by UV (280 nm) during elution were confirmed using, according to need, a micro volume spectrophotometer Xpose (manufactured by Trinean NV) and hydrophobic interaction chromatography.

All fractions containing the compound of interest from the six portions were combined, concentrated using VIVASPIN 20 (10,000 MWCO, manufactured by Sartorius AG), and then buffer-replaced with a 5% sorbitol/10 mM acetate buffer solution (pH 5.5). Finally, the solution was filtered through a filter (Millex-GV, 0.22 µm, PVDF, already sterilized, manufactured by Merck Millipore/Merck KGaA) to obtain 13.03 mg/ml of a Fc-A-[PEG(3)//PEG(12)$_2$-hANP (1-28)]$_4$ solution (5% sorbitol/10 mM acetate buffer solution (pH 5.5)) (13.6 ml).

calculated for the chain of Fc-B-[PEG(3)//PEG(12)$_2$-hANP(1-28)]$_4$(-Lys), M=41469.4; found 41467.9 (deconvolution data).

Results of analyzing the conjugate by mass spectrometry without fragmentation will be given below.

calculated for Fc-B-[PEG(3)//PEG(12)$_2$-hANP(1-28)]$_4$(-Lys), M=82918.8; found 82917.0 (deconvolution data).

calculated for Fc-B-[PEG(3)//PEG(12)$_2$-hANP(1-28)]$_2$(-Lys), M=66391.7; found 66390.8 (deconvolution data).

<Example 4-1> Test on cGMP Elevating Activity of Conjugate

The cGMP elevating activity of compounds 3-1 to 3-6 (FIGS. 27, 29, 33, 35, 38, and 41) prepared in Example 3 was measured by the following method.

CHO/human GC-A cells, which were CHO cells caused to constitutively express human GC-A, were suspended at $2 \times 10^5$ cells/ml in α-MEM, 10% FBS, and 1% penicillin-streptomycin, inoculated at 20 µl/well($4 \times 10^3$ cells/well) to a 384-well plate (manufactured by Corning Inc., 3826), and cultured overnight in a $CO_2$ incubator. On the next day, the medium was removed from this plate, and then, a 1.6 mM IBMX/KRB buffer was added thereto at 10 to 15 µl/well. The plate was stirred on a plate shaker and then incubated at room temperature for 10 minutes. Subsequently, a test substance dissolved in 0.1% BSA/PBS (dilution series were prepared such that the final concentration of each conjugate or native hANP(1-28) was 0.0001, 0.001, 0.01, 0.1, 1, 10 and 100 nM) was added thereto at 5 µl/well. The plate was stirred on a plate shaker and then incubated for 15 minutes in a $CO_2$ incubator. Then, the cGMP level in each well was measured using a cGMP kit (manufactured by Cisbio Bioassays) according to the attached protocol. The activity value (T/C) of the test substance at each concentration was corrected when the measurement value of a well supplemented with only a solvent was defined as 0 and the measurement value of a well supplemented with 1 nM native hANP was defined as 1. On the basis of this correction, the specific activity ($EC_{50}$ value of the test substance/$EC_{50}$ value of native hANP) and $E_{max}$ (the maximum activity value of the test substance in the concentration range) of each test substance were calculated (Table 2).

As seen from the results of Table 2, all the conjugates exhibited cGMP elevating activity. Also, the conjugates had Emax almost equivalent to native hANP. The glycosylated hANP-mAb-A conjugate (compound 3-2 of FIG. 29) was confirmed to have weaker specific activity than that of the hANP-mAb-A conjugate (compound 3-1 of FIG. 27). Also, the glycosylated hANP-CLCH-A conjugate (compound 3-4 of FIG. 35) was confirmed to have weaker specific activity than that of the hANP-CLCH-A conjugate (compound 3-3 of FIG. 33). This suggested that the introduction of a glycan to a hANP peptide tends to reduce in vitro activity. The specific activity of the glycosylated hANP-mAb-A conjugate (compound 3-5 of FIG. 38) having two hANP peptide moieties was attenuated by 4.5 times as compared with the glycosylated hANP-mAb-A conjugate (compound 3-2 of FIG. 29) having four hANP peptide moieties. Also, the specific activity of the glycosylated hANP-CLCH-A conjugate (compound 3-6 of FIG. 41) having two hANP peptide moieties was attenuated by 3.2 times as compared with the glycosylated hANP-CLCH-A conjugate (compound 3-4 of FIG. 35) having four hANP peptide moieties. This suggested that a conjugate having a larger number of hANP peptide moieties tends to exhibit more favorable activity.

All of compound 3-15 exploiting CLCH-B (LALA form of CLCH) as a carrier molecule, compound 3-16 of FIG. 46 exploiting Fc-A (LALA form of the Fc fragment) thereas, and compound 3-17 exploiting Fc-B (wild type Fc fragment) thereas exhibited in vitro activity at the same level as in native hANP.

TABLE 2 cGMP elevating activity of test substance

| Test substance | Specific activity | Emax |
|---|---|---|
| Native hANP | 1 | 1 |
| Compound 3-1 | 1.22 | 1.01 |
| Compound 3-2 | 17.03 | 0.99 |
| Compound 3-3 | 2.03 | 1.03 |
| Compound 3-4 | 13.6 | 0.99 |
| Compound 3-5 | 76.56 | 0.97 |
| Compound 3-6 | 43.42 | 0.98 |
| Compound 3-15 | 6.08 | 0.99 |
| Compound 3-16 | 1.57 | 1.01 |
| Compound 3-17 | 5.75 | 0.99 |

<Test Example 4-2> Test on Duration of Conjugate in Blood of Rat

The duration (the effect of sustainably elevating cGMP in blood and the time for which a test substance was detectable in blood) of each conjugate prepared in Example 3 in the blood of rats was examined by the following method.

(1) Preparation of Plasma Sample
Isoflurane: Japanese pharmacopoeia isoflurane
Needle and syringe for blood collection: Terumo Syringe 25G×1 SR for Tuberculin
Tube for blood collection: CAPIJECT Micro Collection Tube EDTA-2Na 500 µL
Tube for sample storage: MATRIX 4170 Sample Tracking Tube 0.75 mL Each 8- to 9-week-old male Slc:SD rat was subjected to isoflurane inhalation anesthesia (inhalation of an Escain inhalation anesthetic kept at a concentration of 1 to 2%). A solution of a test substance (each conjugate: compounds 3-1 to 3-6) diluted with PBS according to need was rapidly subcutaneously administered at a dose of 100 nmol/kg (1 mL/kg) to the rat. At the point in time selected for each compound from before the administration and 0.25, 0.5, 1, 2, 4, 8, 24, 48, 72, 96, 120 and 168 hours after the administration, blood was sampled (200 µL/sampling) over time from the jugular vein. The blood samples were immediately left on ice.

The collected blood samples were centrifuged at 5000 rpm at 4° C. for 5 minutes using a centrifuge (Sigma 4K15, rotor: Nr12130-H). The separated plasma samples were divided into two types (samples for PK measurement and for cGMP measurement) and preserved at −80° C. until measurement.

(2) Measurement of Plasma cGMP Concentration
The plasma cGMP concentration was measured for the plasma samples diluted 100-fold using Amersham cGMP Enzyme Immunoassay Biotrak™ (EIA) System (dual range) according to the protocol attached to the kit. Change in the obtained plasma cGMP concentration is shown in FIG. 6.

(3) Detection of Test Substance in Plasma Sample

10 µL of each rat plasma sample prepared in the paragraph (1) was diluted 10-fold with Rexxip HN Buffer (manufactured Gyros AB) and further appropriately diluted 10-fold (final: 100-fold dilution) with the same buffer as above, or the resulting dilution was further diluted 10-fold with 1% plasma/Rexxip HN Buffer (final: 1000-fold dilution), according to the need, to prepare a plasma sample for measurement. The primary antibody used was Goat Anti-Human IgG Biotin conjugate (SouthernBiotech) for the measurement of all human Fc-containing molecules (Fc/Fc) in the samples and Mouse Anti-ANP IgG (GeneTex Inc.) for the measurement of a conjugate (ANP/Fc) with hANP(1-28) bonded thereto in the samples. Each primary antibody was adjusted to 700 nM with 0.1% PBS-T. DyLight-labeled Goat Anti-Human IgG (SouthernBiotech) was adjusted as a secondary antibody for detection to 10 nM with Rexxip F Buffer (Gyros AB) for both the primary antibodies. Each solution was loaded in an automatic ELISA apparatus Gyrolab xP workstation and injected to Bioaffy 200 CD (Gyros AB). The content of the test substance (Fc/Fc and ANP/Fc) was measured by sandwich ELISA to calculate a plasma concentration.

Change in the obtained plasma concentration is shown in FIG. 7.

From FIGS. 6 and 7, these various conjugates were confirmed to be GC-A activators possessing all of gradual migration into blood, long retention in blood, and long pharmacological effect duration, as compared with native hANP.

The following was confirmed from FIG. 6.

Compound 3-1 of FIG. 27 which was a hANP-mAb-A conjugate exhibited the highest Emax. Also, compound 3-1 of FIG. 27 exhibited longer pharmacological activity duration than that of compound 3-3 of FIG. 33 which was a hANP-CLCH-A conjugate.

Compound 3-2 of FIG. 29 which was a glycosylated hANP-mAb-A conjugate, and compound 3-4 of FIG. 35 which was a glycosylated hANP-CLCH-A conjugate exhibited slower time to reach Emax and decay rate than those of compound 3-1 of FIG. 27. This probably means that a glycosylated hANP-mAb-A conjugate exhibits longer pharmacological activity duration.

Compounds 3-5 and 3-6 (FIGS. 38 and 41) which were conjugates having two hANP peptide moieties exhibited weaker Emax than that of compounds 3-2 of FIG. 29 and 3-4 of FIG. 35 which were conjugates having four hANP peptide moieties. This probably means that a glycosylated hANP-mAb-A conjugate having a larger number of hANP peptide moieties exhibits stronger pharmacological activity.

The following was confirmed from FIG. 7.

The concentrations in blood of the hANP conjugates were confirmed even 168 hours after administration.

Compound 3-1 of FIG. 27 which was a hANP-mAb-A conjugate had a small divergence between Fc/Fc and ANP/Fc, a high plasma concentration 168 hours after administration, and a slow decay rate, as compared with compound 3-3 which was a hANP-CLCH-A conjugate. This indicates that compound 3-1 of FIG. 27 has longer retention in blood than that of compound 3-3 of FIG. 33.

Compound 3-2 of FIG. 29 which was a glycosylated hANP-mAb-A conjugate had a small divergence between Fc/Fc and ANP/Fc, a high plasma concentration 168 hours after administration, and a slow decay rate, as compared with compound 3-1 of FIG. 27 which was a hANP-mAb-A conjugate. This indicates that compound 3-2 of FIG. 29 has longer retention in blood than that of compound 3-1 of FIG. 27. Compound 3-4 of FIG. 35 which was a glycosylated hANP-CLCH-A conjugate had a small divergence between Fc/Fc and ANP/Fc, a high plasma concentration 168 hours after administration, and a slow decay rate, as compared with compound 3-3 of FIG. 33 which was a hANP-CLCH-A conjugate. This indicates that compound 3-4 of FIG. 35 has longer retention in blood than that of compound 3-3 of FIG. 33.

<Example 4-3> Influence of PEG Linker on cGMP Elevating Activity of Conjugate

This experiment was conducted for the purpose of studying the influence of the PEG linker moiety on cGMP elevating activity using the conjugates synthesized in Example 3-7. The specific activity and Emax of native hANP and a test substance were calculated in the same way as the method described in Example 4-1. The results are shown in Table 3.

The following was confirmed as to the influence of the length or type of the PEG linker on in vitro activity. All the compounds kept Emax to the same extent as in hANP. The specific activity relative to hANP ranged from 0.41 to 2.84 times. Thus, all the compounds had cGMP elevating activity at a given or higher level. A compound having a larger number of ethylene glycol units contained in the PEG linker tended to exhibit more favorable activity. On the other hand, it was suggested that when linker structures have a nearly equal length as a whole, a compound having a linker structure where a smaller number of linker molecules having long PEG are bonded tends to exhibit more favorable activity than that of a compound having a linker structure where a larger number of linker molecules having short PEG (e.g., PEG(6)) are bonded.

TABLE 3

| Test substance | cGMP elevating activity of test substance | |
|---|---|---|
| | Specific activity | Emax |
| Native hANP | 1 | 1 |
| 3-7 | 0.42 | 1.06 |
| 3-8 | 1.11 | 1.06 |
| 3-9 | 0.41 | 1.08 |
| 3-12 | 2.84 | 1.00 |
| 3-13 | 2.19 | 1.01 |
| 3-14 | 1.69 | 1.02 |

<Test Example 4-4> Influence of PEG Linker on Duration of Conjugate in Blood of Rat This experiment was conducted for the purpose of studying the influence of the PEG linker moiety on duration in animal blood using the conjugates synthesized in Example 3-7. Time-dependent change in plasma cGMP concentration after subcutaneous administration of a test substance to rats was examined in the same way as the method described in Example 4-2. The results are shown in FIG. 8.

The following was confirmed as to the influence of the length or type of the PEG linker on in vitro activity. Compound 3-7 having PEG(12)-PEG(12) had the highest Emax, whereas compound 3-9 having PEG(24) had the weakest activity and short duration, contrary to the in vitro results.

<Test Example 4-5> Physical Property Evaluation of Conjugate

Native hANP(1-28) is known to be highly agglutinated. For example, when 7 mg/mL solution of native hANP(1-28) in PBS is incubated at 30° C., gel-like deposits are confirmed within 24 hours and the whole solution is confirmed to become a gel within 48 hours.

Provided that a test is conducted at almost the same concentration based on the number of moles of hANP contained, the agglutination of a hANP conjugate can be indirectly compared. The following test was conducted for the purpose of confirming the agglutination of the conjugate of the present invention.

(1) Accelerated Deterioration Test

Each sample was concentrated using Vivapore 5 (manufactured by Vivascience AG), dialyzed against 25 mM AcONa/5% sorbitol, pH 5.5 (ABSor solution) or PBS, and then adjusted to 70 mg/mL. The solution was filtered through a Spin-X 0.22 μm centrifugal filter (manufactured by CoStar Group, Inc.) and dispensed at 80 μL/tube to 0.5 mL sterilized slim tubes (manufactured by Sumitomo Bakelite Co., Ltd.), which were then hermetically sealed and then left standing at 40° C. for 2 weeks. The sample before and after deterioration was measured using SEC-MALS system (manufactured by Wyatt Technology Corp.) constituted by Agilent 1260 LC, DAWN HELEOS 8, and Eclipse 3+, and analyzed using ASTRA software (manufactured by Wyatt Technology Corp.). The measurement was carried out under conditions of column: Nanofilm SEC-250 7.8'300 mm (manufactured by Sepax Technologies, Inc.), buffer: 0.2 M KPi/0.2 M KCl, pH 7.0, flow rate: 0.5 mL/min, column temperature: 30° C., and detection wavelength: 280 nm. The results are shown in Table 4.

The whole solution of native hANP in PBS becomes a gel within 48 hours, whereas the conjugates were confirmed to have solution fluidity even 2 weeks later and exhibited improved solution stability. The accelerated deterioration treatment increased a high-molecular-weight form of compound 3-3 from 8.2% to 14.2% in the ABSor solution and from 9.2% to 45.7% in the PBS solution. As for compound 3-4 with a glycan introduced near the hANP site of compound 3-3, the accelerated deterioration treatment increased a high-molecular-weight form from 1.8% to 4.5% in the ABSor solution and from 2.8% to 12.8% in the PBS solution. Accordingly, the introduction of a glycan to near a hANP site was found to reduce agglutination remarkably.

TABLE 4

| | | Content ratio of high-molecular-weight form | |
|---|---|---|---|
| Compound No. of test substance | Buffer solution | Before accelerated deterioration treatment | After accelerated deterioration treatment |
| 3-3 | ABSor | 8.2% | 14.2% |
| 3-3 | PBS | 9.2% | 45.7% |
| 3-4 | ABSor | 1.8% | 4.5% |
| 3-4 | PBS | 2.8% | 12.8% |

<Test Example 4-6> Test on Duration of Conjugate in Blood of Monkey

The duration of the conjugates differing in their carrier molecule, prepared in Example 3, in the blood of monkeys was examined by examining the time for which a test substance was detectable in blood according to the following method to study the influence of the carrier molecule on the duration in the blood of the conjugates.

(1) Preparation of Plasma Sample

Needle and syringe for blood collection: Terumo Syringe 25G×1 SR for Tuberculin

Tube for blood collection: CAPIJECT Micro Collection Tube EDTA-2Na or Venoject Vacuum Blood Collecting Vessel EDTA-2Na Tube for sample storage: MATRIX 4170 Sample Tracking Tube 0.75 mL Each 3- to 7-year-old male cynomolgus monkey was subjected to the administration of a test substance and blood collection without anesthesia. A solution of a test substance (each conjugate: compounds 3-2, 3-4, 3-15, 3-16, and 3-17) diluted with PBS according to need was rapidly subcutaneously administered at a dose of 10 nmol/kg (1 mL/kg) to the monkey. At each point in time before administration and 0.25, 0.5, 1, 2, 4, 8, 24, 48, 96, 168, 336, 528 (or 504), and 696 (or 672) hours after administration, blood was sampled (approximately 500 μL/sampling) over time from the vein. The blood samples were immediately left on ice.

The collected blood samples were centrifuged, and the plasma samples thus obtained were preserved at −80° C. until measurement.

(2) Detection of Test Substance in Plasma Sample

To 10 μL of each monkey plasma sample prepared in the paragraph (1), 90 μL of Rexxip HN Buffer (manufactured Gyros AB) was added and then mixed (10-fold diluted sample, MRD: 10), or the resulting dilution was further diluted 10-fold with Rexxip HN Buffer (100-fold diluted sample, MRD: 100) and further diluted 10-fold with 1% plasma/Rexxip HN Buffer (1000-fold diluted sample, MRD: 100) to prepare a plasma sample for measurement. The primary antibody used was Goat Anti-Human IgG Biotin conjugate (SouthernBiotech) for the measurement of all human Fc-containing molecules (Fc/Fc) in the samples and Mouse Anti-ANP IgG (GeneTex Inc.) for the measurement of a conjugate (ANP/Fc) with hANP(1-28) bonded thereto in the samples. Each primary antibody was adjusted to 700 nM with 0.1% PBS-T. DyLight-labeled Goat Anti-Human IgG (SouthernBiotech) was adjusted as a secondary antibody for detection to 10 nM with Rexxip F Buffer (Gyros AB) for both the primary antibodies. Each solution was loaded in an automatic ELISA apparatus Gyrolab xP workstation and injected to Bioaffy 200 CD (Gyros AB). The content of the test substance (Fc/Fc and ANP/Fc) was measured by sandwich ELISA to calculate a plasma concentration.

Change in the obtained plasma concentration is shown in FIG. 9.

From FIG. 9, the hANP conjugates used in this test were confirmed to have a conjugate concentration in blood even 672 hours (28 days) after administration, without being degraded. Compounds 3-4 of FIGS. 35 and 3-15 having CLCH-A and CLCH-B, respectively, as a carrier molecule rapidly decayed from blood, as compared with compound 3-2 having mAb-A as a carrier molecule. On the other hand, compounds 3-16 of FIGS. 46 and 3-17 having Fc-A and Fc-B, respectively, as a carrier molecule decayed more gradually from blood than compound 3-2 of FIG. 29. Hence, a glycosylated hANP-Fc conjugate was found to have the longest duration in the blood of monkeys.

[Example 5] Transglycosylation Reaction Using Two Types of Endo Enzymes

Enzyme A (EndoM-like enzyme) and enzyme B (EndoS-like enzyme) can be properly combined as the two types of Endo enzymes used. Examples of enzyme A can include EndoM, EndoOm, and EndoCC, and EndoM mutants, EndoOm mutants, and EndoCC mutants that exhibit reduced hydrolyzing activity. Examples of enzyme B can include EndoS and EndoS2 (EndoS49), and EndoS mutants and EndoS2 (EndoS49) mutants that exhibit reduced hydrolyzing activity. In the structure of a glycan donor moiety, any substituent other than R=H may be used as substituent R at the anomer site as long as the resulting molecule is synthesizable in a chemical reaction or enzymatic reaction.

<Example 5-1> Measurement of Rate of Transglycosylation Using SGP as Glycan Donor Commercially available trastuzumab was used as mAb-C. Trastuzumab (440 mg/vial, manufactured by Genentech Inc.) was prepared into 51.3 mg/ml of a (Fucα1,6)GlcNAc-trastuzumab solution (50 mM Tris buffer solution (pH 7.4)) (1.65 ml) by use of the method described in Example 3-1. To 51.3 mg/ml of the (Fucα1,6)GlcNAc-trastuzumab solution (50 mM Tris buffer solution (pH 7.4)) (19.5 μl), a 50 mM Tris buffer solution (pH 7.4) (0.5 μl), a SGP (manufactured by Tokyo Chemical Industry Co., Ltd.) (5.82 mg) solution (50 mM Tris buffer solution (pH 7.4)) (29.1 μl), 1 U/ml of an EndoM N175Q solution (manufactured by Tokyo Chemical Industry Co., Ltd.) (5.0 μl) and 2.00 mg/ml of an EndoS D233Q solution (PBS) (10.0 μl) were added, and the mixture was incubated at 28° C. for 48 hours.

At each point in time of 2 hours, 4 hours, 8 hours, 24 hours and 48 hours after the start of the reaction, a portion of this reaction solution was collected, and the degree of progression of the reaction was measured using an Experion electrophoresis station (manufactured by Bio-Rad Laboratories, Inc.). For the measurement, a measurement sample was prepared according to the manual attached to the instrument. In the course of this, the transglycosylation reaction was immediately stopped because of the operation of exposing the collected reaction solution to a solution containing dithiothreitol and heating the reaction solution at 95° C. for 5 minutes.

The obtained measurement sample was transferred to Experion Pro260 Chips and measured according to the manual attached to the Experion electrophoresis station. From the obtained chromatogram, an unreacted product and a transglycosylated form were confirmed as separate peaks. The rate of transglycosylation was calculated according to the following expression from the peak area ratio between the unreacted product and the transglycosylated form.

Rate of transglycosylation(%)=[Peak area of the H chain derived from SG-trastuzumab]/{[Peak area of the H chain derived from (Fucα1,6) GlcNAc-trastuzumab+[Peak area of the H chain derived from SG-trastuzumab]}×100

Similarly, reactions were performed using varying combinations of various Endo enzymes, and the rate of transglycosylation at each point in time of each reaction was calculated (Table 5).

<Example 5-2> Measurement of Rate of Transglycosylation Using SG-Asn as Glycan Donor To 51.3 mg/ml of the (Fucα1,6)GlcNAc-trastuzumab solution (50 mM Tris buffer solution (pH 7.4)) (19.5 μl), a 50 mM Tris buffer solution (pH 7.4) (0.5 μl), a SG-Asn ammonium salt (4.74 mg) solution (50 mM Tris buffer solution (pH 7.4)) (23.7 μl), a 1 U/ml of EndoM N175Q solution (5.0 μl) and 2.00 mg/ml of an EndoS D233Q solution (PBS) (10.0 μl) were added, and the mixture was incubated at 28° C. for 48 hours. The subsequent procedures were performed in the same way as in Example 5-1 to calculate the rate of transglycosylation at each point in time of a reaction (Table 5).

<Example 5-3> Measurement of Rate of Transglycosylation Using EndoCC as Enzyme a To 51.3 mg/ml of the (Fucα1,6)GlcNAc-trastuzumab solution (50 mM Tris buffer solution (pH 7.4)) (19.5 μl), a 50 mM Tris buffer solution (pH 7.4) (0.5 μl), a SGP (manufactured by Tokyo Chemical Industry Co., Ltd.) (5.82 mg) solution (50 mM Tris buffer solution (pH 7.4)) (29.1 μl), a 1.16 U/ml of an EndoCC solution or 2.21 U/ml of an EndoCC N180H solution (Fushimi Pharmaceutical Co., Ltd.) (15.0 μl) and 2.00 mg/ml of an EndoS D233Q solution (PBS) (10.0 μl) were added, and the mixture was incubated at 28° C. or 37° C. for 48 hours. The subsequent procedures were performed in the same way as in Example 5-1 to calculate the rate of transglycosylation at each point in time of a reaction (Table 5).

TABLE 5

Reaction conditions and time-dependent change in rate of transglycosylation

| Example | Enzyme A | Enzyme B | Glycan donor | Temperature | 2 h | 4 h | 8 h | 24 h | 48 h |
|---|---|---|---|---|---|---|---|---|---|
| 5-1-1 | EndoM | EndoS | SGP | 28° C. | 2 | 1 | 1 | <1 | <1 |
| 5-1-2 | EndoM | EndoS D233Q | SGP | 28° C. | 5 | 7 | 8 | 13 | 10 |
| 5-1-3 | EndoM N175Q | EndoS | SGP | 28° C. | 4 | 3 | 2 | 1 | <1 |
| 5-1-4 | EndoM N175Q | — | SGP | 28° C. | 2 | 2 | 4 | 5 | 5 |
| 5-1-5 | — | EndoS D233Q | SGP | 28° C. | <1 | 1 | 1 | 1 | 1 |
| 5-1-6 | EndoM N175Q | EndoS D233Q | SGP | 28° C. | 89 | 93 | 95 | 95 | 93 |
| 5-1-7 | EndoM N175Q | EndoS D233Q/Q303L | SGP | 28° C. | 53 | 72 | 88 | 95 | 93 |
| 5-1-8 | EndoM N175Q | EndoS D233Q/E350Q | SGP | 28° C. | 94 | 97 | 97 | 96 | 95 |
| 5-2 | EndoM N175Q | EndoS D233Q | (SG-)Asn | 28° C. | 70 | 86 | 95 | 97 | 94 |
| 5-3-1 | EndoCC | EndoS D233Q | SGP | 37° C. | <1 | <1 | <1 | <1 | <1 |
| 5-3-2 | EndoCC N180H | EndoS D233Q | SGP | 28° C. | 11 | 16 | 25 | 34 | 35 |
| 5-3-3 | EndoCC N180H | EndoS D233Q | SGP | 37° C. | 42 | 51 | 57 | 52 | 39 |

When an oxazoline form was not used as a glycan donor, the transglycosylation reaction were confirmed to proceed efficiently by mixing two types of Endo enzyme mutants at an appropriate ratio. When enzyme A has high hydrolyzing activity, the rate of transglycosylation is low even if a mutant that exhibits reduced hydrolyzing activity is used as enzyme B. Enzyme Bs that exhibit reduced hydrolyzing activity differ in reaction time until the rate of transglycosylation exceeds 90%, depending on the degree thereof. EndoCC whose optimum reaction temperature is reportedly 50° C. tends to yield a higher rate of transfer at a higher reaction temperature.

A chemically modified glycan structure can be introduced to a Fc-containing molecule by selecting a properly chemically modified glycan donor. For example, provided that ($N_3$—PEG(3)-SG-)Asn-PEG(3)-$N_3$ is used instead of the glycan donor SGP or (SG-)Asn, the corresponding glycan can be transferred to a Fc-containing molecule. Also, mAb, CLCH, or Fc can be appropriately used as the Fc-containing molecule.

<Example 5-4> Preparation of mAb-A-[PEG(3)-$N_3$]$_4$ Using ([N3-PEG(3)]$_2$-SG-)Asn-PEG(3)-$N_3$ mAb-A-[PEG(3)-$N_3$]$_4$ was prepared by the following method using ([$N_3$-PEG(3)]$_2$-SG-)Asn-PEG(3)-$N_3$ as a glycan donor.

To 51.27 mg/ml of the (Fucα1,6)GlcNAc-mAb-A solution (50 mM Tris buffer solution (pH 7.4)) (200 μl), the ([$N_3$-PEG(3)]$_2$-SG-)Asn-PEG(3)-$N_3$ (50.0 mg) solution (50 mM Tris buffer solution (pH 7.4)) (240 μl) prepared in step (1-12A), 1 U/ml of an EndoM N175Q solution (manufactured by Tokyo Chemical Industry Co., Ltd.) (50 μl) and 2.10 mg/ml of an EndoS D233Q/Q303L solution (PBS) (100 μl) were added, and the mixture was incubated at 28° C. for 20 hours. Then, a purification method (purification apparatus and column) and an ultrafiltration method (ultrafiltration membrane) suitable for the reaction scale were selected in accordance with the method described in Example 3-1 to obtain 14.78 mg/mL of a mAb-A-[PEG(3)-$N_3$]$_4$ solution (5% sorbitol/10 mM acetate buffer solution (pH 5.5)) (500 μl). ESI-MS:

calculated for the heavy chain of mAb-A-[PEG(3)-$N_3$]$_4$ (-Lys, pyrGlu), M=52569.9; found 52570.0 (deconvolution data).

calculated for the light chain of mAb-A-[PEG(3)-$N_3$]$_4$, M=23292.9; found 23292.0 (deconvolution data).

<Example 5-5> Preparation of CLCH-B-[PEG(3)-$N_3$]$_4$ Using ([$N_3$-PEG(3)]$_2$-SG-)Asn-PEG(3)-$N_3$ CLCH-B-[PEG(3)-$N_3$]$_4$ was prepared by the following method using ([$N_3$-PEG(3)]$_2$-SG-)Asn-PEG(3)-$N_3$ as a glycan donor.

To 39.2 mg/ml of the (Fucα1,6)GlcNAc-CLCH-B solution (50 mM Tris buffer solution (pH 7.4)) (150 μl), a 50 mM Tris buffer solution (pH 7.4) (50 μl), the ([$N_3$-PEG(3)]$_2$-SG-)Asn-PEG(3)-$N_3$ (53.0 mg) solution (50 mM Tris buffer solution (pH 7.4)) (240 μl) prepared in step (1-12A), 1 U/ml of an EndoM N175Q solution (manufactured by Tokyo Chemical Industry Co., Ltd.) (50 μl) and 2.10 mg/ml of an EndoS D233Q/Q303L solution (PBS) (100 μl) were added, and the mixture was incubated at 28° C. for 20 hours. Then, a purification method (purification apparatus and column) and an ultrafiltration method (ultrafiltration membrane) suitable for the reaction scale were selected in accordance with the method described in Example 3-8 to obtain 8.92 mg/mL of a CLCH-B-[PEG(3)-$N_3$]$_4$ solution (5% sorbitol/10 mM acetate buffer solution (pH 5.5)) (500 ul).

ESI-MS:
calculated for the heavy chain of CLCH-B-[PEG(3)-$N_3$]$_4$(-Lys), M=38706.3; found 38706.1 (deconvolution data).

calculated for the light chain of CLCH-B-[PEG(3)-$N_3$]$_4$, M=11507.8; found 11506.7 (deconvolution data).

<Example 5-6> Preparation of Fc-A-[PEG(3)-$N_3$]$_4$ Using ([$N_3$-PEG(3)]$_2$-SG-)Asn-PEG(3)-$N_3$ Fc-A-[PEG(3)-$N_3$]$_4$ was prepared by the following method using ([$N_3$-PEG(3)]$_2$-SG-)Asn-PEG(3)-$N_3$ as a glycan donor.

To 24.8 mg/ml of the (Fucα1,6)GlcNAc-Fc-A solution (50 mM Tris buffer solution (pH 7.4)) (140 μl), a 50 mM Tris buffer solution (pH 7.4) (60 μl), a solution of ([N$_3$-PEG(3)]$_2$-SG-)Asn-PEG(3)-N$_3$ (60.0 mg) prepared in step (1-12A) in a 50 mM Tris buffer solution (pH 7.4) (240 μl), 1 U/ml of an EndoM N175Q solution (manufactured by Tokyo Chemical Industry Co., Ltd.) (50 μl) and 2.10 mg/ml of an EndoS D233Q/Q303L solution (PBS) (100 μl) were added, and the mixture was incubated at 28° C. for 20 hours.

Then, a purification method (purification apparatus and column) and an ultrafiltration method (ultrafiltration membrane) suitable for the reaction scale were selected in accordance with the method described in Example 3-9 to obtain 4.06 mg/mL of a Fc-A-[PEG(3)-N$_3$]$_4$ solution (5% sorbitol/10 mM acetate buffer solution (pH 5.5)) (500 ul).

calculated for the chain of Fc-B-[PEG(3)-N$_3$]$_4$(-Lys), M=28088.3; found 28085.6 (deconvolution data).

---

The invention claimed is:

1. A method for producing a desired Fc-containing molecule comprising a complex N297 glycan, the method comprising reacting a glycan donor comprising a complex glycan with an unactivated reducing end, an initial Fc-containing molecule comprising an acceptor N297 glycan, an Endo enzyme (enzyme A) which recognizes the complex glycan of the glycan donor but not the acceptor N297 glycan as its substrate, and another Endo enzyme (enzyme B) which recognizes the acceptor N297 glycan as its substrate, in a reaction solution, wherein the glycan donor is (MSG1-) Asn, (MSG2-) Asn, SGP or (SG-) Asn, wherein the acceptor N297 glycan is GlcNAc or (Fuca1, 6) GlcNAc, wherein the enzyme A is EndoM, EndoCC, EndoOm, EndoM N175Q, EndoCC N180H, or EndoOm N194Q, and wherein the enzyme B is EndoS, EndoS2, EndoS D233Q, EndoS D233Q/Q303L, EndoS D233Q/E350A, EndoS D233Q/E350Q, EndoS D233Q/E350D, EndoS D233Q/E350N, or EndoS D233Q/D405A.

2. The method according to claim 1, further comprising purifying the desired Fc-containing molecule from the reaction solution.

3. The method according to claim 1, wherein the glycan donor is a molecule comprising a N-linked glycan or a O-linked glycan.

4. The method according to claim 3, wherein the complex glycan in the glycan donor comprises a non-reducing end which is chemically modified.

5. The method according to claim 1, wherein the complex glycan in the glycan donor comprises a non-reducing end which is chemically modified.

6. The method according to claim 1, wherein the desired Fc-containing molecule is an IgG, CLCH or Fc fragment.

7. The method according to claim 5, wherein the chemical modification on the non-reducing end is introduction of an azide group to the sialic acid in the non-reducing end.

8. The method of claim 7, further comprising the step of reacting a molecule comprising DBCO with the azide group.

* * * * *